United States Patent
Diab et al.

(10) Patent No.: US 11,832,940 B2
(45) Date of Patent: Dec. 5, 2023

(54) NON-INVASIVE MEDICAL MONITORING DEVICE FOR BLOOD ANALYTE MEASUREMENTS

(71) Applicant: Cercacor Laboratories, Inc., Irvine, CA (US)

(72) Inventors: Mohamed K. Diab, Ladera Ranch, CA (US); Kevin Hughes Pauley, Lake Forest, CA (US); Jesse Chen, Foothill Ranch, CA (US); Cristiano Dalvi, Lake Forest, CA (US); Hung The Vo, Fountain Valley, CA (US); Ferdyan Lesmana, Irvine, CA (US); Jeroen Poeze, Rancho Santa Margarita, CA (US); Ruiqi Long, Irvine, CA (US); Venkatramanan Krishnamani, Irvine, CA (US); Frank Lee, Irvine, CA (US)

(73) Assignee: Cercacor Laboratories, Inc., Irvine, CA (US)

( * ) Notice: Subject to any disclaimer, the term of this patent is extended or adjusted under 35 U.S.C. 154(b) by 344 days.

(21) Appl. No.: 17/004,663

(22) Filed: Aug. 27, 2020

(65) Prior Publication Data

US 2021/0113121 A1   Apr. 22, 2021

Related U.S. Application Data

(60) Provisional application No. 62/892,217, filed on Aug. 27, 2019.

(51) Int. Cl.
*A61B 5/145* (2006.01)
*G02B 27/30* (2006.01)
(Continued)

(52) U.S. Cl.
CPC ........ *A61B 5/14532* (2013.01); *A61B 5/1455* (2013.01); *A61B 5/6826* (2013.01); *G02B 27/30* (2013.01)

(58) Field of Classification Search
CPC . A61B 5/14532; A61B 5/1455; A61B 5/6826; A61B 5/0073; A61B 5/7267;
(Continued)

(56) References Cited

U.S. PATENT DOCUMENTS

| 4,960,128 A | 10/1990 | Gordon et al. |
| 4,964,408 A | 10/1990 | Hink et al. |

(Continued)

FOREIGN PATENT DOCUMENTS

WO   WO-2010082444 A1 * 7/2010 ......... A61B 5/02241

OTHER PUBLICATIONS

US 2022/0192529 A1, 06/2022, Al-Ali et al. (withdrawn)
Gannon, "What are the benefits of spring-loaded contacts?", WTWH Media LLC (Year: 2016).*

*Primary Examiner* — Eric F Winakur
*Assistant Examiner* — Jonathan Drew Moroneso
(74) *Attorney, Agent, or Firm* — Knobbe Martens Olson & Bear LLP

(57) ABSTRACT

Systems, methods, and apparatuses for enabling a plurality of non-invasive, physiological sensors to obtain physiological measurements from essentially the same, overlapping, or proximate regions of tissue of a patient are disclosed. Each of a plurality of sensors can be integrated with or attached to a multi-sensor apparatus and can be oriented such that each sensor is directed towards, or can obtain a measurement from, the same or a similar location.

10 Claims, 63 Drawing Sheets

(51) Int. Cl.
*A61B 5/1455* (2006.01)
*A61B 5/00* (2006.01)

(58) Field of Classification Search
CPC ..... A61B 5/0205; A61B 5/0531; A61B 5/442; A61B 5/0071; A61B 5/0075; G02B 27/30
See application file for complete search history.

(56) References Cited

U.S. PATENT DOCUMENTS

| | | | |
|---|---|---|---|
| 5,319,355 A | 6/1994 | Russek | |
| 5,337,744 A | 8/1994 | Branigan | |
| 5,341,805 A | 8/1994 | Stavridi et al. | |
| D353,195 S | 12/1994 | Savage et al. | |
| D353,196 S | 12/1994 | Savage et al. | |
| 5,377,676 A | 1/1995 | Vari et al. | |
| D359,546 S | 6/1995 | Savage et al. | |
| 5,431,170 A | 7/1995 | Mathews | |
| 5,436,499 A | 7/1995 | Namavar et al. | |
| D361,840 S | 8/1995 | Savage et al. | |
| D362,063 S | 9/1995 | Savage et al. | |
| D363,120 S | 10/1995 | Savage et al. | |
| 5,456,252 A | 10/1995 | Vari et al. | |
| 5,479,934 A | 1/1996 | Imran | |
| 5,482,036 A | 1/1996 | Diab et al. | |
| 5,494,043 A | 2/1996 | O'Sullivan et al. | |
| 5,533,511 A | 7/1996 | Kaspari et al. | |
| 5,561,275 A | 10/1996 | Savage et al. | |
| 5,590,649 A | 1/1997 | Caro et al. | |
| 5,602,924 A | 2/1997 | Durand et al. | |
| 5,638,816 A | 6/1997 | Kiani-Azarbayjany et al. | |
| 5,638,818 A | 6/1997 | Diab et al. | |
| 5,645,440 A | 7/1997 | Tobler et al. | |
| 5,671,914 A | 9/1997 | Kalkhoran et al. | |
| 5,726,440 A | 3/1998 | Kalkhoran et al. | |
| D393,830 S | 4/1998 | Tobler et al. | |
| 5,743,262 A | 4/1998 | Lepper, Jr. et al. | |
| 5,747,806 A | 5/1998 | Khalil et al. | |
| 5,750,994 A | 5/1998 | Schlager | |
| 5,758,644 A | 6/1998 | Diab et al. | |
| 5,760,910 A | 6/1998 | Lepper, Jr. et al. | |
| 5,890,929 A | 4/1999 | Mills et al. | |
| 5,919,134 A | 7/1999 | Diab | |
| 5,987,343 A | 11/1999 | Kinast | |
| 5,997,343 A | 12/1999 | Mills et al. | |
| 6,002,952 A | 12/1999 | Diab et al. | |
| 6,010,937 A | 1/2000 | Karam et al. | |
| 6,027,452 A | 2/2000 | Flaherty et al. | |
| 6,040,578 A | 3/2000 | Malin et al. | |
| 6,066,204 A | 5/2000 | Haven | |
| 6,115,673 A | 9/2000 | Malin et al. | |
| 6,124,597 A | 9/2000 | Shehada et al. | |
| 6,128,521 A | 10/2000 | Marro et al. | |
| 6,129,675 A | 10/2000 | Jay | |
| 6,144,868 A | 11/2000 | Parker | |
| 6,152,754 A | 11/2000 | Gerhardt et al. | |
| 6,184,521 B1 | 2/2001 | Coffin, IV et al. | |
| 6,232,609 B1 | 5/2001 | Snyder et al. | |
| 6,241,683 B1 | 6/2001 | Macklem et al. | |
| 6,255,708 B1 | 7/2001 | Sudharsanan et al. | |
| 6,280,381 B1 | 8/2001 | Malin et al. | |
| 6,285,896 B1 | 9/2001 | Tobler et al. | |
| 6,308,089 B1 | 10/2001 | von der Ruhr et al. | |
| 6,317,627 B1 | 11/2001 | Ennen et al. | |
| 6,321,100 B1 | 11/2001 | Parker | |
| 6,334,065 B1 | 12/2001 | Al-Ali et al. | |
| 6,360,114 B1 | 3/2002 | Diab et al. | |
| 6,368,283 B1 | 4/2002 | Xu et al. | |
| 6,411,373 B1 | 6/2002 | Garside et al. | |
| 6,415,167 B1 | 7/2002 | Blank et al. | |
| 6,430,437 B1 | 8/2002 | Marro | |
| 6,430,525 B1 | 8/2002 | Weber et al. | |
| 6,463,311 B1 | 10/2002 | Diab | |
| 6,470,199 B1 | 10/2002 | Kopotic et al. | |
| 6,487,429 B2 | 11/2002 | Hockersmith et al. | |
| 6,505,059 B1 | 1/2003 | Kollias et al. | |
| 6,525,386 B1 | 2/2003 | Mills et al. | |
| 6,526,300 B1 | 2/2003 | Kiani et al. | |
| 6,534,012 B1 | 3/2003 | Hazen et al. | |
| 6,542,764 B1 | 4/2003 | Al-Ali et al. | |
| 6,580,086 B1 | 6/2003 | Schulz et al. | |
| 6,584,336 B1 | 6/2003 | Ali et al. | |
| 6,587,196 B1 | 7/2003 | Stippick et al. | |
| 6,587,199 B1 | 7/2003 | Luu | |
| 6,595,316 B2 | 7/2003 | Cybulski et al. | |
| 6,597,932 B2 | 7/2003 | Tian et al. | |
| 6,606,511 B1 | 8/2003 | Ali et al. | |
| 6,635,559 B2 | 10/2003 | Greenwald et al. | |
| 6,639,668 B1 | 10/2003 | Trepagnier | |
| 6,640,116 B2 | 10/2003 | Diab | |
| 6,640,117 B2 | 10/2003 | Makarewicz et al. | |
| 6,658,276 B2 | 12/2003 | Kiani et al. | |
| 6,661,161 B1 | 12/2003 | Lanzo et al. | |
| 6,697,656 B1 | 2/2004 | Al-Ali | |
| 6,697,658 B2 | 2/2004 | Ai-Ali | |
| RE38,476 E | 3/2004 | Diab et al. | |
| RE38,492 E | 4/2004 | Diab et al. | |
| 6,738,652 B2 | 5/2004 | Mattu et al. | |
| 6,760,607 B2 | 7/2004 | Al-Ali | |
| 6,788,965 B2 | 9/2004 | Ruchti et al. | |
| 6,816,241 B2 | 11/2004 | Grubisic | |
| 6,822,564 B2 | 11/2004 | Al-Ali | |
| 6,850,787 B2 | 2/2005 | Weber et al. | |
| 6,850,788 B2 | 2/2005 | Al-Ali | |
| 6,876,931 B2 | 4/2005 | Lorenz et al. | |
| 6,920,345 B2 | 7/2005 | Al-Ali et al. | |
| 6,934,570 B2 | 8/2005 | Kiani et al. | |
| 6,943,348 B1 | 9/2005 | Coffin, IV | |
| 6,956,649 B2 | 10/2005 | Acosta et al. | |
| 6,961,598 B2 | 11/2005 | Diab | |
| 6,970,792 B1 | 11/2005 | Diab | |
| 6,985,764 B2 | 1/2006 | Mason et al. | |
| 6,990,364 B2 | 1/2006 | Ruchti et al. | |
| 6,998,247 B2 | 2/2006 | Monfre et al. | |
| 7,003,338 B2 | 2/2006 | Weber et al. | |
| 7,015,451 B2 | 3/2006 | Dalke et al. | |
| 7,027,849 B2 | 4/2006 | Al-Ali | |
| D526,719 S | 8/2006 | Richie, Jr. et al. | |
| 7,096,052 B2 | 8/2006 | Mason et al. | |
| 7,096,054 B2 | 8/2006 | Abdul-Hafiz et al. | |
| D529,616 S | 10/2006 | Deros et al. | |
| 7,133,710 B2 | 11/2006 | Acosta et al. | |
| 7,142,901 B2 | 11/2006 | Kiani et al. | |
| 7,225,006 B2 | 5/2007 | Al-Ali et al. | |
| RE39,672 E | 6/2007 | Shehada et al. | |
| 7,254,429 B2 | 8/2007 | Schurman et al. | |
| 7,254,431 B2 | 8/2007 | Al-Ali et al. | |
| 7,254,434 B2 | 8/2007 | Schulz et al. | |
| 7,274,955 B2 | 9/2007 | Kiani et al. | |
| D554,263 S | 10/2007 | Al-Ali et al. | |
| 7,280,858 B2 | 10/2007 | Al-Ali et al. | |
| 7,289,835 B2 | 10/2007 | Mansfield et al. | |
| 7,292,883 B2 | 11/2007 | De Felice et al. | |
| 7,341,559 B2 | 3/2008 | Schulz et al. | |
| 7,343,186 B2 | 3/2008 | Lamego et al. | |
| D566,282 S | 4/2008 | Al-Ali et al. | |
| 7,356,365 B2 | 4/2008 | Schurman | |
| 7,371,981 B2 | 5/2008 | Abdul-Hafiz | |
| 7,373,193 B2 | 5/2008 | Al-Ali et al. | |
| 7,377,794 B2 | 5/2008 | Al-Ali et al. | |
| 7,395,158 B2 | 7/2008 | Monfre et al. | |
| 7,415,297 B2 | 8/2008 | Al-Ali et al. | |
| 7,438,683 B2 | 10/2008 | Al-Ali et al. | |
| 7,483,729 B2 | 1/2009 | Al-Ali et al. | |
| D587,657 S | 3/2009 | Al-Ali et al. | |
| 7,500,950 B2 | 3/2009 | Al-Ali et al. | |
| 7,509,494 B2 | 3/2009 | Al-Ali | |
| 7,510,849 B2 | 3/2009 | Schurman et al. | |
| 7,514,725 B2 | 4/2009 | Wojtczuk et al. | |
| 7,519,406 B2 | 4/2009 | Blank et al. | |
| D592,507 S | 5/2009 | Wachman et al. | |
| 7,530,942 B1 | 5/2009 | Diab | |
| 7,593,230 B2 | 9/2009 | Abul-Haj et al. | |
| 7,596,398 B2 | 9/2009 | Al-Ali et al. | |
| 7,606,608 B2 | 10/2009 | Blank et al. | |

(56) References Cited

U.S. PATENT DOCUMENTS

| | | |
|---|---|---|
| 7,620,674 B2 | 11/2009 | Ruchti et al. |
| D606,659 S | 12/2009 | Kiani et al. |
| 7,629,039 B2 | 12/2009 | Eckerbom et al. |
| 7,640,140 B2 | 12/2009 | Ruchti et al. |
| 7,647,083 B2 | 1/2010 | Al-Ali et al. |
| D609,193 S | 2/2010 | Al-Ali et al. |
| D614,305 S | 4/2010 | Al-Ali et al. |
| 7,697,966 B2 | 4/2010 | Monfre et al. |
| 7,698,105 B2 | 4/2010 | Ruchti et al. |
| RE41,317 E | 5/2010 | Parker |
| RE41,333 E | 5/2010 | Blank et al. |
| 7,729,733 B2 | 6/2010 | Al-Ali et al. |
| 7,761,127 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| RE41,912 E | 11/2010 | Parker |
| 7,880,626 B2 | 2/2011 | Al-Ali et al. |
| 7,909,772 B2 | 3/2011 | Popov et al. |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,941,199 B2 | 5/2011 | Kiani |
| 7,957,780 B2 | 6/2011 | Lamego et al. |
| 7,962,188 B2 | 6/2011 | Kiani et al. |
| 7,976,472 B2 | 7/2011 | Kiani |
| 7,990,382 B2 | 8/2011 | Kiani |
| 8,008,088 B2 | 8/2011 | Bellott et al. |
| RE42,753 E | 9/2011 | Kiani-Azarbayjany et al. |
| 8,028,701 B2 | 10/2011 | Al-Ali et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,130,105 B2 | 3/2012 | Al-Ali et al. |
| 8,182,443 B1 | 5/2012 | Kiani |
| 8,190,223 B2 | 5/2012 | Al-Ali et al. |
| 8,203,438 B2 | 6/2012 | Kiani et al. |
| 8,203,704 B2 | 6/2012 | Merritt et al. |
| 8,219,172 B2 | 7/2012 | Schurman et al. |
| 8,224,411 B2 | 7/2012 | Al-Ali et al. |
| 8,229,532 B2 | 7/2012 | Davis |
| 8,233,955 B2 | 7/2012 | Al-Ali et al. |
| 8,255,026 B1 | 8/2012 | Al-Ali |
| 8,265,723 B1 | 9/2012 | McHale et al. |
| 8,274,360 B2 | 9/2012 | Sampath et al. |
| 8,280,473 B2 | 10/2012 | Al-Ali |
| 8,315,683 B2 | 11/2012 | Al-Ali et al. |
| RE43,860 E | 12/2012 | Parker |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,374,665 B2 | 2/2013 | Lamego |
| 8,388,353 B2 | 3/2013 | Kiani et al. |
| 8,401,602 B2 | 3/2013 | Kiani |
| 8,414,499 B2 | 4/2013 | Al-Ali et al. |
| 8,418,524 B2 | 4/2013 | Al-Ali |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,707 B2 | 6/2013 | Kiani |
| 8,471,713 B2 | 6/2013 | Poeze et al. |
| 8,473,020 B2 | 6/2013 | Kiani et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| D692,145 S | 10/2013 | Al-Ali et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,584,345 B2 | 11/2013 | Al-Ali et al. |
| 8,588,880 B2 | 11/2013 | Abdul-Hafiz et al. |
| 8,630,691 B2 | 1/2014 | Lamego et al. |
| 8,641,631 B2 | 2/2014 | Sierra et al. |
| 8,652,060 B2 | 2/2014 | Al-Ali |
| 8,666,468 B1 | 3/2014 | Al-Ali |
| 8,670,811 B2 | 3/2014 | O'Reilly |
| RE44,823 E | 4/2014 | Parker |
| RE44,875 E | 4/2014 | Kiani et al. |
| 8,688,183 B2 | 4/2014 | Bruinsma et al. |
| 8,690,799 B2 | 4/2014 | Telfort et al. |
| 8,702,627 B2 | 4/2014 | Telfort et al. |
| 8,712,494 B1 | 4/2014 | MacNeish, III et al. |
| 8,715,206 B2 | 5/2014 | Telfort et al. |
| 8,723,677 B1 | 5/2014 | Kiani |
| 8,740,792 B1 | 6/2014 | Kiani et al. |
| 8,755,535 B2 | 6/2014 | Telfort et al. |
| 8,755,872 B1 | 6/2014 | Marinow |
| 8,764,671 B2 | 7/2014 | Kiani |
| 8,768,423 B2 | 7/2014 | Shakespeare et al. |
| 8,771,204 B2 | 7/2014 | Telfort et al. |
| 8,781,544 B2 | 7/2014 | Al-Ali et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,840,549 B2 | 9/2014 | Al-Ali et al. |
| 8,852,094 B2 | 10/2014 | Al-Ali et al. |
| 8,852,994 B2 | 10/2014 | Wojtczuk et al. |
| 8,897,847 B2 | 11/2014 | Al-Ali |
| 8,911,377 B2 | 12/2014 | Al-Ali |
| 8,989,831 B2 | 3/2015 | Al-Ali et al. |
| 8,998,809 B2 | 4/2015 | Kiani |
| 9,066,666 B2 | 6/2015 | Kiani |
| 9,066,680 B1 | 6/2015 | Al-Ali et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,131,881 B2 | 9/2015 | Diab et al. |
| 9,138,180 B1 | 9/2015 | Coverston et al. |
| 9,153,112 B1 | 10/2015 | Kiani et al. |
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,211,095 B1 | 12/2015 | Al-Ali |
| 9,218,454 B2 | 12/2015 | Kiani et al. |
| 9,245,668 B1 | 1/2016 | Vo et al. |
| 9,267,572 B2 | 2/2016 | Barker et al. |
| 9,277,880 B2 | 3/2016 | Poeze et al. |
| 9,307,928 B1 | 4/2016 | Al-Ali et al. |
| 9,323,894 B2 | 4/2016 | Kiani |
| D755,392 S | 5/2016 | Hwang et al. |
| 9,326,712 B1 | 5/2016 | Kiani |
| 9,392,945 B2 | 7/2016 | Al-Ali et al. |
| 9,408,542 B1 | 8/2016 | Kinast et al. |
| 9,436,645 B2 | 9/2016 | Al-Ali et al. |
| 9,445,759 B1 | 9/2016 | Lamego et al. |
| 9,474,474 B2 | 10/2016 | Lamego et al. |
| 9,480,435 B2 | 11/2016 | Olsen |
| 9,510,779 B2 | 12/2016 | Poeze et al. |
| 9,517,024 B2 | 12/2016 | Kiani et al. |
| 9,532,722 B2 | 1/2017 | Lamego et al. |
| 9,560,996 B2 | 2/2017 | Kiani |
| 9,579,039 B2 | 2/2017 | Jansen et al. |
| 9,622,692 B2 | 4/2017 | Lamego et al. |
| D788,312 S | 5/2017 | Al-Ali et al. |
| 9,649,054 B2 | 5/2017 | Lamego et al. |
| 9,697,928 B2 | 7/2017 | Al-Ali et al. |
| 9,717,458 B2 | 8/2017 | Lamego et al. |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,749,232 B2 | 8/2017 | Sampath et al. |
| 9,750,442 B2 | 9/2017 | Olsen |
| 9,750,461 B1 | 9/2017 | Telfort |
| 9,775,545 B2 | 10/2017 | Al-Ali et al. |
| 9,778,079 B1 | 10/2017 | Al-Ali et al. |
| 9,782,077 B2 | 10/2017 | Lamego et al. |
| 9,787,568 B2 | 10/2017 | Lamego et al. |
| 9,808,188 B1 | 11/2017 | Perea et al. |
| 9,839,379 B2 | 12/2017 | Al-Ali et al. |

(56) References Cited

U.S. PATENT DOCUMENTS

| | | |
|---|---|---|
| 9,839,381 B1 | 12/2017 | Weber et al. |
| 9,847,749 B2 | 12/2017 | Kiani et al. |
| 9,848,800 B1 | 12/2017 | Lee et al. |
| 9,861,298 B2 | 1/2018 | Eckerbom et al. |
| 9,861,305 B1 | 1/2018 | Weber et al. |
| 9,877,650 B2 | 1/2018 | Muhsin et al. |
| 9,891,079 B2 | 2/2018 | Dalvi |
| 9,924,897 B1 | 3/2018 | Abdul-Hafiz |
| 9,936,917 B2 | 4/2018 | Poeze et al. |
| 9,955,937 B2 | 5/2018 | Telfort |
| 9,965,946 B2 | 5/2018 | Al-Ali et al. |
| D820,865 S | 6/2018 | Muhsin et al. |
| 9,986,952 B2 | 6/2018 | Dalvi et al. |
| D822,215 S | 7/2018 | Al-Ali et al. |
| D822,216 S | 7/2018 | Barker et al. |
| 10,010,276 B2 | 7/2018 | Al-Ali et al. |
| 10,086,138 B1 | 10/2018 | Novak, Jr. |
| 10,111,591 B2 | 10/2018 | Dyell et al. |
| D833,624 S | 11/2018 | DeJong et al. |
| 10,123,729 B2 | 11/2018 | Dyell et al. |
| D835,282 S | 12/2018 | Barker et al. |
| D835,283 S | 12/2018 | Barker et al. |
| D835,284 S | 12/2018 | Barker et al. |
| D835,285 S | 12/2018 | Barker et al. |
| 10,149,616 B2 | 12/2018 | Al-Ali et al. |
| 10,154,815 B2 | 12/2018 | Al-Ali et al. |
| 10,159,412 B2 | 12/2018 | Lamego et al. |
| 10,188,348 B2 | 1/2019 | Al-Ali et al. |
| RE47,218 E | 2/2019 | Al-Ali |
| RE47,244 E | 2/2019 | Kiani et al. |
| RE47,249 E | 2/2019 | Kiani et al. |
| 10,205,291 B2 | 2/2019 | Scruggs et al. |
| 10,226,187 B2 | 3/2019 | Al-Ali et al. |
| 10,231,657 B2 | 3/2019 | Al-Ali et al. |
| 10,231,670 B2 | 3/2019 | Blank et al. |
| RE47,353 E | 4/2019 | Kiani et al. |
| 10,279,247 B2 | 5/2019 | Kiani |
| 10,292,664 B2 | 5/2019 | Al-Ali |
| 10,299,720 B2 | 5/2019 | Brown et al. |
| 10,327,337 B2 | 6/2019 | Schmidt et al. |
| 10,327,713 B2 | 6/2019 | Barker et al. |
| 10,332,630 B2 | 6/2019 | Al-Ali |
| 10,383,520 B2 | 8/2019 | Wojtczuk et al. |
| 10,383,527 B2 | 8/2019 | Al-Ali |
| 10,388,120 B2 | 8/2019 | Muhsin et al. |
| D864,120 S | 10/2019 | Forrest et al. |
| 10,441,181 B1 | 10/2019 | Telfort et al. |
| 10,441,196 B2 | 10/2019 | Eckerbom et al. |
| 10,448,844 B2 | 10/2019 | Al-Ali et al. |
| 10,448,871 B2 | 10/2019 | Al-Ali et al. |
| 10,456,038 B2 | 10/2019 | Lamego et al. |
| 10,463,340 B2 | 11/2019 | Telfort et al. |
| 10,471,159 B1 | 11/2019 | Lapotko et al. |
| 10,505,311 B2 | 12/2019 | Al-Ali et al. |
| 10,524,738 B2 | 1/2020 | Olsen |
| 10,532,174 B2 | 1/2020 | Al-Ali |
| 10,537,285 B2 | 1/2020 | Shreim et al. |
| 10,542,903 B2 | 1/2020 | Al-Ali et al. |
| 10,555,678 B2 | 2/2020 | Dalvi et al. |
| 10,568,553 B2 | 2/2020 | O'Neil et al. |
| RE47,882 E | 3/2020 | Al-Ali |
| 10,608,817 B2 | 3/2020 | Haider et al. |
| D880,477 S | 4/2020 | Forrest et al. |
| 10,617,302 B2 | 4/2020 | Al-Ali et al. |
| 10,617,335 B2 | 4/2020 | Al-Ali et al. |
| 10,637,181 B2 | 4/2020 | Al-Ali et al. |
| D886,849 S | 6/2020 | Muhsin et al. |
| D887,548 S | 6/2020 | Abdul-Hafiz et al. |
| D887,549 S | 6/2020 | Abdul-Hafiz et al. |
| 10,667,764 B2 | 6/2020 | Ahmed et al. |
| D890,708 S | 7/2020 | Forrest et al. |
| 10,721,785 B2 | 7/2020 | Al-Ali |
| 10,736,518 B2 | 8/2020 | Al-Ali et al. |
| 10,750,984 B2 | 8/2020 | Pauley et al. |
| D897,098 S | 9/2020 | Al-Ali |
| 10,779,098 B2 | 9/2020 | Iswanto et al. |
| 10,827,961 B1 | 11/2020 | Iyengar et al. |
| 10,828,007 B1 | 11/2020 | Telfort et al. |
| 10,832,818 B2 | 11/2020 | Muhsin et al. |
| 10,849,554 B2 | 12/2020 | Shreim et al. |
| 10,856,750 B2 | 12/2020 | Indorf |
| D906,970 S | 1/2021 | Forrest et al. |
| D908,213 S | 1/2021 | Abdul-Hafiz et al. |
| 10,918,281 B2 | 2/2021 | Al-Ali et al. |
| 10,932,705 B2 | 3/2021 | Muhsin et al. |
| 10,932,729 B2 | 3/2021 | Kiani et al. |
| 10,939,878 B2 | 3/2021 | Kiani et al. |
| 10,956,950 B2 | 3/2021 | Al-Ali et al. |
| D916,135 S | 4/2021 | Indorf et al. |
| D917,046 S | 4/2021 | Abdul-Hafiz et al. |
| D917,550 S | 4/2021 | Indorf et al. |
| D917,564 S | 4/2021 | Indorf et al. |
| D917,704 S | 4/2021 | Al-Ali et al. |
| 10,987,066 B2 | 4/2021 | Chandran et al. |
| 10,991,135 B2 | 4/2021 | Al-Ali et al. |
| D919,094 S | 5/2021 | Al-Ali et al. |
| D919,100 S | 5/2021 | Al-Ali et al. |
| 11,006,867 B2 | 5/2021 | Al-Ali |
| D921,202 S | 6/2021 | Al-Ali et al. |
| 11,024,064 B2 | 6/2021 | Muhsin et al. |
| 11,026,604 B2 | 6/2021 | Chen et al. |
| D925,597 S | 7/2021 | Chandran et al. |
| D927,699 S | 8/2021 | Al-Ali et al. |
| 11,076,777 B2 | 8/2021 | Lee et al. |
| 11,114,188 B2 | 9/2021 | Poeze et al. |
| D933,232 S | 10/2021 | Al-Ali et al. |
| D933,233 S | 10/2021 | Al-Ali et al. |
| D933,234 S | 10/2021 | Al-Ali et al. |
| 11,145,408 B2 | 10/2021 | Sampath et al. |
| 11,147,518 B1 | 10/2021 | Al-Ali et al. |
| 11,185,262 B2 | 11/2021 | Al-Ali et al. |
| 11,191,484 B2 | 12/2021 | Kiani et al. |
| D946,596 S | 3/2022 | Ahmed |
| D946,597 S | 3/2022 | Ahmed |
| D946,598 S | 3/2022 | Ahmed |
| D946,617 S | 3/2022 | Ahmed |
| 11,272,839 B2 | 3/2022 | Al-Ali et al. |
| 11,289,199 B2 | 3/2022 | Al-Ali |
| RE49,034 E | 4/2022 | Al-Ali |
| 11,298,021 B2 | 4/2022 | Muhsin et al. |
| D950,580 S | 5/2022 | Ahmed |
| D950,599 S | 5/2022 | Ahmed |
| D950,738 S | 5/2022 | Al-Ali et al. |
| D957,648 S | 7/2022 | Al-Ali |
| 11,389,093 B2 | 7/2022 | Triman et al. |
| 11,406,286 B2 | 8/2022 | Al-Ali et al. |
| 11,417,426 B2 | 8/2022 | Muhsin et al. |
| 11,439,329 B2 | 9/2022 | Lamego |
| 11,445,948 B2 | 9/2022 | Scruggs et al. |
| D965,789 S | 10/2022 | Al-Ali et al. |
| D967,433 S | 10/2022 | Al-Ali et al. |
| 11,464,410 B2 | 10/2022 | Muhsin |
| 11,504,058 B1 | 11/2022 | Sharma et al. |
| 11,504,066 B1 | 11/2022 | Dalvi et al. |
| D971,933 S | 12/2022 | Ahmed |
| D973,072 S | 12/2022 | Ahmed |
| D973,685 S | 12/2022 | Ahmed |
| D973,686 S | 12/2022 | Ahmed |
| D974,193 S | 1/2023 | Forrest et al. |
| D979,516 S | 2/2023 | Al-Ali et al. |
| D980,091 S | 3/2023 | Forrest et al. |
| 11,596,363 B2 | 3/2023 | Lamego |
| 11,627,919 B2 | 4/2023 | Kiani et al. |
| 11,637,437 B2 | 4/2023 | Al-Ali et al. |
| 2001/0034477 A1 | 10/2001 | Mansfield et al. |
| 2001/0039483 A1 | 11/2001 | Brand et al. |
| 2002/0010401 A1 | 1/2002 | Bushmakin et al. |
| 2002/0058864 A1 | 5/2002 | Mansfield et al. |
| 2002/0133080 A1 | 9/2002 | Apruzzese et al. |
| 2003/0013975 A1 | 1/2003 | Kiani |
| 2003/0018243 A1 | 1/2003 | Gerhardt et al. |
| 2003/0144582 A1 | 7/2003 | Cohen et al. |
| 2003/0156288 A1 | 8/2003 | Barnum et al. |
| 2003/0212312 A1 | 11/2003 | Coffin, IV et al. |

(56) References Cited

U.S. PATENT DOCUMENTS

| | | |
|---|---|---|
| 2004/0106163 A1 | 6/2004 | Workman, Jr. et al. |
| 2005/0055276 A1 | 3/2005 | Kiani et al. |
| 2005/0234317 A1 | 10/2005 | Kiani |
| 2006/0073719 A1 | 4/2006 | Kiani |
| 2006/0189871 A1 | 8/2006 | Al-Ali et al. |
| 2007/0027376 A1* | 2/2007 | Todokoro ............. A61B 5/6838 600/344 |
| 2007/0073116 A1 | 3/2007 | Kiani et al. |
| 2007/0180140 A1 | 8/2007 | Welch et al. |
| 2007/0244377 A1 | 10/2007 | Cozad et al. |
| 2008/0064965 A1 | 3/2008 | Jay et al. |
| 2008/0094228 A1 | 4/2008 | Welch et al. |
| 2008/0221418 A1 | 9/2008 | Al-Ali et al. |
| 2009/0036759 A1 | 2/2009 | Ault et al. |
| 2009/0093687 A1 | 4/2009 | Telfort et al. |
| 2009/0095926 A1 | 4/2009 | MacNeish, III |
| 2009/0247984 A1 | 10/2009 | Lamego et al. |
| 2009/0275844 A1 | 11/2009 | Al-Ali |
| 2010/0004518 A1 | 1/2010 | Vo et al. |
| 2010/0030040 A1 | 2/2010 | Poeze et al. |
| 2010/0099964 A1 | 4/2010 | O'Reilly et al. |
| 2010/0234718 A1 | 9/2010 | Sampath et al. |
| 2010/0270257 A1 | 10/2010 | Wachman et al. |
| 2010/0317936 A1* | 12/2010 | Al-Ali ................... A61B 46/10 600/323 |
| 2011/0028806 A1 | 2/2011 | Merritt et al. |
| 2011/0028809 A1 | 2/2011 | Goodman |
| 2011/0040197 A1 | 2/2011 | Welch et al. |
| 2011/0082711 A1 | 4/2011 | Poeze et al. |
| 2011/0087081 A1 | 4/2011 | Kiani et al. |
| 2011/0118561 A1 | 5/2011 | Tari et al. |
| 2011/0137297 A1 | 6/2011 | Kiani et al. |
| 2011/0172498 A1 | 7/2011 | Olsen et al. |
| 2011/0230733 A1 | 9/2011 | Al-Ali |
| 2012/0123231 A1 | 5/2012 | O'Reilly |
| 2012/0165629 A1 | 6/2012 | Merritt et al. |
| 2012/0209084 A1 | 8/2012 | Olsen et al. |
| 2012/0226117 A1 | 9/2012 | Lamego et al. |
| 2012/0283524 A1 | 11/2012 | Kiani et al. |
| 2013/0023775 A1 | 1/2013 | Lamego et al. |
| 2013/0041591 A1 | 2/2013 | Lamego |
| 2013/0060147 A1 | 3/2013 | Welch et al. |
| 2013/0096405 A1 | 4/2013 | Garfio |
| 2013/0296672 A1 | 11/2013 | O'Neil et al. |
| 2013/0345921 A1 | 12/2013 | Al-Ali et al. |
| 2014/0166076 A1 | 6/2014 | Kiani et al. |
| 2014/0180160 A1 | 6/2014 | Brown et al. |
| 2014/0187973 A1 | 7/2014 | Brown et al. |
| 2014/0275871 A1 | 9/2014 | Lamego et al. |
| 2014/0275872 A1 | 9/2014 | Merritt et al. |
| 2014/0316217 A1 | 10/2014 | Purdon et al. |
| 2014/0316218 A1 | 10/2014 | Purdon et al. |
| 2014/0323897 A1 | 10/2014 | Brown et al. |
| 2014/0323898 A1 | 10/2014 | Purdon et al. |
| 2015/0005600 A1 | 1/2015 | Blank et al. |
| 2015/0011907 A1 | 1/2015 | Purdon et al. |
| 2015/0073241 A1 | 3/2015 | Lamego |
| 2015/0080754 A1 | 3/2015 | Purdon et al. |
| 2015/0099950 A1 | 4/2015 | Al-Ali et al. |
| 2016/0196388 A1 | 7/2016 | Lamego |
| 2016/0367173 A1 | 12/2016 | Dalvi et al. |
| 2017/0024748 A1 | 1/2017 | Haider |
| 2017/0042488 A1 | 2/2017 | Muhsin |
| 2017/0173632 A1 | 6/2017 | Al-Ali |
| 2017/0251974 A1 | 9/2017 | Shreim et al. |
| 2017/0311891 A1 | 11/2017 | Kiani et al. |
| 2018/0103874 A1 | 4/2018 | Lee et al. |
| 2018/0242926 A1 | 8/2018 | Muhsin et al. |
| 2018/0247353 A1 | 8/2018 | Al-Ali et al. |
| 2018/0247712 A1 | 8/2018 | Muhsin et al. |
| 2018/0256087 A1 | 9/2018 | Al-Ali et al. |
| 2018/0296161 A1 | 10/2018 | Shreim et al. |
| 2018/0300919 A1 | 10/2018 | Muhsin et al. |
| 2018/0310822 A1 | 11/2018 | Indorf et al. |
| 2018/0310823 A1 | 11/2018 | Al-Ali et al. |
| 2018/0317826 A1 | 11/2018 | Muhsin et al. |
| 2019/0015023 A1 | 1/2019 | Monfre |
| 2019/0117070 A1 | 4/2019 | Muhsin et al. |
| 2019/0200941 A1 | 7/2019 | Chandran et al. |
| 2019/0239787 A1 | 8/2019 | Pauley et al. |
| 2019/0320906 A1 | 10/2019 | Olsen |
| 2019/0374139 A1 | 12/2019 | Kiani et al. |
| 2019/0374173 A1 | 12/2019 | Kiani et al. |
| 2019/0374713 A1 | 12/2019 | Kiani et al. |
| 2020/0060869 A1 | 2/2020 | Telfort et al. |
| 2020/0111552 A1 | 4/2020 | Ahmed |
| 2020/0113435 A1 | 4/2020 | Muhsin |
| 2020/0113488 A1 | 4/2020 | Al-Ali et al. |
| 2020/0113496 A1 | 4/2020 | Scruggs et al. |
| 2020/0113497 A1 | 4/2020 | Triman et al. |
| 2020/0113520 A1 | 4/2020 | Abdul-Hafiz et al. |
| 2020/0138288 A1 | 5/2020 | Al-Ali et al. |
| 2020/0138368 A1 | 5/2020 | Kiani et al. |
| 2020/0163597 A1 | 5/2020 | Dalvi et al. |
| 2020/0196877 A1 | 6/2020 | Vo et al. |
| 2020/0253474 A1 | 8/2020 | Muhsin et al. |
| 2020/0253544 A1 | 8/2020 | Belur Nagaraj et al. |
| 2020/0275841 A1 | 9/2020 | Telfort et al. |
| 2020/0288983 A1 | 9/2020 | Telfort et al. |
| 2020/0321793 A1 | 10/2020 | Al-Ali et al. |
| 2020/0329983 A1 | 10/2020 | Al-Ali et al. |
| 2020/0329984 A1 | 10/2020 | Al-Ali et al. |
| 2020/0329993 A1 | 10/2020 | Al-Ali et al. |
| 2020/0330037 A1 | 10/2020 | Al-Ali et al. |
| 2021/0022628 A1 | 1/2021 | Telfort et al. |
| 2021/0104173 A1 | 4/2021 | Pauley et al. |
| 2021/0117525 A1 | 4/2021 | Kiani et al. |
| 2021/0118581 A1 | 4/2021 | Kiani et al. |
| 2021/0121582 A1 | 4/2021 | Krishnamani et al. |
| 2021/0161465 A1 | 6/2021 | Barker et al. |
| 2021/0236729 A1 | 8/2021 | Kiani et al. |
| 2021/0256267 A1 | 8/2021 | Ranasinghe et al. |
| 2021/0256835 A1 | 8/2021 | Ranasinghe et al. |
| 2021/0275101 A1 | 9/2021 | Vo et al. |
| 2021/0290060 A1 | 9/2021 | Ahmed |
| 2021/0290072 A1 | 9/2021 | Forrest |
| 2021/0290080 A1 | 9/2021 | Ahmed |
| 2021/0290120 A1 | 9/2021 | Al-Ali |
| 2021/0290177 A1 | 9/2021 | Novak, Jr. |
| 2021/0290184 A1 | 9/2021 | Ahmed |
| 2021/0296008 A1 | 9/2021 | Novak, Jr. |
| 2021/0330228 A1 | 10/2021 | Olsen et al. |
| 2021/0386382 A1 | 12/2021 | Olsen et al. |
| 2021/0402110 A1 | 12/2021 | Pauley et al. |
| 2022/0026355 A1 | 1/2022 | Normand et al. |
| 2022/0039707 A1 | 2/2022 | Sharma et al. |
| 2022/0053892 A1 | 2/2022 | Al-Ali et al. |
| 2022/0071562 A1 | 3/2022 | Kiani |
| 2022/0096603 A1 | 3/2022 | Kiani et al. |
| 2022/0151521 A1 | 5/2022 | Krishnamani et al. |
| 2022/0218244 A1 | 7/2022 | Kiani et al. |
| 2022/0287574 A1 | 9/2022 | Telfort et al. |
| 2022/0296161 A1 | 9/2022 | Al-Ali et al. |
| 2022/0361819 A1 | 11/2022 | Al-Ali et al. |
| 2022/0379059 A1 | 12/2022 | Yu et al. |
| 2022/0392610 A1 | 12/2022 | Kiani et al. |
| 2023/0028745 A1 | 1/2023 | Al-Ali |
| 2023/0038389 A1 | 2/2023 | Vo |
| 2023/0045647 A1 | 2/2023 | Vo |
| 2023/0058052 A1 | 2/2023 | Al-Ali |
| 2023/0058342 A1 | 2/2023 | Kiani |
| 2023/0069789 A1 | 3/2023 | Koo et al. |
| 2023/0087671 A1 | 3/2023 | Telfort et al. |
| 2023/0110152 A1 | 4/2023 | Forrest et al. |
| 2023/0111198 A1 | 4/2023 | Yu et al. |
| 2023/0115397 A1 | 4/2023 | Vo et al. |
| 2023/0116371 A1 | 4/2023 | Mills et al. |

* cited by examiner

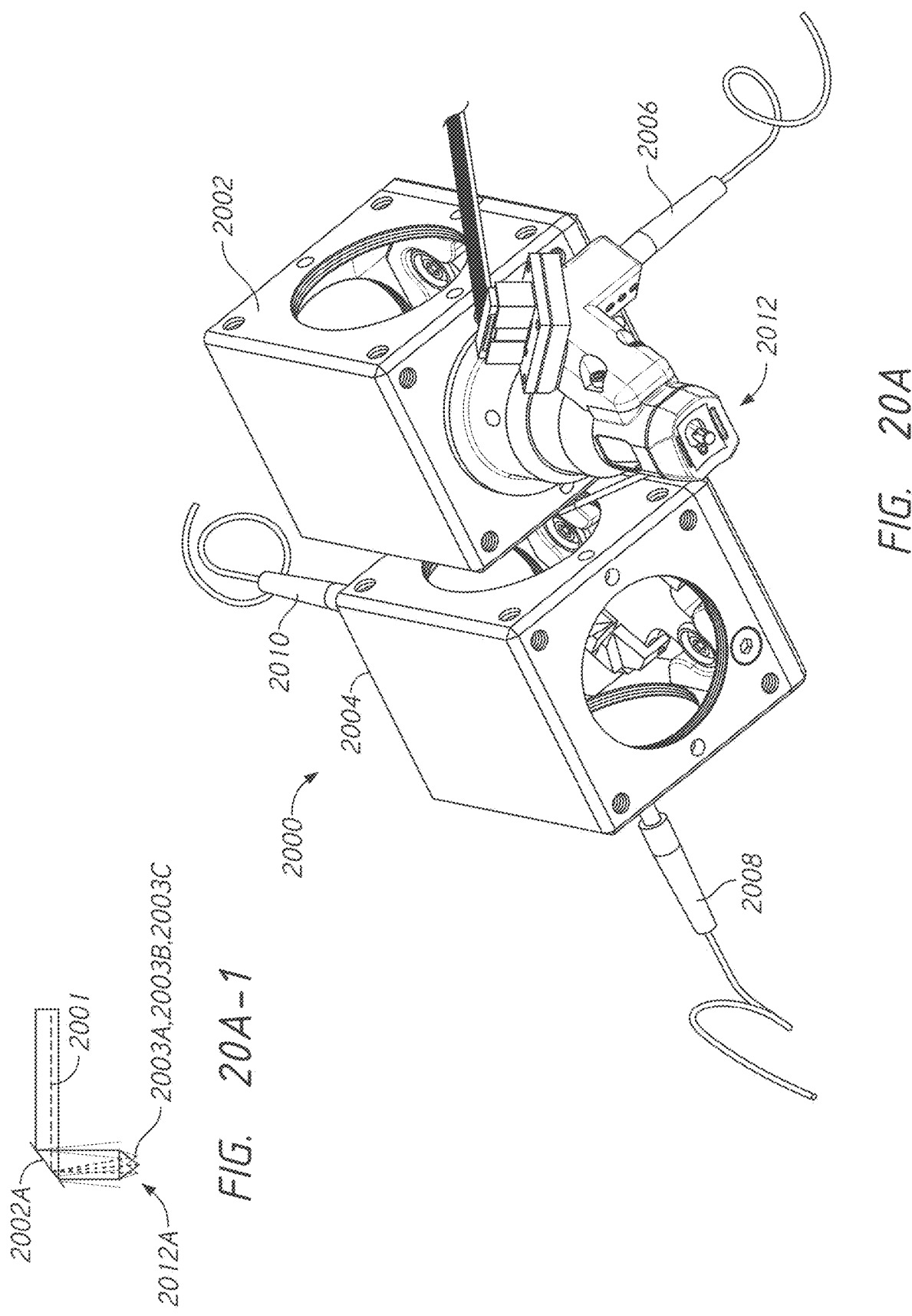

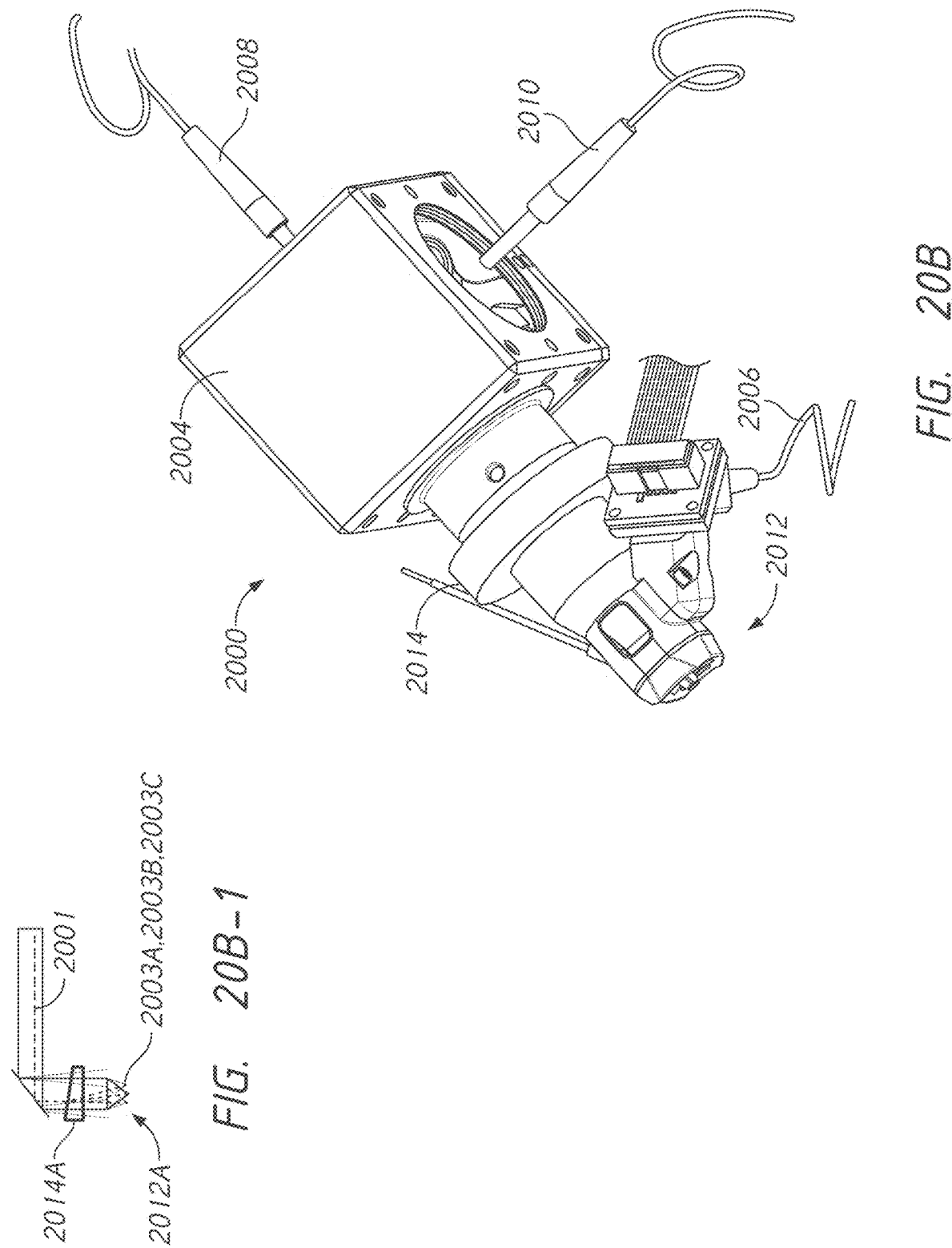

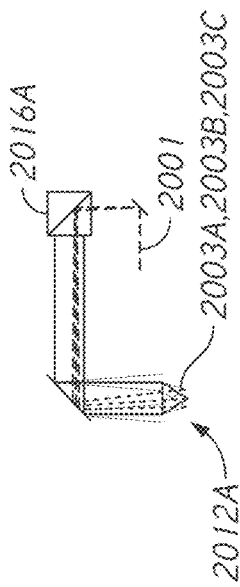
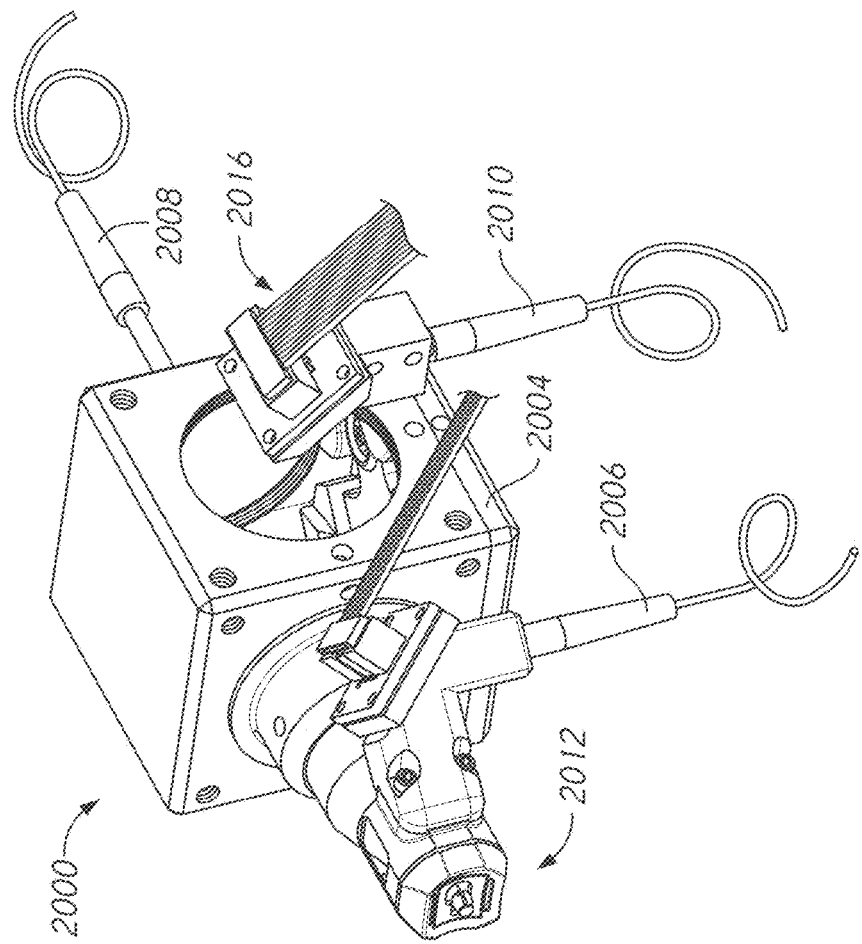

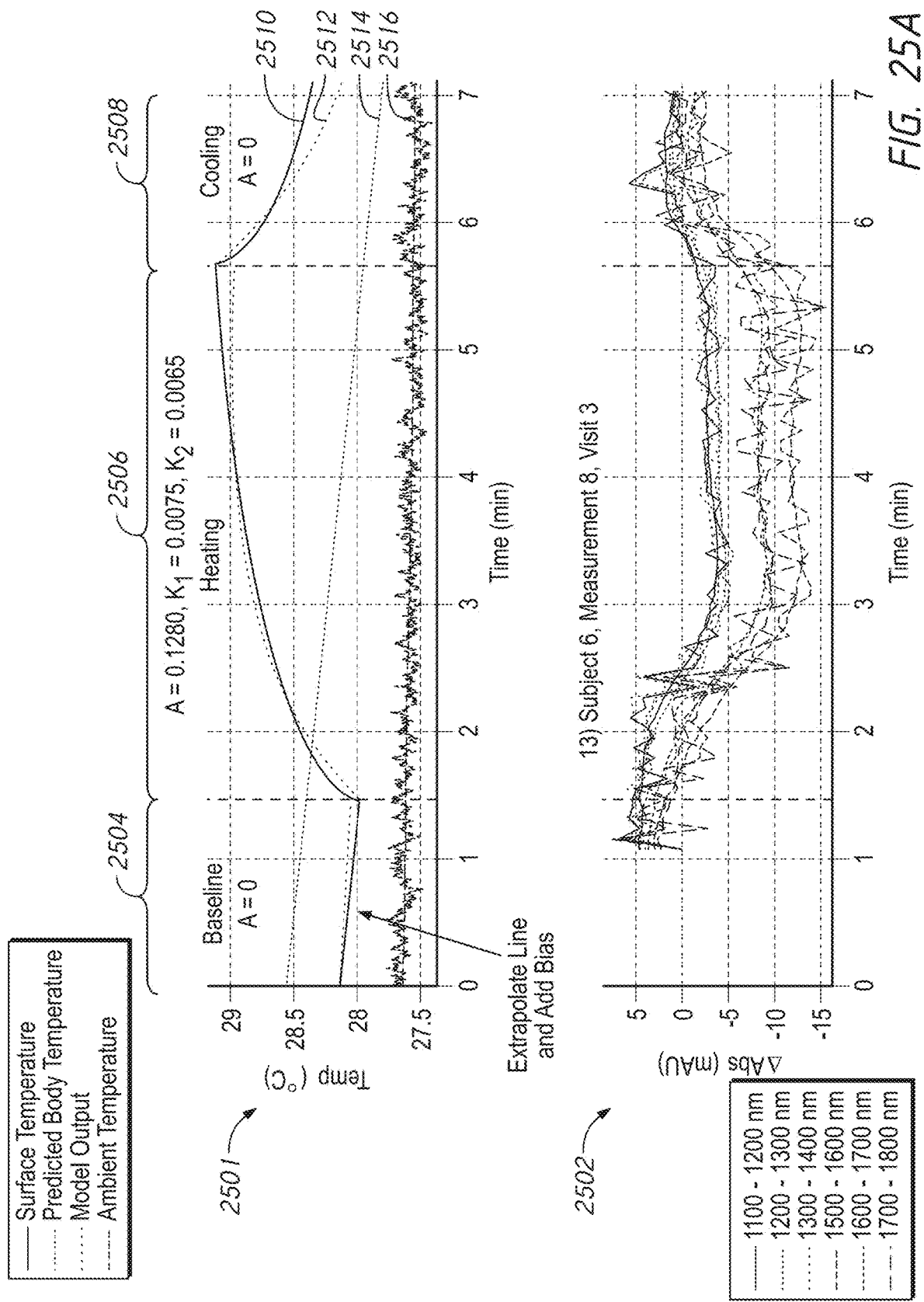

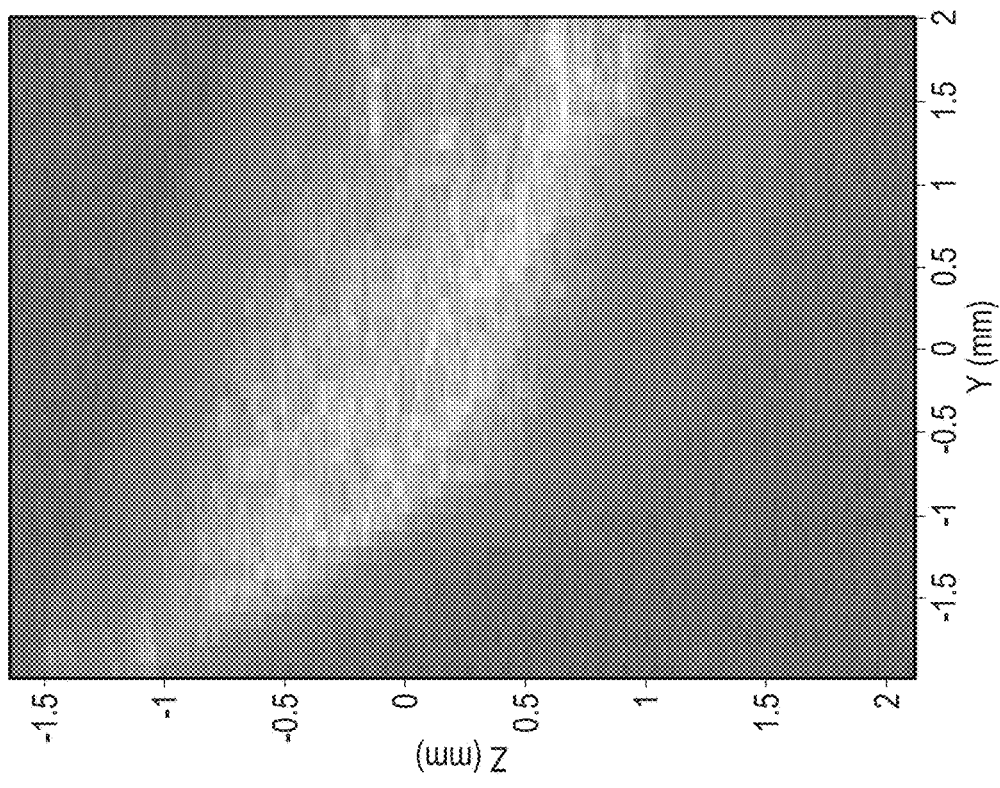
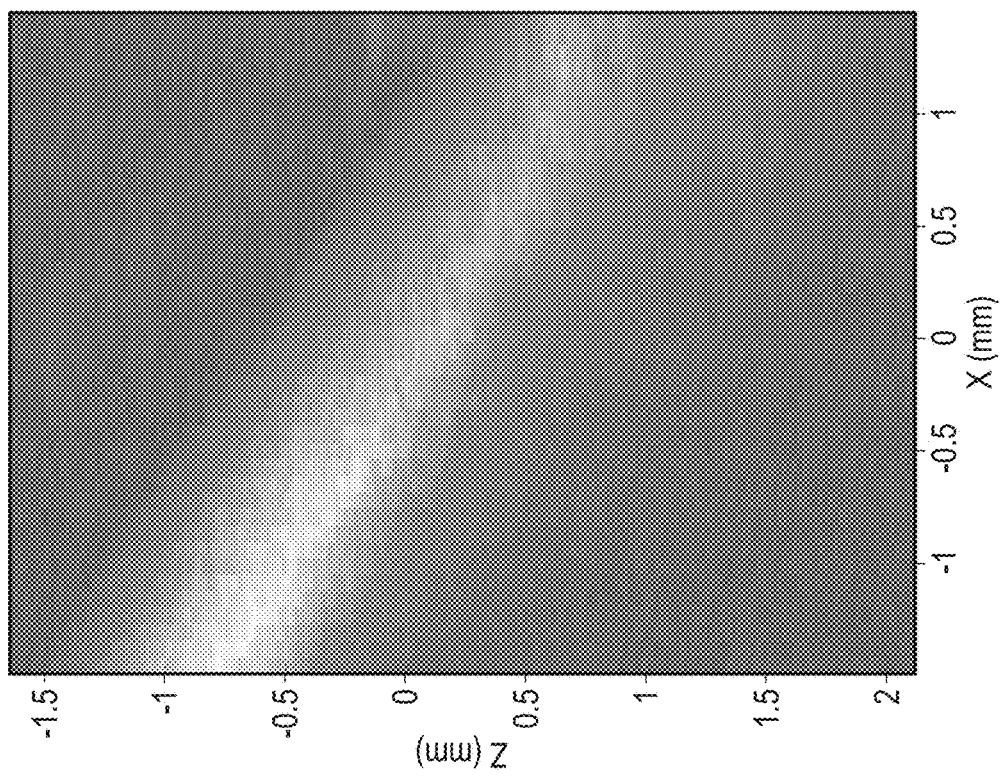
FIG. 34A

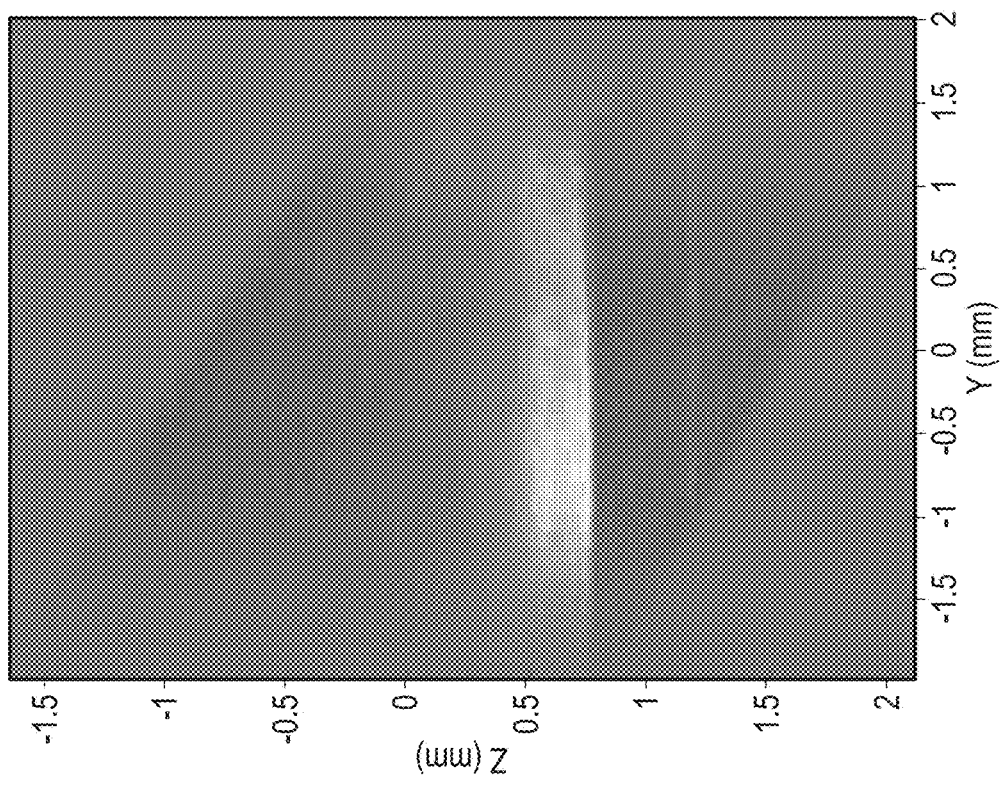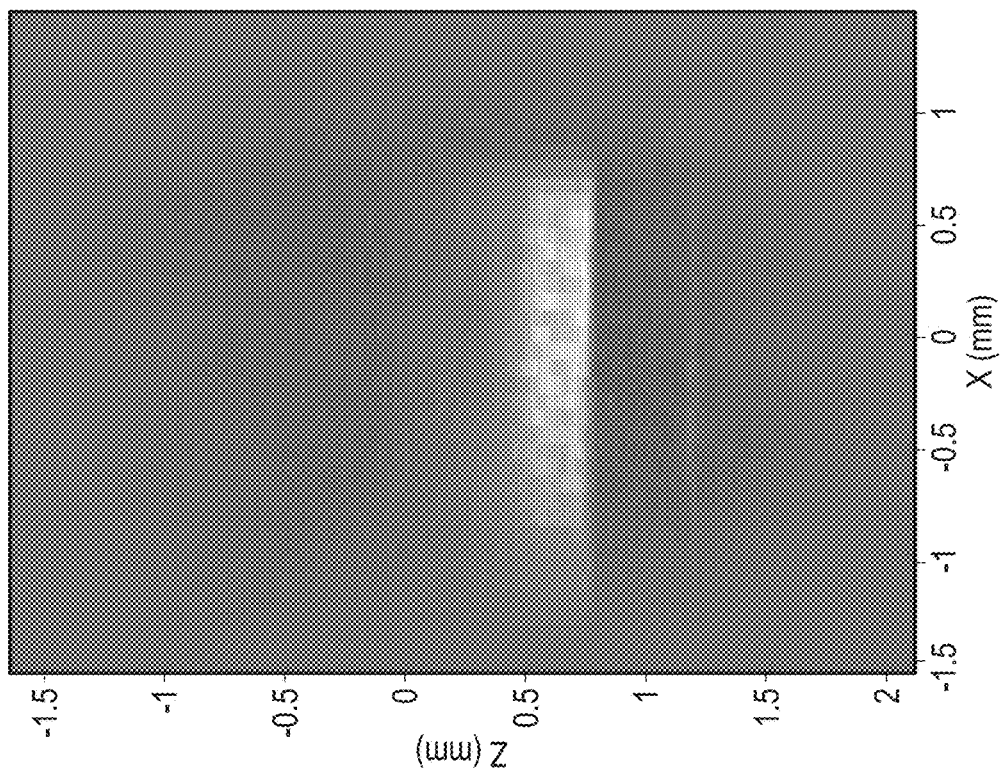
FIG. 34B

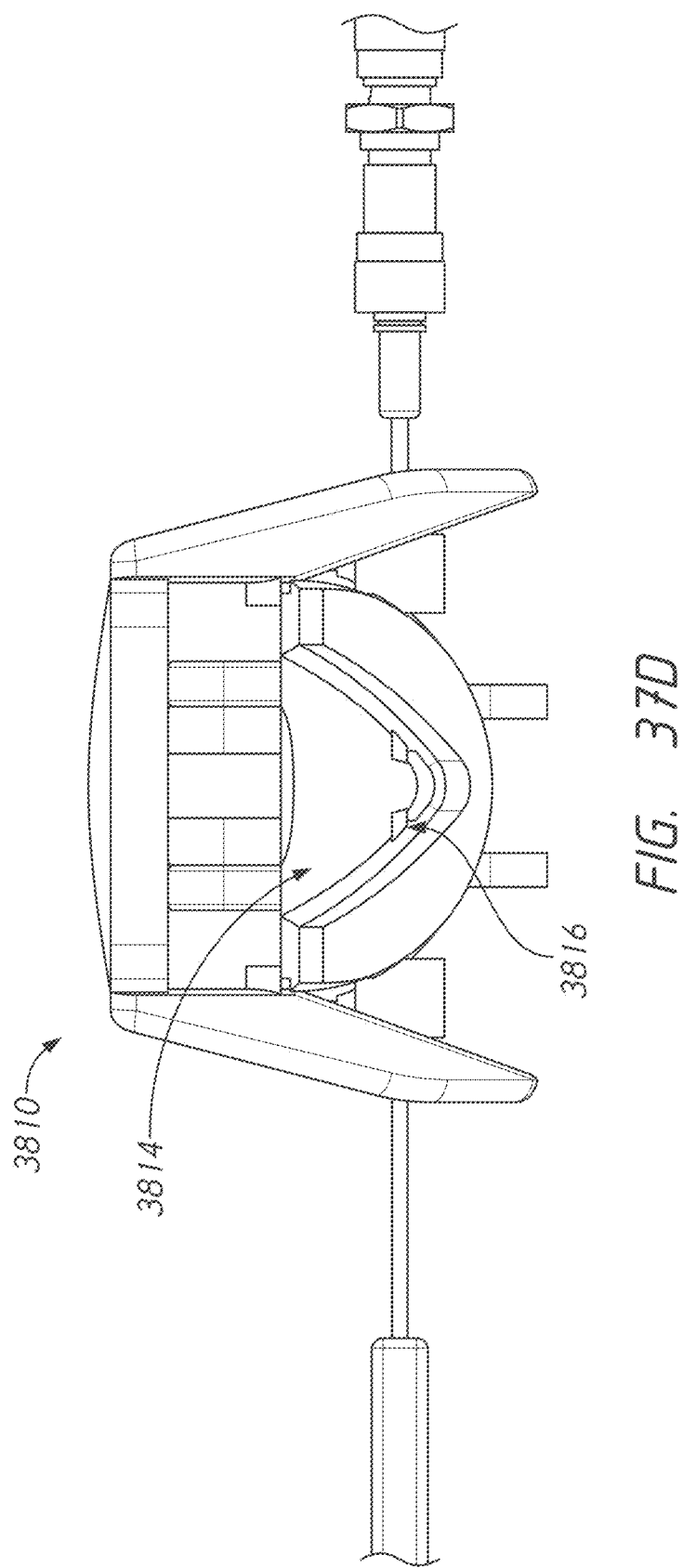

NON-INVASIVE MEDICAL MONITORING DEVICE FOR BLOOD ANALYTE MEASUREMENTS

FIELD

The present disclosure relates to physiological monitoring. More specifically, this disclosure relates to systems, methods, and apparatuses for interrogating overlapping or proximate regions of tissue using a plurality of non-invasive physiological sensors.

BACKGROUND

Monitoring of blood glucose (blood sugar) concentration levels has long been critical to the treatment of diabetes in humans. Current blood glucose monitors involve a chemical reaction between blood serum and a test strip, requiring an invasive extraction of blood via a lancet or pinprick. Small handheld monitors have been developed to enable a patient to perform this procedure anywhere, at any time. But the inconvenience of this procedure—specifically the blood extraction and the use and disposition of test strips—has led to a low level of compliance. Such low compliance can lead to serious medical complications. While a non-invasive method of measuring glucose has long been sought, attempts to create such a device have universally failed due to the difficult nature of detecting glucose in the blood.

SUMMARY

A system for measuring physiological parameters from a tissue site of a patient, the system can include: a plurality of non-invasive sensors configured to obtain physiological data associated with a patient; one or more sensor heads can include: a frame configured to support at least a portion of each of the plurality of noninvasive sensors; an interlocking component configured to couple to the frame and mate with a tissue site attachment component, wherein the tissue site attachment component can be configured to couple to a tissue site of the patient, and wherein the tissue site attachment component has an opening configured to allow at least one of the plurality of noninvasive sensors to obtain physiological data associated with the patient at the tissue site.

The system can include a tissue site clasp configured to accept the tissue site attachment component to stabilize the tissue site while at least one of the plurality of noninvasive sensors obtains physiological data associated with the patient at the tissue site.

The tissue site attachment component can be configured to couple to the tissue site of the patient by an adhesive.

The interlocking attachment can include one or more electrical contacts and wherein the frame can include one or more spring loaded electrical contacts configured to electrically connect with the one or more electrical contacts of the interlocking attachment when the interlocking attachment can be coupled to the frame.

A system for measuring physiological parameters from a tissue site of a patient, the system can include: a plurality of non-invasive sensors configured to obtain physiological data associated with a patient; one or more sensor heads can include a frame configured to support at least a portion of each of the plurality of noninvasive sensors; a movement mechanism configured to couple to the one or more sensor heads, wherein the movement mechanism can be configured to allow for a plurality of degrees of freedom of movement of the one or more sensor heads; a cradle configured to accept a hand of a patient, the cradle can include: a palm rest configured to accept the hand of the patient; a stopping mechanism configured to stop the palm rest on a track; and a release mechanism configured to allow the palm rest to move along the track.

The palm rest can include a heated surface.

A system for measuring physiological parameters from a tissue site of a patient, the system can include: a plurality of non-invasive sensors can include: an emitter configured to emit excitation light; and a detector configured to receive data associated with a physiological parameter at a tissue site of a patient; one or more sensor heads can include: a frame configured to support at least a portion of each of the plurality of noninvasive sensors; one or more scanning mechanisms configured to direct a path of light from the emitter towards a tissue site of a patient; one or more hardware processors configured to: determine a scanning pattern can include a pattern of movement of the excitation light from the emitter towards the tissue site of the patient; actuate the one or more scanning mechanisms to cause the excitation light to follow a path on the tissue site of the patient based on the scanning pattern at a substantially constant speed; detect a plurality of physiological measurements at a plurality of points on the path based on the scanning pattern; and average the plurality of physiological measurements to determine a physiological parameter.

The scanning pattern can include a Lissajous pattern or a raster pattern.

The one or more scanning mechanisms can include at least one of a motorized mirror and a rotary wedge lens.

A system for measuring physiological parameters from a tissue site of a patient, the system can include: a plurality of non-invasive sensors configured to obtain physiological data associated with a patient; one or more sensor heads can include a frame configured to support at least a portion of each of the plurality of noninvasive sensors; and a timing processor in communication with the plurality of non-invasive sensors, the timing processor can include: a timing generator configured to generate a timing signal; a first programmable delay line configured to delay the timing signal according to a first delay; a first signal converters in communication with the plurality of non-invasive sensors, wherein the first signal converter can be configured to receive physiological data from the non-invasive sensors according to the first delay of the timing signal; a second programmable delay line configured to delay the timing signal according to a second delay different from the first delay; a second signal converter in communication with the plurality of non-invasive sensors, wherein the second signal converter can be configured to receive physiological data from the non-invasive sensors according to the second delay of the timing signal; and a deserializer configured to generate one or more data signals from serialized data received from the first signal converter or the second signal converter.

A system for measuring physiological parameters from a tissue site of a patient, the system can include: a first non-invasive sensor can include: a first emitter configured to emit light towards a tissue site of a patient; a first detector configured to receive a first signal can include physiological data associated with the tissue site of the patient; a second non-invasive sensor configured to: a second emitter configured to emit light towards the tissue site of the patient; a second detector configured to receive a second signal can include physiological data associated with the tissue site of the patient; and one or more sensor heads can include: a frame configured to support at least a portion of first non-invasive sensor and the second non-invasive sensor; and a lens system configured to: transmit the first signal from the tissue site of the patient towards the first detector along a central core of an optical path;

transmit the second signal from the tissue site of the patient towards the second detector along a different path than the first signal within the optical path.

A system for detecting an air gap between a surface of a sensor and a tissue site of a patient, the system can include: a plurality of non-invasive sensors configured to obtain physiological data associated with a patient; one or more sensor heads can include: a frame configured to support at least a portion of each of the plurality of noninvasive sensors; and a surface configured to contact a tissue site of the patient; and one or more hardware processors configured to: receive an image of the tissue site of the patient from at least one of the plurality of non-invasive sensors; process the image using a classifier trained by a neural network to determine a likelihood score that the surface of the one or more sensor heads can be in contact with the tissue site of the patient; and cause at least one of the plurality of non-invasive sensors to obtain physiological data associated with the patient based on the likelihood score.

A system for detecting an air gap between a surface of a sensor and a tissue site of a patient, the system can include: a Raman spectrometer configured to obtain Raman spectrographic data associated with a first band of wavenumbers and a second band of wavenumbers at least 500 cm−1 away from the first band, the Raman spectrometer can include: an emitter configured to emit light towards a tissue sample of a patient; a diffraction grating configured to diffract Raman scattered light from the tissue site of the patient towards a first detector and a second detector, wherein: the first detector can be configured to detect Raman scattered light in the first band; and the second detector can be configured to detect Raman scattered light in the second band.

For purposes of summarizing the disclosure, certain aspects, advantages and novel features are discussed herein. It is to be understood that not necessarily all such aspects, advantages or features will be embodied in any particular embodiment of the invention and an artisan would recognize from the disclosure herein a myriad of combinations of such aspects, advantages or features.

BRIEF DESCRIPTION OF THE DRAWINGS

The following drawings and the associated descriptions are provided to illustrate embodiments of the present disclosure and do not limit the scope of the claims.

FIGS. 19B-1 and 19B-2 illustrate example fiber shapes in an example arrangement.

FIGS. 20A and 20A-1 illustrate an example motorized mirror mechanism for a noninvasive sensor.

FIGS. 20B and 20B-1 illustrates an example rotary wedge movement mechanism for a noninvasive sensor.

FIGS. 20C and 20C-1 illustrates an example steering mechanism for a noninvasive sensor.

FIG. 25A illustrates a radiant heating and ambient cooling model.

FIGS. 34A and 34B illustrate example OCT measurements after and before transformation, respectively.

FIGS. 37A-37E illustrate example aspects of an example fiber sensor.

Figure 1:
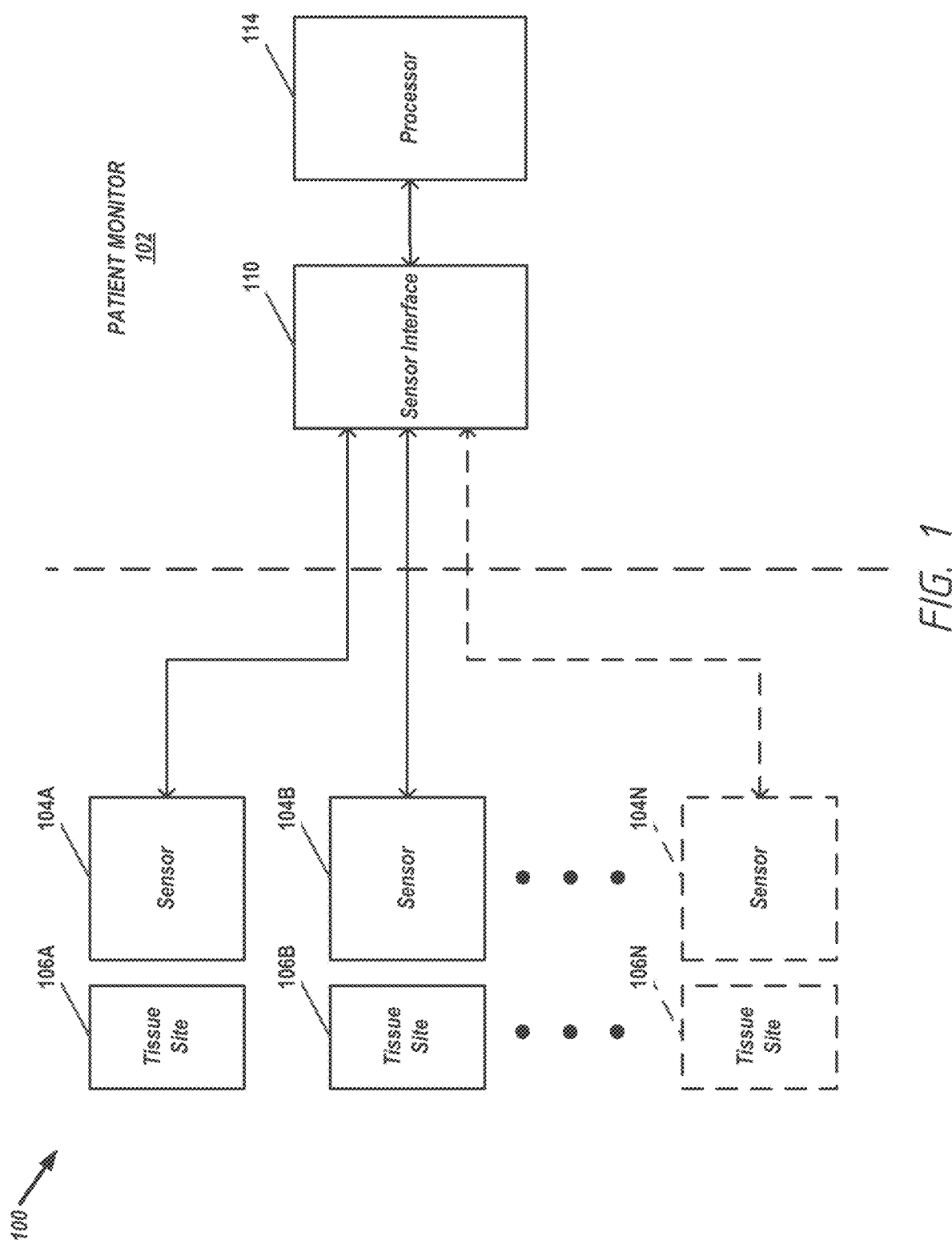
FIG. 1 illustrates an example patient monitoring system that includes a plurality of physiological sensors.

While the foregoing "Brief Description of the Drawings" references generally various embodiments of the disclosure, an artisan will recognize from the disclosure herein that such embodiments are not mutually exclusive. Rather, the artisan would recognize a myriad of combinations of some or all of such embodiments.

DETAILED DESCRIPTION

The present disclosure will now be described with reference to the accompanying figures, wherein like numerals refer to like elements throughout. The following description is merely illustrative in nature and is in no way intended to limit the disclosure, its application, or uses. It should be understood that steps within a method may be executed in different order without altering the principles of the present disclosure. Furthermore, embodiments disclosed herein can include several novel features, no single one of which is solely responsible for its desirable attributes or which is essential to practicing the systems, devices, and methods disclosed herein.

A. INTRODUCTION

Many non-invasive techniques for determining blood glucose have significant shortcomings, such as low accuracy (for example, less accuracy than invasive home monitors) and insufficient specificity of glucose concentration measurement. Accordingly, there is a need for an improved method to non-invasively monitor glucose. Systems and methods disclosed herein address various challenges related to non-invasively determining a patient's blood glucose level by harmonizing data from multiple non-invasive sensors. Each of the non-invasive sensors can interrogate the same or a similar tissue site of a patient, and variables identified using one or more sensors can be utilized to improve data from one or more other sensors. Using these data harmonization techniques, a glucose concentration measurement can be obtained.

In many instances, a single non-invasive sensor may lack the functionality to measure each of the parameters required for an accurate determination of an analyte concentration. As a result, many physiological monitoring techniques include estimations, such as those based on common assumptions, to compensate for the lack of known data. However, due to the sensitivity of analyte measurements, these estimations can result in inaccurate or unreliable determinations.

For example, Beer's Law (also known as the Beer-Lambert Law) relates the attenuation of light to properties of a material. In particular, Beer's law states that absorbance of a material is proportional to the concentrations of the attenuating species in the material sample. The relationship between these parameters is expressed in Equation 1 below:

$$A = \varepsilon * b * c \qquad \text{(Equation 1)}$$

where A is the absorbance of the material at a given wavelength of light, c is the molar absorptivity or extinction coefficient (L mol$^{-1}$ cm$^{-1}$), unique to each molecule and varying with wavelength, b is the length of the light path through the material (cm), and c is the concentration of an analyte of interest (mol L$^{-1}$).

In many cases, the length of the light path through the material (sometimes referred to as the path length) is estimated. For example, a generic finger may be associated with a first estimated path length value, while a generic nose may be associated with a second path length value. However, every person has a unique tissue geometry, which can include, but is not limited to, unique skin structure or skin thickness. Furthermore, because tissue is not uniform throughout a person's body, even tissue sites that are close in proximity, such as two different measurements sites on a patient's finger, can have a different tissue geometry. As noted above, a specific tissue geometry of a particular tissue site can affect the path length value. Accordingly, a non-invasive physiological sensor can be configured to obtain skin geometry data, which can be utilized to calculate a path length associated with a tissue site. In addition or alternatively, the skin geometry data can be utilized to calibrate one or more sensors (for example, select a focal depth of Raman spectrometer), which can result in more accurate analytes measurements, such as blood glucose concentration measurements.

An optical coherence tomography, or OCT, sensor can be utilized to obtain tissue geometry information. OCT is an optical imaging technique using light waves that produce high-resolution imagery of biological tissue. OCT creates its images by interferometrically scanning in depth a linear succession of spots, and measuring backscattered light at different depths in each successive spot. The OCT data can be processed to present an image of the linear cross section. OCT data can be processed to determine tissue geometry information, such as skin geometry. For example, the OCT data can provide data regarding a thickness of one or more skin layers, such as the epidermis, the dermoepidermal junction, or the dermis.

In addition or alternatively, OCT data can be utilized to determine whether successive OCT measurements have occurred in the same or a different location. For example, one reason data harmonization between sensors is available relates to the specific optical profile of a particular tissue site. That is, a particular tissue site retains its specific optical profile, and a different measurement location may have a different optical profile. Thus, in many cases, to maintain data harmonization capabilities, each of the sensors should interrogate the same or a substantially proximate tissue site. One problem associated with interrogating the same or a substantially proximate tissue site relates to the subsequent placement of a sensor after it has been removed from the patient. To solve these and other problems, tissue geometry information associated with OCT data can be utilized to determine whether a later one of successive OCT measurements is taken at the same tissue site as a previous one of the successive OCT measurements.

A bio-impedance or tissue dielectric constant sensor can be utilized to obtain tissue geometry information. For example, bio-impedance or tissue dielectric constant data can provide information relating to one or more skin layers, a hydration of one or more skin layers, or a cellular structure of the tissue.

Raman spectroscopy has exhibited promise with respect to blood glucose detection, for example, due to its capability to gain information about the molecular constitution non-invasively. For example, features such as peaks of the Raman spectra are considered the Raman "fingerprints" of analytes such as glucose. Accordingly, using an isolated or semi-isolated Raman signal, the system can identify physiological data, such as information regarding a patient's blood glucose level.

For various reasons, it has been challenging to isolate a pure Raman signal from a signal obtained from a Raman spectrometer. For example, emission of fluorescence in tissue often overwhelms any signal collected from the Raman spectrometer, thereby hiding Raman features. In addition, attenuation of the signal due to absorption can further affect prediction of analytes using the collected signal. Furthermore, varying tissue geometries at tissue sites increases a difficulty in selecting a focal depth of the Raman spectrometer that will optimize a resolution of the Raman signal.

Systems and methods disclosed herein address one or more of these or other challenges by utilizing data associated with one or more sensors to calibrate or improve an accuracy of one or more other sensors. For example, a value for path length can be obtained from skin geometry data, which can improve a pulse oximetry sensor such as a near infrared (NIR), reflectance, or transmittance sensor. As another example, the present disclosure addresses various challenges related to leveraging the Raman scattering signatures for prediction of glucose by harmonizing data from a plurality of non-invasive physiological sensors. For instance, a focal depth of the Raman spectrometer can be selected based on tissue geometry data, which can improve the Raman spectrometer, and possibly increase an accuracy of a blood glucose measurement. Similarly, using data from one or more sensor, the Raman signal can be isolated by reducing or removing an effect of Fluorescence on a collected signal, or removing an effect of attenuation of the signal due to absorption.

1. System Overview

FIG. 1 illustrates an example patient monitoring system 100 that includes a patient monitor 102, a first sensor 104A, and a second sensor 104B. In addition, the patient monitoring system 100 can include one or more other sensors 104N. Sensors 104A, 104B, and 104N can interrogate tissue sites 106A, 106B, and 106N, respectively, of a patient. In some cases, tissue sites 106A, 106B, and 106N can be the same or substantially proximate tissue sites, while in other cases one or more of the tissue sites 106A, 106B, or 106N can be different. Sensor data from the sensors 104A, 104B, or 104N can be utilized to determine one or more physiological parameters or patient vitals. For example, the patient monitor 102 can receive a signal from the one or more of the sensors 104A, 104B, or 104N and can determine, based on the received signal(s), one or more physiological parameters or one or more measurements that can be used to determine a physiological parameter.

The sensors 104A, 104B, and 104N can each be the same type of sensors, or one or more of the sensors 104A, 104B, and 104N can be different from each other. For example, the sensors 104A, 104B, and 104N can include, but are not limited to, any combination of an optical coherence tomography (OCT) device, a spectrometer (for example, a Raman spectrometer), a plethysmograph sensor such as a pulse oximetry device (for example, a near infrared (NIR), reflectance and/or transmittance device), a pressure sensor, an electrocardiogram sensor, a bioimpedance sensor, or acoustic sensor, among other sensors.

Two or more of the sensors 104A, 104B, or 104N can be configured to interrogate the same tissue site. For example, two or more of the senor sensors 104A, 104B, or 104N can be positioned proximate each other such that they can interrogate the same tissue, such as a finger, a thumb, a thenar space, a hand, a wrist, a forearm, a nose, a limb, a head, an ear, a neck, an upper body, or a lower body. In addition or alternatively, two or more of the sensors 104A, 104B, or 104N can be configured to interrogate different tissue sites.

In some cases, one or more of the sensors 104A, 104B, or 104N can be integrated into an apparatus, such as an apparatus that is wearable by a user. For example, one or more of the sensors 104A, 104B, or 104N can be integrated into a glove that when worn by a user allows the sensor(s) to interrogate one or more tissue sites. Similarly, one or more of the sensors 104A, 104B, or 104N can be incorporated in or attached to various other apparatuses, including, but not limited to, a sock, a shirt, a sleeve, a cuff, a bracelet, a glove, or the like.

In some cases, data from a single sensor 104A, 104B, or 104N does not provide enough reliable information to determine certain physiological parameters. For example, a number of factors can affect an accuracy of sensor data including, but not limited to, patient movement, sensor placement, interference, and type of sensor being used, the expansion and contraction of the patient's vascular system, assumptions made during calculations, skin temperature, pressure, or the like. In addition or alternatively, the determination of some physiological parameters (for example, glucose concentration) may require more information than a single sensor can provide.

To solve this and other problems, the patient monitor 102 (or one or more of the sensors) can harmonize or compare data from two or more sensors, which can allow for a determination of more accurate or reliable data, or can allow for a determination of one or more additional physiological parameters, such as blood glucose concentration.

As one example, the patient monitor 102 receives a first signal from a first sensor 104A, the first signal corresponding to an interrogation of the first tissue site 106A by the first sensor 104A. Further, the patient monitor 102 receives a second signal from a second sensor 104B, the second signal corresponding to an interrogation of the second tissue site 106B by the second sensor 104B. Based on the first signal, the patient monitor 102 can make adjustments to modify the second sensor or the second measurement to improve the accuracy or reliability of the second sensor or the second measurement. For instance, adjustments can include, but are not limited to, adjusting an intensity, power, position, or timing of the second sensor 104b or adjusting values corresponding to the measurement of the second physiological parameter. For example, the patient monitor 102 can modify the second measurement or calculations for a physiological parameter (for example, introduce an offset, adjust assumed or estimated values, filter a signal, etc.) to account for information from the first sensor. In addition or alternatively, the patient monitor can adjust a confidence value associated with the first, second, or another measurement.

As described above, based at least in part on the first and second signals, the patient monitor 102 can determine a physiological parameter. The physiological parameter can be a value which may not be independently determinable from data from either of the first sensor or the second sensor alone. For example, data from the first sensor can be utilized to determine a path length, data from the second sensor can be utilized to determine an absorbance, and the physiological parameter can include a concentration of an analyte, such as glucose. As another example, data from the first sensor can be utilized to determine a path length or absorbance, the second sensor can correspond to a Raman spectrometer, and the physiological parameter can include a concentration of an analyte, such as glucose.

The patient monitor 102 can include a digital signal processor (DSP) that receives the signals generated by the one or more sensors 104A, 104B, or 104N (for example, through a front-end unit) and determines parameters, for example, those indicative of the physiological condition of the patient, using the received signals. The patient monitor 102 can, for example, determine physiological parameters corresponding to the patient, such as an amount of light absorbed, transmitted through, or reflected at a tissue site, path length (for example, distance that light travels through the material), concentration of an analyte, bioimpedance, tissue dielectric constant, pulse rate (PR), pulse pressure variation (PPV), pleth variability index (PVI'), stroke volume (SV), stroke volume variation (SVV), peripheral capillary oxygen saturation ($SpO_2$), mean arterial pressure (MAP), central venous pressure (CVP), pulse pressure (PP), perfusion index (PI), total hemoglobin (SPHB®), carboxyhemoglobin(SPCO®), methemoglobin(SPMET®), oxygen content)(SPOC®), or acoustic respiration rate (RRA®), among other parameters. In some aspects, the patient monitor 102 can derive or use one or more relationships (for instance, a set of linear equations) from two or more of the determined parameters. The patient monitor 102 can utilize the one or more relationships to determine the patient's glucose levels, systemic vascular resistance (SVR), CO, or arterial blood pressure (BP), among other parameters.

The patient monitor 102 can further compare or analyze one or more of the determined parameters (for instance, at least two of the determined parameters or one determined parameter and a previous or model parameter) to adjust how a parameter is measured or calculated to make the measured parameter more accurate or reliable, to adjust a sensor to make the measured parameter more accurate or reliable, to calculate, derive or determine an accuracy or a confidence value of a measured parameter, to isolate a parameter, or to determine another parameter based on the one or more parameters. The sensors, in addition to or alternatively than the patient monitor, can coordinate with each other to coordinate data or adjust calculations to enhance an accuracy or reliability of measurements. In addition or alternatively, the patient monitor 102 can use the data to increase an accuracy of one or more calculations, calculate a previously unknown or estimated physiological parameter, calibrate data, or compensate for various circumstances that might otherwise result in inaccurate or unreliable data.

2. Additional Implementations

The patient monitor 102 can be connected to one or more (for instance, three, four, five, or six) sensors, such as the sensors 104A, 104B, or 104N, that are detecting from a patient and use the signals received from the sensors to determine one or more physiological parameters including, but not limited to, glucose, $SpO_2$, PPR, PVI® (for instance, via a palm, thumb or finger plethysmography sensor), SV, MAP, CVP, PP, or PI (for instance, via a palm, thumb or finger plethysmography sensor), among other parameters such as those described herein.

Moreover, the patient monitor 102 can utilize any of the techniques described herein to determine whether any measurement described herein (using any of the sensors described herein) is valid. The patient monitor 102 can be configured to show (for example, on a display) information about a valid or invalid measurement, activate an indicator light (such as an LED), trigger an alarm, adjust one or more sensors or parameters (for instance, based on a received sensor signal), or display any data.

The patient monitor 102 can wirelessly or using wires receive, via an input of the patient monitor 102, a signal from one of the sensors 104A, 104B, or 104N. The received signal may take various forms, such as a voltage, a current, or charge. An operational amplifier (op-amp) of the patient monitor 102 can increase the amplitude, as well as transform the signal, such as from a current to a voltage. An anti-aliasing filter (AAF) of the patient monitor 102 can then process of the output signal from the op-amp to restrict a bandwidth of the output signal from the op-amp to approximately or completely satisfy the sampling theorem over a band of interest. An analog-to-digital convertor (ADC) of the patient monitor 102 can convert the output signal from the AAF from analog to digital. The output signal from the ADC can then be sampled by a first processor of the patient monitor 102 at a relatively high speed. The result of the sampling can next be down-sampled by a second processor of the patient monitor 102, which may be the same or different from the first processor, before waveform analysis may be performed by a DSP.

Figure 2:
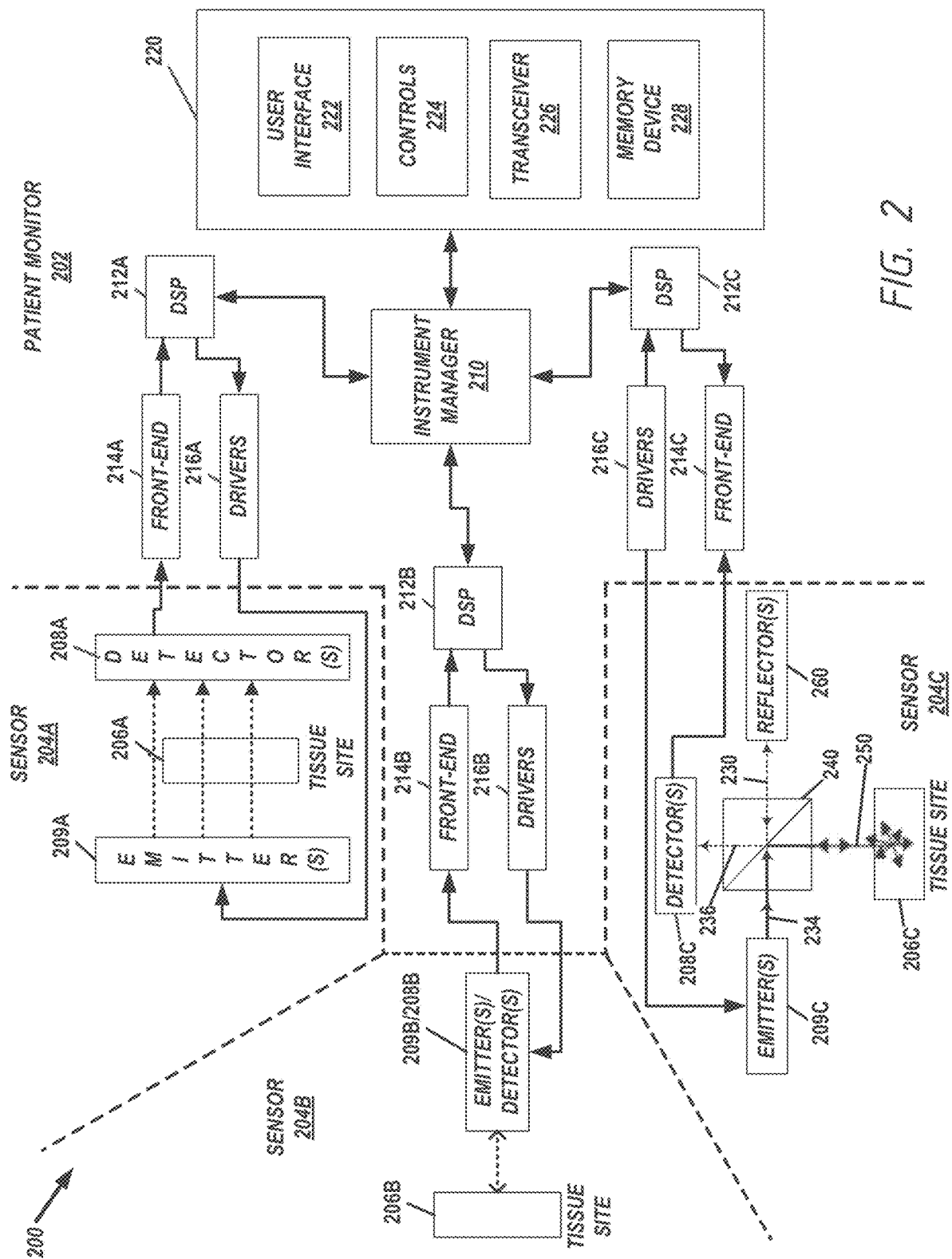
FIG. 2 illustrates a block diagram of an example patient monitoring system.

FIG. 2 illustrates a block diagram of an example patient monitoring system 200, which can be an embodiment of the patient monitoring system 100. The patient monitoring system 200 can include a patient monitor 202, a first non-invasive physiological sensor 204A, a second non-invasive physiological sensor 204B, or a third non-invasive physiological sensor 204C. Furthermore, it should be noted that fewer, additional, or different sensors may be included in patient monitoring system 200.

The sensors 204A, 204B, or 204C can respectively detect from tissue sites 206A, 206B, and 206C of a patient. Each of the sensor can measure from the same or a similar tissue site. For example, sensor 204A can take a measurement and sensor 204B can take a subsequent measurement on the same tissue or at the same location. This may allow the system to more easily harmonize the data from the sensors or use data from one sensor to improve data or calculation based on another sensor. The tissue sites 206A, 206B, and 206C can be different. As a non-limiting example, tissue site 206A can include a thenar space of a patient's hand, and tissue sites 206B, 206C include a thumb of the patient, such as a base of the thumb. It should be noted, however, that fewer, more or different sensors can be include in system 200.

The DSP 212A can communicate via drivers 216A with the plethysmography sensor 204A and receive via a front-end 214A one or more light intensity signals indicative of one or more physiological parameters of the patient or one or more measurements that can be used to determine one or more physiological parameters. For example, a signal can be indicative of an intensity of light reflected, refracted, scattered, absorbed, or transmitted at a tissue site. The drivers 216A can convert digital control signals into analog drive signals capable of driving emitters 209A to illuminate the tissue site 206A. For example, the light emitted by emitters 209A can have an infrared (IR), near infrared (NIR), red, ultra-violet (UV), visible, or other wavelength. The detector(s) 208A can, in turn, generate one or more composite analog light intensity signals responsive to light detected by the detector(s) 208A after attenuation, reflection, refraction, scattering, absorption, etc. at the tissue site 206A. The emitter(s) 209A or detector(s) 208A include a fiber-optic component for illumination and collection, respectively. For example, the emitter(s) 209A can be positioned on a tissue site 206A (for example, on top, on the bottom, on the side, etc.) and the detector(s) 208A can be positioned on an opposite portion of the tissue site 206A.

The front-end 214A can convert the one or more composite analog light intensity signals from the detector(s) 208A into digital data and input the digital data into the DSP 212A. The digital data from the front-end 214A can correspond to at least one of a plurality of physiological parameters as described herein. For example, the digital data from the front-end 214A can be representative of a change in the absorption of particular wavelengths of light as a function of the changes in the tissue site 206A resulting from pulsing blood.

The DSP 212A can include one or more data or signal processors configured to execute one or more programs for determining physiological parameters from input data. The DSP 212A can perform operations that include calculating or outputting one or more physiological measures, such as absorbance, path length, PVI® and other parameters described herein. The operations performed by the DSP 212A can be implemented in software, firmware or other form of code or instructions, or logic or other hardware, or a combination of the above.

The DSP 212B can receive via a front-end 214B one or more light intensity signals indicative of one or more physiological parameters of the patient. The drivers 216B can convert digital control signals into analog drive signals capable of driving emitters/detectors 209B/208B to illuminate the tissue site 206B. For example, the light emitted by emitters/detectors 209B/208B can be infrared (IR), near infrared (NIR), red, ultra-violet (UV), visible, or other wavelength, the like, or a combination thereof in discrete or continuous wavelengths. The emitters/detectors 209B/208B can, in turn, generate one or more composite analog light intensity signals responsive to light detected by the emitters/detectors 209B/208B light is reflected, refracted, scattered, absorbed, or attenuated at a tissue site 206B. The emitters/detectors 209B/208B include a fiber-optic bundle that has illumination and detection fibers. In addition, for example, as described with respect to FIG. 1, the emitters/detectors 209B/208B can be separate.

The front-end 214B can convert the one or more composite analog light intensity signals from the emitters/detectors 209B/208B into digital data and input the digital data into the DSP 212B. The digital data from the front-end 214B can correspond to at least one of a plurality of physiological parameters, as described herein. The digital data from the front-end 214B can be representative of a change in the absorption/reflection of particular wavelengths of light as a function of the changes in the tissue site 206B resulting from pulsing blood.

The DSP 212B can include one or more data or signal processors configured to execute one or more programs for determining physiological parameters from input data. The operations performed by the DSP 212B can be implemented in software, firmware or other form of code or instructions, or logic or other hardware, or a combination of the above.

Sensor 204C includes a detector 208C, a light source 209C, a beam splitter 240, and a reflector 260. The light source 209C can emit light having an approximately equal wavelength, a spectrum of wavelengths, or a few different wavelengths, for example, two. For example, the wavelengths can be selected based on the absorption spectrum.

As illustrated, light beams from the light source 209C are split using the beam splitter 240 into reference arm light beams 230 and sample arm light beams 250. After the light beams 234 are split, the reference arm light beams 230 travel down the reference arm to interact with the reflector 260, and the sample arm light beams 250 travel down the sample arm to interact with the tissue 206C, for example, from the base of a patient's thumb.

The tissue site 206C can absorb, reflect, scatter, or refract the sample arm light beams 250. Some of the sample arm light beams 250 are reflected back to the beam splitter 240. The beam splitter 240 can direct at least some of the reflected sample arm light beams 250 to the detector 208C.

The light beams traveling down the reference arm interact with a reflector 260 and are reflected back to the beam splitter 240 Similar to the reflected sample arm light beams 250, the reflected reference arm light beams 230 are also directed to the detector 208C by the beam splitter 240. Reflected signals from the sample arm and reference arm and are presented to photodetector 208C for measurement.

The tissue volume with which the light interacts (referred to as the interaction volume) can be determined by the spot size of the imaging optics (surface area) and the coherence length of the light (depth). Thus, the reference arm can determine the depth within the interaction volume from which scattered light is measured. The patient monitor 200 uses the detected signals obtained from the interference of the reflected sample arm light beams 250 and the reflected reference arm light beams 230 to calculate tissue geometry data, such as a skin geometry of one or more skin layers.

Although not illustrated in FIG. 2, imaging optics can also be used to focus the sample arm light beams 250 prior to interacting with the tissue site 206C. Furthermore, the end of the sample arm and imaging optics can be placed in close proximity to the tissue site 206C. The reference arm and reflector 260 are configured such that appropriate wavelength and polarization selected such that the appropriate depth of the tissue is measured.

The DSP 212C can receive via a front-end 214C one or more signals indicative of one or more physiological parameters of the patient, such as path length. The drivers 216C can convert digital control signals into analog drive signals capable of driving emitters 209C to illuminate the tissue site 206C. The detectors 208C can, in turn, generate one or more composite analog signals responsive to light detected by the detectors 208C.

The front-end 214C can convert the one or more composite analog signals from the detectors 208C into digital data and input the digital data into the DSP 212C. The digital data from the front-end 216C can correspond to at least one of a plurality of physiological parameters, as described herein. The DSP 212C can include one or more data or signal processors configured to execute one or more programs for determining physiological parameters from input data. The operations performed by the DSP 212C can be implemented in software, firmware or other form of code or instructions, or logic or other hardware, or a combination of the above.

One or more of the components relating to signal acquisition or processing (for example, front end 214A, 214B, 214C, drivers 216A, 216B, 216C, DSP 212A, 212B, 212C, etc.) can be incorporated into one or more connecting cables, the sensors themselves, or are otherwise closer to the sensor sites. As such, the patient monitor 202 can include primarily the input or output devices 220 and the instrument manager 210, (if appropriate). In addition, some of the components are illustrated as separate units but can be combined. For instance, front end 214A, 214B, 214C can be combined into one or more front ends, drivers 216A, 216B, 216C, can be combined into one or more drives, DSP 212A, 212B, 212C can be combined into one or more DSPs, etc. By reducing the number of components included in the patient monitor 102, 202, the monitor can be smaller in size or more portable, which can be more convenient for home or "spot check" use.

The instrument manager 210 can communicate with one or more non-invasive psychological sensors, such as 204A, 204B, or 204N. The instrument manager 210 can communicate with one or more input or output devices 220. The one or more input or output devices 220 can include a user interface 222, controls 224, a transceiver 226, and a memory device 228.

The user interface 222 can include a numerical or graphical display that provides readouts of measures or parameters, trends and bar graphs of measures or parameters, visual indications of measures or parameters, visual indicators like LEDs of various colors that signify measurement magnitude, or device management interfaces, which can be generated by LEDs, LCDs, or CRTs, for example. The user interface 222 can include an audible output device that provides readouts or audible indications of measures or parameters. The user interface 222 can include one or more input devices like a keypad, touch screen, pointing device, voice recognition device, and computer that can be used to supply control or configuration data, such as initialization settings, from the user interface 222 to the instrument manager 210. In some implementations, the user interface 222 can be an interface for devices as well as users.

The controls 224 can be outputs to medical equipment, such as drug administration devices, ventilators, or fluid IVs, so as to control the amount of administered drugs, ventilator settings, or the amount of infused fluids. Additionally or alternatively, the controls 224 can include an interface between, for example, the user interface 222 and the Instrument Manager 210. The patient monitor 202 can use the controls 224 to automatically treat the patient (for instance, provide fluid to the patient, provide medication to the patient, turn on a fan to cool the patient, or adjust a temperature of a room to heat or cool the patient) in response to determining that the patient may benefit from treatment.

The transceiver 226 via an antenna or wires can transmit information about operation of the patient monitor 202 to an electronic device or receive control or configuration data for operating the patient monitor 202. The transceiver can, for example, communicate via a computer network or intermediary device or directly with the electronic device using electromagnetic radiation.

The memory device 228 can be used to store information about operation of the patient monitor 202 and other relevant information to the operation of Patient Monitor 202 (such as calibration etc). This information can, for example, include readouts of measures or parameters, trends and bar graphs of measures or parameters, visual indications or indicators.

Although not illustrated in FIG. 1 or 2 patient monitors 102, 202, or cables connecting the patient monitors to the sensors can further include one or more outputs that supply the signal(s) from one or more of the sensors to one or more other electronic devices for further processing. As one example, the signal(s) from one or more of the sensors can be output in parallel by one or more of the sensors or the cables that couple the one or more sensors to the patient monitor 102, 202. In another example, the patient monitors 102, 202 can include one or more outputs for outputting copy(ies) of the signal(s) from one or more of the sensors. The copy(ies) of the signal(s) can also be adjusted relative to the original(s) with filtering, scaling, or other changing operation prior to being provided to the one or more other electric devices.

3. Tissue Geometry

Figure 3A:
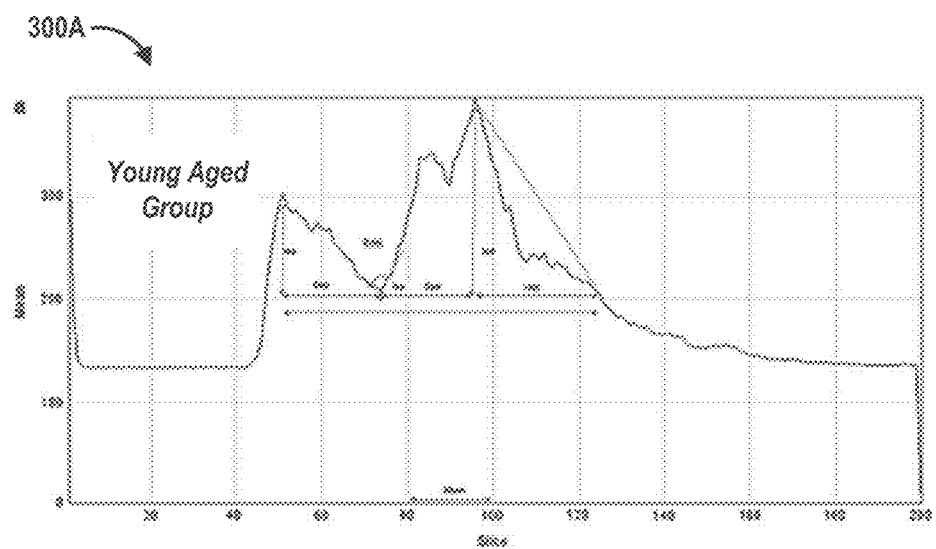
FIGS. 3A-3C illustrate optical scattering differences in skin geometries among various age groups.
Figure 3B:
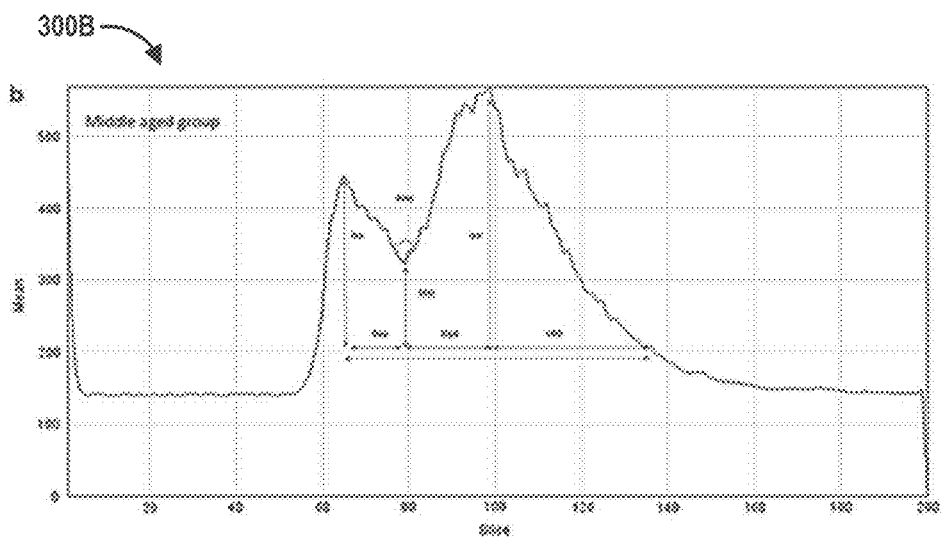
Figure 3C:
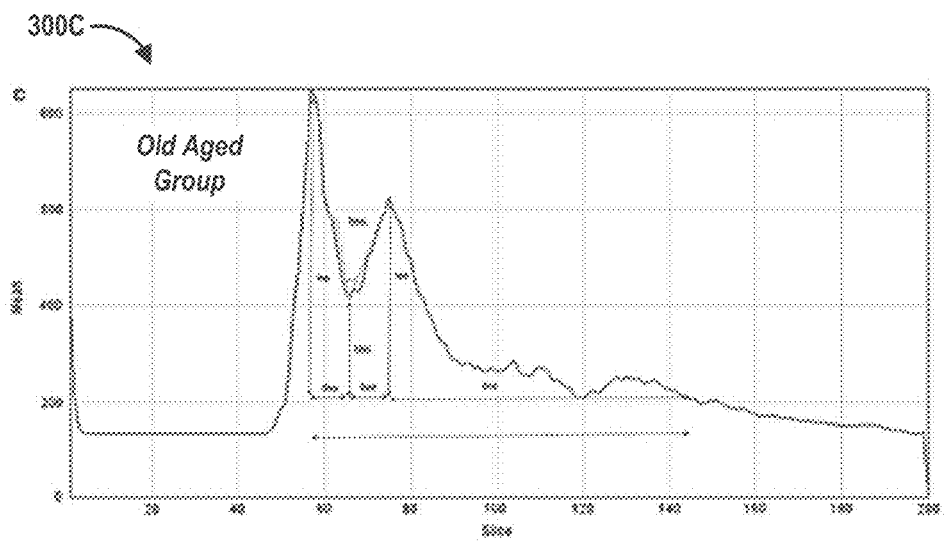

Tissue geometry can vary greatly between individuals. For example, skin structure or skin thickness can vary across races, ages, or the like. Even individuals having similar demographics can have different skin geometries. FIGS. 3A-3C illustrate optical scattering differences in skin geometries among various age groups. FIG. 3A corresponds to 20-39 year olds, FIG. 3B corresponds to 40-59 year-olds, and FIG. 3C corresponds to 60-79 year-olds. In these examples, the x-axis corresponds to a compaction of the skin and is measured from 0 to 200 units, where one unit is 3 μm, and the y-axis corresponds to brightness (for example, backscattered intensity) of the skin and is measured from 0 to 800 AU (absorbance units). As evidenced by these graphs 300A, 300B, 300C, the general skin structure or thickness is not constant throughout the population.

Tissue geometry can also vary greatly between tissue sites of a particular individual. For example, each of a finger, a thumb, a thenar space of a hand, a wrist, a forearm, a nose, an ear, a neck, or other tissue site can have a different skin geometry. Even tissue sites that are in close proximity, such an upper part of a finger and a lower part of a finger, can have a different skin geometry.

4. Optical Coherence Tomography

Optical coherence tomography, or OCT, is an optical imaging technique using light waves that produces high-resolution imagery of biological tissue. OCT creates its images by focusing a beam of light into a medium and interferometrically scanning the depth of a linear succession of spots and measuring the absorption and/or the scattering of the light at different depths in each successive spot. In some cases, the data can be processed to present an image of the linear cross section of the medium scanned.

A light source can output a beam of light having a broad spectrum of wavelengths. The beam of light can be collimated and pass a beam splitter such that a portion of the beam of light is directed towards the tissue and a portion of the beam of light is directed toward a reference arm. The light can be either polarized, partially polarized, or non-polarized. A polarizer located on one edge of the beam splitter can polarize the light linearly, elliptically, or circularly, as desired. The path length of the reference arm can be changed based on the desired measurement depth into the tissue. The wavelength can be centered at, for example, 1310 nm with a 50 nm bandwidth. In other cases, the wavelength can be 1060 nm with a 70 nm bandwidth. The light source can be selected to have a center wavelength anywhere between 400 nm and 1700 nm with a broad bandwidth. For example, the bandwidth can be up to 150 nm. It is understood that different light sources with different center wavelengths and bandwidths can be chosen to optimize penetration depth into the tissue and optimize the depth resolution of sensitivity to skin structures. The reflected light from the tissue can be collected using a converging lens and be directed back through the beam splitter to a photodetector where it is recombined with a portion of the reference arm beam to form an interference pattern. A processor can use the signals from the photodetector to render an image of the tissue.

OCT can provide a non-invasive method for identifying one or more characteristics of a tissue's structure. For example, OCT data (which can be referred to as tissue geometry data) can include an indication of a boundary between the main skin layers, such as the epidermis (outermost layer of the skin), the dermis (layer beneath the epidermis), or the hypodermis (layer directly below the dermis and serves to connect the skin to the underlying fibrous tissue of the bones or muscles). The epidermis is further divided into five, separate layers (Stratum Corneum, Stratum Lucidum, Stratum Granulosum, Stratum Spinosum, and Stratum Basale) and the dermis is divided into two, separate layers (the papillary dermis and the reticular dermis). In some cases, OCT data can provide an indication of a boundary between any of these layers. In addition or alternatively, OCT data can include an indication of a thickness of any of the epidermis, dermis, or hypodermis, or their individual layers.

Figures 4A, 4B:
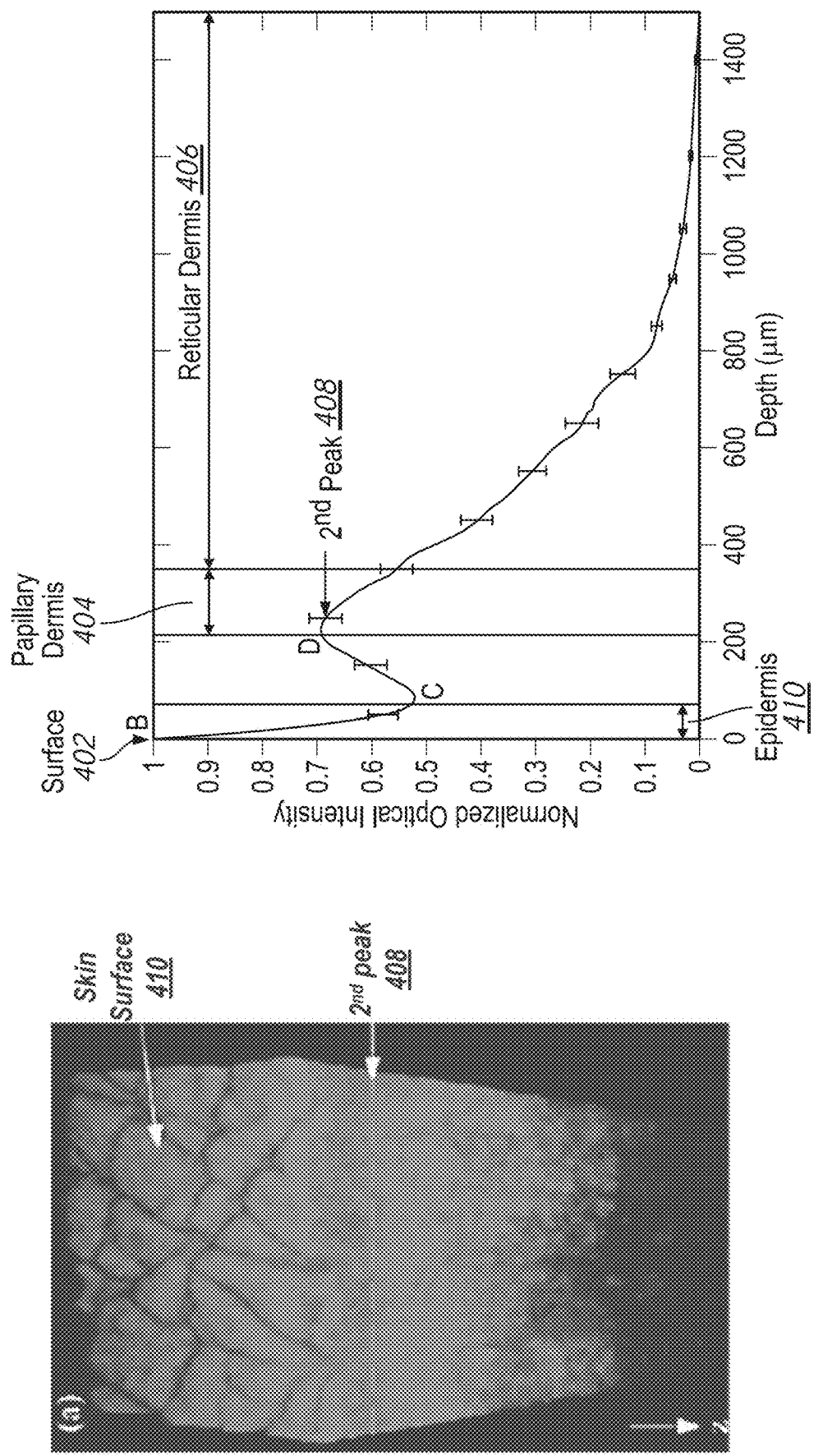
FIG. 4A illustrates an example 3D OCT image obtained from a volar side of forearm skin.
FIG. 4B illustrates an example one-dimensional distribution of light intensity versus depth graph obtained by averaging scans of the image of FIG. 4A.

For example, FIG. 4A illustrates an example 4D OCT image obtained from a volar side of forearm skin, and FIG. 4B illustrates an example one-dimensional distribution of light intensity vs. depth obtained by averaging Amplitude scans (A-scans) in the reconstructed OCT 4D image of FIG. 4A. The slope of the line of FIG. 4B is indicative of index of refraction of tissue. A difference in the index of refraction, or a difference in slope, can indicate a new skin or tissue layer because each layer may have a different index of refraction. As illustrated, the first peak 402 corresponds to the skin surface, and the second peak 408 corresponds to the dermoepidermal junction, which is the area of tissue that joins the epidermis 410 and the dermis layers (for example, the papillary dermis 404) of the skin. Accordingly, using OCT data, the system 200 can determine a thickness of one or more of various skin layers such as, but not limited to, the epidermis 410, the dermoepidermal junction, the papillary dermis 404, the reticular dermis 406, or the like.

In some cases, OCT data can provide an indication that an OCT sensor is interrogating an unfavorable tissue site. An unfavorable tissue site can include any tissue site that might provide distorted or inaccurate OCT data (relative to desired OCT data), such as tissue sites that include at least a portion of a hair follicle, a pore, a bone, a finger- or toe-nail, a pimple, a mole, a scar, a blister, a callous, debris, other skin imperfection, or the like.

A particular tissue site can retain its specific optical profile over time, and that optical profile can be different from another tissue site. Accordingly, to maintain data harmonization capabilities, it can be advantageous for sensors to interrogate the same or a substantially proximate tissue site. One problem associated with interrogating the same or a substantially proximate tissue site relates to the subsequent placement of a sensor after it has been removed from the patient or when it is shifted in some way from its original positioning. For example, a subsequent OCT measurement or set of measurements can occur minutes, hours, days, weeks, or some other period of time after the first measurement, and it can be unreasonable to require a patient to wear or interact with the OCT sensor for the duration of that period of time. Nonetheless, even though the OCT sensor has been separated from the patient or shifted from its original position, it can be advantageous for the subsequent OCT measurement(s) to occur at the same location as the first measurement. For example, as described herein, a first tissue site may have a different tissue structure, density, depth, hydration, analyte concentration, or the like than a second, different tissue site. Thus, if the OCT sensor is placed at the same location for each measurement, then previous calculations, determinations, or the like can be utilized, which can simplify any calibrations or corrections to sensor data, among other things.

To solve these and other problems, tissue geometry information associated with OCT data can be utilized to determine whether a subsequent placement of the OCT sensor allows the OCT sensor to interrogate the tissue site corresponding to the tissue site of the first OCT measurement(s). For example, a processor can compare the first tissue geometry data associated with the first OCT measurement(s) with the subsequent tissue geometry data associated with the subsequent OCT measurement(s). If the subsequent tissue geometry data does not correspond to the first tissue geometry data, then the processor can cause one or more actions to occur. For example, the processor can cause an output to indicate that the subsequent tissue geometry data does not correspond to the first tissue geometry data. In other words, the processor can cause an output to indicate that the subsequent placement of the OCT sensor is incorrect, or is different from the first OCT sensor placement, or the processor can cause an output to indicate a probe-off condition. In addition or alternatively, the processor can cause the OCT sensor to be re-positioned. For example, based on the comparison, the processor can suggest a new placement of the OCT sensor, which may more closely correspond to the first placement of the OCT sensor. In addition or alternatively, the processor can control a motorized component to re-position to the OCT sensor such that it more closely corresponds to the first placement of the OCT sensor. Still, in some implementations, the processor can calibrate other sensors based on the subsequent tissue geometry data, rather than the first tissue geometry data.

Alternatively, if the subsequent tissue geometry data does correspond to the first tissue geometry data, then the processor can cause one or more other actions to occur. For example, the processor can cause an output to indicate that the subsequent tissue geometry data does correspond to the first tissue geometry data. In other words, the processor can cause an output to indicate that the subsequent placement of the OCT sensor is correct, as compared to the first placement of the OCT sensor. In addition or alternatively, the processor can calibrate other sensors based on the first tissue geometry data or the subsequent tissue geometry data.

5. Raman Spectroscopy

The Raman effect is a light-scattering phenomenon that can provide insight as to one or more characteristics of an analyte in a sample. When light irradiates a tissue, a fraction of the light is scattered, meaning it emerges in directions other than that of the incident (incoming) beam. Most of this scattered light, generally referred to as Rayleigh scattering, emerges at the original frequency ($f_0$) and wavelength of the incident beam. A small portion of the scattered light, however, emerges at some shifted frequency ($f_s$) that is different from, and usually lower than, the original frequency ($f_0$) and has wavelengths different from that of the incident light. The process leading to this small portion of the scattered light is termed the Raman effect or Raman scattering.

Raman scattering can occur with a change in vibrational or rotational energy of a molecule. Accordingly, the Raman spectra can contain information about the specific chemical substance in the irradiated tissue. For example, Raman scattering yields a set of characteristic peaks in a spectrum, which is a "fingerprint" of a specific chemical substance. Therefore, Raman has high specificity in glucose measurements.

Raman spectroscopy has exhibited promise with respect to blood glucose detection, for example, due to its capability to gain information about the molecular constitution non-invasively. For example, features (such as peaks) of the Raman spectra are considered the Raman "fingerprints" of analytes, such as glucose. Accordingly, using an isolated or semi-isolated Raman signal, the system can identify physiological data, such as information regarding a patient's blood glucose level. However, for various reasons, it has been challenging to isolate a pure Raman signal from a signal obtained from a Raman spectrometer.

The signal collected through Raman spectroscopy is based at least in part on the collection optics and the focal distance/depth of the optics into the tissue. In some cases, the system can use data from one or more sensors to select an appropriate focal depth. For example, a focal depth can be selected that may provide a high or the highest resolution of the Raman or collected signal. In addition or alternatively, a focal depth can be selected that will allow the Raman spectrometer to focus on a particular location of the tissue, such as the capillary beds. For example, OCT, bioelectrical impedance, or tissue dielectric constant measurements may provide tissue geometry data (for example, structural and functional information) that can be used to select a focal depth into the tissue. For example, the selection can be based at least in part on a water content of a portion of the tissue, a thickness of one or more skin layers, or a particular location of tissue, such as the capillary beds.

Although complex, an approximation of a measurement obtained from a Raman spectrometer can be determined using one or more of the following equations:

$$I_1 = I_0 e^{-A_1} \quad \text{(Equation 2)}$$

$$R_0 = R_A I_1 \quad \text{(Equation 3)}$$

$$F_0 = \Phi I_1 \quad \text{(Equation 4)}$$

$$I_2 = \Sigma((R_0 + F_0) e^{-A_2}) \quad \text{(Equation 5)}$$

where $I_0$ is an intensity of excitation light, $I_1$ is an intensity of scattered light over a mean path length, $A_1$ is a first interrogation volume, $R_A$ represents Raman activity, $R_0$ is an intensity Raman scattering at a specific wavelength of light, $F_0$ is an intensity of Florescence at the specific wavelength of light, $\Phi$ represents quantum efficiency, $A_2$ represents a second interrogation volume, and $I_2$ is an intensity of emitted light from isotropic Raman activity. From these relationships, it can be seen that the intensity of measured light ($I_2$) is dependent on the intensity of Raman scattering ($R_0$), the intensity of Fluorescence ($F_0$), the first interrogation volume ($A_1$), or the second interrogation volume ($A_2$), among other things. Due to the nature of the Raman spectroscopy, the intensity of Raman scattering ($R_0$) is often of very low intensity. In various aspects, a controller can reduce or remove an effect of Fluorescence or absorption on the measured signal, thereby isolating or improving the Raman signal ($R_0$).

6. Fluorescence

A challenge in the implementation of Raman spectroscopy to obtain physiological data is the emission of fluorescence. Accordingly, if fluorescence is generated, it often overwhelms the Raman signal, effectively hiding the Raman features. Thus, in some cases, is can be advantageous to isolate the Raman signal.

Figure 5:
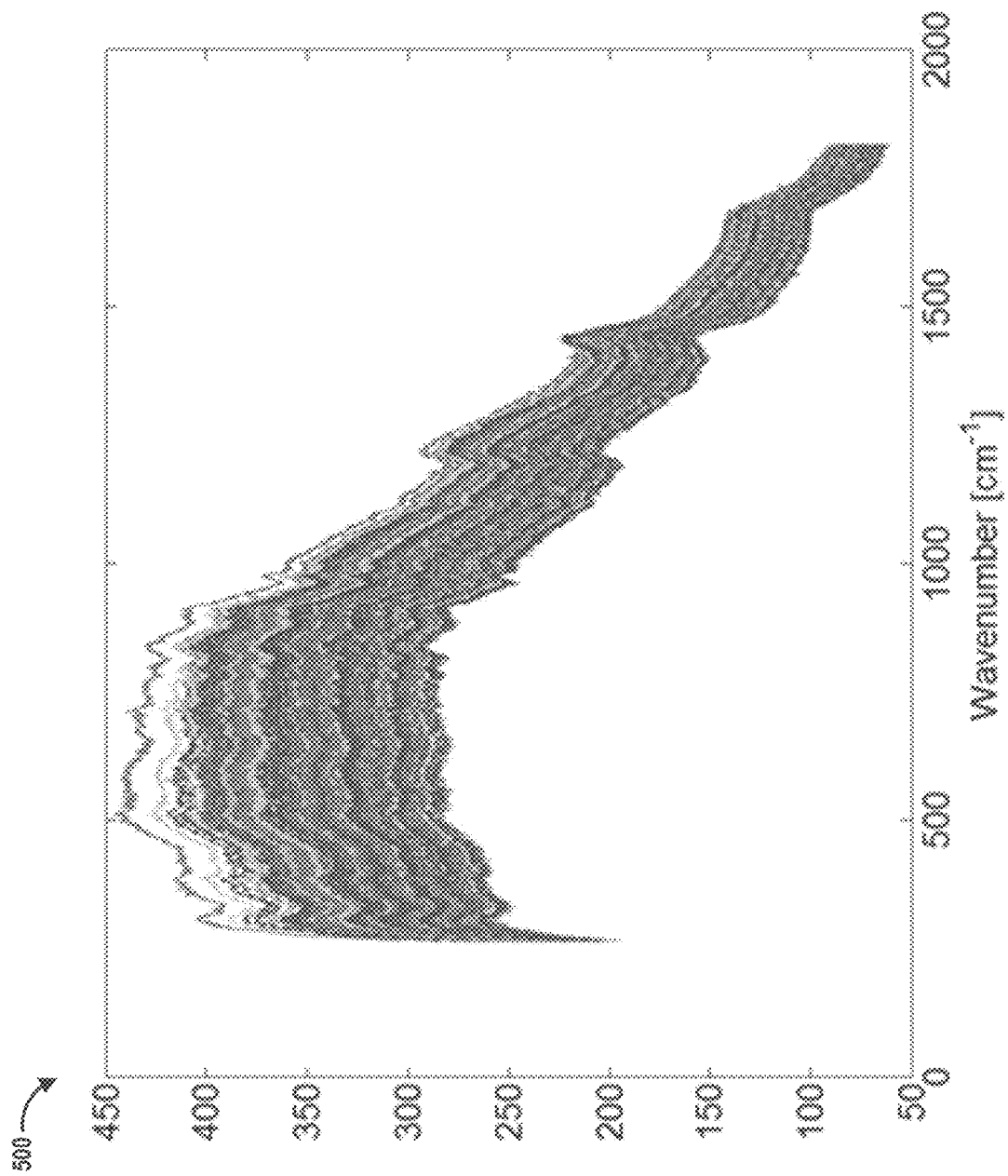
FIG. 5 shows a graph illustrating various example light intensity signals acquired at a patient's wrist.

FIG. 5 shows a graph 500 illustrating various example light intensity signals acquired at a patient's wrist. In this example, the y-axis corresponds to arbitrary intensity units, while the x-axis corresponds to a wavenumber shift (in $cm^{-1}$). Because the Raman signal is dependent on the excitation wavelength, it can be convenient to use wavenumber to indicate the change of wavelength compared to excitation wavelength. Wavelength change is also photo energy change that is often described by wavenumber change in the frequency domain, because wavenumber is used to describe wavelength in the frequency domain. Wavelength can convert to wavenumbers by dividing one centimeter by wavelength.

As described herein, the light intensity signal acquired from a Raman spectrometer is influenced by the emission of florescence. For example, fluorescence is often much more intense than Raman scattering, and fluorescence can overwhelm or mask a Raman measurement in the light intensity signal. This can be seen in each of the signals of the graph 500. For example, the overall shape of each signal of the graph 500 is attributable to the fluorescence, while the subtle oscillations of each signal are attributable to Raman. Because the fluorescence tends to mask the Raman spectrum, it can be desirable to remove or reduce an effect of the fluorescence on the light intensity signal.

Various techniques for removing or reducing an effect of the fluorescence on the light intensity signal are known, including, but not limited to, confocal configuration, photobleaching, chemical bleaching, deployment of laser excitation at longer wavelengths, filtering with respect to pixel frequency (or wavenumber frequency), signal decomposition by various forms of component subtraction from a priori information, photobleaching curve fitting to subtract away an approximated fluorescence signal, frequency offset Raman methods, spatial offset Raman methods, or the like.

For example, irradiating tissue with intense laser light for a long period of time (sometimes referred to as photobleaching) can reduce a level of fluorescence emission in the light intensity signal, thus increasing the signal to noise (S/N) ratio of a Raman measurement. That is because the fluorescence signal of skin will decrease over time (experiencing an exponential decay) as a source is continually shining, while a Raman signal will not change. By looking at the exponential decay (in time) of photobleaching, the system can obtain a fluorescence approximation by curve fitting.

As another example, a system can use a first excitation wavelength to characterize the fluorescence, and then can subtract the fluorescence from a signal of a second excitation wavelength to isolate the Raman. For example, a location of peaks of the fluorescence emission are independent of excitation wavelength, whereas a location of peaks and compactness of emission of Raman spectra are dependent on excitation wavelength. Using this information, the system can remove or reduce an effect of fluorescence emission in the light intensity signal. Fluorescence can also be removed by taking sequential measurements of the tissue over time.

For example, the fluorescence signal can be isolated by the change of the measured spectrum overtime.

Figure 6:
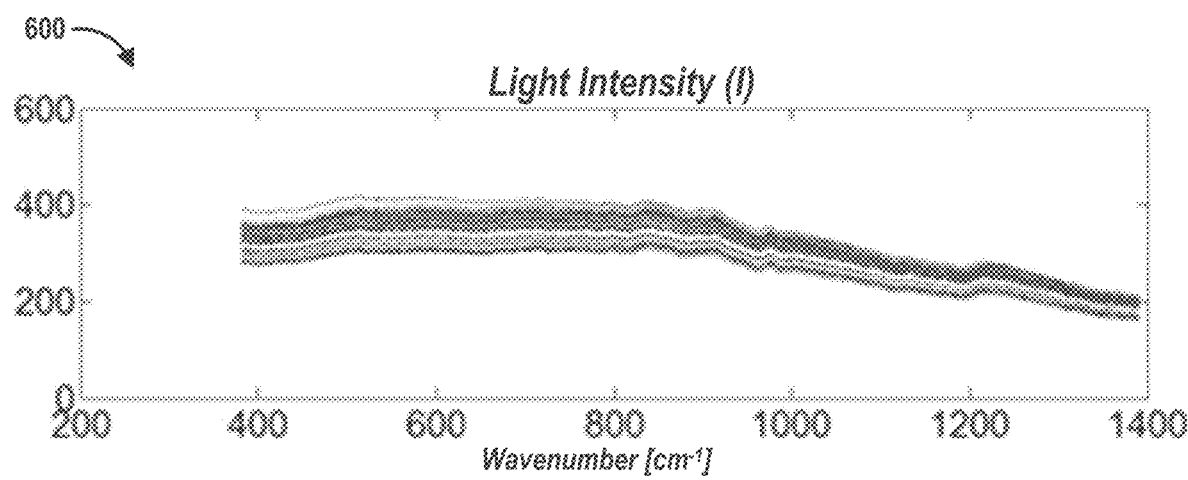
FIG. 6 illustrates a scaled view of the various example light intensity signals of FIG. 5

FIG. 6 illustrates a scaled view of the various example light intensity signals of FIG. 5. As described herein with respect to FIG. 5, the light intensity signals are influenced by, among other things, fluorescence, Raman scattering, and tissue absorption. For example, the light intensity signals can include a significant fluorescence baseline.

Figure 7:
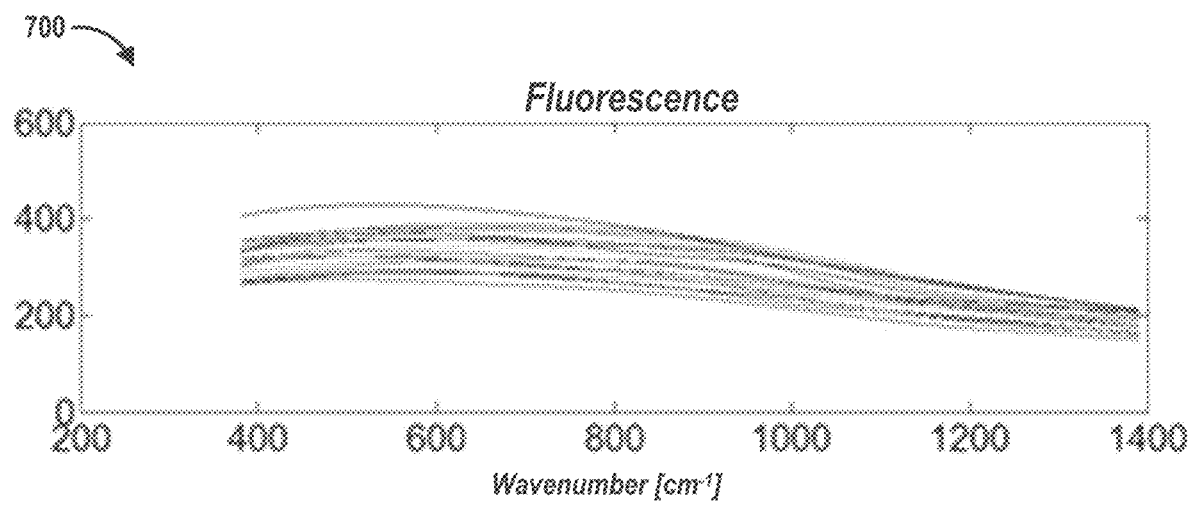
FIG. 7 illustrates an approximation of an intensity of the fluorescence portion of the light intensity signals of FIG. 6.

FIG. 7 illustrates an approximation of an intensity of the fluorescence portion 700 of the light intensity signals 600 of FIG. 6. This approximation of fluorescence can be determined using various techniques, such as those described herein. The system can utilize photobleaching curve fitting to subtract away an approximated fluorescence signal. For example, over time, the Raman signal ($R_0$) will remain constant while the fluorescence $F_0$ will experience an exponential decay. By looking at the exponential decay (in time) of photobleaching, the system can obtain a fluorescence approximation by curve fitting.

Figure 8:
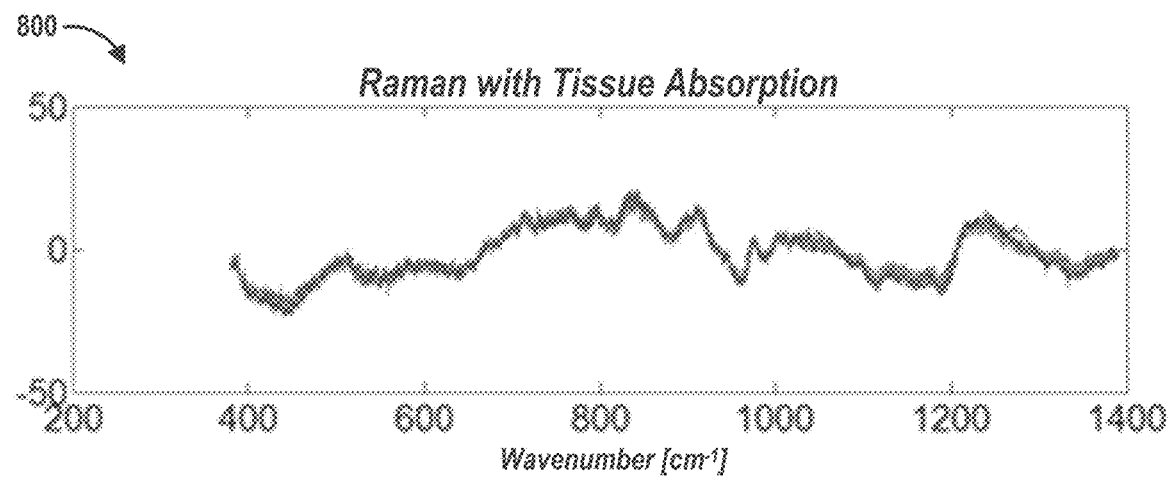
FIG. 8 illustrates an approximation of an intensity of the isolated Raman with tissue absorption signals of FIG. 6.

FIG. 8 illustrates an approximation of an intensity of the isolated Raman with tissue absorption signals of FIG. 6. In this example, at least some of the effect of florescence (for example, illustrated in FIG. 7) has been removed or reduced. Accordingly, the graph 600 of FIG. 6 can be approximately equal to the Raman and tissue absorption portion (for example, the $\Sigma(R_0 e^{-A_2})$ portion of Equation 6) of the light intensity signals of FIG. 5. As can be seen from a comparison of FIGS. 7 and 9, the presence of fluorescence in the light intensity signals 600 can mask many of the Raman features, such as the peaks, valleys, amplitude, compaction, and the like. By removing or reducing the presence of fluorescence in the light intensity signals 600, the system can isolate the Raman signal.

Figure 9:
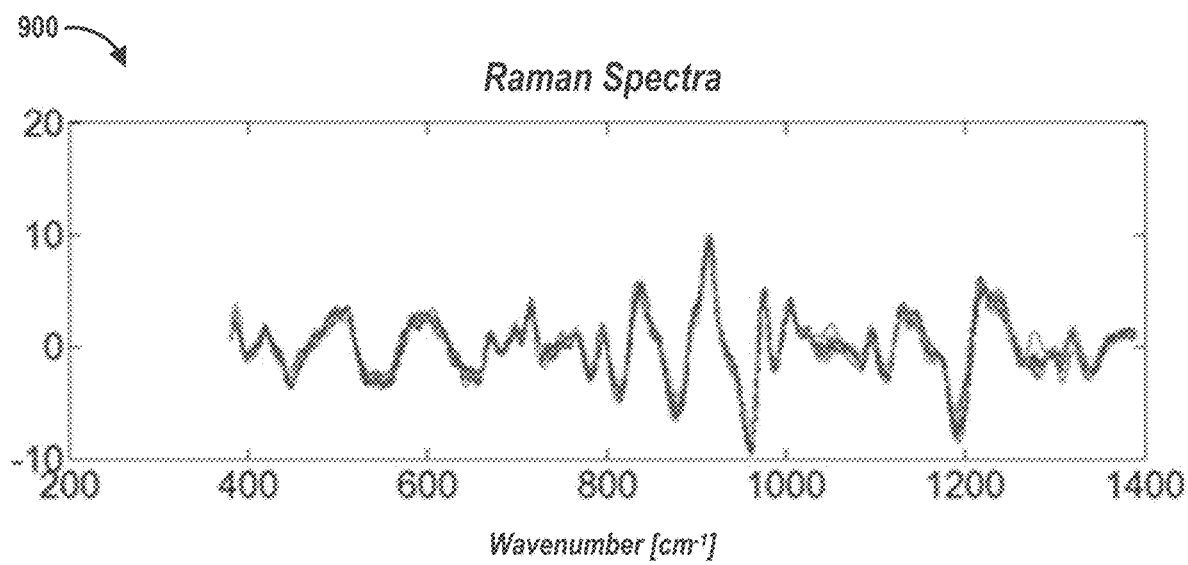
FIG. 9 illustrates an approximation of an intensity of the isolated Raman with tissue absorption signals of FIG. 6.

FIG. 9 illustrates an approximation of an intensity of the isolated Raman with tissue absorption signals of FIG. 6. In this example, the signal of graph 800 of FIG. 8 has been filtered to reduce or remove at least some of a remaining effect of florescence. For example, the system can filter the signal using a band pass or high pass filter.

7. Absorption

Another challenge in the implementation of Raman spectroscopy to obtain physiological data is the attenuation of the signal due to absorption. In some cases, the Raman signal can be isolated or improved by reducing or removing an effect of absorption on the measured signal. For example, sensor data from one or more sensors, such as a near infrared (NIR), reflectance, transmittance, or pulse oximetry sensor, can be utilized to determine absorption, which can be removed from one or more other measurements, such as a Raman measurement.

An effect of the tissue absorption (for example, the $e^{-A}$ portion of Equation 6) may be removed or reduced in various ways. For example, the absorption data, transmission data, reflectance data, or the like may be determined using data from one or more sensors, such as, but not limited to, a near infrared (NIR), reflectance, transmittance, or pulse oximetry sensor. Based on the sensor data, a processor can further process the signal (for example, signal 800 or 900) to reduce or subtract an effect of the attenuation of the signal due to absorption.

8. Bioelectrical Impedance (Bioimpedance)

Impedance can be characterized as a physical variable describing the resistance characteristics acting on an electric current. Bioelectrical impedance is based on the principle that tissues or fluids of a patient have different impedances, that is, opposition to the flow of the electric current, which in turn may be dependent on variables such as water and electrolyte content, to name a few. Using a bioelectrical impedance, analysis can be performed to examine electrical, capacitive, or resistive characteristics of tissue to provide information on a noninvasive basis.

Mathematically, bioelectrical impedance can be represented as a complex number including a real component (resistance) and an imaginary dimension (reactance). For example, the bioelectrical impedance can be calculated using the following equation below:

$$Z=R+jX=|Z|e^{j\theta} \quad \text{(Equation 6)}$$

where R is resistance, X is reactance, |Z| is amplitude, and $\theta$ is phase.

A number of physiological characteristics or parameters can be calculated or estimated using determined bioelectrical impedance characteristics, such as water content, body cell mass (BCM), extra cellular mass (ECM), extracellular fluid (ECF), extracellular water (ECW), fat-free mass (FFM), fat mass (FM), total body water (TBW), electrolyte composition, cell membrane mass, cell membrane function and the like.

Biological tissues can have complex electrical impedance which is dependent, for instance, on the frequency of the electrical applied field or tissue cellular structure. Therefore, the electrical impedance of tissue is a function of its structure and it can be used to differentiate or determine characteristics of one or more layers to tissue.

The system can include a bioimpedance sensor configured to apply an electrical signal to the tissue, which can include one or more of various voltages, currents, frequencies (for example, 1 kHz to 2.5 GHz), or fields. In some cases, the path length of the signal can vary based on the applied electrical signal. For example, low frequency signals may primarily reflect the extracellular environment, while high frequency signals may reflect both the intra- and extracellular environment. In addition, the bioimpedance sensor can be configured to measure characteristics of the applied electrical signal as it passes (or after it has passed) through tissue. For example, the bioimpedance sensor can measure a voltage, current, frequency, magnetic field, etc., which can be indicative of a voltage difference across tissue or a biological impedance of a tissue, to name a few.

Figure 10:
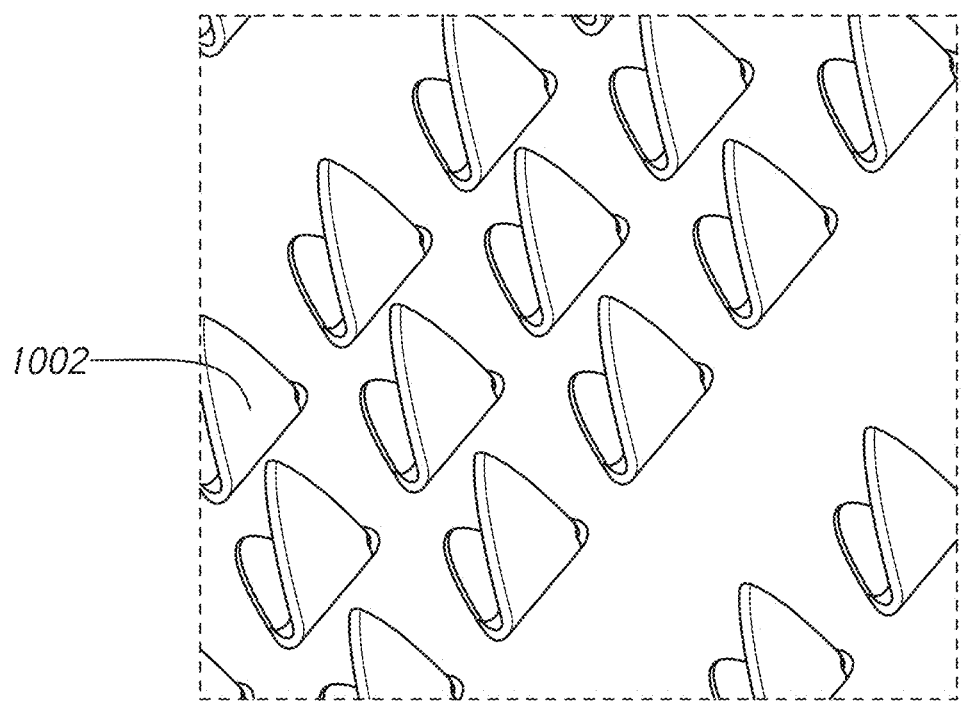
FIG. 10 illustrates example micro-invasive elements of a bioimpedance sensor.

One or more properties of skin may disturb or disrupt bioimpedance measurements. For example, the stratum corneum can limit bioimpedance measurements. Accordingly, as illustrated in FIG. 10, the bioimpedance sensor can include a micro-invasive element 1002 that is configured to penetrate the stratum corneum layer. For example, the bioimpedance sensor can include spikes or other elements that penetrate approximately 10-20 μm deep.

Figure 11:
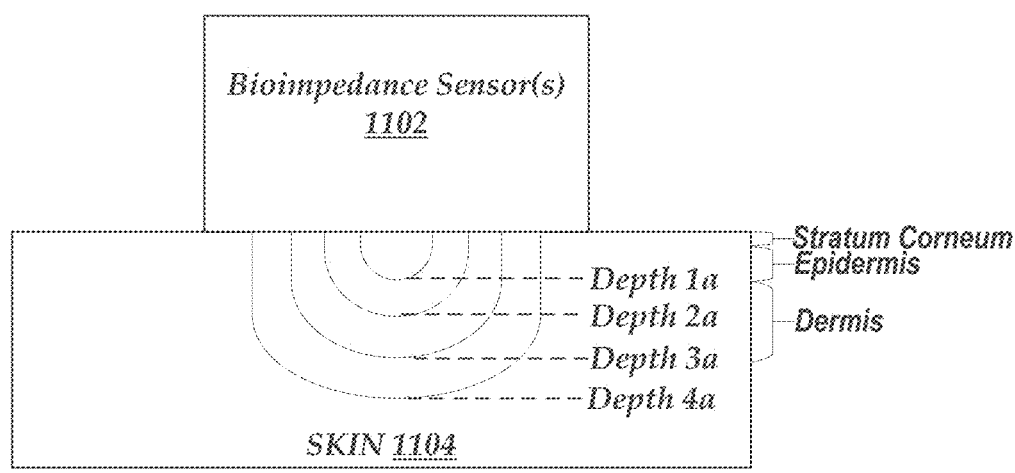
FIG. 11 illustrates an example bioimpedance sensor.

FIG. 11 illustrates an example bioimpedance sensor 1102. The sensor 1102 can include multiple channels of spiked regions configured to penetrate the skin. As shown, spacing between the channels can allow for shallow and deep penetration, such that the bioimpedance sensor 1102 can measure impedance at various depths, such as Depths 1a, 2a, 3a, or 4a.

Using information from the bioelectric sensor(s) 1102, the system 200 can determine information about the tissue geometry. For example, based on bioelectric sensor data, the system can determine a cellular structure of the tissue, which may affect various physiological parameters, such as path length or absorption. In addition, based on bioelectric sensor data, the system can determine information related to hydration of the skin or tissue. For example, water content can be directly related to skin thickness. As described herein, in some cases, the system can select a focal depth of the Raman spectrometer based at least in part on tissue geometry data.

9. Tissue Dielectric Constant

In addition or alternatively to bioimpedance or OCT, the system can utilize one or more tissue dielectric constant sensors to determine various tissue geometries or tissue information, including, but not limited to a dielectric constant of tissue. For example, the system 200 can include a plurality of probes for different measuring depths, such as 0.5 mm, 1.5 mm, 2.5 mm, and 5 mm effective depths, and the system can determine a dielectric value at each of the different depths. In addition or alternatively, the system 200 can include one or more probes that are each configured to measure at different depths, such as 0.5 mm, 1.5 mm, 2.5 mm, and 5 mm effective depths, and the system can determine a dielectric value at each of the different depths. The dielectric value can correlate with water content, which can be tied to tissue structure.

Accordingly, the tissue dielectric constant can provide information which can be combined with other sensor information (for example, OCT, bioimpedance, reflectance or transmission measurements, Raman measurements) to determine more accurate physiological measurements, such as blood glucose levels. For example, the bioimpedance or tissue dielectric constant data can provide information that correlates with local tissue hydration, or can provide information about different skin layers or cellular structure information. Furthermore, bioimpedance or tissue dielectric constant sensors can provide real-time measurements that can provide information about physiological "noise" within the tissue, which can be used to calibrate other measurements or calculations. As described herein, in some cases, the system can select a focal depth of the Raman spectrometer based at least in part on tissue geometry data.

B. EXAMPLE DATA HARMONIZATION

Figure 12A:
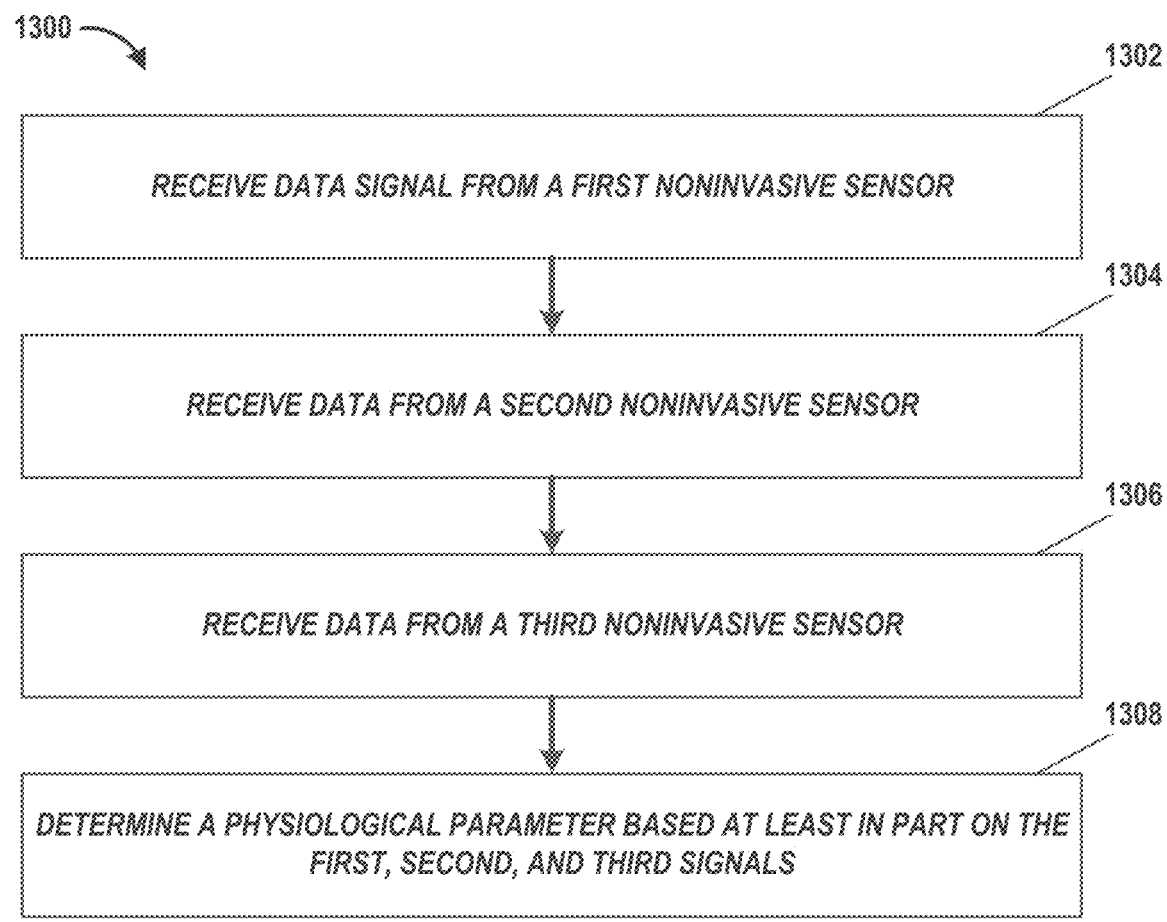
FIG. 12A illustrates a flow diagram illustrative of an example routine for harmonizing data from a plurality of non-invasive sensors.

FIG. 12A illustrates a flow diagram illustrative of an example routine for harmonizing data from a plurality of non-invasive sensors. One skilled in the relevant art will appreciate that the elements outlined for routine 1300 may be implemented by one or many computing devices/components, such as in hardware, with a front end component, with a sensor interface, or with a processor, such as one or more processors housed in a patient monitor, one or more remote processors, one or more processors housed in the sensors, etc. Accordingly, although routine 1300 has been logically associated as being generally performed by a processor, the following illustrative embodiments should not be construed as limiting.

At block 1302, a processor can receive data from one or more first noninvasive sensors. The one or more first noninvasive sensors can include an optical coherence tomography (OCT) sensor. As described herein, the OCT sensor can provide a non-invasive method for identifying one or more characteristics of a tissue's structure. The data received by the processor from the OCT sensor can include OCT data, which can be referred to as tissue geometry data.

In addition or alternatively, the one or more first noninvasive sensors can include a bioimpedance sensor or a tissue dielectric constant sensor. As described herein, the bioimpedance sensor or tissue dielectric constant sensor can provide a non-invasive method for identifying one or more characteristics of a tissue's structure. The data received by the processor from the bioimpedance sensor or tissue dielectric constant sensor can include bioimpedance data, which can include tissue geometry data, hydration data, or the like.

At block 1304, a processor can receive data from one or more second noninvasive sensors. The one or more second noninvasive sensors can include a pulse oximetry sensor, such as a reflectance or transmission sensor. As described herein, the pulse oximetry sensor can provide a non-invasive method for identifying or more of various physiological parameters.

At block 1306, a processor can receive data from one or more third noninvasive sensors. The one or more second noninvasive sensors can include a Raman spectrometer. As described herein, the Raman spectrometer can provide a non-invasive method for identifying or more of various physiological parameters.

At block 1308, the processor can harmonize the data received from two or more of the non-invasive sensors. By harmonizing the data from two or more non-invasive sensors, the system may be able to compensate for circumstances that might otherwise result in inaccurate or unreliable data. For example, using skin geometry information (for example, skin thickness), the processor can weight or prioritize longer or shorter path length detectors. In addition or alternatively, the various sensor data, such as skin geometry information, can allow the processor compensate for sensor or probe placement. For example, a location, coupling, or pressure can be compensated by the processor by adjusting path length, which can be determined from the various sensor data, such as skin geometry information. Similarly, the processor can utilize the various sensor data, such as skin geometry information, to detect drift or motion at the tissue site.

As a non-limiting example, the data received at block 1302 from the OCT sensor, the bioelectrical impedance sensor, or the tissue dielectric constant sensor can include tissue geometry information. Based at least in part on the tissue geometry data, the processor can determine a path length corresponding to a tissue site interrogated by the one or more first noninvasive sensors. In some cases, the determined path length can be utilized with the pulse oximetry sensor to determine a concentration of an analyte, such as blood glucose. For example, based on the data received at block 1304 from the one or more second noninvasive sensors, the processor can determine an absorbance corresponding to a tissue site interrogated by the one or more second noninvasive sensors. Using one or more relationships derived from Beer's law (Equation 1), the concentration, c, of one or more analytes can be determined using the absorbance, A, determined from the pulse oximetry sensor data, and the path length, b, determined from the tissue geometry data.

As another non-limiting example, the processor can utilize the tissue geometry data to select a focal depth or focal length, wavelength, refractive index, or other parameter associated with the Raman spectrometer. For example, the tissue geometry data can provide an indication of a particular location of tissue, such as the capillary beds. The processor can select a focal depth or focal length of the Raman spectrometer such that the Raman spectrometer can focus on this particular location. As a result, the processor can determine a more accurate indication of glucose concentration from the Raman signal.

As another non-limiting example, the processor can utilize the pulse oximetry data to filter data received from a Raman Spectrometer to isolate a Raman Spectra. For example, as described herein, a direct measurement of glucose can be determined based on features of the isolated Raman signal. Using the pulse oximetry data, the processor can filter out an effect of absorbance on the Raman Spectra.

Additionally or alternatively, the processor can utilize the measurement result from the pulse oximetry data to better understand the components in the tissue that produce the Raman Spectra.

In addition or alternatively, using the various sensor data, the processor can create calibrations for one or more individuals. For example, although skin geometry may vary between individuals, one or more groups of individuals may have similar skin geometries, which can allow for more accurate physiological parameter estimations of for individuals in those groups. For example, using the various sensor data, such as the skin geometry, Raman, or NIR data, the processor can determine calibrations for different groups, such as different skin populations, different ages, or the like.

The various blocks of process 1300 described herein can be implemented in a variety of orders, and that the system can implement one or more of the blocks concurrently or change the order, as desired. For example, the system 100 can concurrently receive any of the sensor data, or receive the sensor data in any order. Similarly, the system can make one or more calculations or determinations in any order, such as before or after receiving data from one or more sensors.

It will be understood that any of the first, second, or third sensors can interrogate the same or a different tissue site. Furthermore, it will be understood that fewer, more, or different blocks can be used as part of the routine 1300. Likewise, fewer, more, or different sensors can be used by the system. For example, the routine 1300 can include blocks for receiving data associated with additional non-invasive sensors or determining various other physiological parameters. Furthermore, the routine 1300 can include causing a display to display one or more of various indications of the any other the sensor data, calculations, or determinations.

Figure 12B:
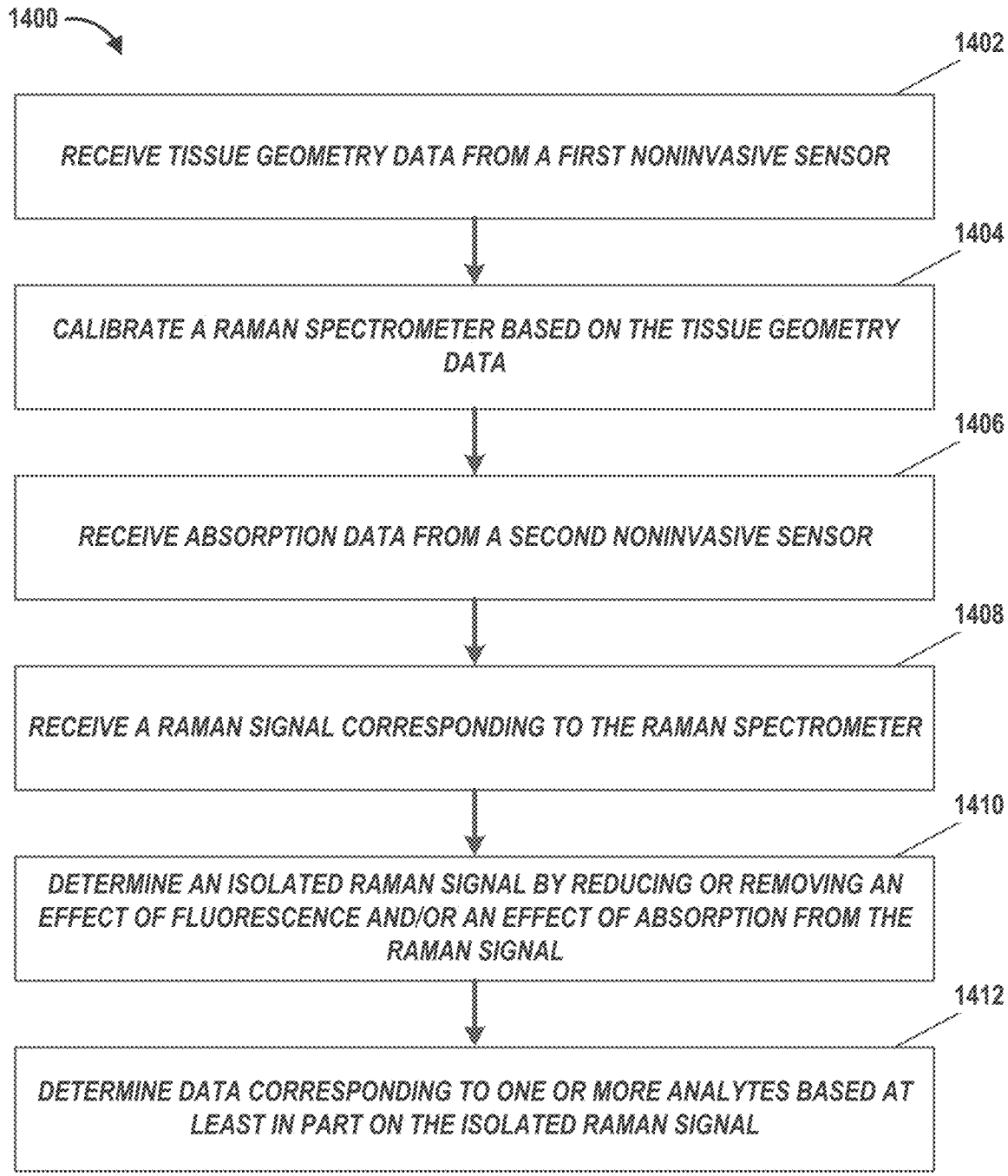
FIG. 12B illustrates a flow diagram illustrative of an example routine for harmonizing data from a plurality of non-invasive sensors.

FIG. 12B illustrates a flow diagram illustrative of an example routine for harmonizing data from a plurality of non-invasive sensors. One skilled in the relevant art will appreciate that the elements outlined for routine 1400 may be implemented by one or many computing devices/components, such as in hardware, with a front end component, with a sensor interface, or with a processor, such as one or more processors housed in a patient monitor, one or more remote processors, one or more processors housed in the sensors, etc. Accordingly, although routine 1400 has been logically associated as being generally performed by a processor, the following illustrative embodiments should not be construed as limiting.

At block 1402, the process 1400 can receive tissue geometry data from a first noninvasive sensor. As described herein, the first non-invasive sensor can include a combination of one or more of an OCT sensor, a bioimpedance sensor, a tissue dielectric constant sensor, or any other sensor configured to measure or determine tissue geometry data. The tissue geometry data can include various information corresponding to the skin, fluids, bones, or the like. For example, tissue geometry data can include, but is not limited to, a thickness of one or more skin layers (for example, the epidermis, the dermoepidermal junction, the papillary dermis, the reticular dermis, etc.), cellular structure information, a water content of a portion of the tissue, etc.

At block 1404, the process 1400 can calibrate a Raman Spectrometer based at least in part on the tissue geometry data received at block 1402. For example, the tissue geometry data can provide insight about the tissue site, which can allow the process 1400 to optimize one or more settings of the Raman spectrometer. For example, based at least in part on the tissue geometry data, the process 1400 can select a focal depth or focal length, wavelength, refractive index, or other parameter associated with the Raman spectrometer. By adjusting one or more settings or positioning of the Raman spectrometer based on the tissue geometry data, the process can enhance a signal received by the Raman spectrometer. For example, the new settings can increase the collection efficiency, the resolution, the signal-to-noise ratio, or the like of the Raman signal.

At block 1406, the process 1400 can receive absorption, transmission, reflectance, or other data from a second non-invasive sensor. As described herein, the second non-invasive sensor can include one or more of a pulse oximetry sensor, a reflectance sensor, a transmittance sensor, or another sensor from which absorption, transmission, reflectance, or other tissue related data can be determined. In some cases, the second noninvasive sensor can include a light source configured to emit light and a detector and configured to detect light. Depending on the type of sensors, the detector can be configured to detect light after having it has passed through, reflected, refracted, or scattered at a tissue site of a patient. In some cases, the tissue site corresponding to the second sensor (for example, the tissue site at which the second sensor takes a measurement) is the same tissue site (or within a close proximity) as the tissue site of the second sensor. For example, the first and second sensors can be configured to interrogate the tissue site at different periods of time. However, in some cases, the first and second sensors can be configured to interrogate different tissue sites.

At 1408, the process 1400 can receive a Raman signal corresponding to the Raman spectrometer. As described herein, the light intensity signal acquired from a Raman spectrometer may be influenced by the emission of fluorescence.

At block 1410, the process 1400 can determine an isolated Raman signal by reducing or removing an effect of fluorescence or an effect of absorption from the Raman signal received at block 1408. As described herein, fluorescence can overwhelm or mask a Raman measurement in the light intensity signal. As such, the process 1400 can use one or more techniques described herein to reduce or remove an effect of the fluorescence on the Raman signal. In addition or alternatively, the process 1400 can reduce or remove an effect of absorption on the Raman signal. For example, using the absorption data acquired at block 1406, the process 1400 can filter, subtract, reduce, or remove an effect of absorption on the Raman signal. By reducing or removing an effect of fluorescence or an effect of absorption from the Raman signal, the process 1400 can determine an isolated (or semi-isolated) Raman signal.

At block 1412, the process 1400 can determine data corresponding to one or more analytes based at least in part on the isolated Raman signal. For example, features of the Raman spectra (such as peaks, valleys, concentrations, etc.) can corresponds to analytes such as glucose. Accordingly, using the isolated or semi-isolated Raman signal, the system can identify physiological data, such as information regarding a patient's blood glucose level. Thus, the process 1400 can harmonize data from various non-invasive sensors to non-invasively determine a patient's blood glucose level, or other analytes.

It will be understood that the various blocks of process 1400 described herein can be implemented in a variety of orders, and that the system can implement one or more of the blocks concurrently or change the order, as desired. Furthermore, it will be understood that fewer, more, or different blocks can be used as part of the routine 1400. For example, fewer, more, or different sensors can be used by the system. Furthermore, the routine 1400 can include blocks for receiving data associated with additional non-invasive sensors or determining various other physiological parameters. Furthermore, the routine 1400 can include displaying one or more of various indications of the any other the sensor data, calculations, or determinations.

C. EXAMPLE SIGNAL PROCESSING

Figure 13:
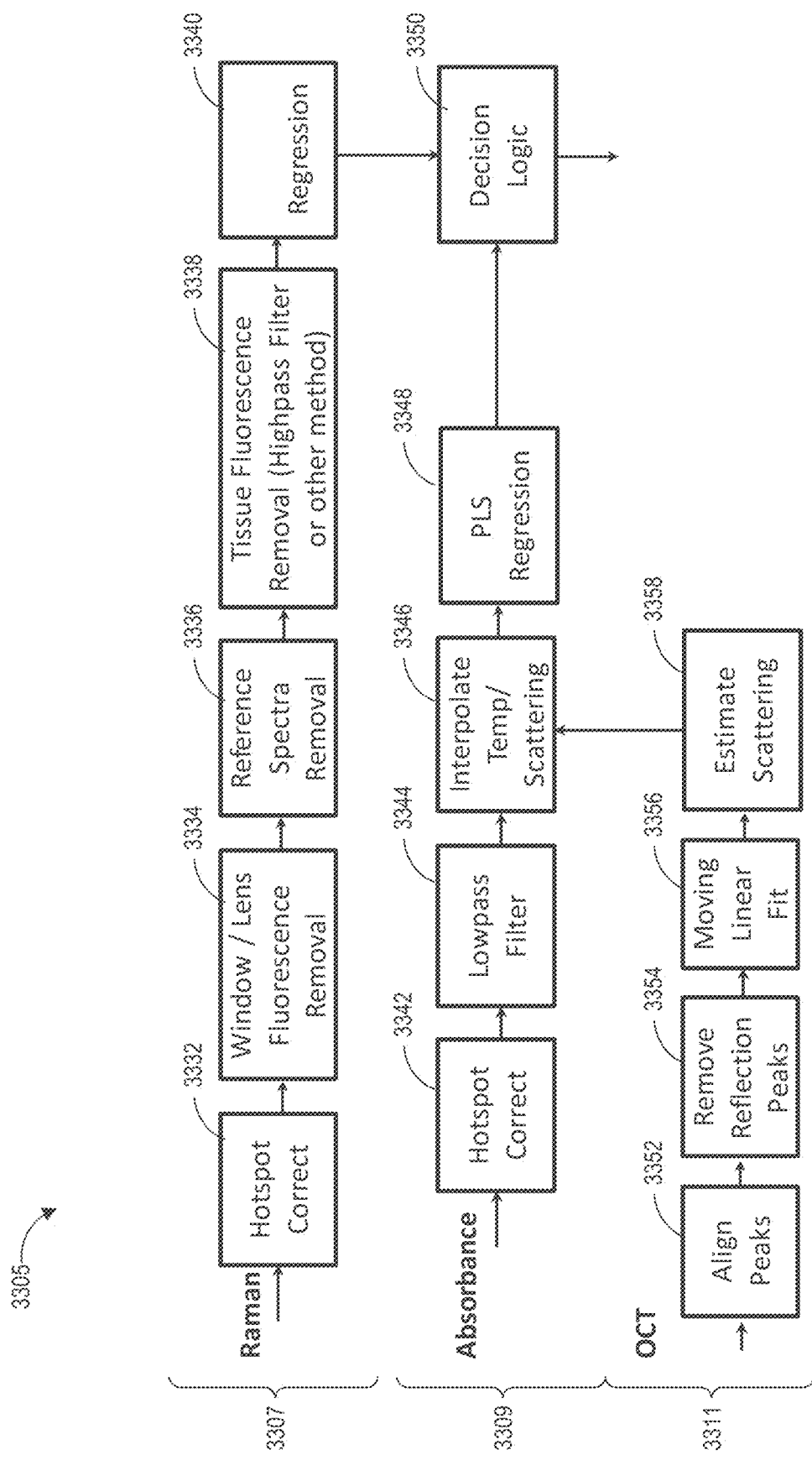
FIG. 13 illustrates a block diagram of signal processing with multiple measurements.

FIG. 13 illustrates example signal processing 3305 that may be part of a process to harmonize physiological measurements made by the system 100. For example, as illustrated in FIG. 13, a system 100 can include Raman measurements, absorbance measurements, and OCT measurements. Signal processing 3305 can include Raman processing blocks 3307, absorbance processing blocks 3309, and OCT processing blocks 3311.

Raman processing blocks 3307 can include one or more blocks for processing or extracting a Raman signal from Raman measurements. For example, Raman processing blocks 3307 can include a hotspot correction block 3332, a window fluorescence removal block 3334, a reference spectra removal block 3336, a tissue fluorescence removal block 3338, and a regression block 3340. The input of the Raman processing blocks 3307 can include a Raman signal.

In some examples, a hotspot correction block 3332 can include one or more processes for correcting or accounting for a peak in intensity or hotspot of an illumination profile in a Raman signal that may be the result of instrument geometry or another source.

A window fluorescence removal block 3334 can include one or more processes for removing or reducing fluorescence in a Raman measurement that may have occurred as a result of excitation of one or more instrument components, such as a window or lens in the system 100.

A reference spectra removal block 3336 can include one or more processes for removing portions of the Raman measurement that correspond to reference components of the tissue sample. Reference spectra may include a priori Raman spectra of individual or aggregate tissue constituents, which can represent a constant or varying background of the signal.

A tissue fluorescence removal block 3338 can include one or more processes for removing or reducing fluorescence in a Raman measurement that may have occurred as a result of fluorescence excitation at the tissue site being measured.

A regression block 3340 can include one or more processes for analyzing a Raman measurement to produce a Raman signal, such as a partial least squares regression. The Raman signal can include a Raman spectra with peaks associated with one or more components of the tissue sample, such as blood glucose. Additionally or alternatively, the Raman signal can include information associated with the Raman measurement, such as an analyte concentration determined based on a Raman spectra.

Absorbance processing blocks 3309 can include one or more blocks for processing or extracting an absorbance signal from absorbance measurements. For example, absorbance processing blocks 3309 can include a hotspot correction block 3342, a filter block 3344, an interpolation block 3346, and a regression block 3348. The input of the absorbance processing blocks 3309 can include an absorbance signal.

In some examples, a hotspot correction block 3342 can include one or more processes for correcting or accounting for a peak in intensity or hotspot of an illumination profile in an absorbance signal that may be the result of instrument geometry or other source.

A filter block 3344 can include one or more filter processes for filtering an absorbance measurement. For example, a filter block 3344 can apply a low pass filter (or other smoothing technique) to help reduce the noise of the signal that may result from adjacent pixels being close in wavelength. The closeness in wavelength can result in adjacent pixels having similar optical properties and little high frequency information. Thus, advantageously, a filter or other smoothing technique can help reduce noise.

An interpolation block 3346 of the absorbance processing blocks 3309 may use an OCT signal, such as described below, to interpolate data associated with the absorbance measurement or tissue site. A regression block 3340 can include one or more processes for analyzing the interpolated data from block 3346 to produce an absorbance signal, such as a partial least squares regression.

OCT processing blocks 3311 can include one or more blocks for processing or extracting an OCT signal from OCT measurements. For example, OCT processing blocks can include a peak alignment block 3352, a reflection peak removal block 3354, a moving linear fit block 3356, and a scattering estimate block 3358. The output of OCT processing blocks 3311 can include an OCT signal. A peak alignment block 3352 can be used to compensate for drifts in the system, such as temperature, which would shift peaks from their expected locations. A reflection peak removal block 3354 can remove peaks generated from multiple reflection events, since the peaks of interest are from single reflections which describe the structure of the tissue. A moving linear fit block 3356 can be used to smooth the signal and extract the slope of the signal. The scattering estimate block 3358 uses the signal and its derivative to predict the scattering coefficient of the layers of the tissue.

The Raman signal or the absorbance signal may be processed by a decision logic block 3350 to determine a physiological parameter, such as an analyte concentration.

D. EXAMPLE PATIENT MONITORING SYSTEM

1. Finger Guide

Consistency in repeated measurements can be an issue when a sensor (for example, sensors 104 of FIG. 1 or sensor 204 of FIG. 2) interrogates a tissue site of a patient due to changes in positioning of the sensor with respect to the tissue site from measurement to measurement. In some cases, even small changes in positioning can result in widely varied measurements due to changes in composition of the tissue site at different positions of the sensor on the tissue site. For example, a tissue site may be a fingernail. A sensor may perform a first measurement at one position on the fingernail and a second measurement at a slightly different position on the fingernail. The slightly different position may result in a change in detected measurement due to an increased blood flow or other composition change at the second position from the first position. Described herein are systems and methods for repeatedly securing a tissue site with respect to a sensor so that repeated measurements can be performed at approximately the same tissue site location on the patient.

Figure 14A:
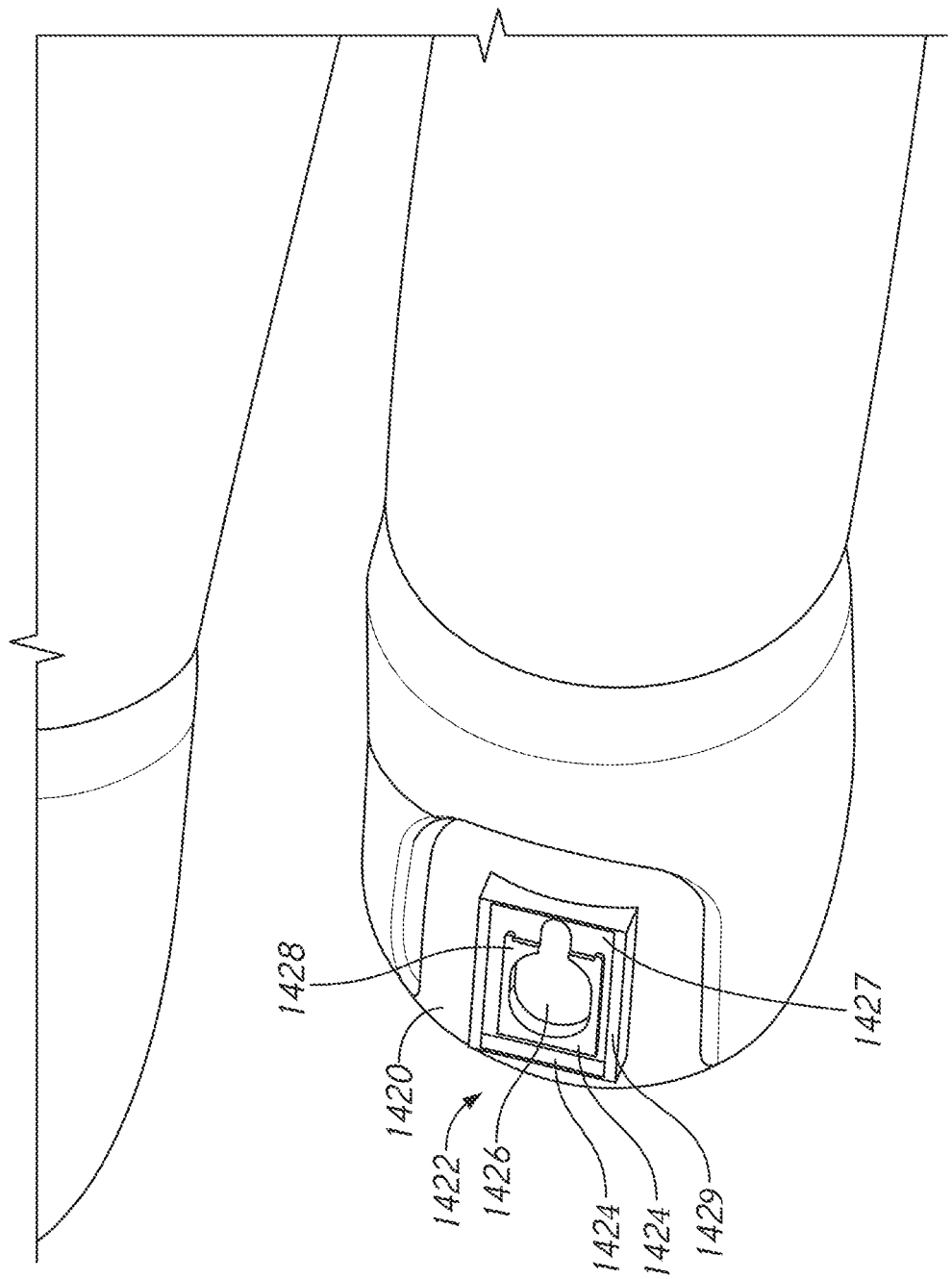
FIG. 14A illustrates an example sensor finger guide for use with a Raman and OCT sensors.
Figure 14B:
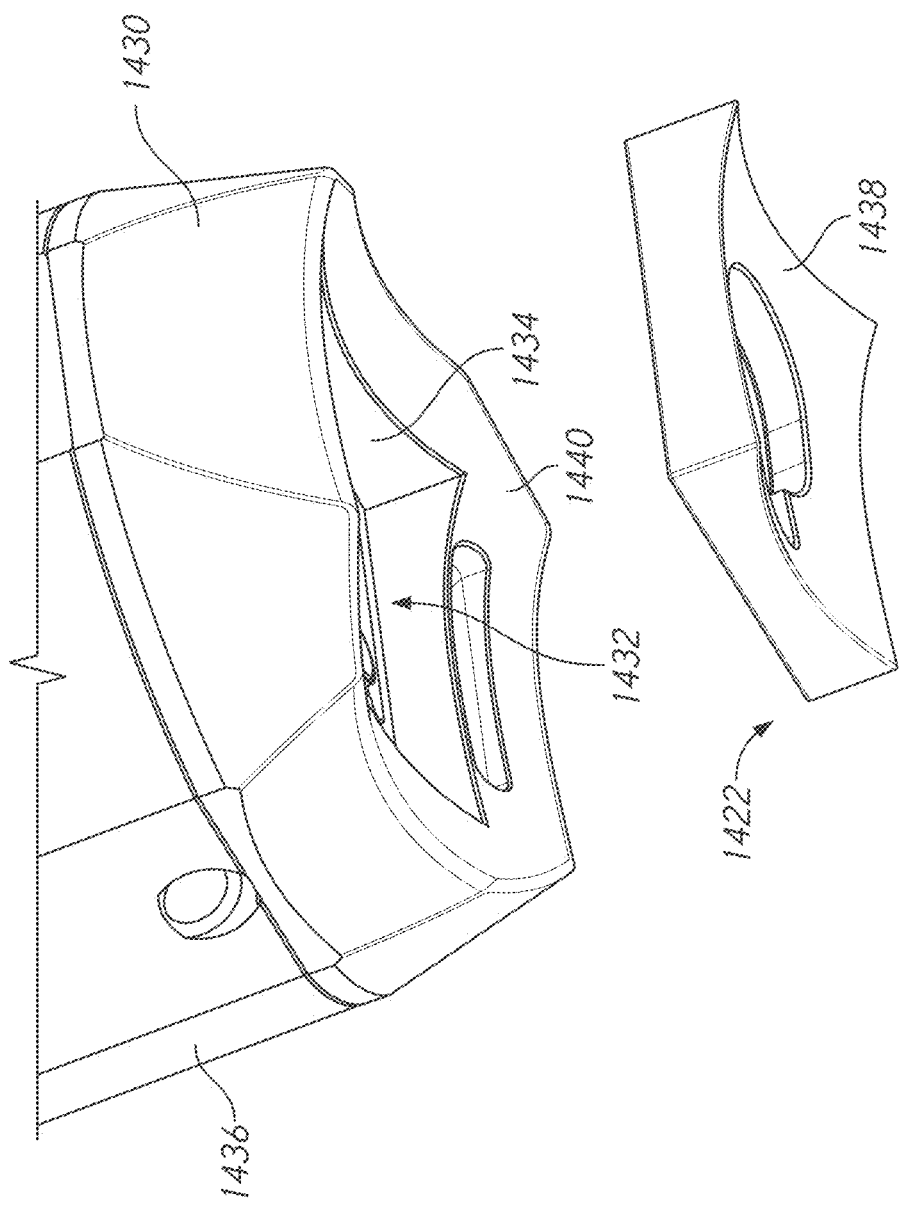
FIG. 14B illustrates how an example guide may mate with a sensor head.
Figure 14D:
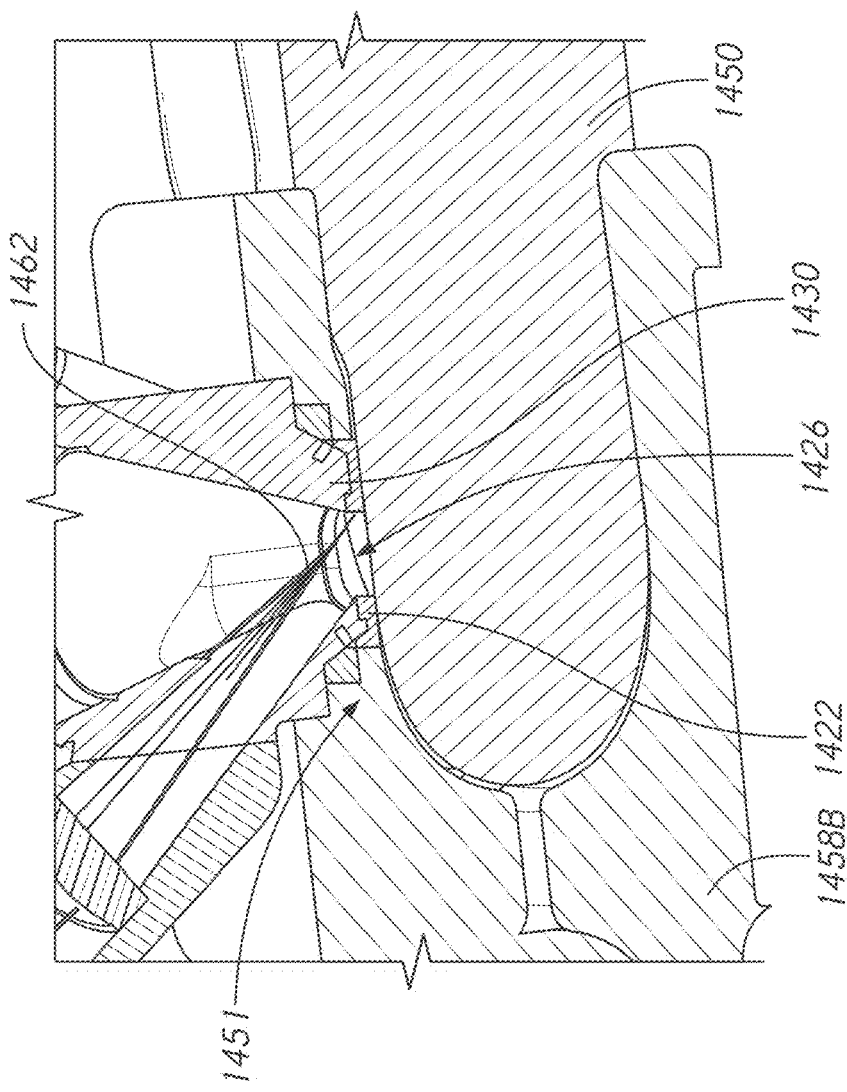
FIGS. 14C, 14D, and 14E illustrate example views of an external enclosure mechanism for mating a finger guide with a sensor head.
Figure 14C:
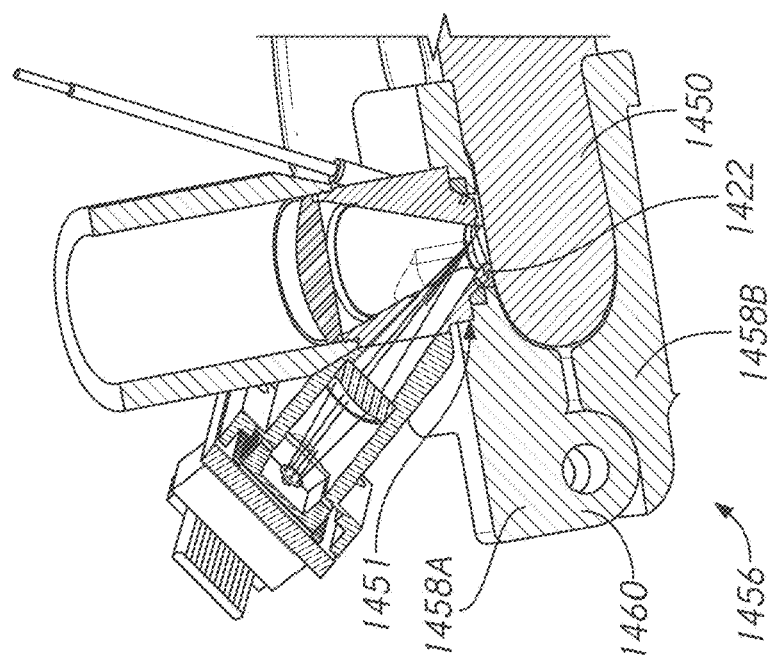
Figure 14F:
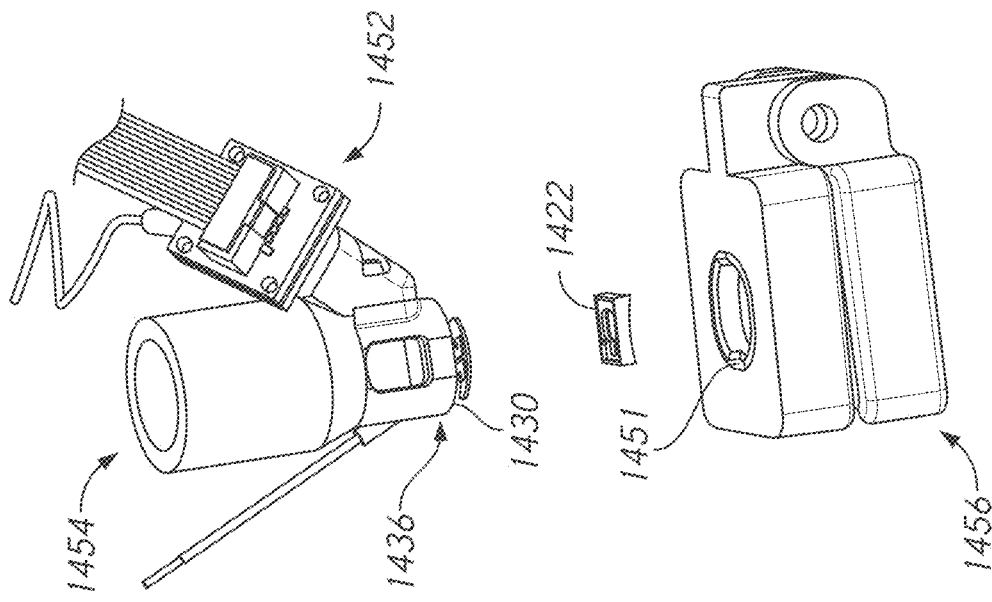
FIG. 14F illustrates an exploded view of the finger guide and sensor assembly.
Figure 14E:
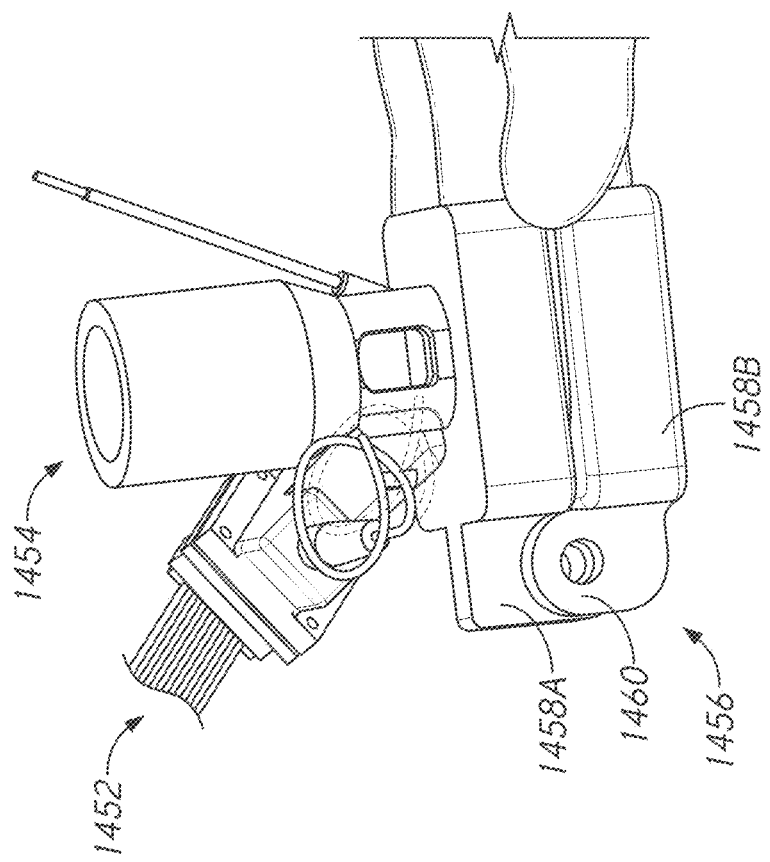
Figure 15A:
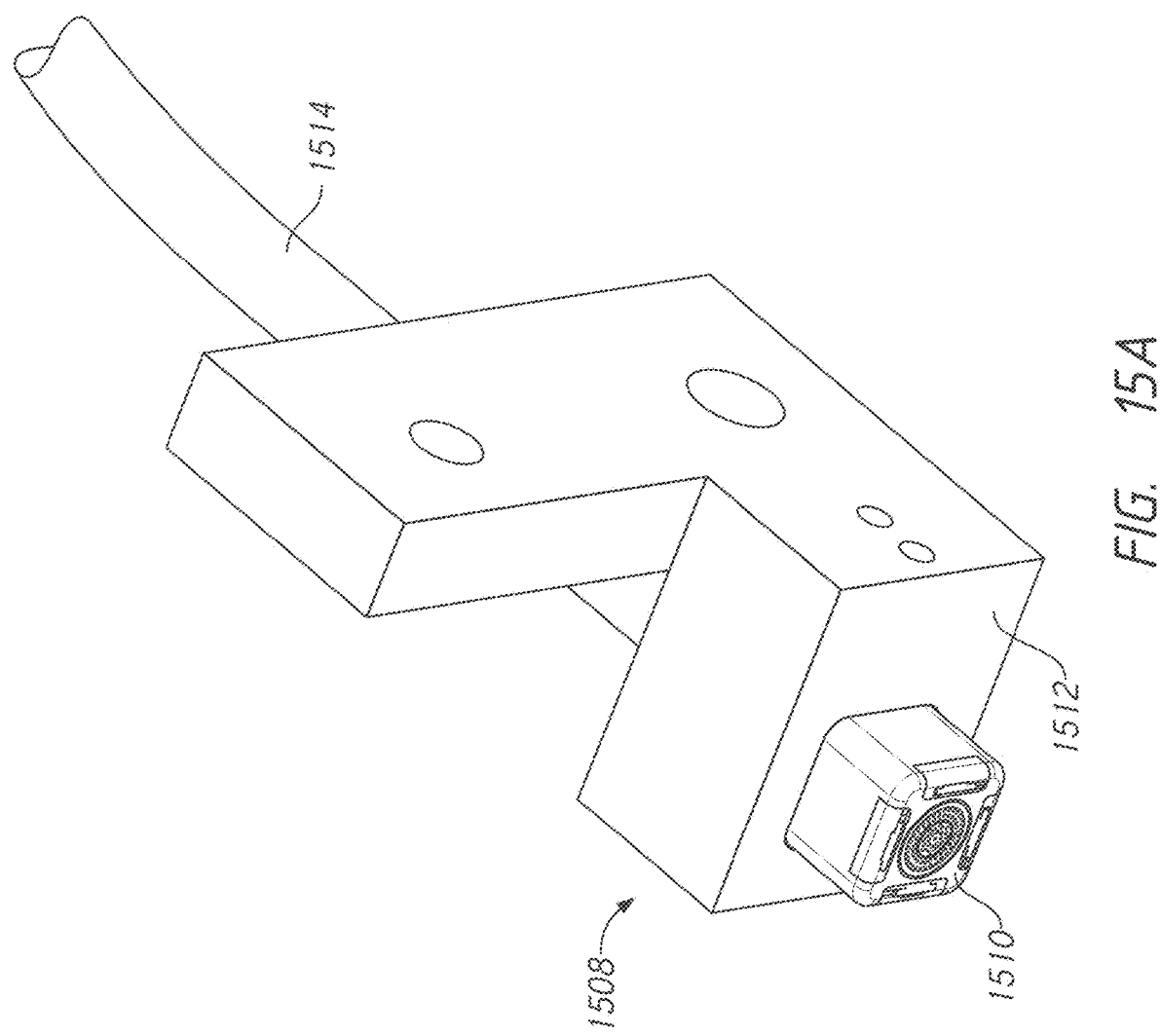
FIG. 15A illustrates an example absorbance head probe that may mate with an absorbance finger guide.
Figure 15B:
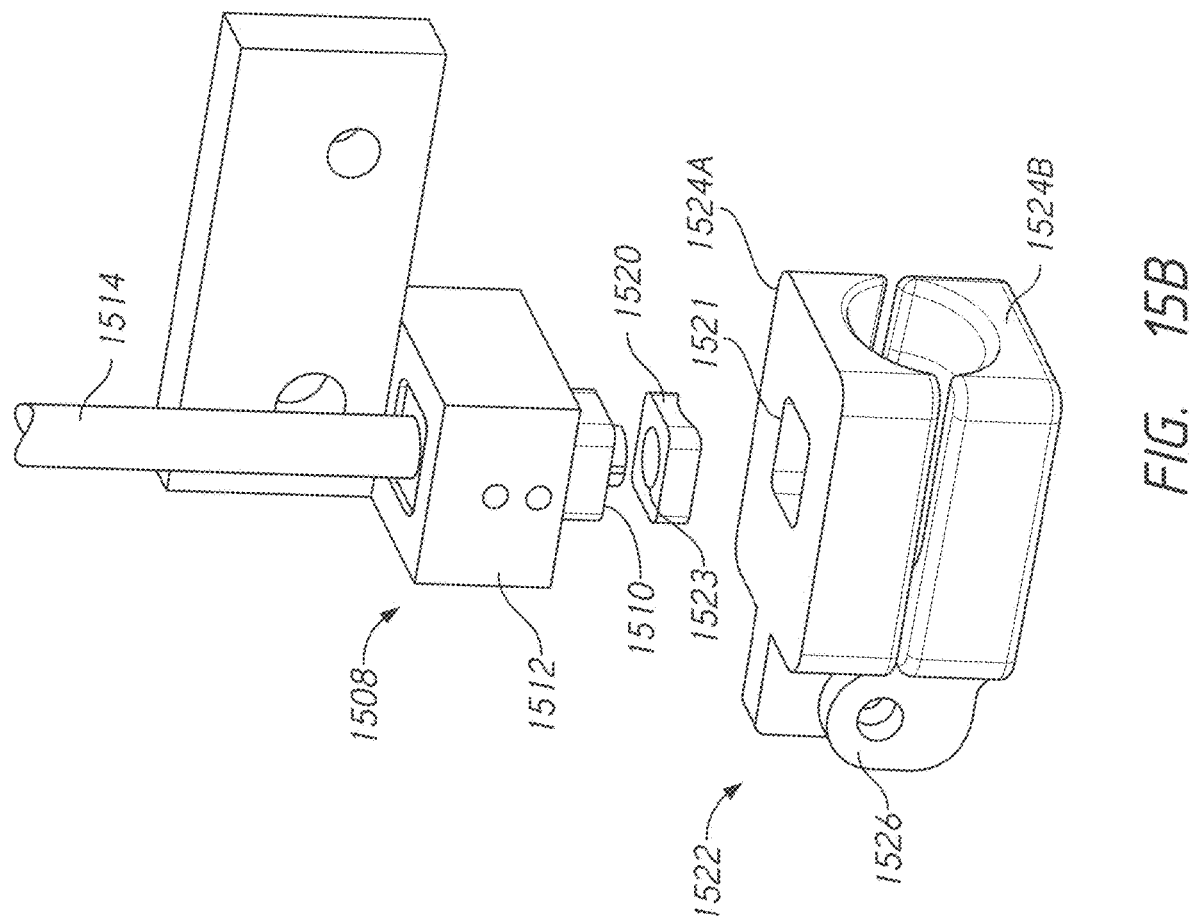
FIG. 15B illustrates an exploded view of the finger guide and absorbance probe assembly.

FIGS. 14A-15B illustrate components of an example system for securing a tissue site to one or more sensors. The system 100 can include one or more tissue site attachment and interlock components that may mate with each other. In some examples, an interlock component may be part of or coupled to a sensor head of one or more sensors of the system 100. The interlock component may uniquely or nonuniquely mate with one or more tissue site attachment components tissue site attachment components. For example, different probe heads in the system 100 can include different interlock components that may mate with different tissue site attachments. In another example, different probe heads in the system 100 can include interlock components that may mate with a single tissue site attachment or single type of tissue site attachment component. FIGS. 14A-14E illustrate example interlock and tissue site attachment components for use with a Fusion probe head 1436. FIGS. 15A and 15B illustrate example interlock and tissue site attachment components for use with an absorbance probe head 1510.

As illustrated in FIG. 14A, a tissue site attachment component 1422, that may mate to an interlock component associated with a sensor head (such as the Fusion probe head 1436 of FIG. 14B), can be attached to a tissue site 1420. The attachment component 1422 can include a mating structure 1424 and an opening 1426.

The mating structure 1424 can be a structure capable of mating with an interlock component associated with a sensor head (such as the Fusion probe head 1436 of FIG. 14B). For example, the mating structure 1424 can include a central raised portion 1428 capable of fitting into a mating cavity of similar size and shape to the central raised portion 1428. Additionally or alternatively, the mating structure 1424 can include one or more walls 1429 that may be raised above a top surface 1427 of the attachment component 1422. The one or more walls 1429 may be capable of securing the attachment component within a mating cavity that may be part of an interlocking component (such as the interlocking component 1430 of FIG. 14B). For example, as illustrated in FIGS. 14C and 14D, the walls 1429 of the attachment component 1422 can form an area capable of receiving a portion of an interlocking component such that the interlocking component does not significantly move horizontally.

The attachment component 1422 can include an open area 1426. The open area can be of a suitable size and shape through which a sensor, such as a Raman sensor, can measure physiological parameters. For example, the open area 1426 can be large enough to include the spot size of an excitation source that may be part of the Raman sensor. Additionally or alternatively, the open area 1426 can be large enough to allow for the excitation source of the sensor to scan the tissue site or to account for movement of the excitation source during use or manufacture. In some examples, the open area 1426 can be part of the mating components 1424 such that the one or more portions of the open area 1426 can be capable of accepting one or more portions of the interlocking component 1430.

The attachment component 1422 can be coupled to the tissue site of a patient or user by any suitable means. For example, the attachment component 1422 can be attached to the tissue site of a patient using a permanent or temporary adhesive, by permanent or temporary implantation, via a wearable device, or other suitable means of temporarily, semi-permanently, or permanently securing a component to a tissue site. In some examples, the attachment component 1422 may be secured to a tissue site of a patient via a semi-permanent adhesive capable of securing the attachment component for a day or more. For example, the attachment component 1422 may be secured to a tissue site with a medical adhesive, glue, tape, or other means of adhering components to a tissue site.

As illustrated in FIG. 14B, an interlock component 1430 may be coupled to or part of the sensor head 1436. The interlock component 1430 can include a cavity 1434 of a size and shape capable of accepting the tissue site attachment component 1422. The cavity 1434 can include an area 1432 through which a Raman sensor can measure a tissue site.

The interlock component 1430 may have a surface 1440 of a similar curvature to the curvature of a surface 1438 of attachment component 1422. The curvature of the surface 1440 and surface 1438 can be of similar curvature to that of the area of the measured tissue site. For example, the tissue site may be a finger nail and the curvature of can follow the approximate curvature of the finger nail. In some examples, the curvature can be specific to the curvature of the tissue site of the user. For example, the surface 1438 or surface 1440 can be molded, formed, or otherwise shaped according to the shape of the tissue site. In other examples, the curvature can be generic to the approximate curvature of the tissue site of the user. For example, the surface 1438 or 1440 can be molded, formed, or otherwise shaped according to the approximate curvature of an adult human finger nail where the tissue site is a finger nail.

FIGS. 14C and 14D illustrate example views of an external enclosure mechanism for mating a finger guide with a sensor head. For example, a system 100 can include an enclosure mechanism 1456 in which a patient can place the tissue site (for example, a finger 1450) to which an attachment component 1422 may be coupled. The enclosure mechanism 1456 may include a top portion 1458A, a bottom portion 1458B, and a hinge mechanism 1460. The top portion 1458A and the bottom portion 1458B may come together to form a cavity capable of accepting a tissue site of a patient. The top portion 1458A and/or the bottom portion 1458B may move to open and accept the tissue site of the patient via the hinge mechanism 1460. The top portion 1458A may include an open portion 1451 capable of accepting or securing an interlocking mechanism 1430 or attachment component 1422 of a sensor head 1436. For example, the open portion 1451 can include an open area of a similar size and shape to the exterior footprint of the attachment mechanism 1422 such that the attachment mechanism 1422 can fit inside the open area. Additionally or alternatively, the open portion 1451 can include an open area of a similar size and shape to the interlocking mechanism 1430 such that the interlocking mechanism 1430 can fit inside the open area.

FIG. 14E illustrates an exploded view of the interlocking components and sensor head assembly. For example, as illustrated in FIG. 14E, the external mechanism 1456 can accept attachment component 1422 into an open portion 1451. Additionally or alternatively, the external mechanism 1456 can accept an interlocking component 1430 that may be associated with a sensor head 1436 for Raman sensor components 1452 and 1454.

FIGS. 15A-15B illustrate components of example attachment component(s) that may mate interlocking components associated with an absorbance probe head 1508. For example, FIG. 15A illustrates an example absorbance head probe 1508 that may include a sensor end 1510, a holder 1512, and a fiber optic cable 1514. The sensor end 1510 may be capable of measuring a tissue of a patient. The sensor end 1510 may be held in place within a system 100 with a holder 1512.

FIG. 15B illustrates an exploded view of example interlocking components and absorbance probe assembly. For example, as illustrated in FIG. 15B, an external mechanism 1456 can accept attachment component 1520 into an open portion 1521. Additionally or alternatively, the external mechanism 1522 can accept a sensor end 1510 of the absorbance head 1508.

The attachment component 1520 can include an open area 1523. The open area 1523 can be of a suitable size and shape to accept the sensor end 1510 or through which absorbance probe can measure physiological parameters. For example, the open area 1523 can be large enough to include the spot size of an excitation source that may be part of the Absorbance probe. Additionally or alternatively, the open area 1523 can be large enough to allow for the excitation source of the sensor to scan the tissue site or to account for movement of the excitation source during use or manufacture.

The attachment component 1520 can be coupled to the tissue site of a patient or user by any suitable means. For example, the attachment component 1520 can be attached to the tissue site of a patient using a permanent or temporary adhesive, by permanent or temporary implantation, via a wearable device, or other suitable means of temporarily, semi-permanently, or permanently securing a component to a tissue site. In some examples, the attachment component 1520 may be secured to a tissue site of a patient via a semi-permanent adhesive capable of securing the attachment component for a day or more. For example, the attachment component 1520 may be secured to a tissue site with a medical adhesive, glue, tape, or other means of adhering components to a tissue site.

In some examples, the tissue site attachment component or interlock component can include one or more anti-counterfeiting components or measures. An anti-counterfeiting component or measurement can include one or more passive or active components in the tissue site attachment component or interlock component that may interact or with another component of the system 100 to authenticate the attachment component or interlock component. For example, an anti-counterfeiting component can include a resistor, identifiable material, barcode, or other method, device, or material capable of authenticating an attachment component or interlock component.

2. Clinical System Environment

Figure 16A:
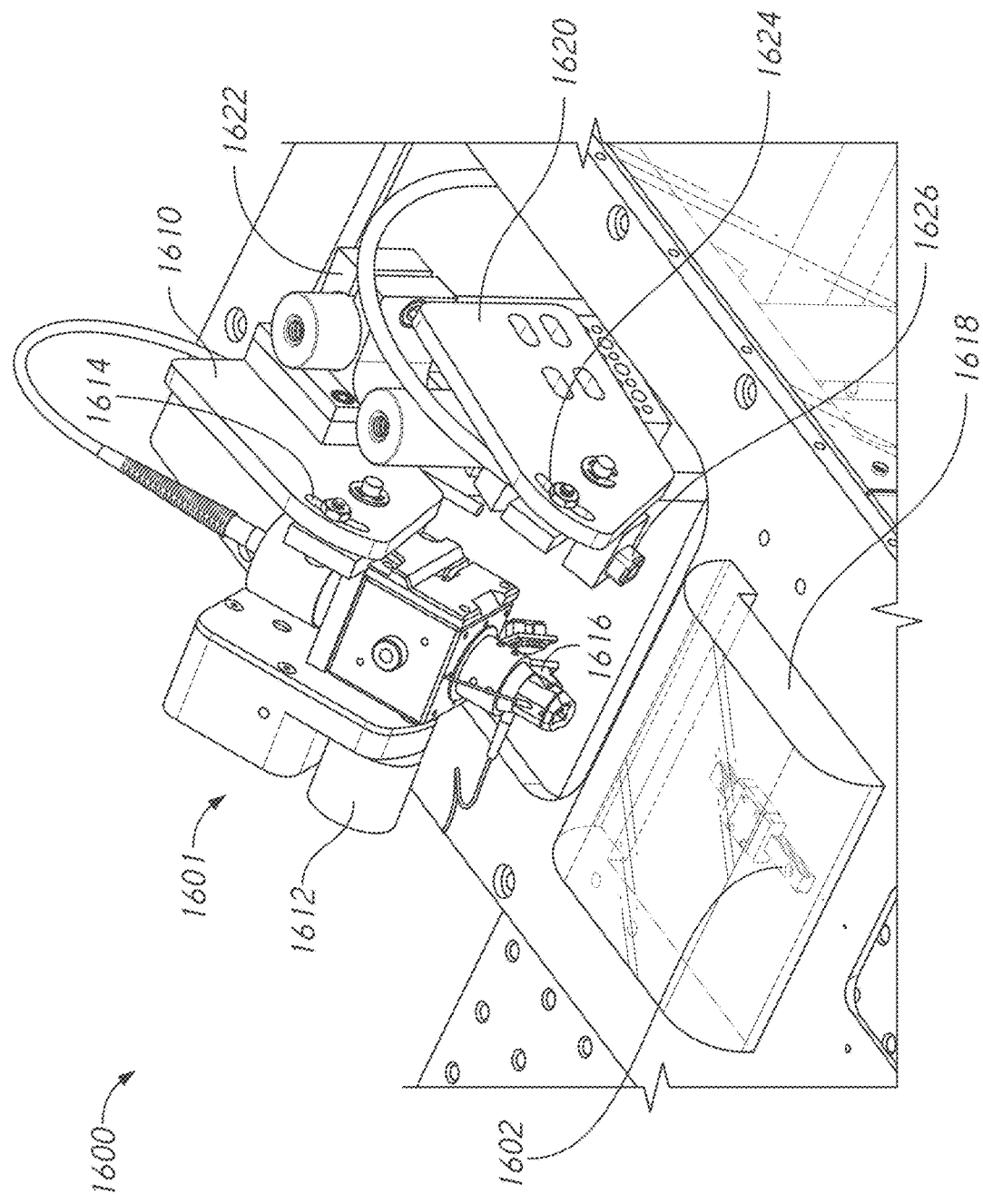
FIG. 16A illustrates an example probe head assembly and cradle.
Figure 16B:
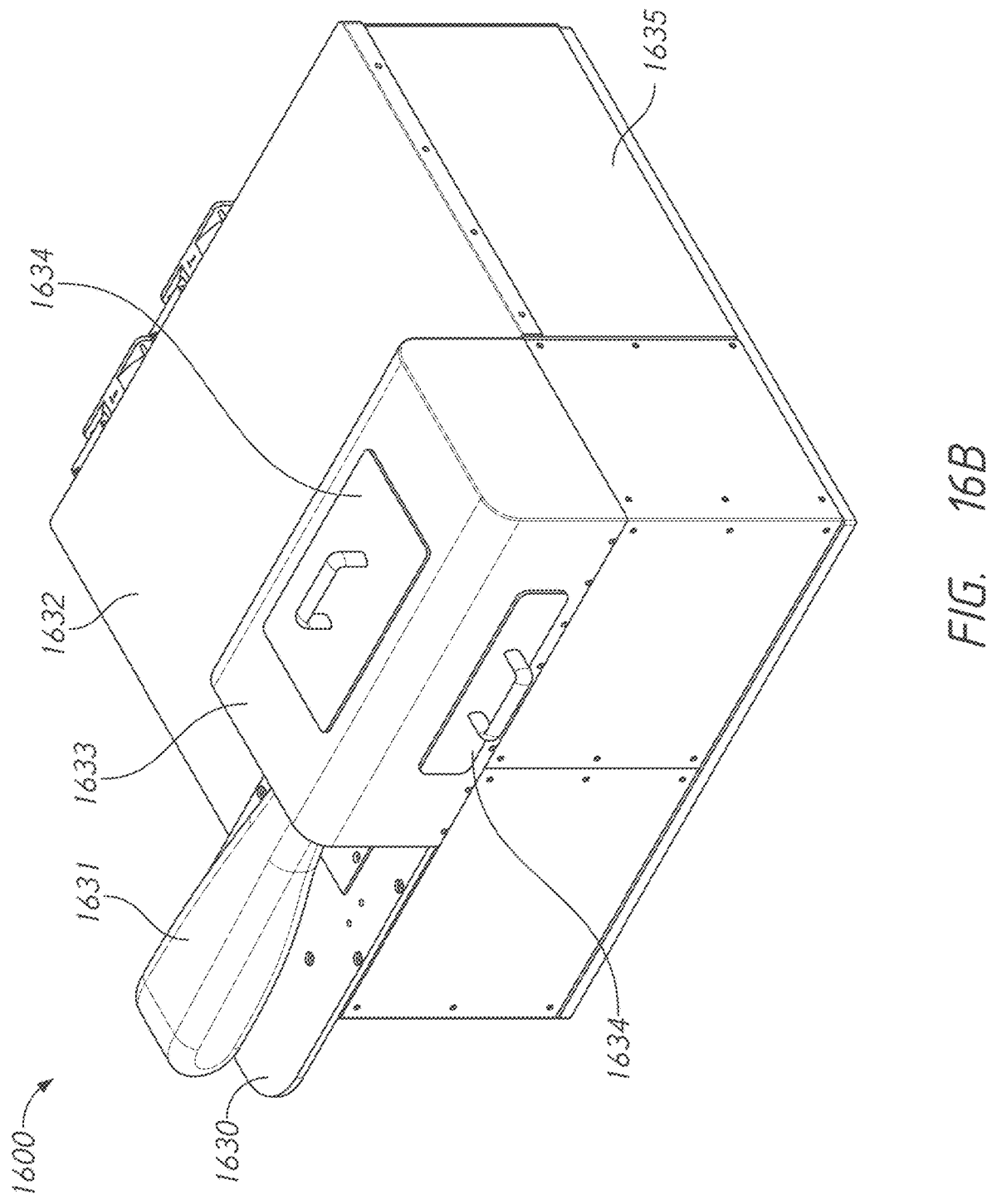
FIG. 16B illustrates an example exterior view of the sensor system.
Figure 16C:
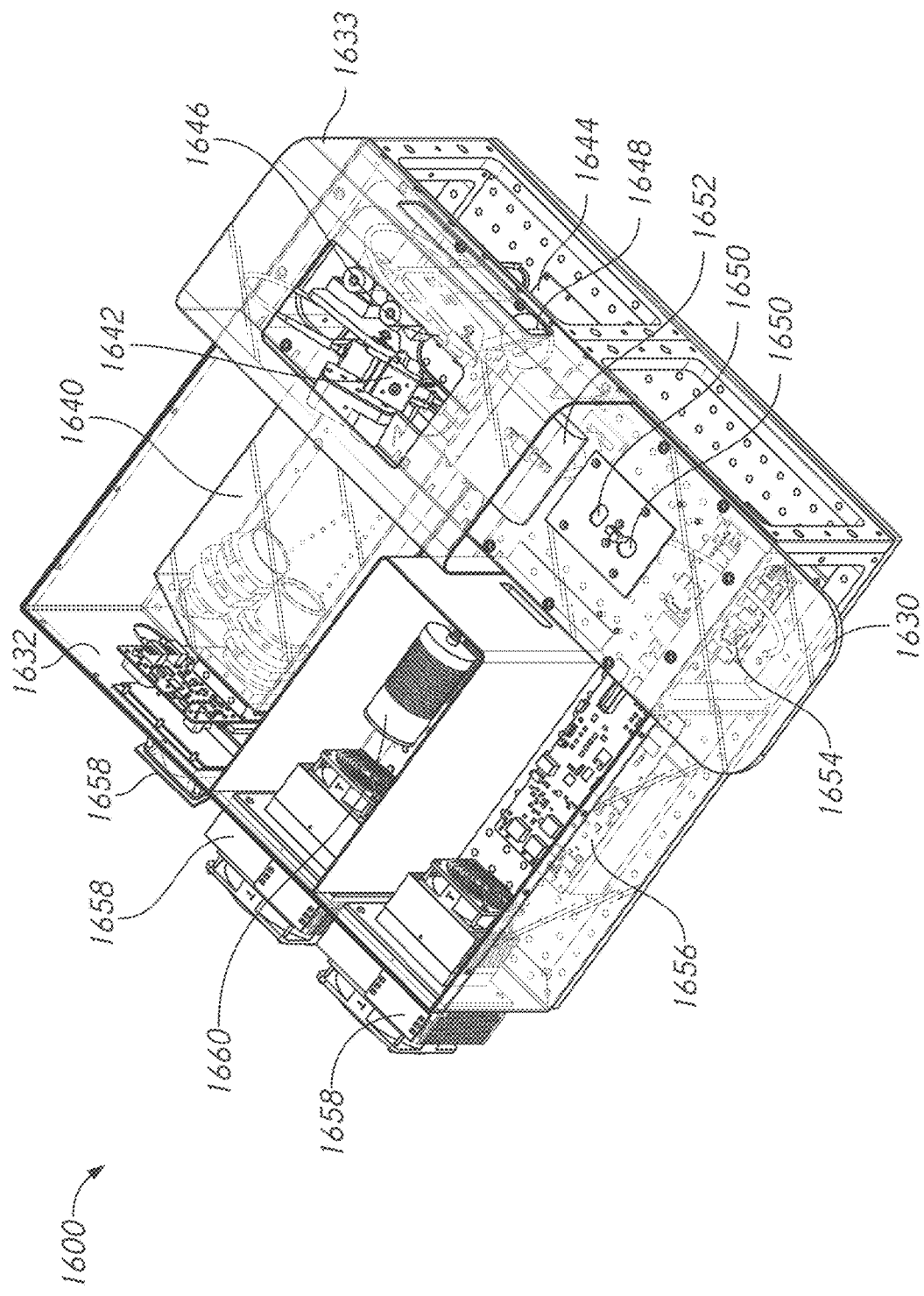
FIG. 16C illustrates an example interior layout of the sensor system.
Figure 16D:
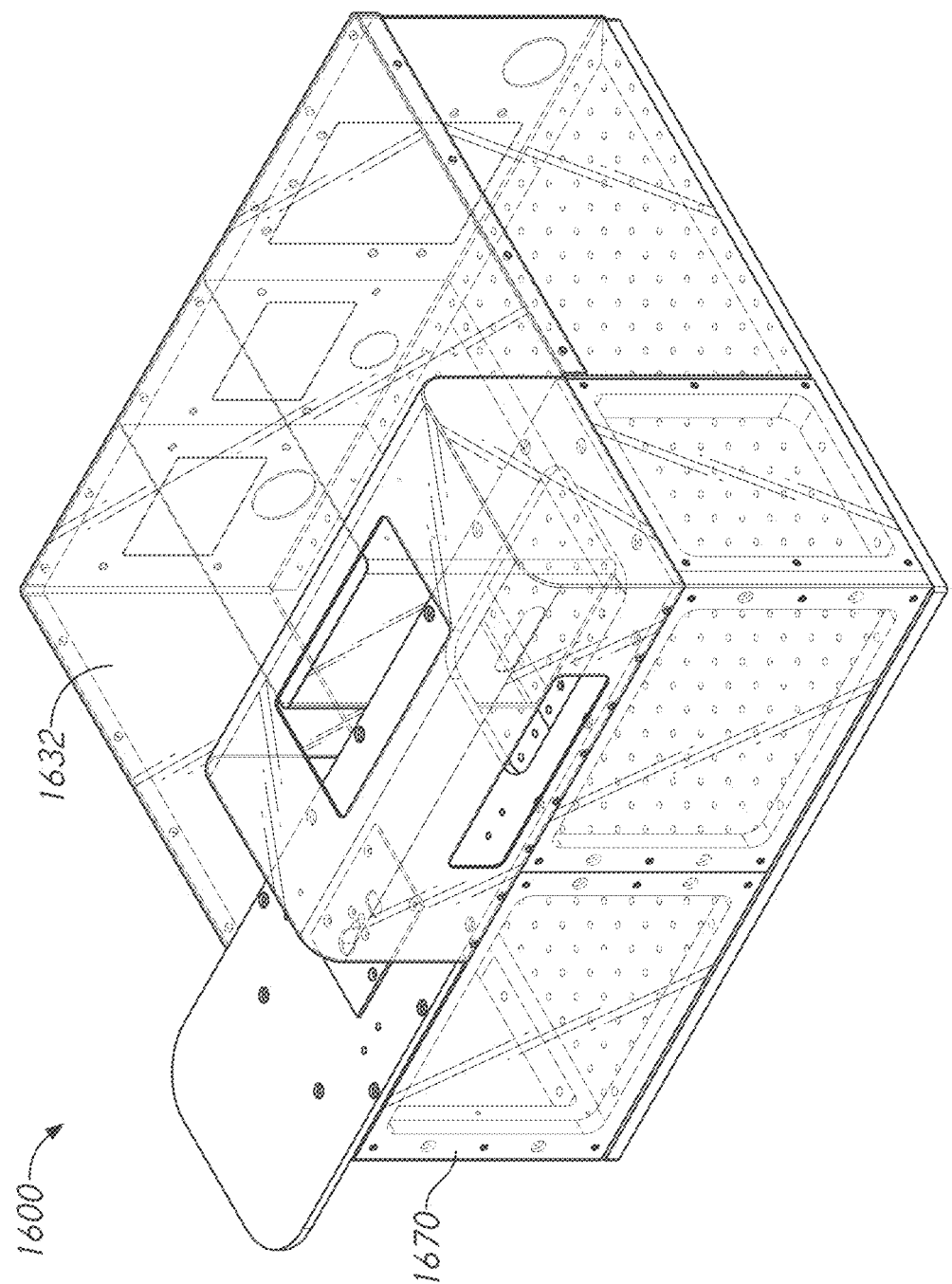
FIG. 16D illustrates an example frame of the sensor system.

FIGS. 16A-16D illustrate example views of the layout of an example sensor system 1600 that may be part of a system 100. For example, FIG. 16A illustrates an example probe head assembly 1601 and cradle 1602 that may be part of a sensor system 1600. FIG. 16B illustrates an example exterior view of the sensor system. FIG. 16C illustrates an example interior layout of the sensor system. FIG. 16D illustrates an example frame of the sensor system.

As illustrated in FIG. 16A, a probe head assembly 1601 can include one or more sensors, such as a Raman sensor 1616 and an absorbance probe 1626. The probe head assembly 1601 may include one or more components that allow for one or more degrees of freedom of movement. For example, the Raman sensor 1616 can be coupled to one or more movement stages 1612 and sensor head holders 1610. Additionally or alternatively, the absorbance probe 1626 can be coupled to one or more movement stages 1622 and sensor head holders 1620. The movement stages 1612, 1622 can be configured to allow one or more sensors 1616, 1626 to have one or more degrees of freedom of movement, including, but not limited to rotation, tilting, up, down, left, and right. The sensor head holders 1610, 1620 can include one or more securing mechanisms 1614, 1624. The securing mechanism(s) 1614, 1624 can include an adjustable mechanism to move or secure a sensor 1616, 1626. For example, the securing mechanism(s) 1614, 1624 can include a slit capable of receiving a screw that may tighten into the sensor 1616, 1626.

With continued reference to FIG. 16A, a cradle 1602 can include a palm rest 1618. The palm rest 1618 can include a heater (not shown). The heater may heat a surface of the palm rest 1618 or other surface of the cradle 1602. Advantageously, the heater may enhance blood circulation of the tissue site. For example, the tissue site may be a portion of a patient's hand and the palm rest 1618 may contain a heated surface capable of increasing circulation of the palm.

The palm rest 1618 can include a movement mechanism 1628 to adjust the location of the palm rest 1618. For example, the movement mechanism 1628 can include a sliding mechanism to move the palm rest 1618 forward and backward. Additionally or alternatively, the movement mechanism 1628 can include other types of movement mechanisms, such as a translational or rotational stage, to allow other types of movement, such as rotation, tilting, raising, lowering, right and left or other movement. The movement mechanism 1628 can include one or more stopping, locking, or securing mechanisms. For example, the movement mechanism 1628 can include a brake, quick latch and release, or other mechanism to secure the palm rest 1618 once the palm rest 1618 is in the desired location for measurement of the tissue site.

As illustrated in FIG. 16B, one or more components of a sensor system 1600 can be contained in a housing 1632. The housing 1632 can include a hand support 1630, a fixture portion 1633, one or more covers to cover a hand at a fixture entrance (not shown), doors 1634, and one or more sheet metal covers 1635.

The hand support 1630 include an area capable of receiving a portion of a patient's hand or arm. The hand support 1630 may support portions of the patient's arm while the system 1600 is in use. For example, the system 1600 may measure a tissue site on the patient's hand, such as a finger nail. The patient may rest their arm on the hand support 1630 while the system 1600 measures physiological parameters at the patient's finger nail. The hand support 1630 can include a shelf wide enough for a person to rest their forearm 1631. In some examples, the palm rest 1618 may be coupled to or otherwise placed on top of the hand support 1630 such that a patient's palm rests on the palm support 1618 while the patient's arm is supported by the hand support 1630.

The fixture portion 1633 of the housing 1632 can be configured to house one or more sensor components or receive the tissue site of the patient for measuring physiological parameters. For example, the fixture portion 1633 can include a Raman sensor and an absorbance probe (not shown) that may be capable of measuring physiological parameters at one or more tissue sites on a patient's hand. In some examples, the fixture portion 1633 may be large enough to fit some or all of one or more probe heads capable of measuring physiological parameters at one or more tissue sites of the patient. In order to perform the measurements, the fixture portion 1633 can include an opening or entrance (not shown) capable of comfortably receiving at least a portion of a patient's hand or arm. For example, the fixture portion 1633 can include an entrance having a width that is 1.2 times, 1.5 times, or 2 times the width of a typical adult patient's hand and a height that is 1.2 times, 1.5 times, or 2 times the height of a typical adult patient's hand. Other sizes or ratios of height to width are possible. Additionally or alternatively, the fixture portion 1633 may be large enough or deep enough to fit the tissue site of the patient or a larger portion of the patient's body that may include the tissue site.

For example, the fixture portion 1633 may be deep enough to fit some or all of the patient's hand or fingers where a tissue site is a fingernail. In some examples, the fixture portion 1634 can include a covering, such as a black cloth, that may fit over part of the received portion of the patient's hand or arm such that the fixture portion 1633 is substantially enclosed around the tissue site of the patient.

The fixture portion 1633 of the housing 1632 can include one or more doors 1634. The doors 1634 may be positioned on the fixture portion 1633 so as to provide access to or a view of one or more of the probe heads that may be contained within the fixture portion 1633. For example, a door 1634 may be positioned on the top of the fixture portion 1633 in order to access one or more sensor components. Additionally or alternatively, the doors 1634 may be positioned on the fixture portion 1633 so as to provide access to other components of the system 1600. For example, a door 1634 may be positioned on the side of the fixture portion 1633 so as to provide access to a moving mechanism of the palm rest 1618. The door(s) 1634 may be quick snap doors. For example, the door(s) 1634 may be mechanically aligned and latch via one or more magnets.

The housing 1632 can include one or more metal covers 1635. The metal cover(s) 1635 may be removable so as to provide access to components contained within the housing 1632. The metal cover(s) 1635 may be made of a light weight and high strength metal, such as 6061 aluminum alloy. The metal cover(s) 1635 can be coated. For example, the outside of the metal cover(s) 1635 can be coated in an anodized coating or other coating capable of reducing the effects of weathering or other damage that may occur during use of the system 1600. In another example, the inside of the metal cover(s) 1635 can be coated in an optical absorption material, such as broadband optical absorption Krylon paint.

As illustrated in FIG. 16C, the housing sensor system 1600 can include a Raman spectrometer 1640, a Fusion probe head assembly 1642, an absorbance probe head assembly 1646, an absorbance system 1644, an imaging system 1648, one or more openings 1650 for the fusion and absorbance probes, a controller 1654 for thermistors, an Optical Coherence Tomography (OCT) system 1656, one or more cooling components cooling components 1658, and a temperature control compartment 1660 for an excitation source.

The Raman spectrometer 1640 can be used to measure a Raman spectrum at a tissue site through a fusion probe head 1642. The Raman spectrometer 1640 can be cooled by cooling components, such as one or more cooling components 1658. The one or more cooling components 1658 can be dedicated to the Raman spectrometer 1640 or shared with other system components. The one or more cooling components 1658 can include some combination of thermoelectric cooling components and fans. Additionally or alternatively, cooling or other temperature control be done by other types of temperature control methods such as using liquid cooling.

The Absorbance system 1644 can be used to measure physiological parameters at a tissue site through an absorbance probe head 1646. The Absorbance system can be cooled by cooling components, such as one or more cooling components 1658. The one or more cooling components 1658 can be dedicated to the Absorbance system 1644 or shared with other system components.

The OCT system 1656 can be used to measure OCT data a tissue site through a probe head 1642. The OCT system 1656 can be cooled by cooling components, such as one or more cooling components 1658. The one or more cooling components 1658 can be dedicated to the OCT system 1656 or shared with other system components.

An excitation source can be cooled by cooling components, such as a fan 1658. Additionally or alternatively, the system 1600 can include a temperature control compartment 1660 for the excitation source. Advantageously, the temperature control compartment 1660 can allow for greater control over the temperature of the excitation source and other system components by reducing the potential heat exchange between excitation source components and other system components, such as the Raman spectrometer 1640, Absorbance system 1644, and OCT system 1656.

The system 1600 can include one or more openings 1650 for measuring physiological parameters with the fusion probe head 1642 or absorbance probe head 1646. For example, the fusion probe head 1642 or absorbance probe head 1646 can measure physiological parameters through an opening 1650 on the shelf 1630 on which a portion of a patient's hand or arm may rest. Additionally or alternatively, the system 1600 can measure physiological parameters at a site on a patient's finger site within the fixture portion 1633 of the housing 1632.

A system 1600 can include an imaging system 1648. The imaging system 1648 may be a camera capable of monitoring the positioning of the tissue site of the patient with respect to the one or more probe heads 1642, 1646. For example, the camera may be mounted on or near the shelf 1630, palm rest 1618, or other area capable of receiving a tissue site of a patient. The camera may have one or more degrees of freedom available to locate or track a tissue site of a patient during placement of the tissue site near one or more of the probe heads 1642, 1646. Images from the imaging system 1648 can be used by the patient or a care provider to guide the tissue site to a suitable location by which the one or more probe heads 1642, 1646 can measure physiological parameters at the tissue site. Additionally or alternatively, images from the imaging system 1648 can be used by the patient, care provider, or controller to guide system components into place for measuring physiological parameters at the tissue site. For example, a controller can guide one or more probe heads 1642, 1646 to rest at a suitable measuring position relative to the tissue site of the patient using tissue site location information and probe head location information obtained using images from the imaging system 1648.

A system 1600 can include one or more heaters (not shown) The one or more heaters can be placed so as to heat parts of a patient that may increase circulation to a tissue site being measured. For example, the system 1600 can include heaters directly placed onto the patient, heaters within a portion of the system 1600 on which a patient rests a part of their body, or other suitable area. In another example, heaters can include one or more heating pads coupled to or attached to the support 1618, a heating blanket around the patient arm 1631, or a localized heating element around a probe head 1642, 1646. The heaters may be monitored by one or more temperature sensors, such as thermistors, thermocouples, resistance temperature detectors (RTDs), the like, or some combination thereof. The one or more temperatures sensors may be controlled by a multiple input/output board 1654.

As illustrated in FIG. 16D, the housing 1632 can include a frame 1670. The frame 1670 can include materials that may optimize strength and reduce weight of the system 1600 while protecting, storing, sealing in light, reducing vibration, and maintaining temperature. For example, the frame can include CNC AL6061 and sheet metal AL6061 parts. As illustrated with reference to FIG. 16B, the housing 1632 can include covers 1635 that may fit onto the frame 1670. The covers 1635 may be removable and allow for quick access to different hardware contained within the housing 1632. In some examples, the housing 1632 can include brackets for securing components to the frame 1670. The brackets (not shown) can be made of plastic or other lightweight material so as to further reduce weight and cost.

Figure 17A:
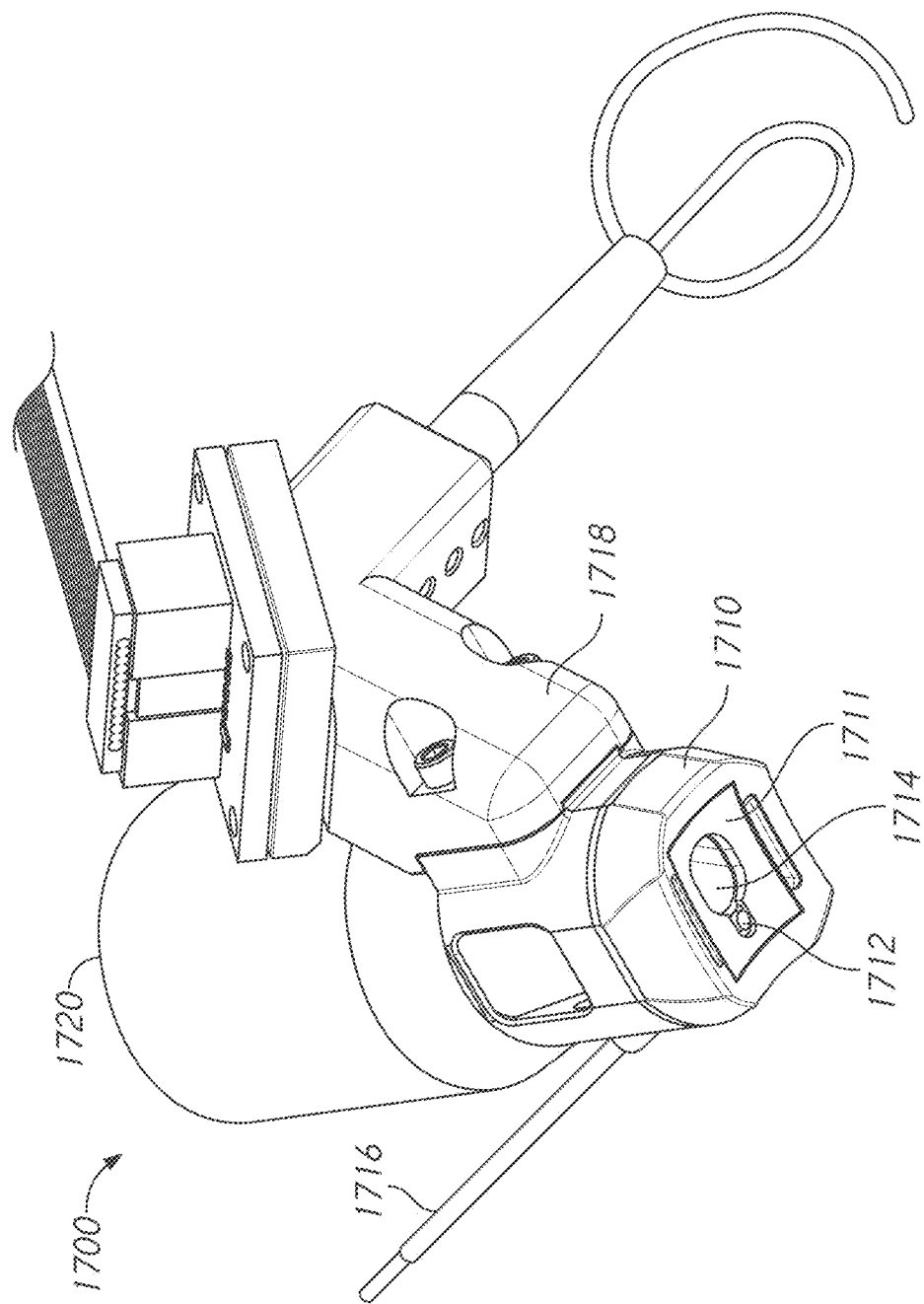
FIG. 17A illustrates an example probe head.
Figure 17B:
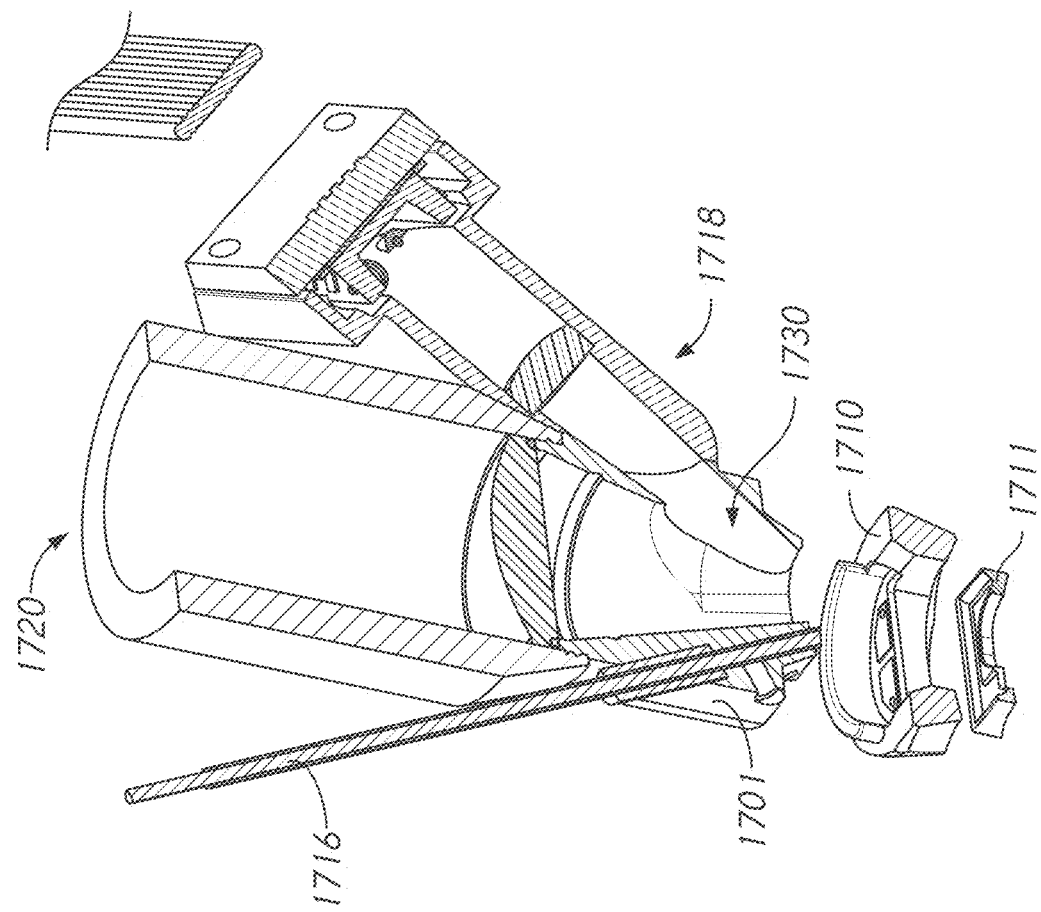
FIG. 17B illustrates an example cross sectional view of the probe head of FIG. 17A.
Figure 17C:
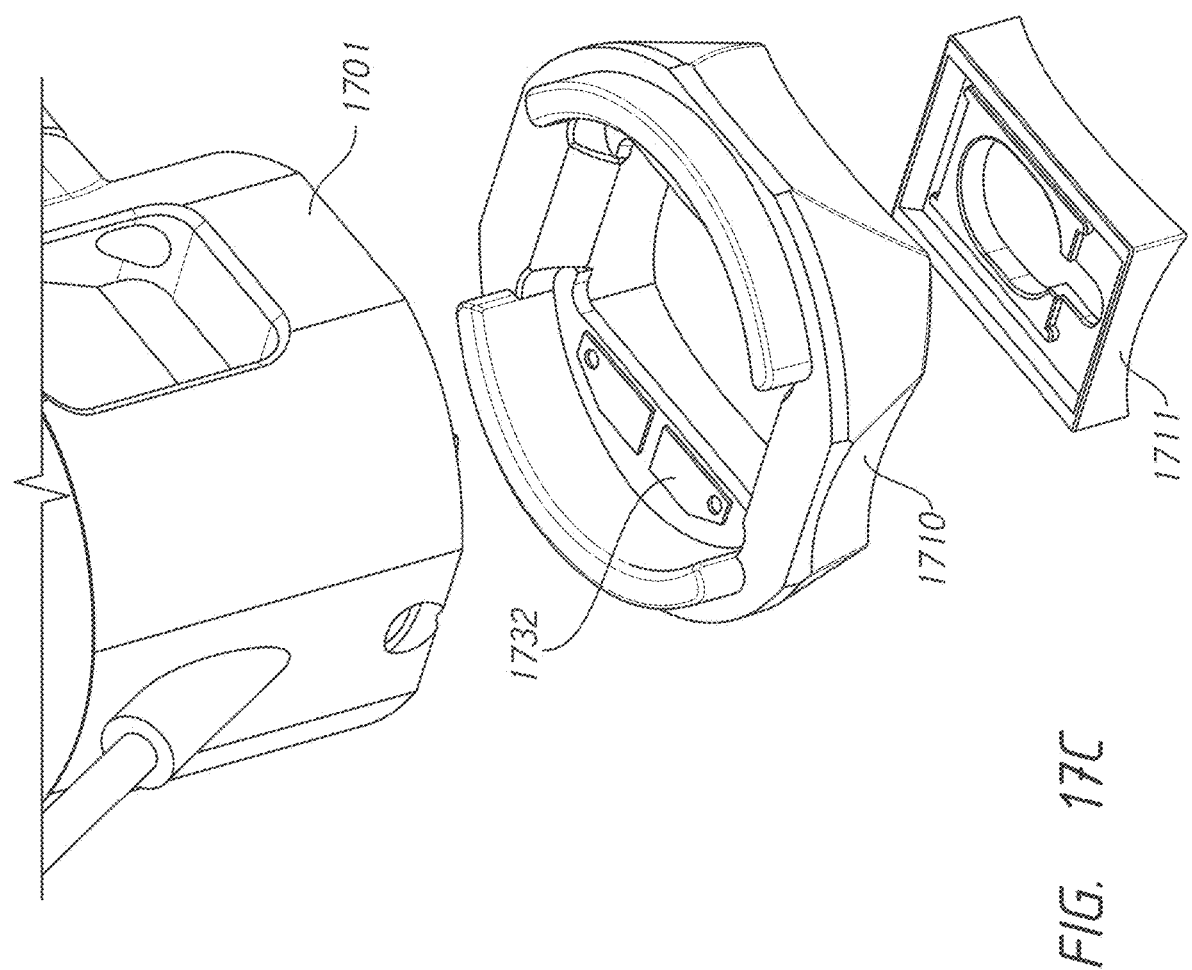
FIG. 17C illustrates an exploded view of an example probe head.
Figure 17D:
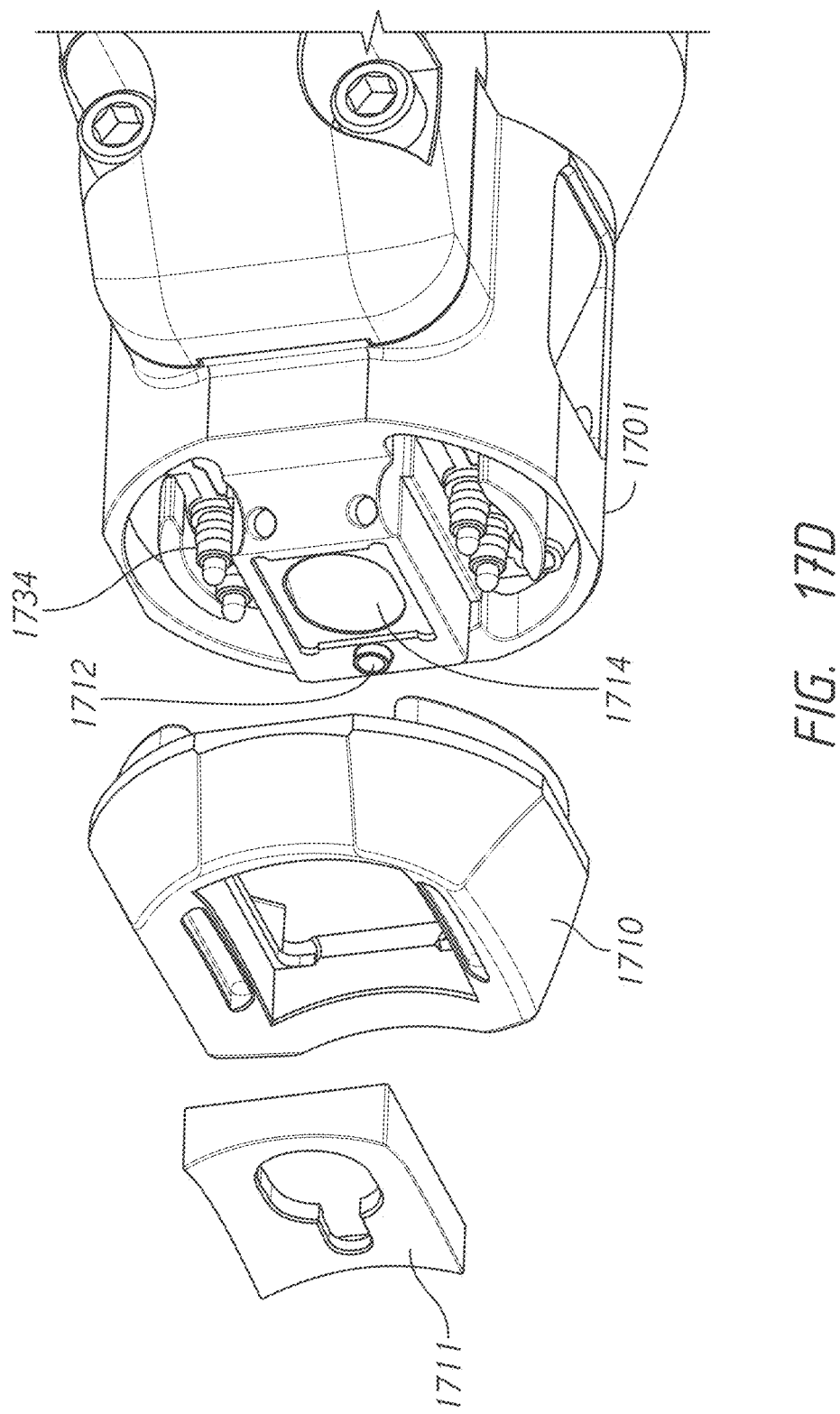
FIG. 17D illustrates another exploded view of an example probe head.

FIGS. 17A-17D illustrate example views of the probe heads that may be part of the sensor system. For example, FIG. 17A illustrates an example probe head. FIG. 17B illustrates an example cross sectional view of the probe head of FIG. 17A. FIGS. 17C and 17D illustrate example exploded views of an example probe head.

As illustrated in FIG. 17A, a probe assembly 1700 can include an interlocking component 1710, an attachment component 1711, an fiber optic end 1712, a sensor window 1714, a fiber 1716, an OCT device 1718, and a Raman sensor 1720. The components of the probe assembly 1700 can be oriented in such a way so that the OCT device 1718 and Raman sensor 1720 can, in use, obtain measurements from essentially the same, overlapping, or proximate regions of tissue. By orienting and/or positioning the sensors to interrogate or analyze essentially the same, overlapping, or proximate regions of tissue, the probe assembly 1700 can ensure that each of the sensors 1718, 1720 obtain measurements corresponding to tissue having the same or similar properties (non-limiting examples: the same or similar optical profile, the same or similar tissue geometry, or the like). As a result, in some embodiments, data from the one or more sensors can be utilized to improve, calibrate, or confirm data and/or calculations related to another sensor, thereby improving a determination or an accuracy of one or more physiological parameters. It will be understood that fewer, additional, or different sensors can be included in the probe assembly 1700.

Advantageously, the sensor window 1714 and fiber 1716 may be large enough to accommodate absorbance measurements at the Raman band using a broadband light source. An attachment component 1711 that may mate with an interlocking component 1710 can include an opening or cutout that may expose the majority of the window 1714 so that a tissue site can be measured through the opening. Additionally or alternatively the opening or cutout may include an area that may expose the majority of the fiber 1716 so that a tissue site can be measured via the fiber 1716 through the opening.

As illustrated in FIG. 17B, the OCT sensor 1718 and Raman sensor 1720 may detect physiological parameters by emitting or detecting light through a shared space 1730 within the probe head 1701. Advantageously, the shared space may allow the probe head 1701 to have a smaller footprint, resulting in a lighter and more efficient probe head 1701.

As illustrated in FIG. 17C, an interlocking component 1710 can include one or more electrical contacts 1732. The one or more electrical contacts 1732 can be electrically connected to one or more sensors that may be within or coupled to the interlock component 1710 or attachment component 1711. The one or more sensors can be any sensor for measuring proper fit of the interlock component 1710 with the attachment component 1711, temperature of the tissue site, proximity of the tissue site, impedance, identity of the attachment component or patient, or other suitable sensor for measuring data associated with the tissue site, interlock component 1710, or attachment component 1711.

As illustrated in FIG. 17D, the probe head 1701 can include one or more electrical components 1734. The electrical components 1734 can protrude so as to make contact with the electrical contacts 1732 of the interlock attachment 1710. In some examples, the one or more electrical components 1734 can be spring loaded so that the one or more electrical components 1734 are compressed against the electrical contacts 1732 of the interlock attachment 1710 while the interlock attachment 1710 is coupled to the probe head 1701. Other forms of electrical connection between the probe head 1701 and interlock component 1710 or attachment component 1711 are also possible.

3. Timing Processor

Figure 18A:
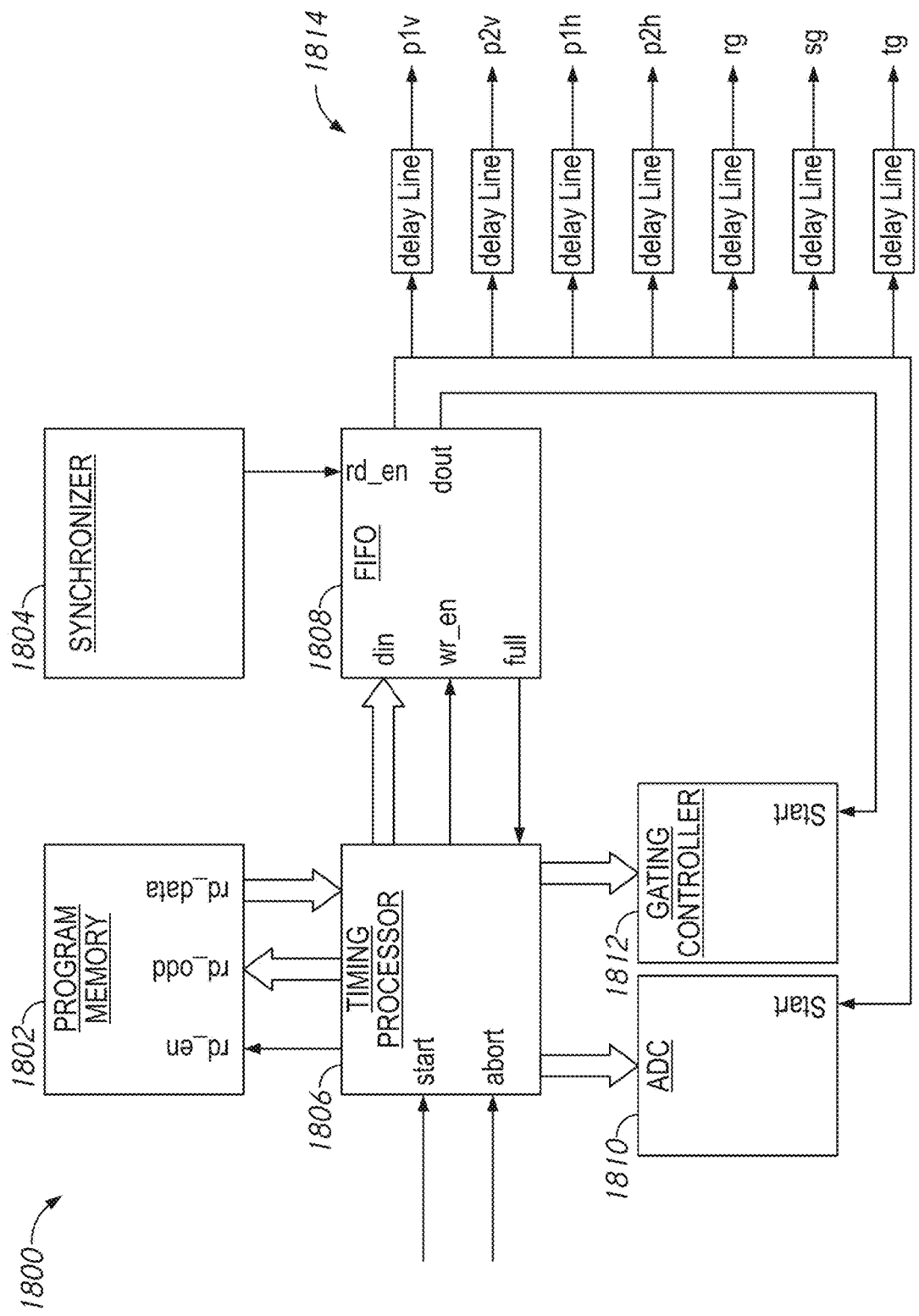
FIGS. 18A and 18B show block diagrams of example timing processors that may be used in association with the example sensor system.
Figure 18B:
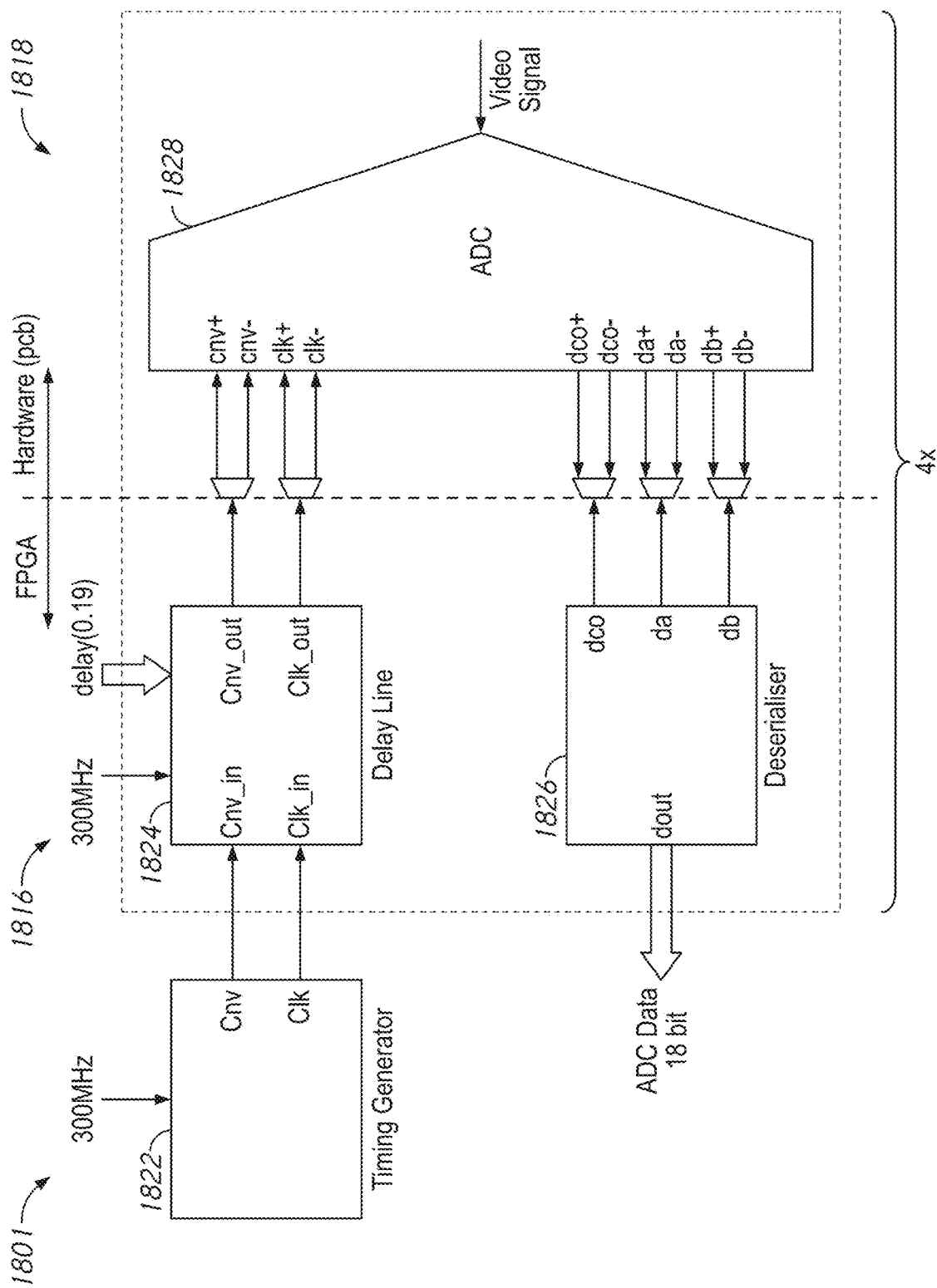

FIGS. 18A and 18B show block diagrams of example timing processor systems 1800 and 1801 that may be used in association with the example sensor system 100. Advantageously, the timing processor systems 1800 and 1801 may be programmable. The programmable nature of the systems 1800 and 1801 may allow for adjustments to windows and timings during sampling and probing of one or more sensors which may in turn increase the signal to noise ratio (SNR) of measured data. For example, the systems 1800 or 1801 may allow for asymmetric binning or running of a CCD in different modes. In another example, the timing processor system 1800, 1801 may allow for optimally timed and oversampled readout. In some examples, the timing processor system 1800, 1801 may allow for a sampling rate of 1 to 15 MSPS.

For example, as illustrated in FIG. 18A, a timing processor system 1800 can include a program memory 1802, a synchronizer 1804, a timing processor 1806, a first input first output (FIFO) module 1808, an ADC controller 1810, a gating controller 1812, and one or more delay lines 1814.

The timing processor 1806 can include a processor capable of reading program memory or generating one or more signals. The one or more signals can include timing signals. Timing signals can include a signal for synchronizing different parts of a processing system. For example, a timing signal can include a signal that oscillates between a high and a low state to coordinate actions of circuits in the system 1800. The timing processor 1806 can interact with other components of the system 1800, such as the program memory 1802, FIFO 1808, ADC 1810, and gating controller 1812. For example, the timing processor 1806 may read instructions from the program memory 1802 for generating timing signals or for other processes. In another example, the timing processor 1806 may output timing or other signals to the FIFO 1808 or receive data from the FIFO 1808. In another example, the timing processor 1806 may output timing or other signals to an ADC controller 1810 or a gating controller 1812. Interactions with other modules or computing components are also possible.

The program memory 1802 can include any suitable memory for holding a program or executable instructions. For example, the program memory 1802 can include a hard drive or solid state drive (SSD). The program memory 1802 may interact with the timing processor 1806 to, for example, read data from the program memory 1802. For example, the timing processor 1806 can send a read enable signal (rd_en) and a control signal for the program memory 1802 to allow access to the data (rd_data) in the program memory.

The FIFO 1808 can include any suitable module for managing data or signals used in the system 1800. For example, the FIFO 1808 can include a module for holding or buffering data or signals. The FIFO 1808 can buffer data (for example, a timing signal) from the timing processor 1806 according to any suitable criteria. For example, timing signals from the timing processor 1806 may be stored in the FIFO 1808. A synchronizer 1804 may send a timing signal to the FIFO 1808. The FIFO 1808 may then output buffered data based on the timing signal from the synchronizer 1804. The FIFO 1808 may output the buffered data to any number of computing modules or components, such as the ADC controller 1810 or the gating controller 1812.

Once a module, such as an ADC controller 1810 or gating controller 1812, receives data from the FIFO 1808, the module may output data or operate a process. For example, the module may output a signal to one or more delay lines 1814. A delay line 1814 can include a module configured to insert a delay into the path of a signal. The output of a delay line 1814 can be a signal to any number of hardware components of the sensor system 100.

In another example, as illustrated in FIG. 18B, a timing processor system 1801 can include a field-programmable gate array (FPGA) 1816 and hardware, such as a printed circuit board (PCB) 1816. The FPGA 1816 can include a timing generator 1822, one or more delay lines 1824, and one or more deserializers 1826. The PCB 1816 can include one or more ADCs 1828. In some examples, a system 1801 can include a single timing generator 1822 and multiple delay lines 1824, ADCs 1828, and deserializers 1826. For example, the system can include four delay lines 1824, four ADCs 1828, and four deserializers 1826. Other combinations of components are also possible.

The timing generator 1822 can include a processor capable of reading program memory or generating one or more signals. The one or more signals can include timing signals. Timing signals can include a signal for synchronizing different parts of a processing system 1801. For example, a timing signal can include a signal that oscillates between a high and a low state to coordinate actions of circuits in the system 1801. The timing generator 1822 can interact with other components of the system 1801, such as one or more delay lines 1824.

A delay line 1824 can include a module configured to insert a delay into the path of a signal. The output of a delay line 1824 can be a signal to any number of hardware components of the sensor system 100, such as an ADC controller 1828. The delay line 1824 can introduce a determined delay on a scale 1830, such as described with reference to FIG. 18C. In some examples, there may be a plurality of delay lines 1824 for one or more ADCs 1828. Each delay line 1824 may be configured to transmit a signal at a specific programmed delay on the scale 1830 such that an ADC 1828 connected to a delay line 1824 may receive or transmit signals according to the specific programmed delay associated with the delay line 1824.

An ADC controller 1828 can receive a signal from one or more noninvasive sensors. Additionally or alternatively, the ADC controller 1828 can transmit data to one or more computing components, such as a deserializer 1826. The deserializer 1826 can allow the system 1801 to convert serial data from an ADC 1828 into parallel data.

Figure 18C:
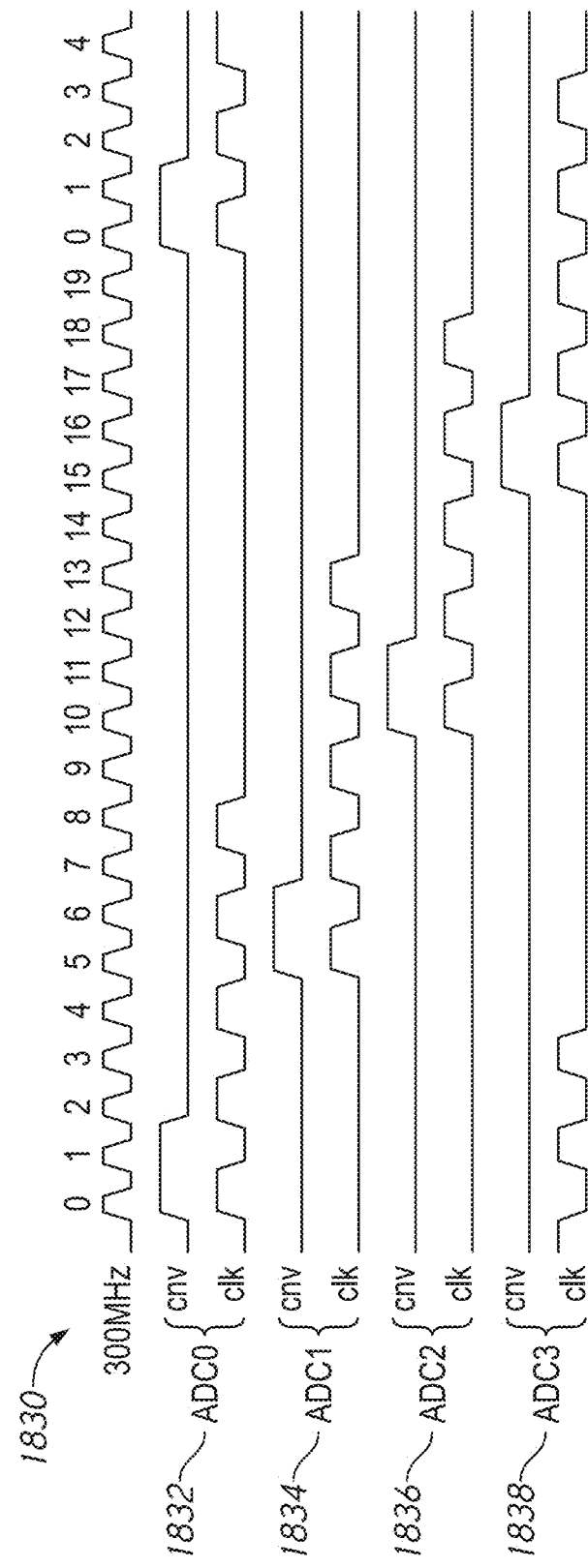
FIG. 18C illustrates an example programmable delay that may be used by the example timing processor of FIG. 18B.

As illustrated in FIG. 18C, the one or more delay lines 1824 may include a conversion start or clock delay for each ADC. The delay for each ADC may be programmable. For example, as illustrated in FIG. 18C, the ADC can be delayed on a scale 1830 anywhere from 0 to 19 on 300 MHz clock cycles. In the illustrated example, there are 4 ADCs, each with a different programmed delay. For example, ADC 0 may have a programmed delay 1832 that includes a conversion start at 0. In another example, ADC 1 may have a programmed delay 1834 that includes a conversion start at 5. In another example, ADC 2 may have a programmed delay 1836 that includes a conversion start at 10. In another example, ADC 3 may have a programmed delay 1838 that includes a conversion start at 15. Those skilled in the arts may recognize that the amount of delay can be any combination, including, but not limited to, no delay.

4. Example Fiber Bundle

An interrogation volume, for example, of a tissue of a patient, may contain multiple layers of varying optical properties, such as absorption and scattering coefficient, anisotropy, refractive index, thickness, etc. A bulk absorbance measurement may contain the summation of a plurality of these properties. This summation can make it difficult to distinguish the contribution of individual analytes to the absorbance measurement.

Figure 19A:
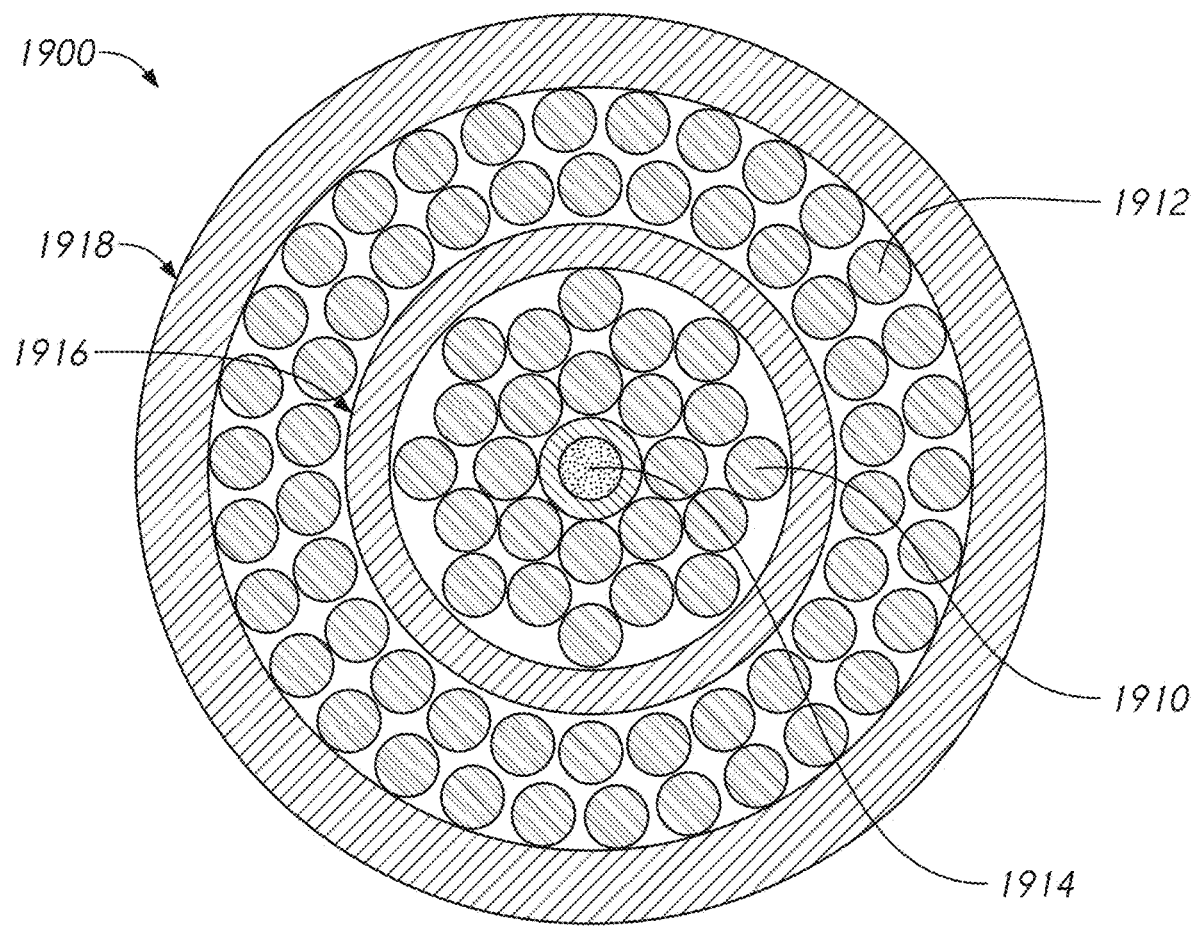
FIG. 19A illustrates an example fiber arrangement in an example absorbance probe head.

FIG. 19A illustrates an example absorbance probe head fiber bundle 1900 that may be part of a Multi-Path Length Probe Head. Advantageously, the probe head fiber bundle 1900 may help reduce the number of unknowns in an absorbance measurement by narrowing the probability distribution of the penetration depth of the light to, for example, photons traveling from the source to detector fibers. Thus, the bundle 1900 can limit the number of unknowns in the absorbance measurement, allowing optical properties of an interrogation volume to be solved within a certain known region of the interrogation volume.

As illustrated in FIG. 19A, an absorbance probe head fiber bundle 1900 can include a set of short path length light source fibers 1910, a set of long path length light source fibers 1912, and one or more detector fibers 1914. The light source fibers 1910, 1912 can be oriented to surround the detector fiber 1914. For example, the detector fiber 1914 can be in the center of fiber bundle 1900. The light source fibers 1910, 1912 can be oriented to encircle the detector fiber 1914. In some examples, the short path length light source fibers 1910 may encircle the detector fiber 1912 to form a central bundle 1916. In some examples, the long path length light source fibers 1912 may encircle the central bundle 1912 to form a larger bundle 1918.

The interrogation volume contains multiple layers of varying optical properties, such as absorption and scattering coefficient, anisotropy, refractive index, thickness, etc. However, a bulk absorbance measurement contains the summation of all these properties, making it very difficult to distinguish the contribution of individual analytes. This probe head narrows the probability distribution of the penetration depth of the light by only accepting photons traveling from the source to detector fibers. Thus, the optical properties can be solved to be within a certain known region, thereby limiting the number of unknowns.

Figures 2, 19B:
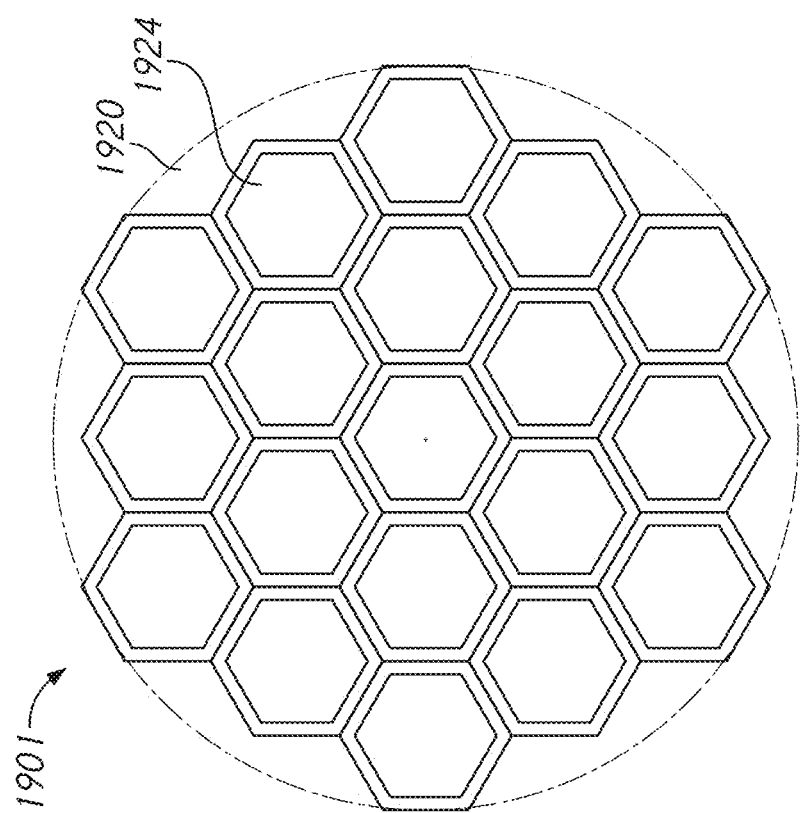
Figures 1, 19B:
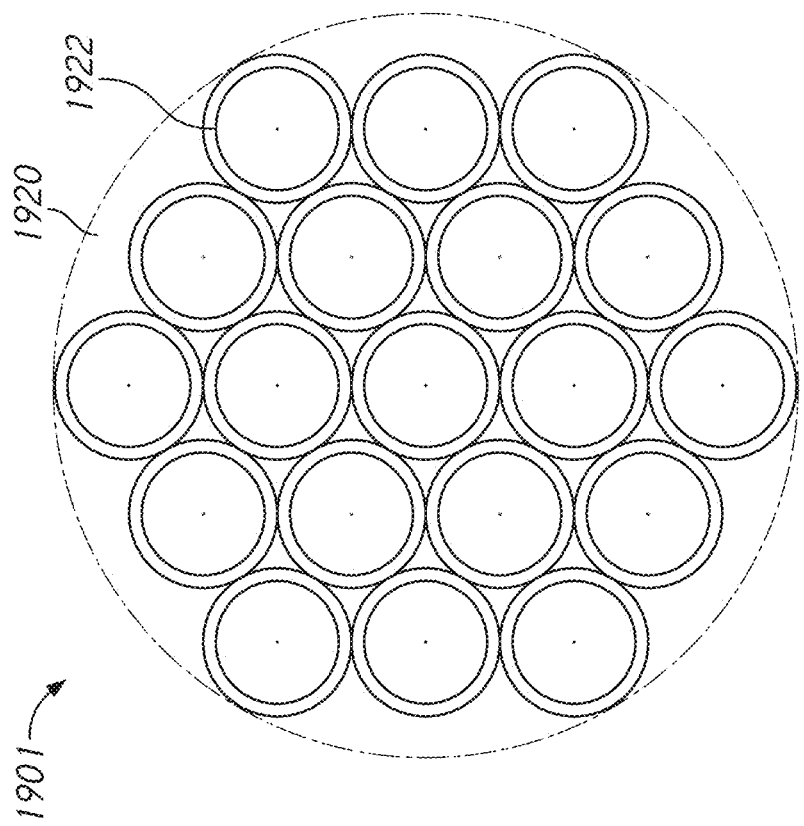

A fiber bundle can include multiple fibers of approximately the same or different shapes or sizes. FIGS. 19B-1 and 19B-2 illustrate example fiber shapes in an example fiber bundle 1901 that may be part of the system 100. For example, the fiber bundle 1901 can be part of an illumination source that may be used with one or more sensors in the system 100. For example, as illustrated in FIGS. 19B-1 and 19B-2, a fiber bundle 1901 can include an illumination or detection area 1920 having multiple fibers. As illustrated in FIG. 19B-1, the area 1920 can include a number of circular fibers 1922 (for example, 19 circular fibers, 20 circular fibers, 11 circular fibers) having a diameter equivalent to five times the diameter of an individual fiber 1922.

The efficiency of illumination or detection through the fiber bundle 1901 within the area 1920 may be affected by the packing density in the area 1920. For example, an increased packing density can increase the efficiency of the fiber bundle 1901. Packing density can be affected by the cross sectional area or shape of individual fibers in the fiber bundle. For example, use of a hexagonal fiber 1924 may increase the packing density in the fiber bundle over use of a circular fiber 1922. As illustrated in FIG. 19B-2, a hexagonal fiber 1924 can reduce or eliminate gaps between fibers within the area 1920. For example, the hexagonal shape of fibers 1924 may allow for packing sides of the hexagonal fibers 1924 to touch. In contrast, the fibers 1922 may have limited contact area between fibers due to their circular shape. Advantageously, use of hexagonal fibers 1924 can result in a packing efficiency of 84 percent, which may in turn improve the efficiency of the fiber bundle 1901, allowing for reductions in weight, size, and cost of the fiber bundle 1901. However, other shapes and packing densities are also possible.

Figure 19C:
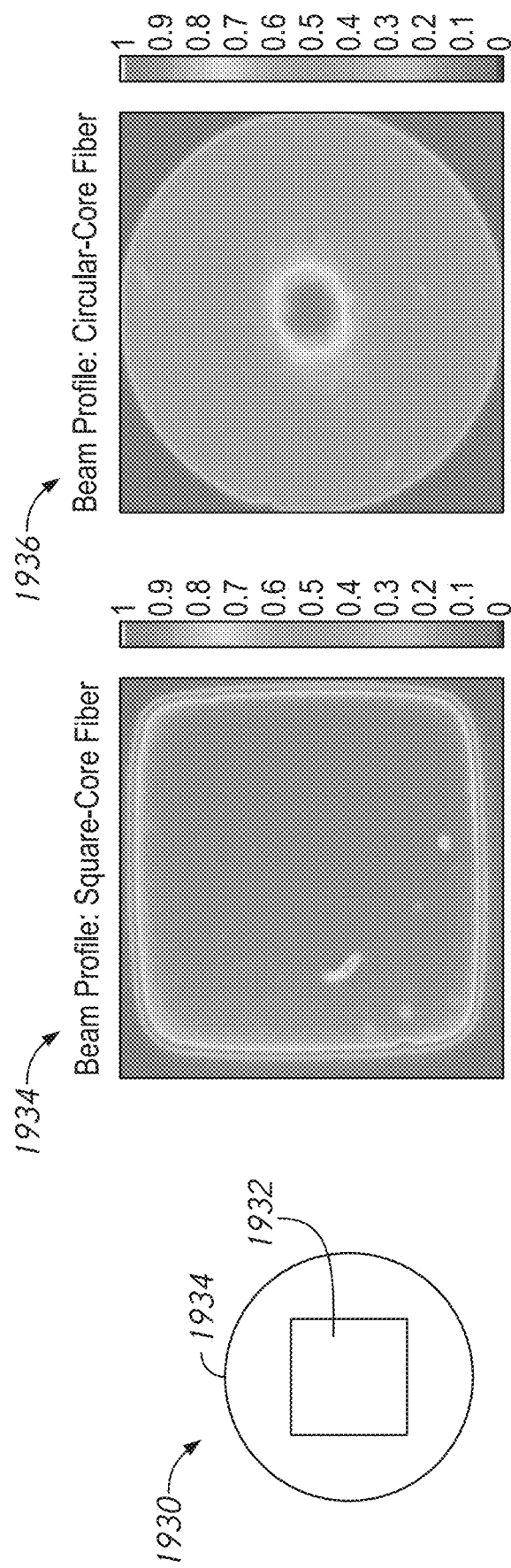
FIG. 19C illustrates an example beam profile associated with different example fiber shapes.

The shape of the fiber core can advantageously improve the beam profile in an illumination source. For example, a cross sectional shape can change the beam profile or intensity of illumination or across the cross section of a fiber core due to differences in mode mixing within the fiber. FIG. 19C illustrates an example beam profile associated with different example fiber shapes. For example, as illustrated in FIG. 19C, a fiber 1930 can include a square core 1932. A cladding 1934 surrounding the square core 1932 can be any suitable shape, such as circular, square, hexagonal, or other shape. Advantageously, a square core 1932 can improve the consistency of illumination intensity across the cross section of the fiber core in comparison to a circular fiber core (not shown) due to improved mode mixing. For example, as shown in inset 1934, the illumination profile of a square fiber core can include mostly consistent or flat output throughout the cross section of the core. In contrast, as shown in inset 1936, the illumination profile of a circular fiber core can include a hot spot in the center of the core corresponding to a Gaussian profile across the cross section of the core. Advantageously, an approximately flat output from a square fiber core (or other suitably shaped fiber core) can improve a patient experience with system measurements by reducing the likelihood that the patient will be burned by a hot spot within the beam.

5. Example Optical Scanning

Patient experience with noninvasive, light-based physiological measurements, such as with the sensors described above can be improved with improved distribution of optical energy in time and space. For example, distributing optical energy can reduce the likelihood that a patient will be burned by an illumination source at a measured tissue site. One way to distribute optical energy is through optical scanning. Advantageously, distributing optical energy, by for example, optical scanning, can allow the system 100 to measure a tissue site of a patient with a more powerful illumination source without burning the patient. The increase in power can increase a signal to noise ratio of a measured signal. The increased signal to noise ratio can not only improve the accuracy of the measurement, but also has the potential to reduce the amount of measurement time needed to perform a measurement.

In some examples, the system 100 can optically scan a tissue site of a patient using a distributed light pattern formed on the tissue site of the patient. The distributed light pattern can be any suitable pattern, such as a Lissajous pattern, raster scan, or other pattern. The optical scanning can be performed within any suitable time frame over any volume. For example, the optical scanning can be performed within a 10 second, 30 second, 1 minute, 5 minute, or any other time frame. The optical scanning can be done continuously or at any fraction of time during the data acquisition time to help optimize the amount of signal from the tissue site at any given measurement time while helping to maximize the comfort of the patient. In another example, the optical scanning can be performed over a tissue site of any suitable size, including but not limited to the full or partial area of a patient's finger nail bed, an area of a patient's skin on their hand, nose, tongue, or other suitable site. In some examples, the interrogated area may be a square centimeter, 2.5 square centimeters, a square centimeter, a square millimeter, 25 square millimeters, or any other suitable size. The optical scanning can be performed at any suitable rate. For example, the optical scanning can be performed at an approximately constant rate over the entire pattern or at a varied rate. Advantageously, performing the scan at a constant rate can provide for a more accurate measurement across the entire tissue site by ensuring measurements are distributed evenly across the tissue site. For example, the tissue site of the patient can be a portion of a patient's finger nail that includes the nail bed. The system 100 can scan, at an approximately constant speed, an illumination source in a distributed light pattern across the patient's finger nail in a Lissajous pattern over a period of one minute to measure a physiological parameter. However, other patterns, time frames, interrogation volumes, or rates of scanning are possible. For example, a scanning speed may be varied in so as to maximize or increase the intensity at any given region of the tissue site.

The system 100 can average detected values or parameters over the scanned interrogation volume or area. Advantageously, averaging the detected values or parameters can create a more reproducible measurement by reducing the effects of noise in individual measurements. For example, the system 100 may scan a tissue site. An individual measurement (of, for example, blood analyte concentration) at a portion of the tissue site may result in an inaccurate result due to, for example, decreased blood volume at that location. Taking and averaging multiple measurements at nearby locations at the tissue site may, therefore, decrease the contribution of that inaccurate measurement to the resulting determined physiological parameter.

The system 100 can scan a tissue site using any number of suitable systems and methods for optically scanning a volume with a sensor probe. FIGS. 20A-20C illustrate example views of mechanisms for scanning a sensor probe. For example, FIG. 20A illustrates an example mirror tilting mechanism for scanning both an excitation and collection beam of a sensor probe. FIG. 20B illustrates an example rotary wedge scanning mechanism. FIG. 20C illustrates an example scanning mechanism for just the excitation beam of a sensor probe.

As illustrated in FIG. 20A, a probe assembly 2000 can include a probe head 2012, a beam steering mirror 2002, a dichroic mirror 2004, an OCT fiber and mirror 2006, a Raman collection fiber 2008, and a Raman laser 2010. The Raman laser 2010 can be configured with respect to the dichroic mirror 2004 so that the Raman laser 2010 (or other excitation source for a Raman sensor) transmits light through the probe head 2012. The Raman collection fiber 2008 can be configured with respect to the dichroic mirror 2004 so that a Raman signal measured through the probe head 2012 propagates back towards the Raman collection fiber 2008. A mirror 2002 can be placed between the probe head 2012 and the dichroic mirror 2004 such that the mirror 2002 falls along the beam path of both the laser light from the Raman laser 2010 and the Raman signal. The system 100 can tilt or otherwise move the mirror 2002 to modify the beam path of both the laser light from the Raman laser 2010 and the Raman signal. For example, as illustrated in FIG. 20A-1, a mirror 2002A (such as the mirror 2002 in FIG. 20A) can tilt to alter a beam path 2001 such that at a probe head 2012A (such as the probe 2012 in FIG. 20A), the beam 2001 moves to different locations 2003A, 2003B, 2003C.

As illustrated in FIG. 20B, a probe assembly 2000 can include a probe head 2012, an OCT fiber and mirror 2006, a Raman collection fiber 2008, a Raman laser 2010, and a rotary wedge 2014. The Raman laser 2010 (or other excitation source for a Raman sensor) can be configured so that the Raman laser 2010 (or other excitation source for a Raman sensor) transmits light through the probe head 2012. The Raman collection fiber 2008 can be configured so that a Raman signal measured through the probe head 2012 propagates back towards the Raman collection fiber 2008. A rotary wedge 2014 can be placed between the probe head 2012 and the Raman laser 2010 or Raman collection fiber 2008 such that the rotary wedge 2014 falls along the beam path of the laser light from the Raman laser 2010 and/or the Raman signal. The system 100 can rotate or otherwise move the rotary wedge 2014 to modify the beam path of both the laser light from the Raman laser 2010 and the Raman signal. For example, as illustrated in FIG. 20B-1, a wedge 2014A (such as the rotary wedge 2014 in FIG. 20B) can rotate to alter a beam path 2001 such that at a probe head 2012A (such as the probe 2012 in FIG. 20B), the beam 2001 moves to different locations 2003A, 2003B, 2003C.

As illustrated in FIG. 20C, a probe assembly 2000 can include a probe head 2012, an OCT fiber and mirror 2006, a Raman collection fiber 2008, a Raman laser 2010, and a beam steering mirror 2016. The Raman laser 2010 can be configured so that the Raman laser 2010 (or other excitation source for a Raman sensor) transmits light through the probe head 2012. The Raman collection fiber 2008 can be configured so that a Raman signal measured through the probe head 2012 propagates back towards the Raman collection fiber 2008. A mirror 2016 can be placed between the probe head 2012 and the Raman laser 2010 such that the mirror 2016 falls along the beam path of the laser light from the Raman laser 2010. The system 100 can tilt or otherwise move the mirror 2016 to modify the beam path of the laser light from the Raman laser 2010. For example, as illustrated in FIG. 20C-1, a mirror 2016A (such as the mirror 2016 in FIG. 20C) can tilt to alter a beam path 2001 such that at a probe head 2012A (such as the probe 2012 in FIG. 20C), the beam 2001 moves to different locations 2003A, 2003B, 2003C.

6. Example Lens System

In some examples of the system 100, a laser or collection beams of one or more sensors may share an optical path. In examples where a collected signal includes Raman or Fluorescence, noise as a result of the Raman or Fluorescence can overwhelm or otherwise adversely affect other portions of the signal. For example, a system 100 can include a Raman sensor and an OCT sensor. Excitation or collection beams from the Raman sensor and the OCT sensor can be configured to share the same or approximately the same optical path. The structural and optical properties derived from OCT may coincide with changes in the Raman signal when the same optical path is shared.

Figure 21A:
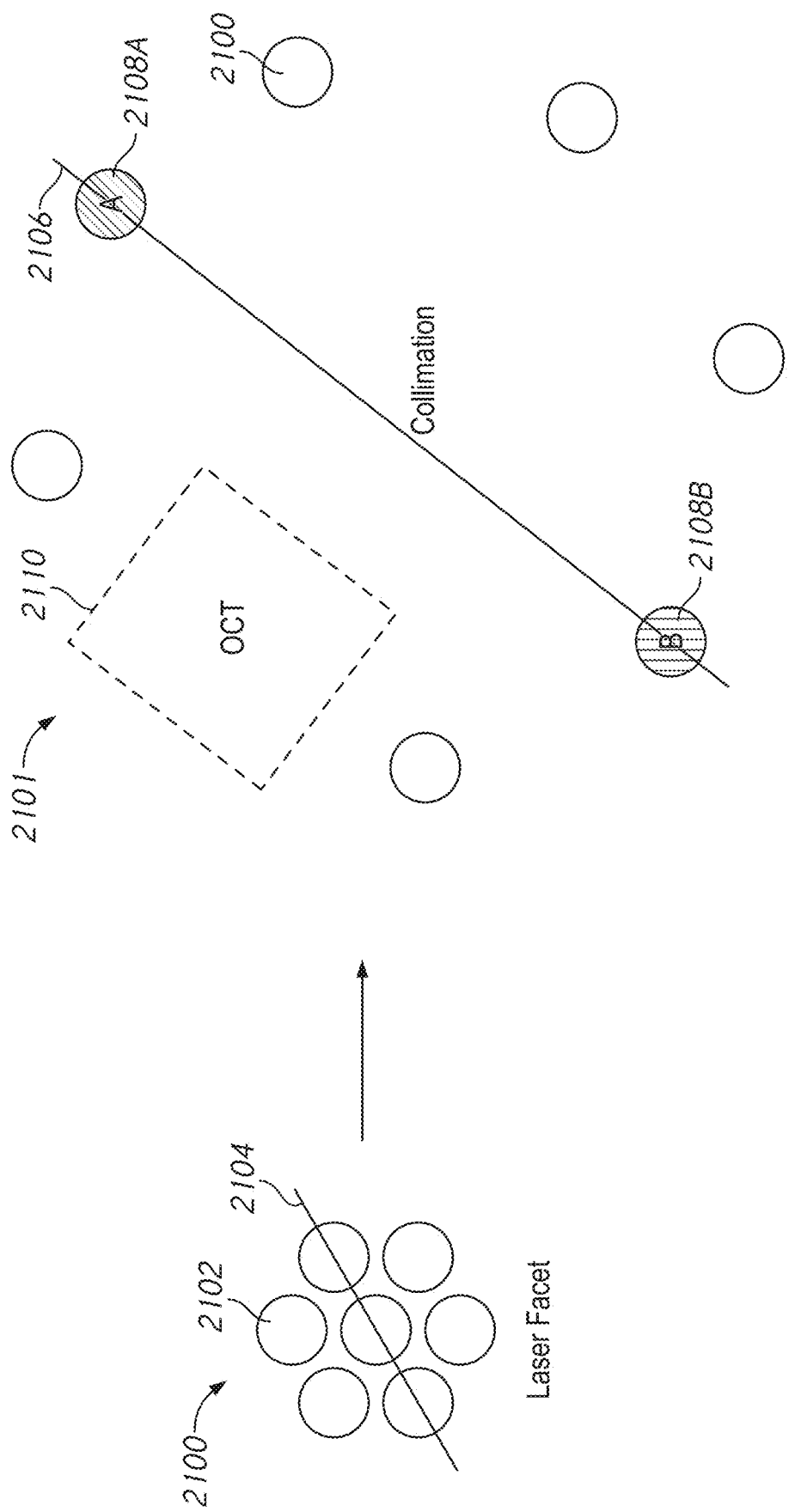
FIG. 21A illustrates an example configuration of sensor lasers that may be transmitted towards an example lens system in a sensor system.
Figure 21B:
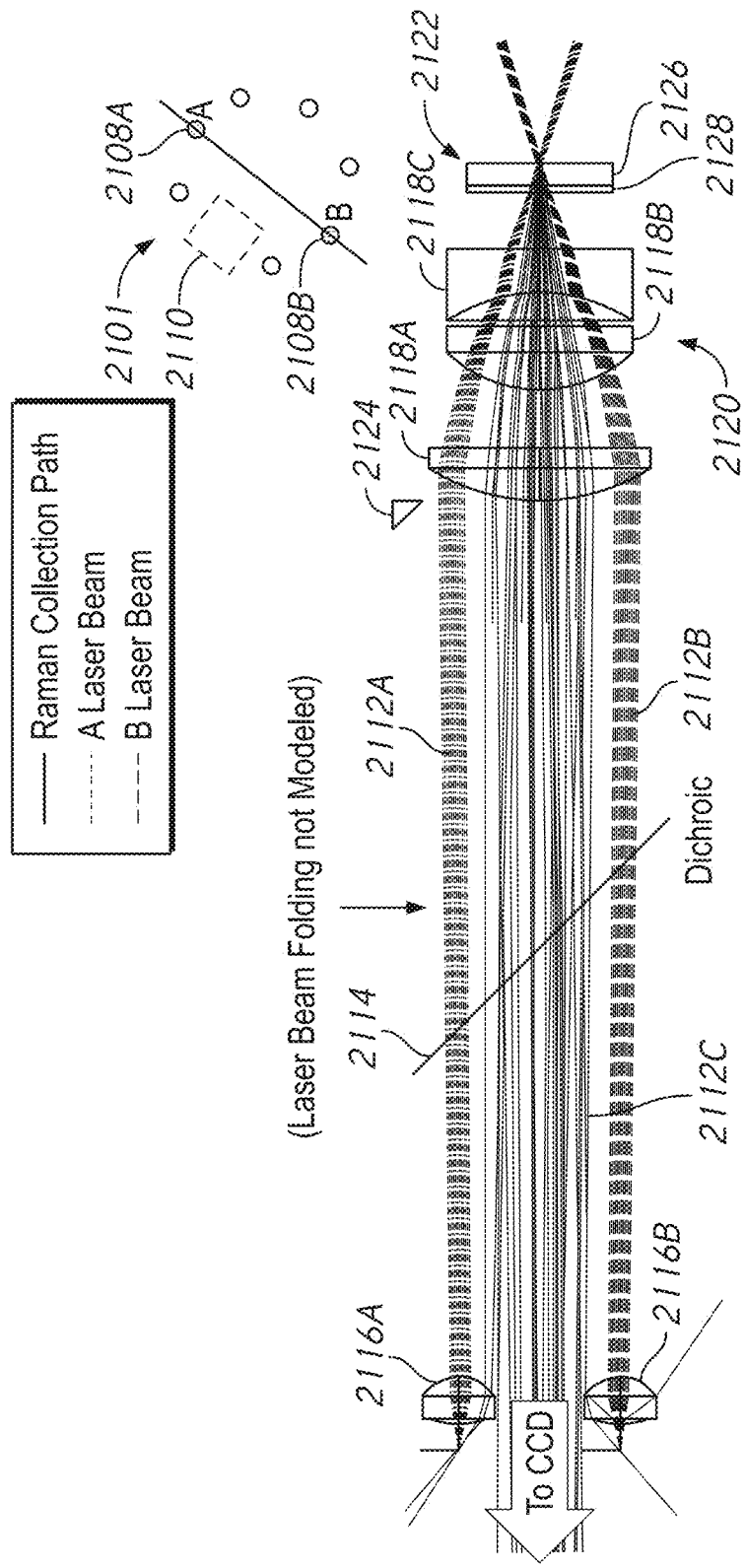
FIG. 21B illustrates an example beam path of different sensor lasers that may be transmitted through an example lens system.
Figure 21C:
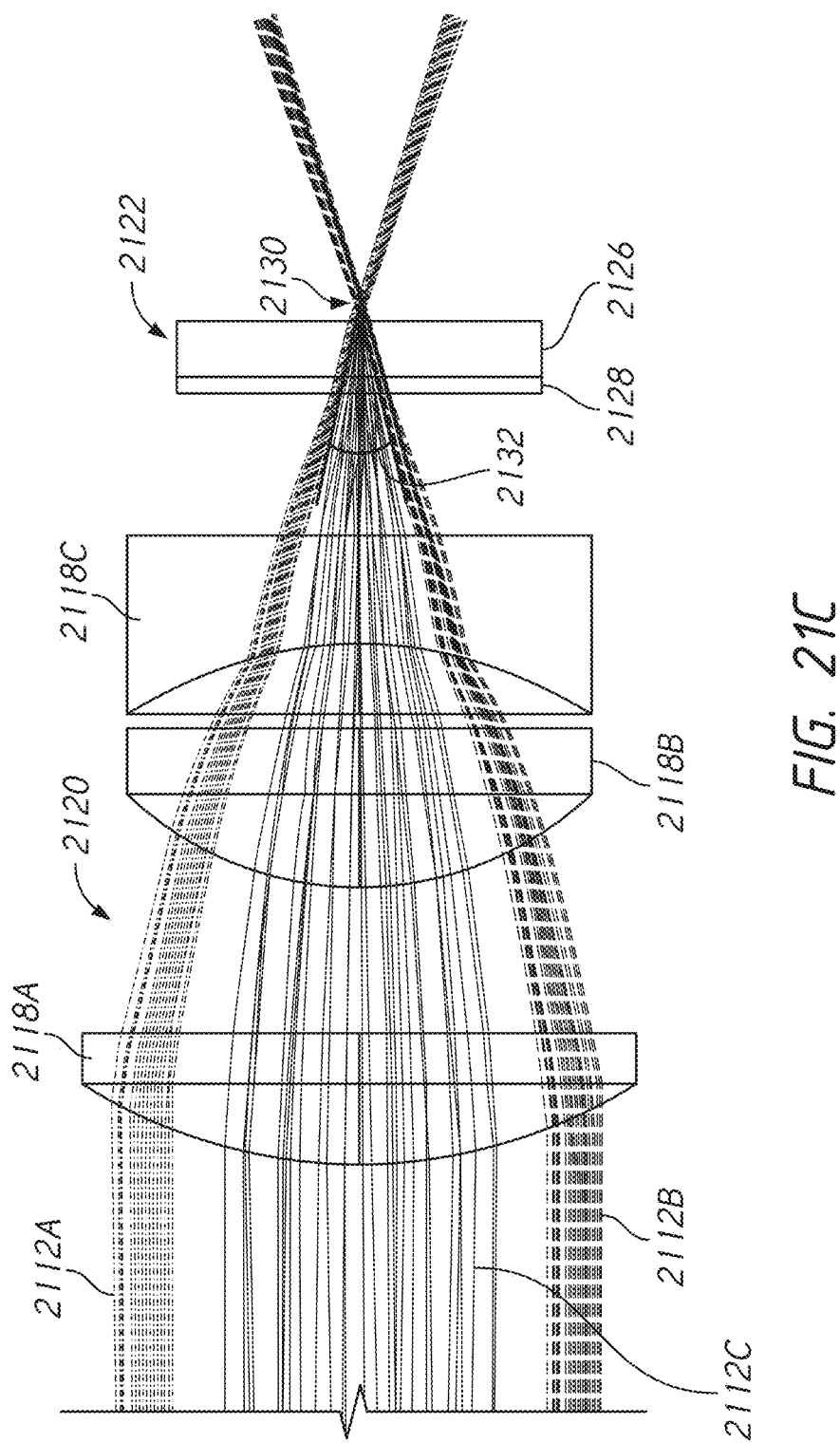
FIG. 21C illustrates an example cone angle of an example collection path.

FIGS. 21A-21C illustrates example lens systems that may help bypass unwanted signals (such as Raman and Fluorescence from superficial layers containing no or few analytes of interest) and preserving wanted signals (such as Raman analytes of interest like glucose) where an optical path may be shared between sensor collection beams in a sensor system 100.

A system 100 may include multiple sensors. The multiple sensors may include one or more excitation or collection beams. In some examples, an excitation source for one or more sensors can include a single fiber source (for example, a single 100 micron fiber to deliver light). In other examples, the excitation source for one or more sensors can include one or more fiber bundles. For example, as illustrated in FIG. 21A, an example sensor bundle 2101 can include one or more fiber bundles 2100 of sensor lasers.

As illustrated in FIG. 21A, a sensor bundle 2101 can include one or more fiber bundles 2100 of multiple fibers 2102 each. Any number of configurations of fibers 2102 and fiber bundles 2100 are possible. The fibers 2102 in the fiber bundle 2100 may be any suitable size and shape. For example, the fibers 2102 may be 50 micron in diameter circular fibers. In another example, the fibers 2102 may be 70 micron in diameter hexagonal fibers. In another example, the fibers 2102 may be 40 micron in width square fibers. A width or diameter 2104 of a fiber bundle 2100 can be any suitable size, such a 165 micron, 200 micron, 100 micron or other size.

With continued reference to FIG. 21A, a sensor bundle 2101 can include any number of configurations of fibers 2102, fiber bundles 2100, 2108A, 2108B or other sensor components (such as an OCT illumination source 2110). For example, a sensor bundle 2101 can include multiple fiber bundles 2100, 2108A, 2108B and one or more OCT illumination sources 2110 in a circular configuration. However, the configuration can be any suitable size and shape, such as a square, triangle, star, or other shape. The fiber bundles 2100, 2108A, 2108B may be spaced such that light from the fiber bundles 2100, 2108A, 2108B or one or more OCT illumination source 2110 is collimated and configured to propagate towards a tissue sample. For example, the light from multiple fiber bundles 2100, 2108A, 2108B and one or more OCT illumination sources 2110 can have a collimation spacing 2106 of 11 mm, 15 mm, 5 mm or other suitable size.

FIG. 21B illustrates an example beam path through an example lens system 2120 of excitation and collection beams that may be emitted by illumination sources in an example sensor bundle 2101. For example, laser light 2112A may be emitted by a fiber or fiber bundle, such as fiber bundle 2108A, in sensor bundle 2101. The laser light 2112A may be collimated by collimating optics 2116A and propagate towards a tissue site 2122. In another example, laser light 2112B may be emitted by a fiber or fiber bundle, such as fiber bundle 2108B, in sensor bundle 2101. The laser light 2112B may be collimated by collimating optics 2116B and propagate towards a tissue site 2122. Laser light from other fibers, fiber bundles, or illumination sources can be similarly collimated and propagate towards a tissue site 2122 along a substantially parallel beam path to light 2112A and 2112B.

With continued reference to FIG. 21B, a lens system 2120 can refract light 2112A, 2112B or other light along the beam path of 2112A, 2112B to converge at or near a tissue site 2122. The lens system 2120 can include focusing optics, such as one or more convex or plano-convex lenses 2118A, 2118B, one or more concave or plano-concave lenses 2118C, or other type of lens or optical element. The lens system 2120 can be configured to cause laser light 2112A, 2112B or other light to converge at any number of depths at or near the tissue site 2112. For example, a tissue site 2122 can include an epidermis layer 2128 and a dermis layer 2126. The laser light 2112A, 2112B can be configured to converge at a focal point 2130 that may be within the dermis layer 2126 or at another point at or near the tissue site 2122. However, other depths are possible.

A signal 2112C that may be emitted from the tissue site 2122 can follow a collection path to a detector (not shown). FIG. 21C illustrates an example collection cone angle 2132 of an example collection path. The cone angle 2132 can correspond to an acceptance angle of a collection fiber (not shown). The cone angle 2132 can be any suitable angle, such as 15 degrees, 20 degrees, 26 degrees, 40 degrees or other angle.

Figure 22A:
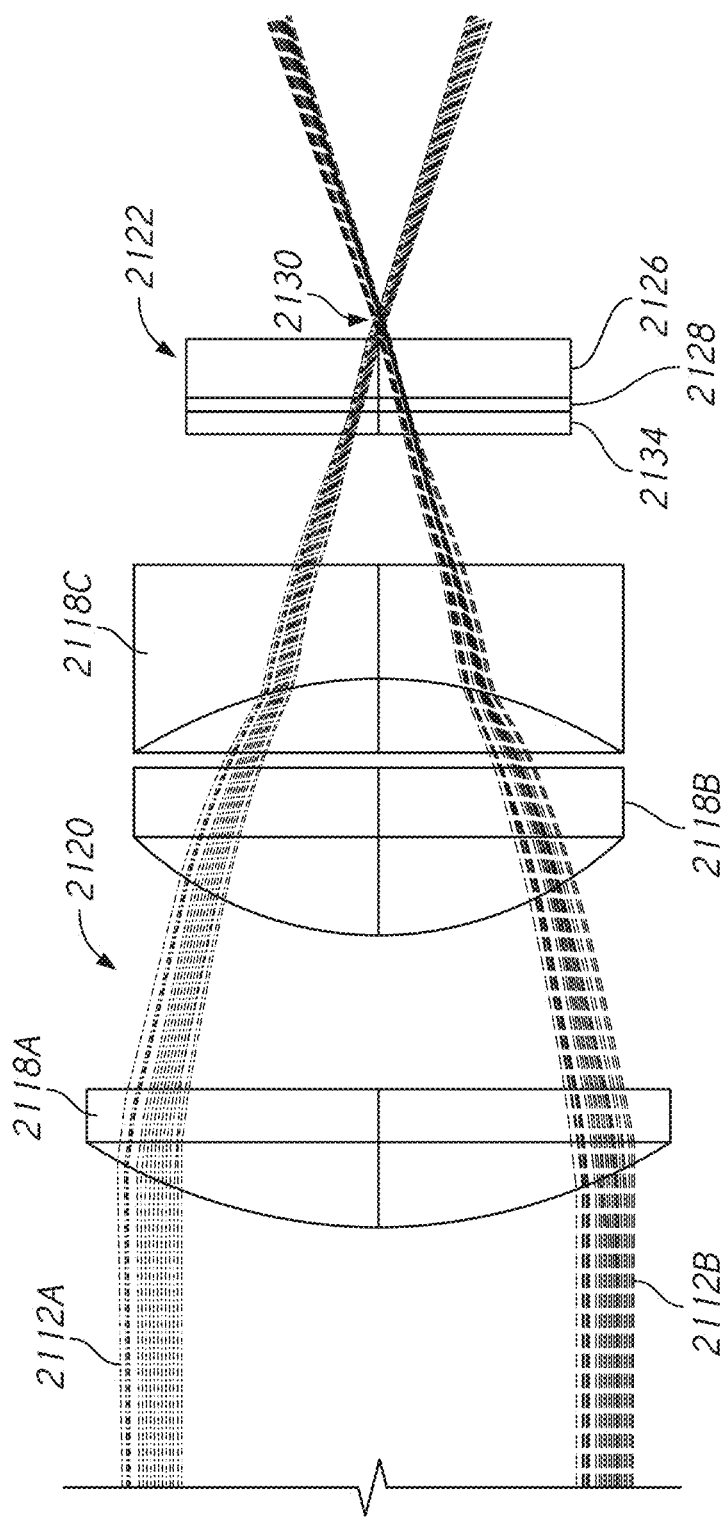
FIG. 22A illustrates an example measurement through an example window.
Figure 22B:
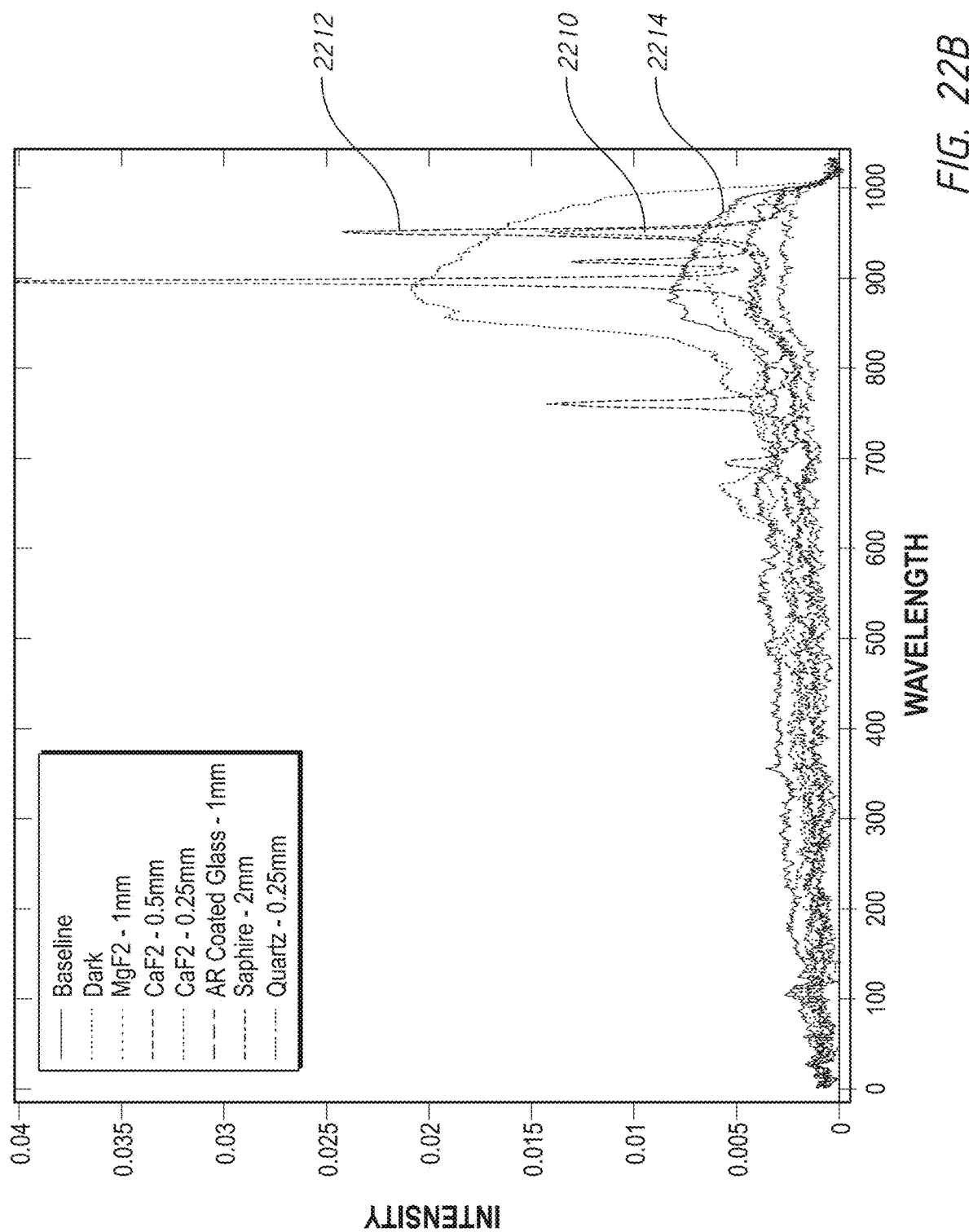
FIG. 22B illustrates an example measurement using a variety of windows that can include CaF2.

As illustrated in FIG. 22A, a system 100 can include a window 2134. The window 2134 can be placed between the lens system 2120 and a tissue site 2122. Advantageously, the choice of material for the window 2134 can reduce the amount of unwanted Fluorescence that is coming from window substrates at the tissue site while still protecting the optics inside from outside environment. The window 2134 can be any suitable material, including but not limited to Calcium Fluoride, Magnesium Fluoride, Sapphire, and Quartz. The window 2134 can be any suitable thickness, including but not limited to 0.25 mm, 0.5 mm, 1 mm, or other thickness. Advantageously, as illustrated in FIG. 22B, different window configurations can change the amount of Fluorescence collected by the system 100. For example, a Calcium Fluoride window of 0.5 mm thickness, represented by line 2212, or a Calcium Fluoride window of 0.25 mm thickness, represented by line 2210, can reduce the amount of measured Fluorescence by up to two times less than baseline, represented by line 2214. The reduced Fluorescence can advantageously help to improve the tissue signal to noise ratio.

Figure 23A:
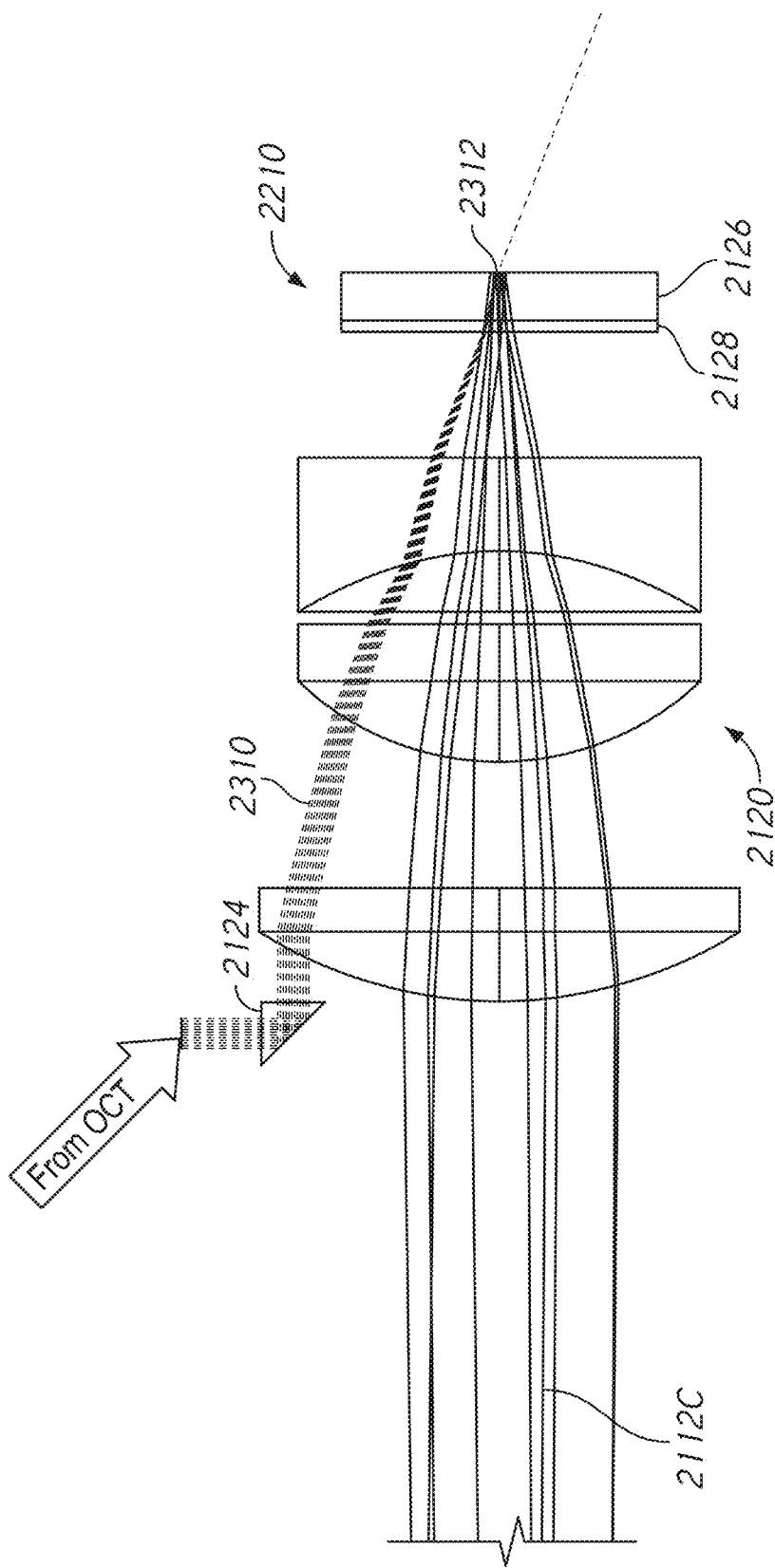
FIGS. 23A-23C illustrates an example beam path of a sensor source that may use an example OCT and Mirror lens.
Figure 23B:
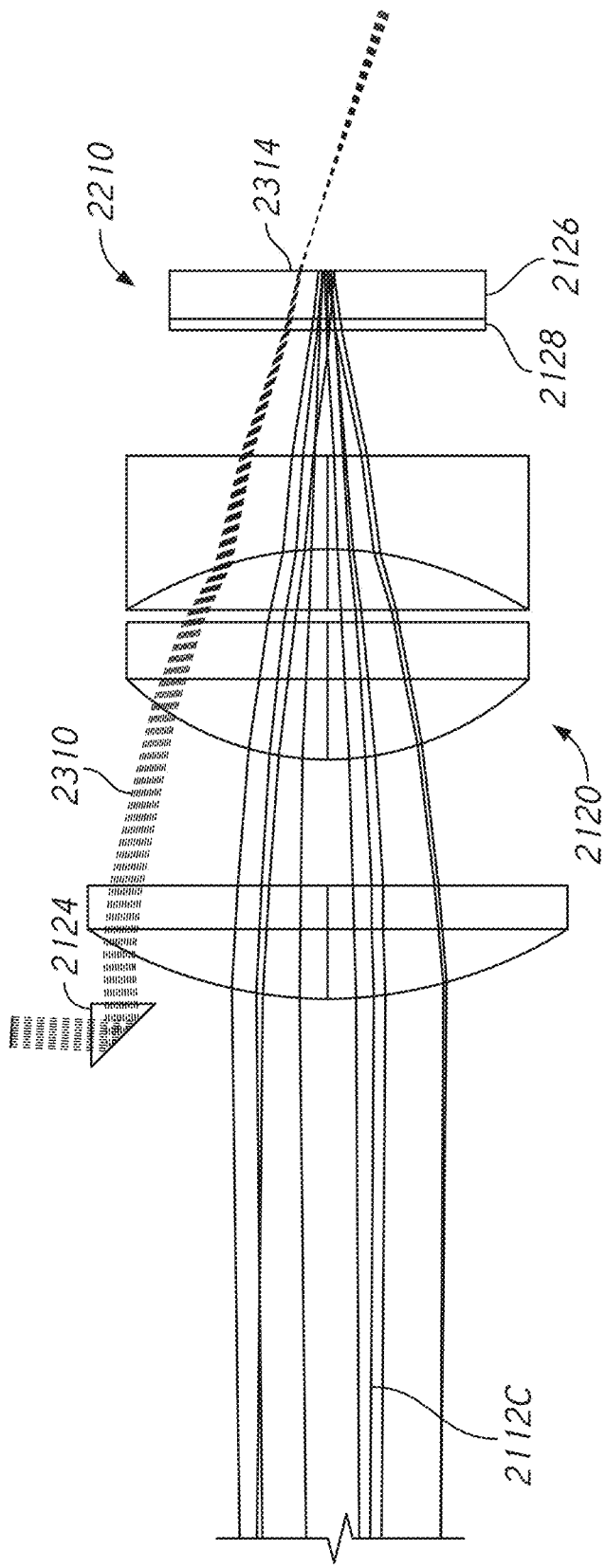
Figure 23C:
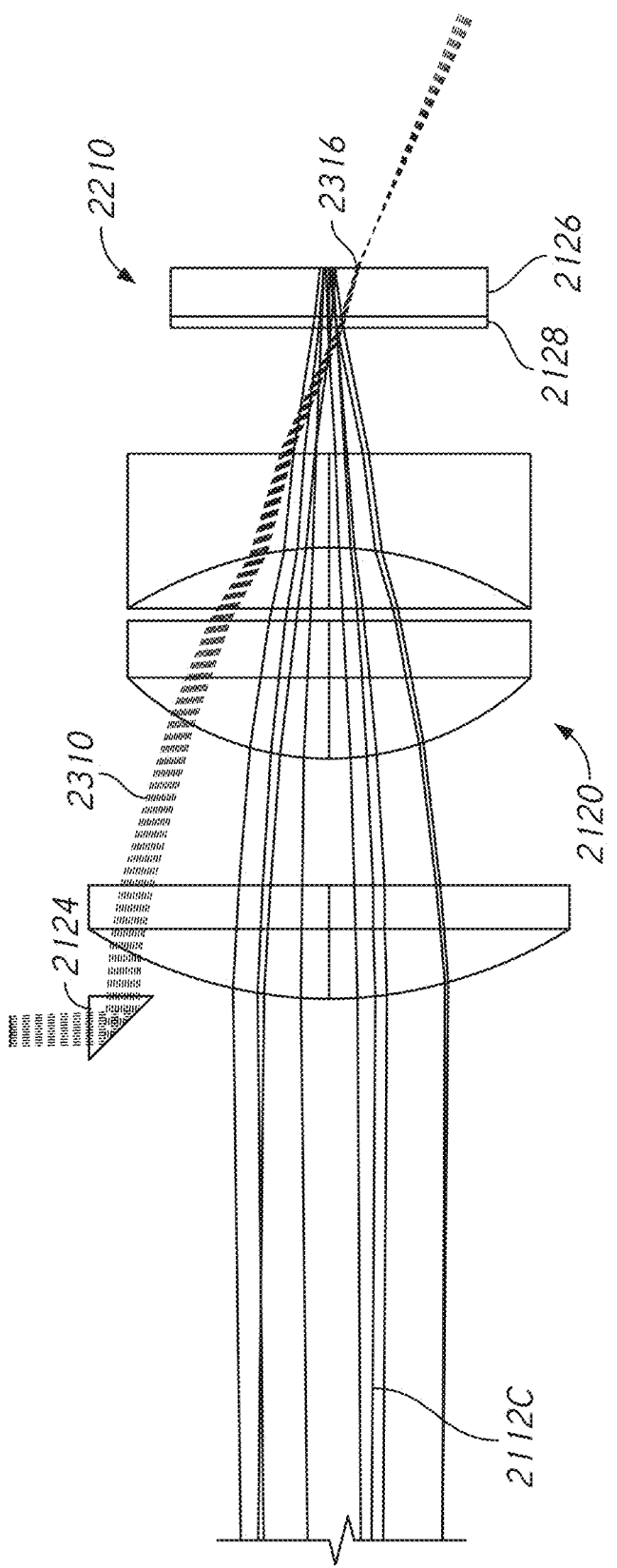

In some examples, the lens system 2120 can include a prism lens 2124. The prism lens 2124 can orient an illumination source beam 2130, such as an OCT illumination beam from an OCT illumination source, to travel along a similar path as the excitation beams 2112A, 2112B, and collection beams 2112C. An orientation of the prism lens 2124 with respect to other components of the lens system 2120 can allow an illumination source beam 2130 to interrogate an area or volume of the tissue site 2210 at or near the area or volume of the tissue site 2210 interrogated by the excitation beams 2112A, 2112B or other beams associated with other sensor. FIGS. 23A-23C illustrate various configurations of an example prism lens that may be part of the lens system 2120 that may correspond to different interrogated areas or volumes of the tissue site 2210. For example, as illustrated in FIG. 23A, the prism can be oriented to direct the beam 2310 to interrogate a location 2312 of the tissue site corresponding to a center or approximate center of the area or volume interrogated by the excitation beams 2112A, 2112B or other beams associated with other sensor. In another example, as illustrated in FIG. 23B, the prism can be oriented to direct the beam 2310 to interrogate a location 2314 of the tissue site corresponding to an area or volume near the area or volume interrogated by the excitation beams 2112A, 2112B or other beams associated with other sensor. In another example, as illustrated in FIG. 23C, the prism can be oriented to direct the beam 2310 to interrogate a location 2316 of the tissue site corresponding to another area or volume near the area or volume interrogated by the excitation beams 2112A, 2112B or other beams associated with other sensor.

Advantageously, the lens system 2120 can allow the system 100 to bypass regions of useless tissue signal, as described above. Additionally, the lens system 2120 can reduce the chance of burning a patient at the tissue site by spreading out the excitation light over a larger area of the tissue in comparison to a single beam. Additionally, the lens system 2120 can allow for a smaller probe head by allowing for OCT and Raman to coexist in a similar beam path in comparison to separating OCT and Raman beams.

7. Example Heating System

A system 100 can include a heating system for increasing the temperature of the tissue site of the patient. Advantageously, in some examples, heating a tissue site of a patient can improve a signal. In some examples, heating a tissue site of a patient can give information about water content or properties of the tissue, such as specific heat, density, or volume. In some examples, heating a tissue can provide patient specific data due to differences in patient response to heating.

Figure 24:
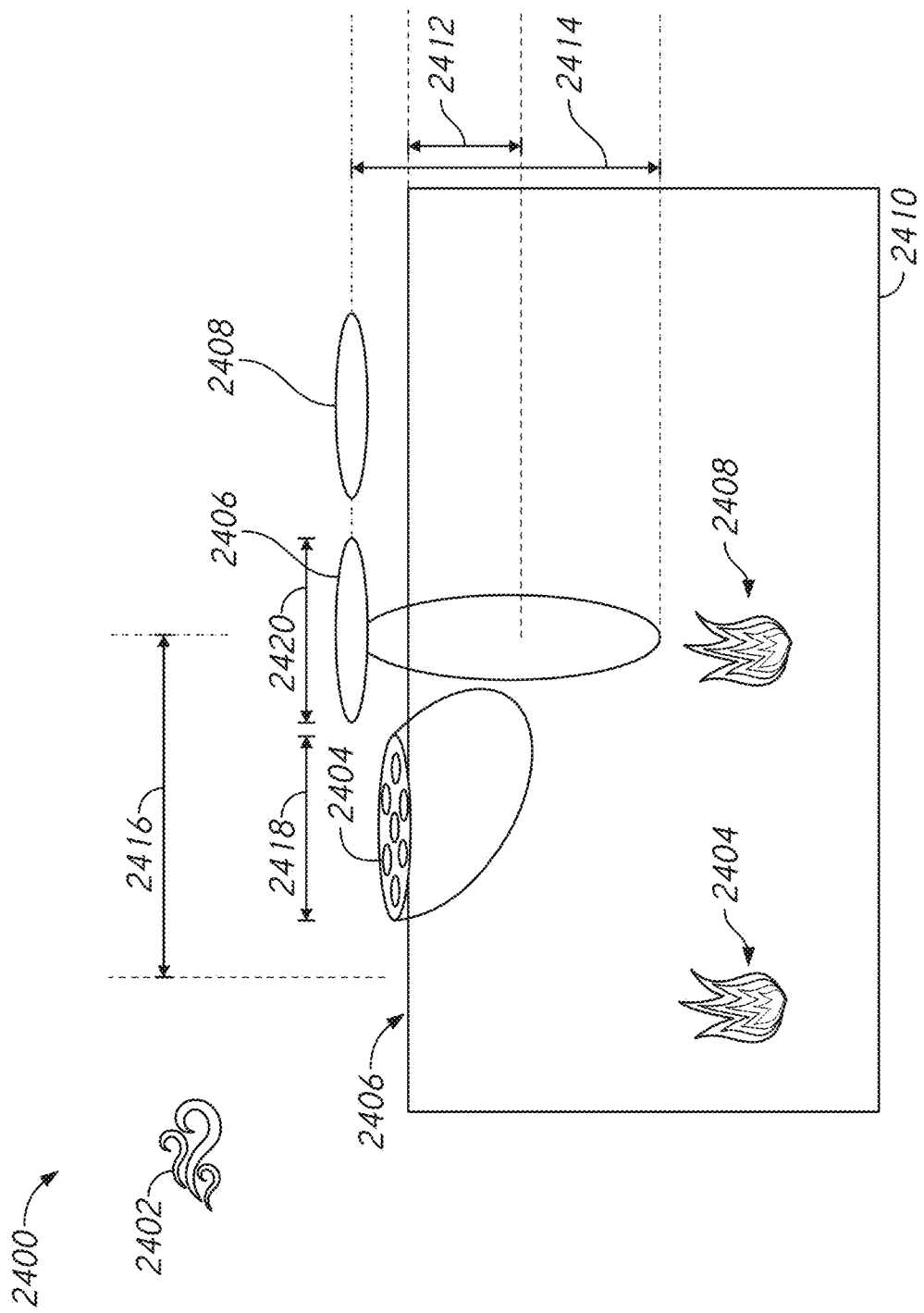
FIG. 24 illustrates an example heating environment that may be part of a sensor system.

FIG. 24 illustrates an example temperature environment 2400 in which a sensor system 100 may operate. For example, a temperature environment 2400 can include an ambient temperature 2402, a body temperature 2404, a surface temperature 2406, and radiant heating 2408. In some examples, a temperature environment 2400 can include an absorbance sensor 2404, a Raman sensor 2406, or an OCT sensor 2408. Need different number for surface temperature and/or Raman sensor; OCT sensor and/or radiant heating; Absorbance sensor and/or body temperature.

An absorbance sensor 2404 can interrogate the tissue 2410 of the patient at a depth 2412 over an area inside the tissue 2410 with a width 2418. The depth 2412 can correspond to a focal point of an absorbance sensor 2404 below the surface of the tissue. The depth 2412 can be any number of depths, including but not limited to 1.4 mm, 1.5 mm, 1.6 mm, or other depths. The width 2418 can include any number of widths, including but not limited to 2.5 mm, 3 mm, 3.5 mm, or other width. A Raman sensor 2406 can interrogate the tissue 2410 of the patient at a depth 2414 over an area with a width 2420. The depth 2414 can be any number of depths, including but not limited to 4.4 mm, 4.5 mm, 4.6 mm, or other depths. The width 2420 can include any number of widths, including but not limited to 2.25 mm, 2.5 mm, 3 mm, or other width. In some examples, the interrogation volume can overlap in whole or in part or can be separate within the tissue site. For example, a total cross section of the measured interrogation volume can have any number of widths, including but not limited to 4 mm, 5, mm, or 6 mm.

The temperature environment 2400 can affect the signal associated with different sensors, such as an absorbance sensor 2404, Raman sensor 2406, or OCT sensor 2408. For example, different sensors may interrogate a tissue site at different depths or cross sections within a tissue 2410. Temperature at the different depths or cross sections can vary. For example, the surface temperature 2406 of the tissue 2410 can be cooler than an interior body temperature 2404 that may be at a deeper depth within the tissue 2410 or than a temperature within an tissue site that may be heated by radiant heating 2408 due to sensor excitation sources, such as a laser associated with a Raman sensor 2406. Additionally or alternatively, an ambient temperature 2402 of the air or other medium surrounding the tissue site 2410 or the natural body temperature of the patient can cool the tissue site 2410. Thus, sensors that interrogate volumes at different depths or cross sections within the tissue 2410 can change based on the temperature within that volume.

The temperature in the tissue site 2410 can be determined by solving a set of differential equations. For example, the temperature in an interrogation volume may be determined by both radiant heating and cooling. A change in temperature over time (dT/dt) due to radiant heating by a laser can be modeled by the following equation:

$$\frac{dT}{dt} = \frac{A(T)*P}{\rho*V*c}\frac{dT}{dt} = \frac{A(T)*P}{\rho*V*c}$$ (Equation 7)

where A(T) is absorbance of the tissue site 2410 as a function of temperature, P is laser power, p is the density of the interrogation volume, V is interrogation volume, and c is specific heat. A change in temperature over time (dT/dt) due to cooling as a result of the ambient temperature can be modeled by the Newton's law of cooling:

$$\frac{dT}{dt} = -k1(T - T_a)$$ (Equation 8)

where k1 is a constant characteristic of the system and $T_a$ is an ambient temperature of the environment surrounding the tissue 2410. The solution of the above differential equation is:

$$(t)=(T_0-T_a)e^{-k1t}+T_a$$ (Equation 9)

A change in temperature over time (dT/dt) due to heating or cooling as a result of the ambient temperature of the body (body heat) can be modeled by Newton's law of cooling:

$$\frac{dT}{dt} = -k2(T - T_b)$$ (Equation 10)

where k2 is a constant characteristic of the system and $T_b$ is the body temperature. The solution of the above differential equation is:

$$T(t)=(T_0-T_b)e^{-k2t}+T_a b$$ (Equation 11)

Using the above equations, a model of temperature as a function of laser heating, ambient cooling, and body heat can be determined. For example, using Euler's method, a change in temperature can be modeled as:

$$dT[n] = \frac{A(T)*P}{\rho*V*c} - k_1(T[n] - T_a[n]) - k_2(T[n] - T_b[n])$$ (Equation 12)

where n corresponds to a point in time. Using the above equation, a temperature at a time n can be determined by calculating the incremental change in temperature:

$$T[n+1]=T[n]+dT[n]*dt$$ (Equation 13)

FIG. 25A illustrates an example heating of an interrogation volume over time at different wavelengths of a laser that may radiantly heat the interrogation volume. For example, in the illustrated example, a radiant heating cycle can include a baseline portion 2504, a heating portion 2506, and a cooling portion 2508. The baseline portion 2504 can include a period of time in which there is no added radiant heating from a sensor excitation source, such as a Raman laser. The heating portion 2506 can include a period of time in which an excitation source, such as a Raman laser, is incident on a tissue site or otherwise transfers energy to the tissue site. The cooling portion 2508 can include a period of time in which an excitation source, such as a Raman laser, is no longer incident on a tissue site or otherwise transferring energy to the tissue site.

With continued reference to FIG. 25A, graph 2501 shows surface temperature of a tissue site 2410 as a function of time (represented by line 2510), a modeled output of temperature as function of time (represented by line 2512), a predicted body temperature as a function of time (represented by line 2514), and an ambient temperature (represented by line 2516).

The model associated with model output 2512 of graph 2501 includes an absorbance, A, of 0.128, a first constant, k1, of 0.0075, and a second constant, k2, of 0.0065. The model may be initialized using surface temperature data obtained during a baseline 2504 measurement. As illustrated in graph 2501, a model output 2512 of temperature can approximately track the surface temperature 2510 over time during a heating 2506 and cooling 2508 cycle.

With continued reference to FIG. 25A, graph 2502 shows change in absorbance over time at different wavelengths of an excitation source, such as a Raman laser over the baseline 2504, heating 2506, and cooling 2508 cycles.

Additionally or in the alternative to the model of temperature of the tissue sample as a function of time described above, temperature can be modeled using Legendre polynomials. For example, temperature can be modeled using a discrete legendre transform (DLT):

$$L_x(k) = \frac{2k+1}{N}\sum_{t=-1}^{t=1} x(t) \cdot P_k(t)$$ (Equation 14)

where the inverse discrete Legendre transform (IDLT) is:

$$x(t) = \sum_{k=0}^{k=k_{max}} L_x(k) \cdot P_k(t)$$ (Equation 15)

Figure 25B:
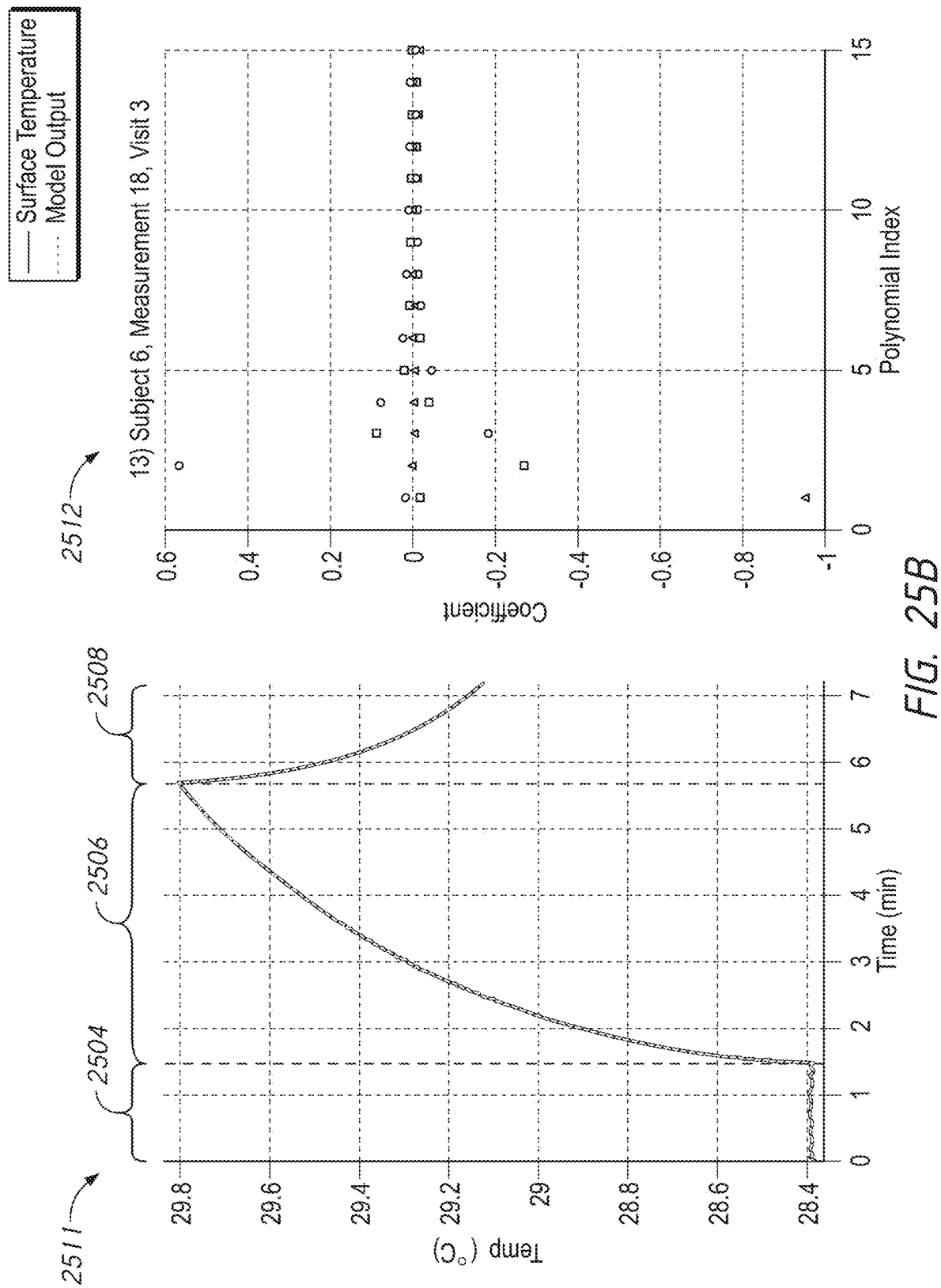
FIG. 25B illustrates a Legendre polynomial heating model.

FIG. 25B shows a graph 2511 that includes a Legendre polynomial model and surface temperature over a radiant heating cycle that can include a baseline portion 2504, a heating portion 2506, and a cooling portion 2508. The model may be initialized using surface temperature data obtained during a baseline 2504 measurement. As illustrated in graph 2511, the Legendre polynomial model of temperature can approximately track the surface temperature over time during a heating 2506 and cooling 2508 cycle.

With continued reference to FIG. 25B, graph 2512 shows a Legendre polynomial coefficient value as a function of polynomial index for the example Legendre polynomial model in graph 2511.

8. Air Gap Detection

Patient movement or poor tissue site placement during measurement by a noninvasive sensor can adversely affect data quality. For example, patient movement or poor tissue site placement can result in air gaps between the sensor surface and the tissue site. The presence of these air gaps may deviate from the designed working parameters of a sensor instrument and reduce the quality of collected data. Thus, detecting such events can be important to filter out data with an air gap by, for example, post-processing or development of regression algorithms to predict a physiological parameter. Additionally or alternatively, if such events can be detected during measurement, data collection procedures can be actively corrected to improve the quality of the data.

Figure 26:
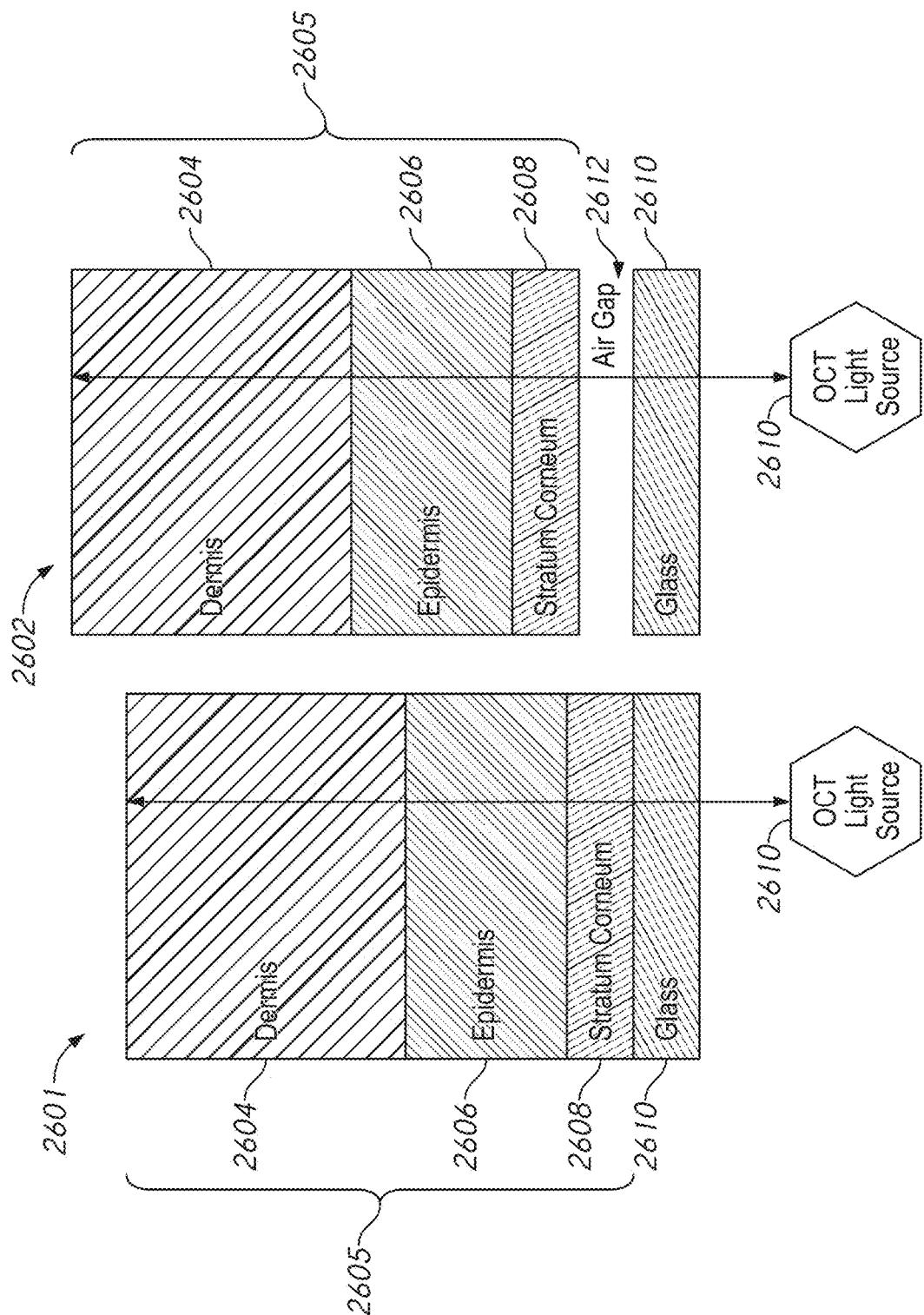
FIG. 26 illustrates an example representation of a patient measurement site interacting with a probe head surface.

FIG. 26 illustrates example representations of a patient measurement site interacting with a sensor or probe head surface both with and without an air gap. For example, representation 2601 shows tissue layers 2605 (which can include the dermis 2604, epidermis 2606, and stratum corneum 2608) of a tissue site of a patient touching or adjacent to sensor surface 2610 through which a sensor light source 2610 may transmit light. In another example, representation 2602 shows tissue layers 2605 above a sensor surface 2610 such that there is an air gap 2612 between the top tissue layer 2608 and the sensor surface 2610.

Figure 27:
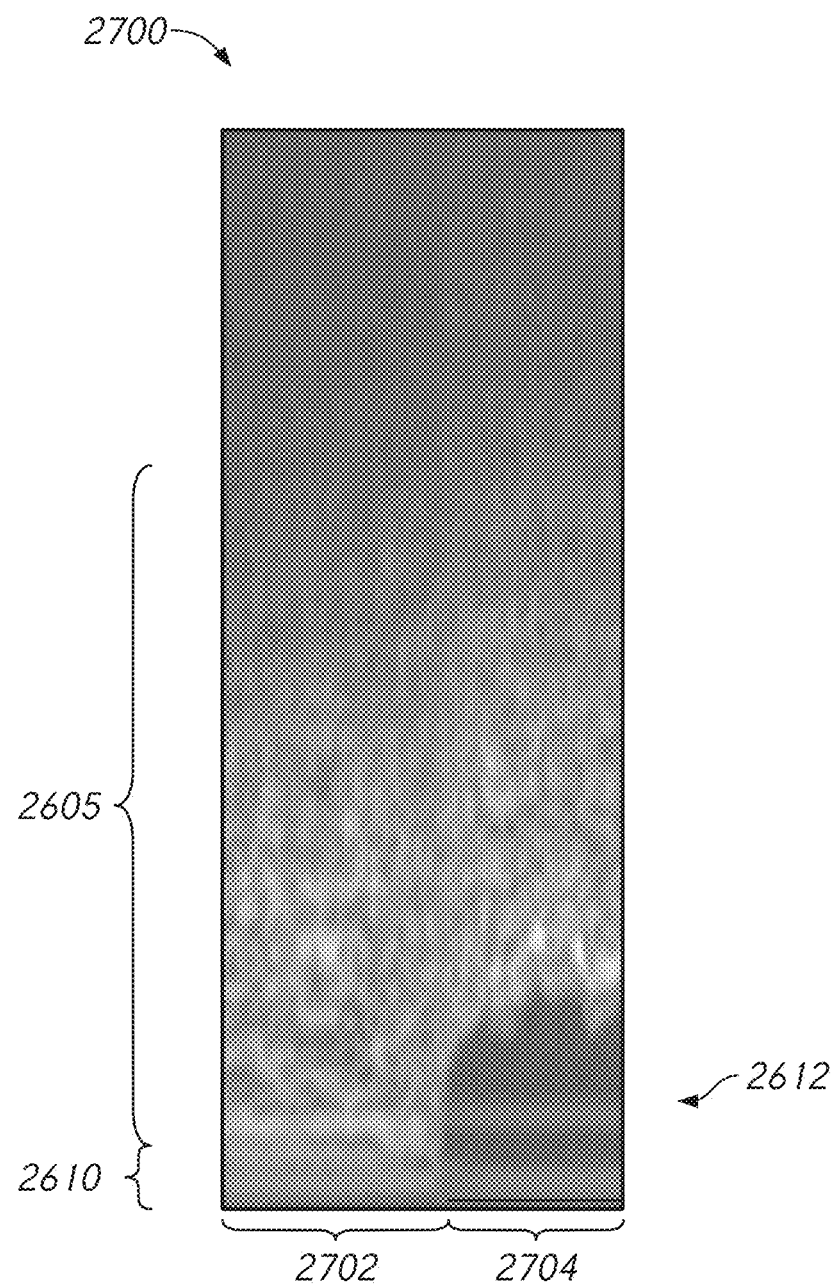
FIG. 27 illustrates an example measurement with an air gap.

FIG. 27 illustrates example OCT sensor data 2700 where a patient moves the tissue site to produce an air gap 2612 during measurement. For example, data 2700 can include 75 A-scans by an OCT sensor of tissue layers 2605. In the first 35 frames 2702, the patient keeps the tissue site against the glass 2610. In the last 40 frames 2704, the patient moves the tissue site so that the there is an air gap 2612 between the tissue layers 2605 and the glass 2610.

Figure 28:
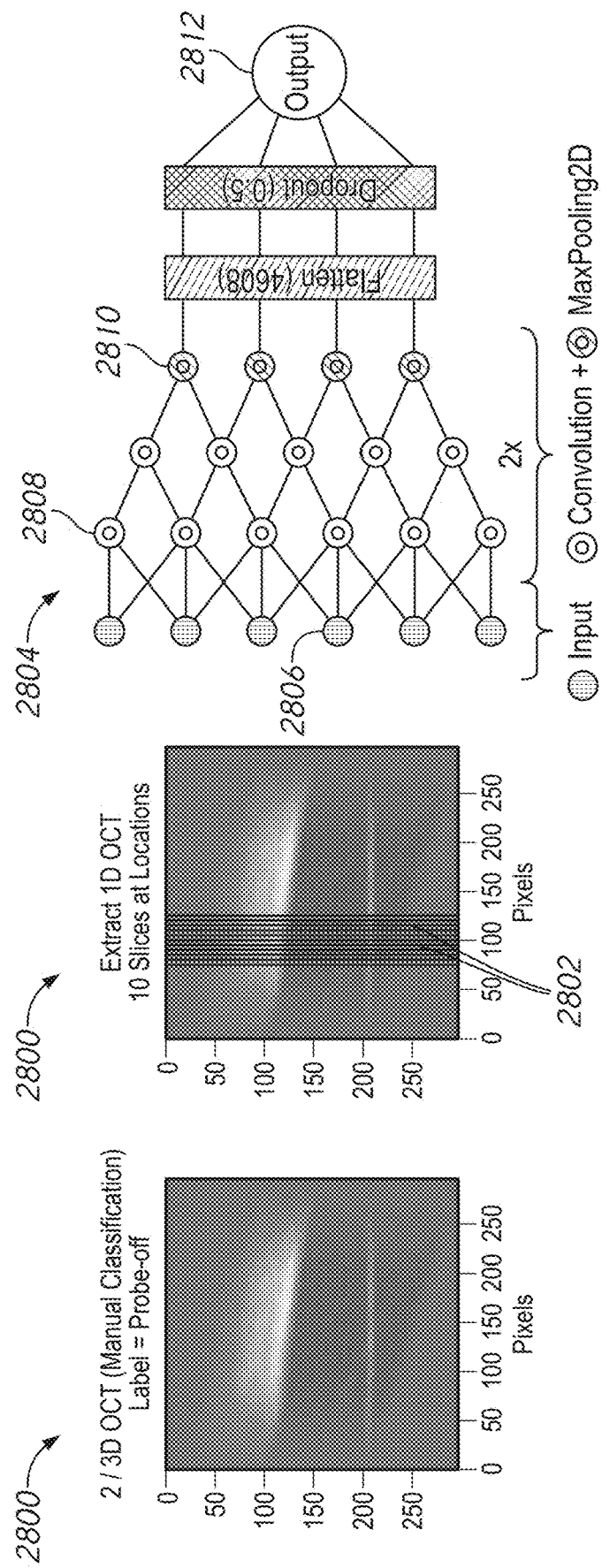
FIG. 28 illustrates an example air gap detection process.

One method for detecting an air gap is by machine learning. FIG. 28 illustrates an example air gap detection process using machine learning. For example, the air gap detection process may involve training a machine learning algorithm, such as a convolutional neural network (CNN), using a training set of OCT images that are sorted, for example, into classes, such as a "probe on"/contact class or "probe off"/air-gap class.

A Convolutional Neural Network (CNN) is a Deep Learning algorithm which takes in an input image, assigns importance (or weights) to various areas in the image and be able to differentiate one from the other. The architecture of a CNN is inspired by the organization of the Visual Cortex and designed to mimic the connectivity pattern of Neurons in the Human Brain. Individual neurons respond to stimuli only in a localized subregion of the entire visual field, also known as the Receptive Field. A collection of such overlapping subfields is used in a CNN architecture to cover the entire visual area of the image.

As illustrated in FIG. 28, an OCT image 2800 can be manually or otherwise classified as being a "probe off" image such that there is an air gap in the image 2800 or a "contact" image such that there is no or minimal air gap in the image 2800. The system 100 can then extract data from the image 2800, such as one dimensional (1D) slices 2802 of the image 2800 at different pixel locations within the image 2800. The extracted data may be used to train a machine learning algorithm, such as a convolutional neural network (CNN) 2804. The trained CNN 2804 may predict whether an image is a "probe on"/contact image or a "probe off"/air-gap image. For example, data from acquired images may be accepted by the CNN 2804 at one or more inputs 2806. The data may then be processed through one or more convolutional layers 2808 or pooling layers 2810. The system 100 may perform further processing of the data before predicting an output 2812. The output 2812 can include a prediction of a whether the image is a contact image or a probe off image.

A CNN is able to successfully capture the spatial dependencies and relationships in an image through the application of several filters or alternatively also called a kernel or feature detector. Each filter performs a transformation of the original image to extract a certain representation, for example detecting edges, sharpen, blurring, curves detection, line detection, etc. among many others. These transformations are learnt to specifically adapt to the problem, in this case air gap detection, during the training process of CNN Deep Learning Algorithm. During the training procedure, the neural network is mathematically directed to understand link between all the images in the training set and its corresponding image classes. Once trained, the network is output as a set of weights, which can now detect the difference between the classes: airgap and contact. These weights can be reused to classify new OCT image data previously unseen by the neural network during the training procedure.

Figure 29:
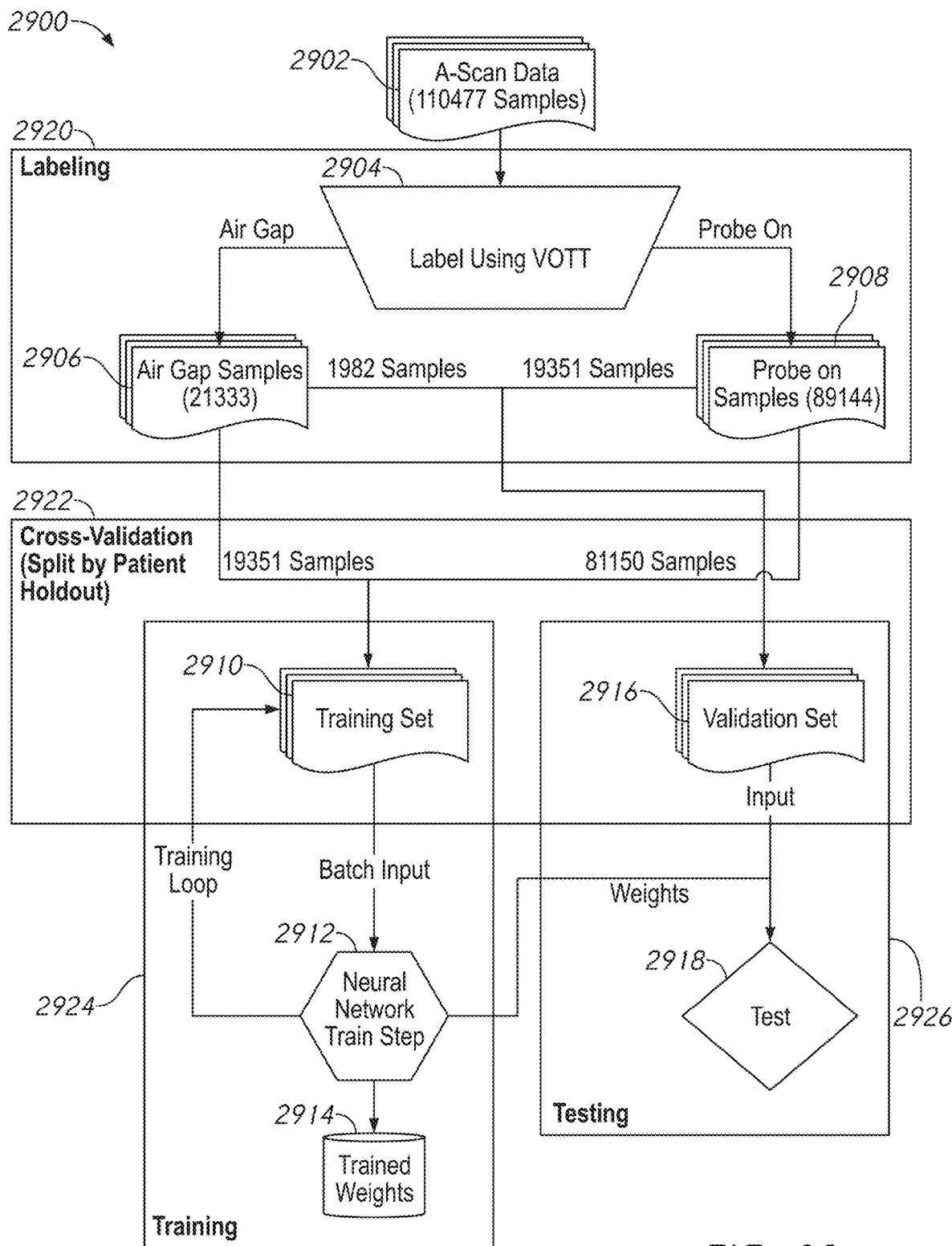
FIG. 29 illustrates an example procedure for training a neural network to determine the presence of an air gap.

FIG. 29 illustrates an example procedure for training a neural network to determine the presence of an air gap. For example, a training procedure 2900 can include a labeling step 2920, a cross validation step 2922, a training loop 2924, and a testing loop 2926.

The labeling step 2920 can include labeling data 2902, such as A-scan OCT data. For example, the locations of air gaps/"probe off" or "probe on" can be labeled manually using, for example, an open source tool called VOTT 2904 released by Microsoft research. In some examples, a total of 110,477 A-scans were classified manually into 89144 "probe on" 2908 and 21333 "probe off" 2906 classes, which can also be referred to as ground-truth labels. The labeled dataset could then be used to train and validate a convolutional neural network by cross-validation.

The cross-validation step 2922 can include dividing the dataset from step 2920 into a training set 2910 and a validation set 2916. In some examples, the division can be done by holding out all samples from a single patient (all visits) into the validation set 2916. The rest of the data can be used as the training set 2910. In some examples, multiple instances of the neural network can be trained by holding out data from different patients. In one example, four independent networks were trained by holding out patients 4, 17, 22 and 33, who all had 5 separate visits to the clinical study. For example, by holding out patient number 4, the training set 2910 consisted of 100501 samples (A-scan) and 9976 samples in the validation set 2916.

The training loop 2924 can include a training step 2912 for determining trained weights 2914 based on the training set 2910. For example, each A-Scan within a training set 2910 can be treated as an image with reduced dimensions, such as 1×296 pixels (or a 1D "slice" of an OCT image). At the training step 2912, the CNN can capture the spatial relationship of the image data. The CNN may then perform a fit to the image dataset to determine one or more weights 2914 that reduce error in predicted classifications 2918 of images as contact or air gap images during a test loop 2926.

Figure 30:
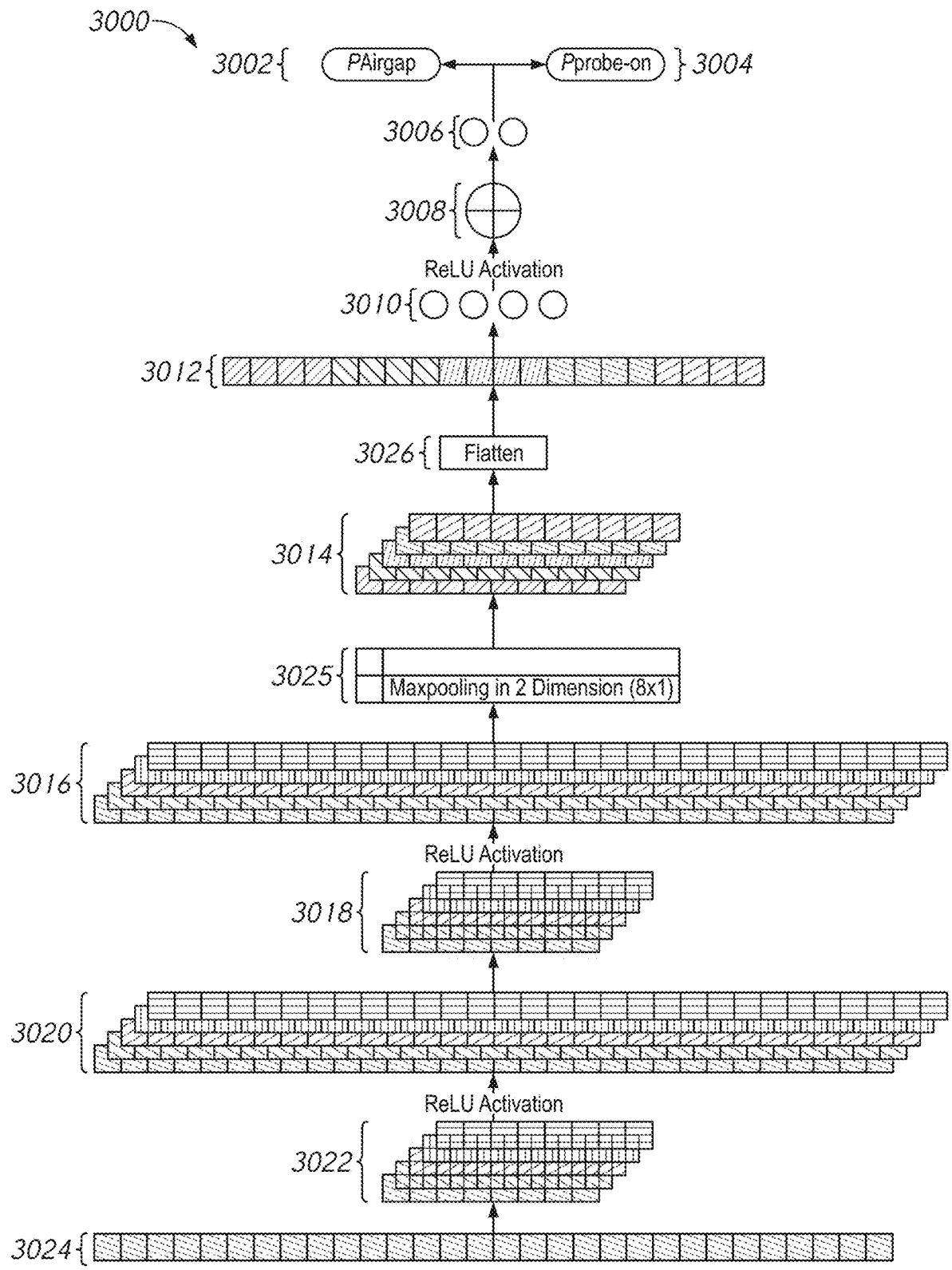
FIG. 30 illustrates an example neural network architecture for air gap detection.

FIG. 30 illustrates an example neural network topology 3000 for air gap detection. For example, the topology 3000 can include an input image 3024 which is processed into a convolution layer 3022, a first convolved image 3020, a convolution layer 3018, a second convolved image 3016, a maxpooling layer 3025, a maxpooled image 3014, a flattening layer 3026, a flattened image 3012, a first dense layer 3010, dropout 3008, a second dense layer 3006, and an air gap classification 3002 or a probe on (or contact) classification 3004. One or more of the neural network layers may have a set of associated weights. One or more of the neural network layers, such as the maxpooling layer 3025, flattening layer 3026 or dropout 3008, may lack a set of associated weights.

The input image 3024 can include a 1D OCT A-scan. The input image 3024 can have the dimensions of 296×1 pixels or any other suitable dimensions. The input image 3024 can be processed in a convolutional layer 3022 to produce a first convolved image 3020. The convolutional layer 3022 can filter or generate features from the input image 3024 using weights, such as the weights 2914 discussed with reference to FIG. 29. In some examples, the input image can be convolved through 8 different filters in the first convolutional layer 3022 which results in an image 3020 having dimensions of 296×1×8 pixels or any other suitable dimensions. The dimensions may vary according to the number of filters chosen in the convolutional layer 3022. The first convolved image 3020 can be processed by a Rectified linear unit (ReLU) activation layer or other suitable activation layer that may apply a nonlinear transformation function to its pixel values. This first convolved image 3020 after applying ReLU activation can be additionally processed in a convolutional layer 3018 consisting of 4 filters to produce a second convolved image 3016. The convolutional layer 3018 can filter or otherwise generate a set of features from the first convolved image 3020 using weights, such as the weights 2914 discussed with reference to FIG. 29. The second convolved image 3018 can have reduced or otherwise different dimensions from the first convolved image, such as the dimensions of 296×1×4 pixels or any other suitable dimensions which is dependent on the number of filters in the convolutional layer 3018. The second convolved image 3018 can be processed by a Rectified linear unit (ReLU) activation layer or other suitable activation layer that may apply a nonlinear transformation function to its pixel values. The second convolved image 3018 after applying a nonlinear transformation can be processed by one or more pooling layers to reduce the dimensionality of the second convolved image 3018 to a maxpooled image 3014. The maxpooled image 3014 can have reduced or otherwise different dimensions from the second convolved image 3016, such as the dimensions of 36×1×4 pixels or any other suitable dimensions. Such a maxpooled layer can serve the function of picking the "most important" features from the convolved image 3016. The maxpooled image 3014 may then be flattened into a flattened image 3012. The flattened image 3012 can have dimensions such as 144×1 pixels or any other suitable dimensions. A flattened image is a simple transformation to rearrange the pixels to create a two-dimensional array to facilitate mathematical operations of the following layers. The flattened image 3012 may be processed in a dense layer or fully connected layer 3010 to determine which features in the flattened image 3012 correlate to a probe on class 3002 or a probe off class 3004. The first dense layer 3010 may determine any number of features associated with the flattened image 3012, such as 4 features. The output of the first dense layer 3010 can be processed by a Rectified linear unit (ReLU) activation layer or other suitable activation layer that may apply a nonlinear function. The output of the ReLU or other layer can be processed to dropout units in the CNN. A dropout layer 3008 may be applied during the training procedure to "stabilize" the mathematical operations that assign weights to all the layers in the CNN. Dropout is a technique where randomly selected neurons from the previous layer, in this case first dense layer 3010, is ignored during training. The dropout process 3008 can include a dropout of, for example, 75 percent of the units in the CNN. Dropout layer 3008 may be removed from the network during classification of new OCT image data previously unseen by the neural network. The second dense layer 3006 may determine any number of features associated with the output of the dropout process 3008, such as 2 features. The CNN may analyze the output of the second dense layer 3006 to determine a probability that the input image 3024 should have an air gap "probe off" probability 3002 or a contact "probe-on" probability 3004.

With continued reference to FIG. 30, the training procedure of CNN starts by randomly initializing the weights associated with each neural network layer except for max-pooling layer 3025, flattening layer 3026 and dropout 3008. A first forward pass of the training procedure predicts a set of "probe on" probability 3004 and "probe off" probability for a given pair of OCT image and associated ground-truth label determined from labeling procedure The difference between the predicted probabilities and ground-truth label may be calculated as a gradient and this gradient can be mathematically propagated through the weights in neural network layers, this step can also be referred to as back-propagation. Backpropagation adjusts the weights in the neural network layers such that the probability prediction moves slightly closer towards the ground-truth label. Then the procedure forward pass and backpropagation can be repeated for as many times as necessary to obtain a user-defined performance level in classifying a given OCT image into "probe off" or "probe on" classes.

Figure 31:
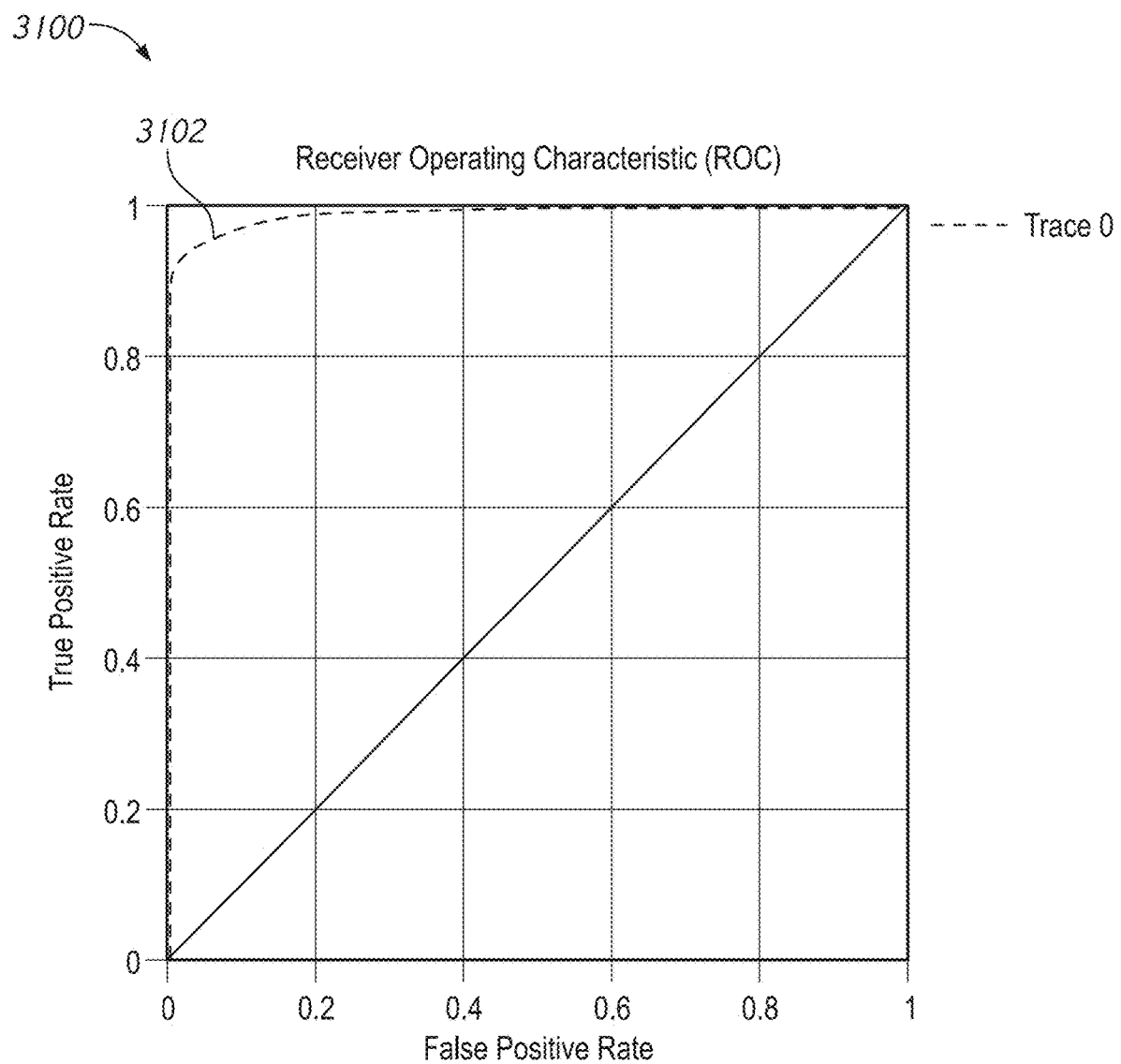
FIG. 31 illustrates an example network performance.

FIG. 31 illustrates an example network performance 3100 of a CNN with an architecture of FIG. 30. For example, as illustrated in FIG. 31, a CNN with architecture 3000 was able to classify input images within 10 epochs of training (in other words, using 10 times the number of images in the training set), where the number of evolution of accuracy over a number of epochs is represented by line 3102.

9. OCT Signal Processing

Figure 32:
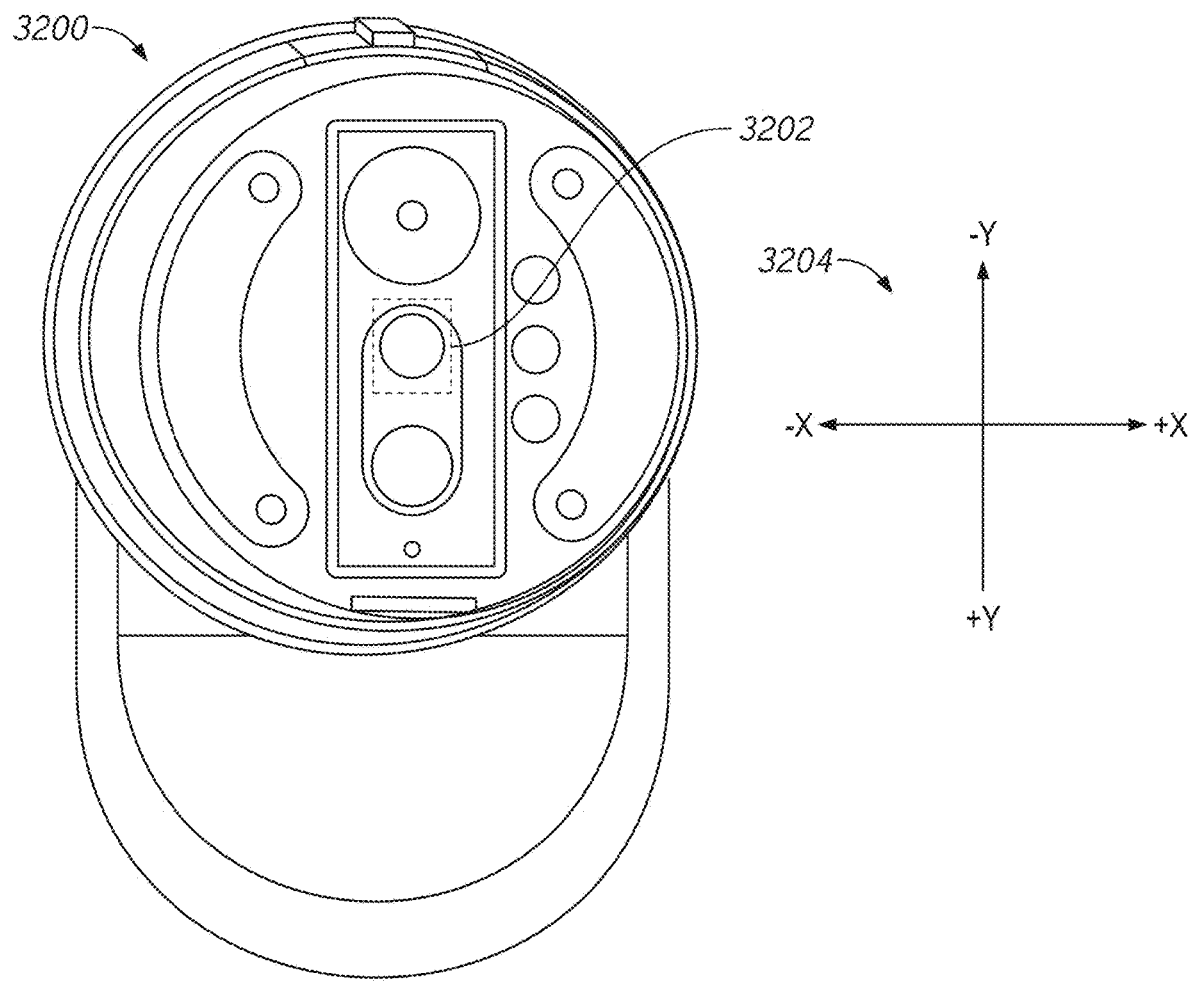
FIG. 32 illustrates an example view of the axes of an OCT sensor head.

In some examples, data from an OCT sensor may be skewed or otherwise not directly representative of the spacing of a tissue site. For example, as illustrated in FIG. 32, an OCT sensor 3200 may receive data with one or more measurement artifacts 3202, such as a skew or distortion relative to a coordinate frame 3204. The coordinate frame 3204 may correspond to a coordinate frame of the sensor 3200 or a tissue site of a patient.

Figure 33:
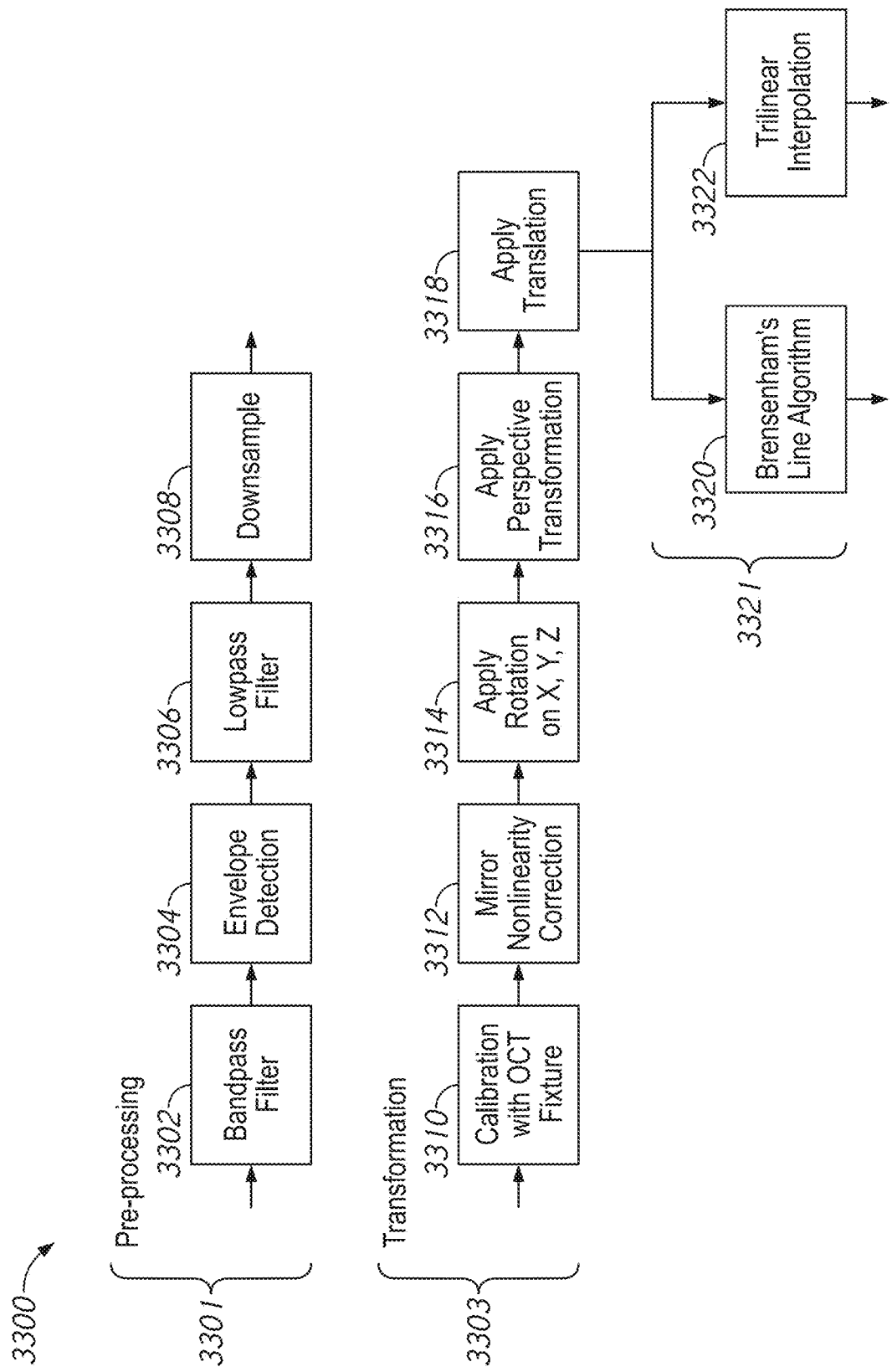
FIG. 33 illustrates a block diagram of example OCT signal processing.

To account for or correct the skew or other measurement artifacts 3202, a system 100 may perform one or more processes. For example, as illustrated in FIG. 33, OCT data signal processing 3300 can include pre-processing blocks 3301, transformation blocks 3303, and image blocks 3321.

The pre-processing blocks 3301 can include a first filter block 3302, an envelope detection block 3304, a second filter block 3306, and a downsample block 3308. The first filter block 3302 can include any suitable filter for selecting wavelengths of an OCT signal. For example, the first filter block 3302 can include a bandpass filter to extract the interference pattern generated between the coherent light from the sample and reference arm. An envelope detection block 3304 can include any suitable detector for determining an envelope of an OCT signal, which is proportional to the probability of a photon residing at that a certain depth. The second filter block 3306 can include a suitable filter for removing residual high frequencies from the envelope detection. For example, the second filter block 3306 can include a lowpass filter. The downsample block 3308 can include any suitable process or algorithm for downsampling an OCT signal, by, for example, reducing the dimensionality, sample size, or other process to reduce the size of the OCT file for ease of processing.

The transformation blocks 3303 can include a calibration block 3310, a nonlinearity correction block 3312, a rotation block 3314, a perspective transform block 3316, and a translation block 3318. The calibration block 3310 can include one or more processes for calibrating the OCT signal for example by applying a known sample of known dimension with known orientation and then comparing the OCT image from this sample. The mirror nonlinearity correction block 3312 accounts for the nonlinear relationship between the voltage applied to the mirror and angle of tilt, which can be found in the MEMS mirror specifications. The rotation block 3314 can include one or more algorithms or processes for applying a rotation transform along one or more axis in a coordinate frame, such as an OCT sensor coordinate frame or tissue site coordinate frame. The perspective transform block 3316 can include one or more algorithms or processes for applying a perspective transform to the OCT signal, to compensate for the distortion caused from viewing from a single point. The translation block 3318 can include one or more algorithms or processes for applying a translation transform to the OCT signal in a coordinate frame, such as an OCT sensor coordinate frame or tissue site coordinate frame. The output of the translation block 3318 or other transformation will go into the image block 3321

The image blocks 3321 can include one or more blocks to produce an OCT image from an OCT signal. For example, the image blocks 3321 can include a line algorithm block 3320, and an interpolation block 3322. The line algorithm block 3320 can include one or more line drawing algorithms or processes of approximating a line segment in discrete graphic data (for example, OCT data), such as Bresenham's line algorithm. The interpolation block 3322 can include one or more algorithms or processes for interpolating data on a multidimensional grid, such as trilinear interpolation.

FIGS. 34A and 34B illustrate example OCT measurements 3401, 3402 before and after signal processing respectively. For example, as illustrated in FIG. 34A, an OCT measurement 3401A or 3402A can include measurement artifacts, such as distortion. The OCT measurement 3401A or 3402A may be processed by the system (for example using processing 3300 discussed with reference to FIG. 33) to produce one or more transformed images 3401B or 3402B as illustrated in FIG. 34B, which may reduce the effects of one or more measurement artifacts in the OCT measurements.

Figure 35A:
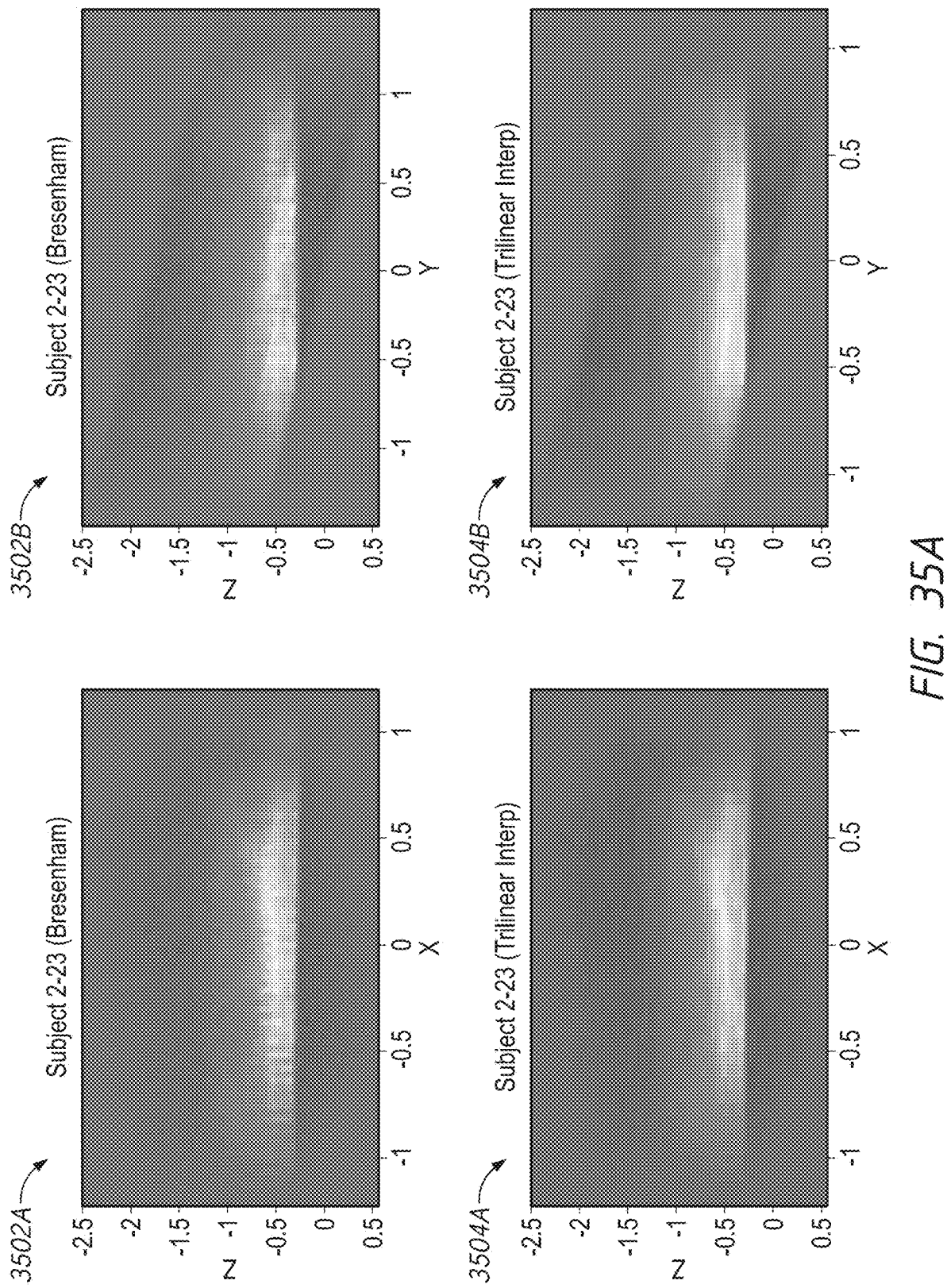
FIGS. 35A and 35B illustrate example OCT measurements after transformation without an air gap and with an air gap, respectively.
Figure 35B:
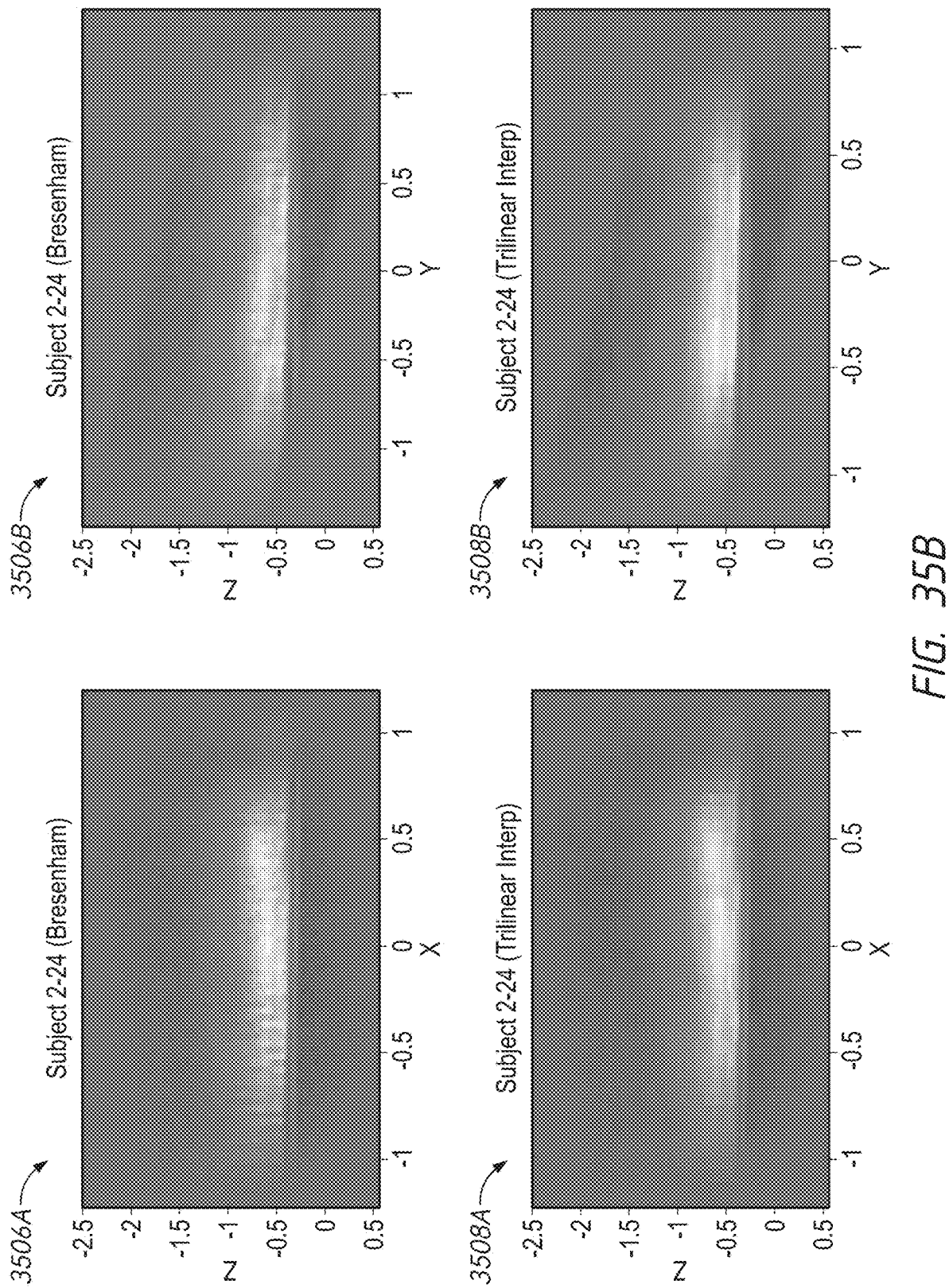

Advantageously, processing the OCT measurements to produce transformed images can allow for the system to better identify air gaps in OCT measurements (by for example an air gap detection process such as described above). FIGS. 35A and 35B illustrate example OCT measurements after transformation without an air gap and with an air gap respectively.

As illustrated in FIGS. 35A and 35B, after performing one or more transformation processes, such as a calibration, nonlinear correction, rotation, perspective transform, or translation, an OCT measurement can be processed to output an OCT image using one or more interpolation algorithms according to image block 3321. For example, as illustrated in FIG. 35A, using Bresenham's line Algorithm 3320, the OCT signal are transformed into OCT images 3502A and 3502B. OCT image 3502A is the image from scanning in the X direction. OCT image 3502B is the image from scanning in the Y direction. Using the same OCT signal, a Trilinear Interpolation technique 3322 would result in the OCT images 3504A and 3504B. As illustrated in FIG. 35B, illustrates an example with a different subject than FIG. 35A, where using Bresenham's line Algorithm 3320, the OCT signal are transformed into OCT images 3506A and 3506B. OCT image 3506A is the image from scanning in the X direction. OCT image 3506B is the image from scanning in the Y direction. Using the same OCT signal, a Trilinear Interpolation technique 3322 would result in the OCT images 3508A and 3508B.

10. Dual Band Raman Spectrometer

A Raman spectra may include useful information relating to analyte concentration of a tissue sample in multiple wavenumber ranges. For example, a Raman spectra can include useful information in a 200 to 1800 $cm^{-1}$ wavenumber range and in 2800 to 3800 $cm^{-1}$ wavenumber range. However, not all areas of a Raman spectra may contain useful information. In order to efficiently measure physiological parameters, such as analyte concentration, a system may utilize a spectrometer capable of selectively detecting data in useful wavenumber ranges.

Figure 36:
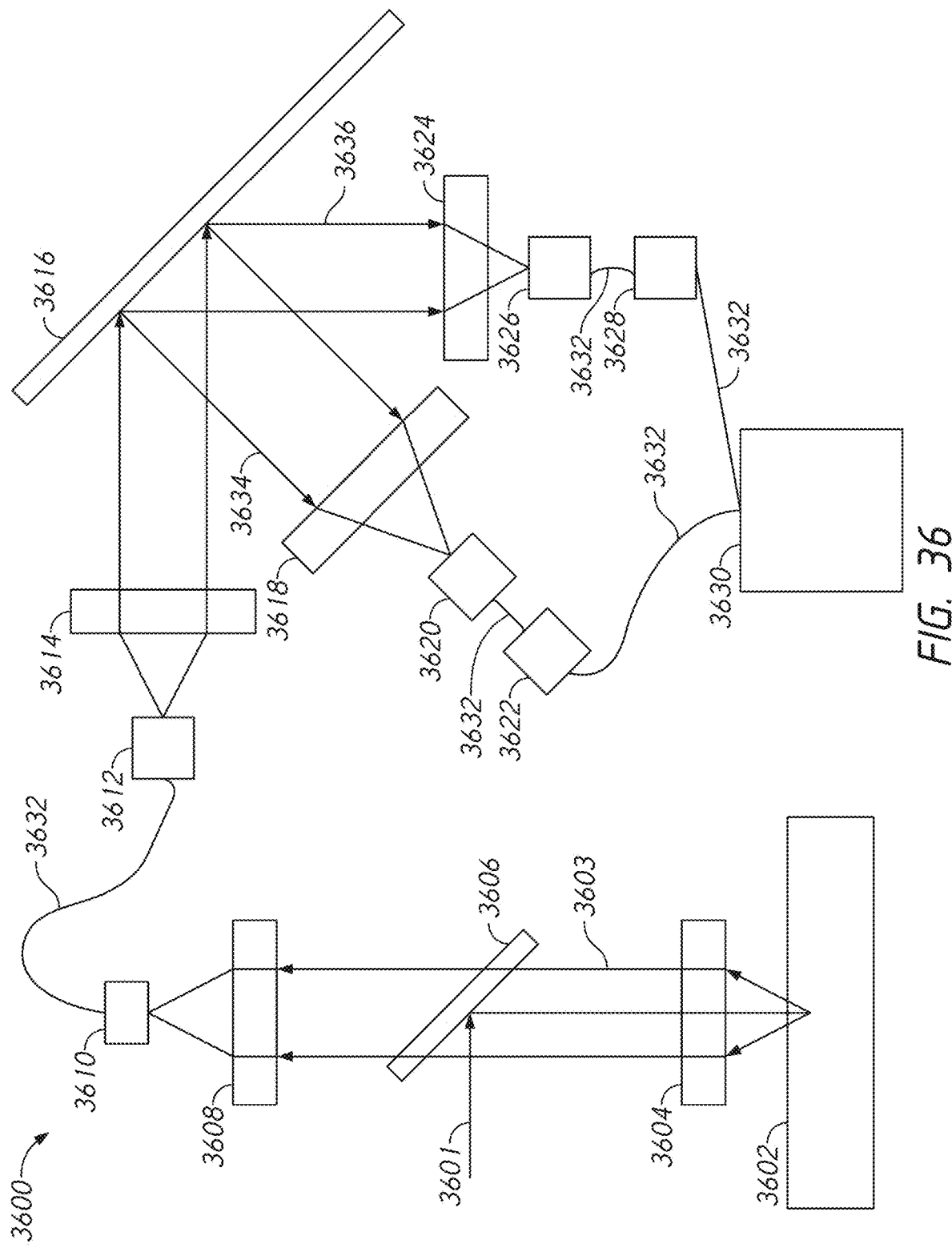
FIG. 36 illustrates an example dual band Raman spectrometer that may be used as part of a non-invasive sensor system.

FIG. 36 illustrates a dual band spectrometer 3600 that may be used to efficiently measure physiological parameters at a tissue site 3602 by detecting Raman spectra in two wavenumber ranges. For example, a dual band spectrometer 3600 can include one or more optical components 3604, 3608, 3618, 3624, one or more spectrometer slits 3614, one or more optical outputs 3612, one or more dichroic mirrors 3606, one or more detectors 3610, 3620, 3626, one or more gratings 3616, For example, light 3601 from a light source, such as a Raman excitation source, may be directed to interrogate a tissue site 3602. Light 3601 from the light source may be directed towards the tissue site by reflecting off a dichroic mirror 3606 towards one or more optical components 3604. The one or more optical components 3604 can include collimating optics or focusing optics, such as one or more convex or plano-convex lenses 2118A, 2118B, one or more concave or plano-concave lenses 2118C, or other type of lens or optical element as described with reference to FIGS. 21A-23C.

Emitted light 3603 that may include spectrographic data from the interrogated tissue site 3602 can be collected by the spectrometer 3600. Light 3603 may follow collection path that can include a collection cone, such as described with reference to FIGS. 21A-23C. Light 3603 in the collection cone can be collimated (by for example, the one or more optical components 3604) and transmitted through a dichroic mirror 3606 towards one or more optical components 3608. The one or more optical components 3608 can include collimating optics or focusing optics that may allow a pickup fiber 3610 to collect the light 3603. The optical input 3610 may transmit detected light towards an optical output 3612 via the fiber 3632. The measurement medium 3602 may emit the detectable light towards one or more spectrometer slits 3614. Those skilled in the art may recognize that 3632 can be a fiber or other form of light guide.

The detected light may be transmitted through one or more spectrometer slits 3614 towards a diffraction grating 3616. The grating 3616 may diffract light from the slit 3614 into a plurality of light beams. The structure and type of grating 3616 can help determine the wavenumber range the spectrometer 3600 may detect. For example, the groove frequency of a grating can help determine a wavenumber coverage of the spectrometer and a blaze angle of the grating can help determine a shape of the diffraction curve, which may affect the diffraction efficiency at different wavenumbers. A diffraction grating 3616 of a dual band spectrometer 3600 may be configured to diffract light in one or more wavenumber ranges between 200 and 3800 $cm^{-1}$. A 1200 line per mm holographic grating may be used to achieve the optimal resolution and throughput. The blaze wavelength used can be 700 nm or other suitable blaze wavelength. An expert in the field will see how this can be applied in different but standard configurations to yield the same result.

The grating 3616 may diffract light towards one or more optical components 3618, 3624 and one or more electronic components 3620, 3626, 3630. For example, diffracted light 3634 in a first band may be collected by a first set of one or more optical components 3618. The first band can include light with wavenumbers in a 200 to 1800 $cm^{-1}$ wavenumber range. The first set of one or more optical components 3618 can include collimating optics or focusing optics that may allow a detector 3620 to collect light in the first band. The collected light from the first band may be processed by processing electronics 3622. In some examples, the processed light signal may be transmitted towards an output or other electronic component. Additionally or alternatively, diffracted light in a second band 3636 may be collected by a second set of one or more optical components 3624. The second band can include light with wavenumbers in a 2800 to 3800 $cm^{-1}$ wavenumber range. The second set of one or more optical components 3624 can include collimating optics or focusing optics that may allow a detector 3626 to collect light in the second band. The collected light from the first band may be processed by processing components 3628. In some examples, the processed light signal may be transmitted towards an output or other electronic component.

11. Example Raman Spectrometer Entrance Slit

A spectrometer slit, such as slit 3614 of spectrometer 3600 as described with reference to FIG. 36, may determine how much of the detected light enters a detector plane. The width of the slit can affect aspects of the resulting Raman spectra. For example, the width of the slit can affect spectral resolution and intensity of the signal. A larger slit width may result in increased signal by allowing the use of bigger fiber but may also reduce spectral resolution due to the increase in the spot size. The slit width can be any suitable width, including but not limited to 5 micron, 50 micron, 100 micron, 200 micron, or 500 micron. Advantageously, in a Raman spectrometer that may be part of a system 100, such as the dual band spectrometer 3600, increasing a slit width may result in improved signal to noise ratio (SNR) when measuring physiological parameters without sacrificing much in terms of the spectral resolution. For example, a slit width that corresponds to a wavenumber range of 20 $cm^{-1}$ may improve the SNR by approximately 3-4 times over a slit width that corresponds to a wavenumber range of 10 $cm^{-1}$ based on the instantiation from within our device due to use of fibers. Even though the resolution drops, the resulting resolution is still within the acceptable limit of discretization of raman spectra.

12. Fiber Sensor

FIGS. 37A-37E illustrate aspects of an example fiber sensor configuration. A fiber sensor 3800 may be configured to have an initial intensity (10) detector 3804, a light source 3806, a tissue receiving portion 3810, and at least one detector 3802, 3812. In some examples, the light source 3806 may include at least one LED. For example, the light source 2806 may include a multiple LED package.

Figure 37A:
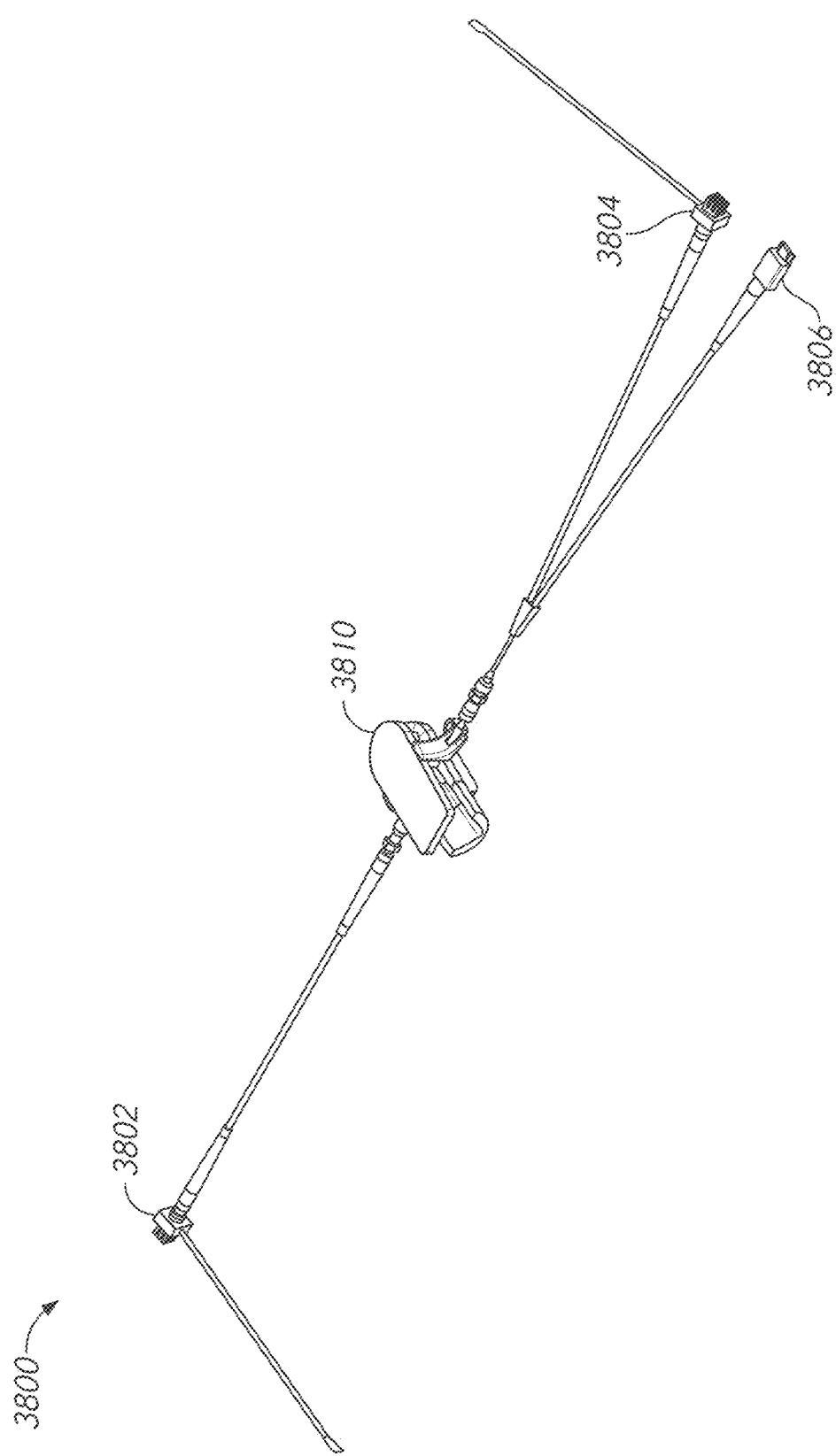
Figure 37B:
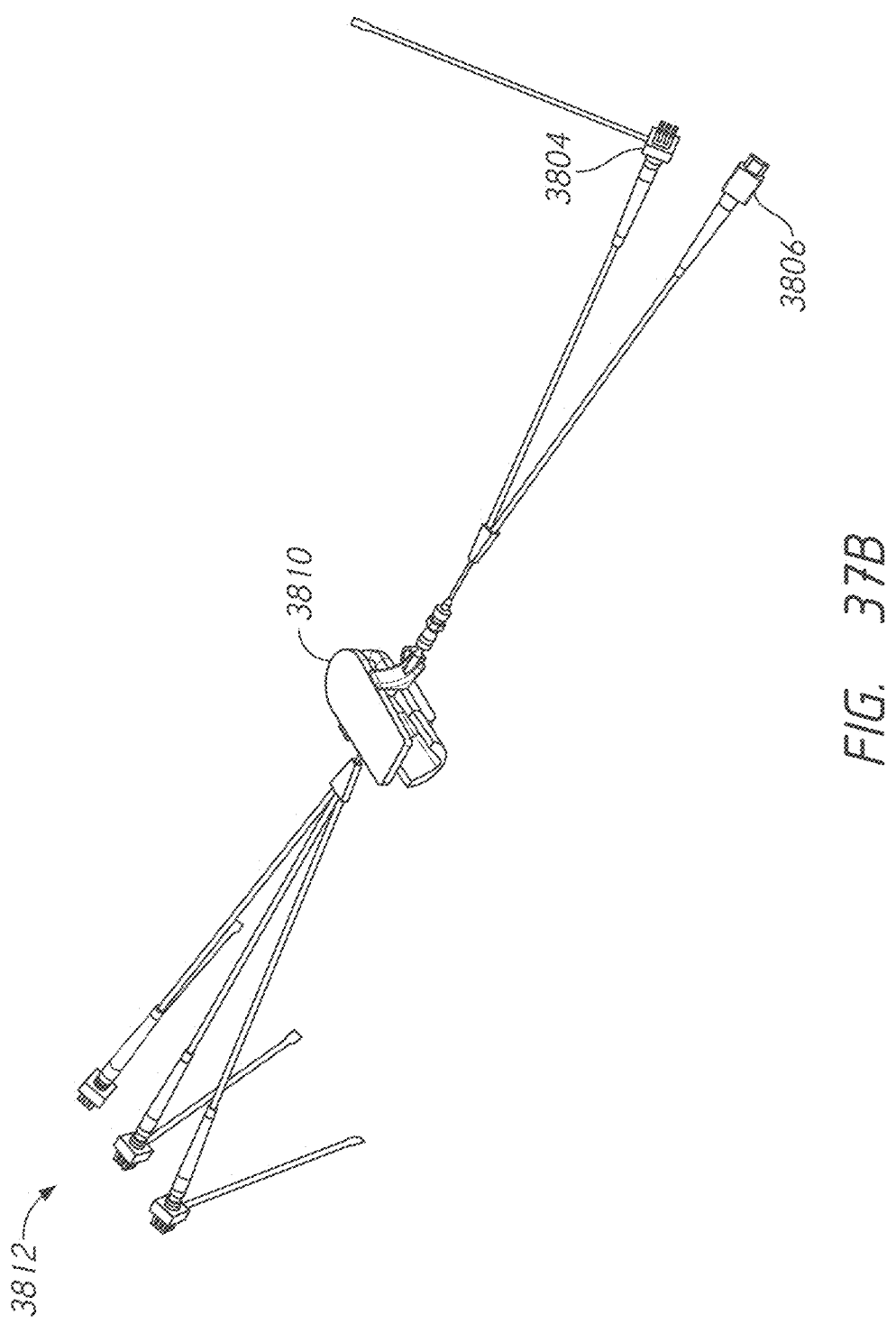
Figure 37C:
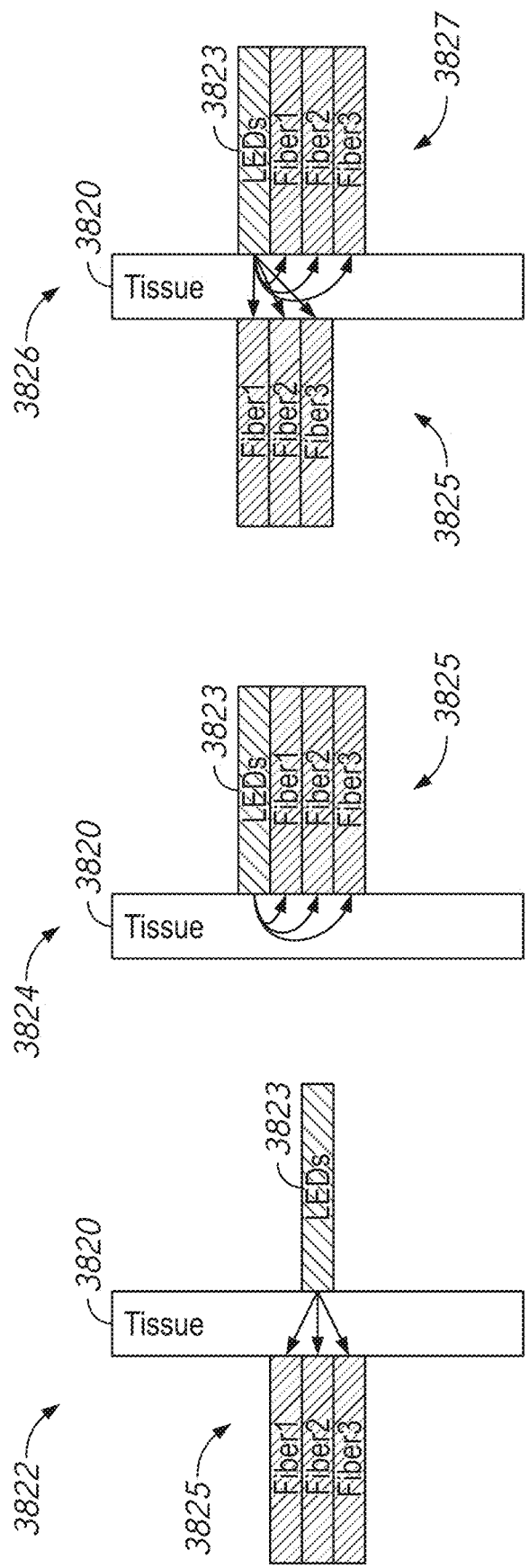

In some examples, as illustrated in FIG. 37A, the fiber sensor 3800 may include a single may include a single path length detector 3802. In some examples, as illustrated in FIG. 37B, the fiber sensor 3800 may include multiple path length detectors 3812. For example, the fiber sensor 3800 may include three path length detectors. The configuration of detectors in the fiber sensor may include, but are not limited to, variations such as illustrated in FIG. 37C. For example, in a first configuration 3822 (or a transmission configuration), a sensor 3800 may include a light source 3823 configured to emit light into the tissue 3820 of a patient. The light may be attenuated and received by a plurality of detectors or fibers associated with the detectors 3825 on an opposite side of the tissue 3820 of the patient so as to detect transmitted light. In another example, in a second configuration 3824 (or a reflection configuration), a sensor 3800 may include a light source 3823 configured to emit light into the tissue 3820 of a patient and a plurality of detectors 3825 configured to detect reflected light attenuated by the tissue 3820 of the patient. In the second configuration 3824, the light source 3823 and the detectors or fibers associated with the detectors 3825 may be on substantially the same side of the tissue site 3820 of the patient or at a position for the detectors 3825 to receive reflected attenuated light. In a third configuration 3826 (or a transflection configuration), a sensor 3800 may include a light source 3823 configured to emit light into the tissue 3820 of a patient, a first plurality of detectors 3825 configured to detect transmitted light attenuated by the tissue of the patient 3820, and a second plurality of detectors 3827 configured to detect reflected light attenuated by the tissue 3820 of the patient.

FIG. 37C illustrates an example tissue receiving portion 3810 of a sensor 3800. For example, a tissue receive portion 3810 may be configured to receive a tissue site of a patient, such as a fingertip, toe, nose, earlobe, or other suitable tissue site. In some examples, a receiving cavity 3814 may be configured to accept a tissue site of a patient. In some examples, the receiving cavity 3814 may be configured to allow at least one fiber of the fiber sensor 3800 to transmit or detect light from the tissue site of the patient. For example, an end 3816 of at least one fiber may be adjacent to or within the receiving cavity 3814 so as to allow for placement of the tissue site next to the end 3816. In some examples, a fiber end 3816 may include a connector or a protective cover.

Figure 37E:
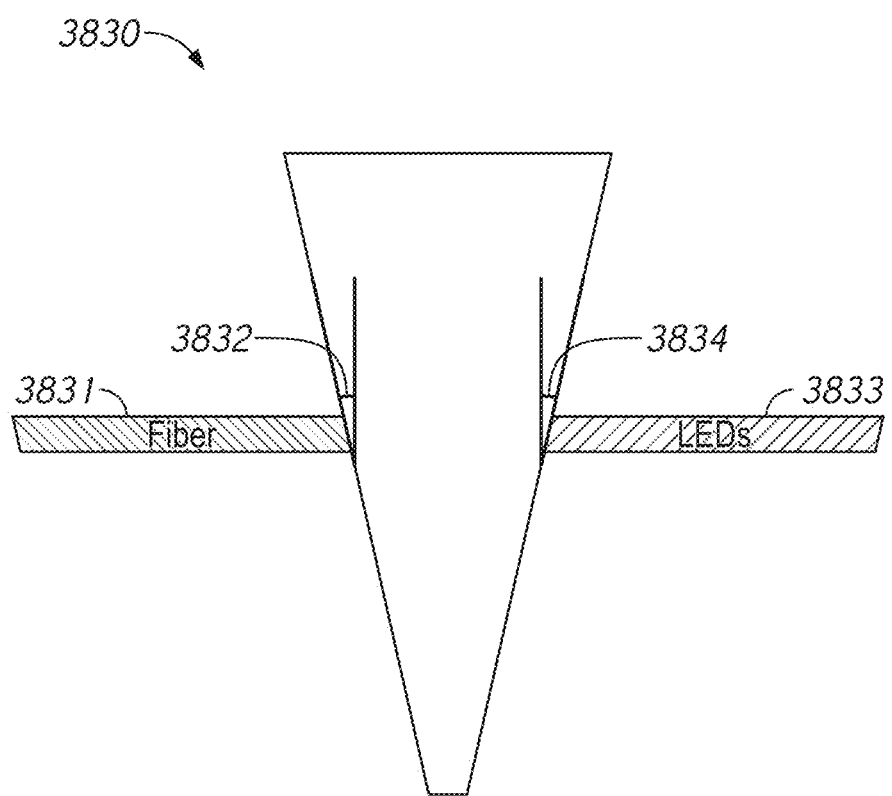

As illustrated in FIGS. 37D and 37E, in some examples, a fiber end 3816 may form an angle θ with respect to a plane perpendicular to the length of the optical fiber. In some examples, an angle 3832 of a detector fiber 3831 may be the same or different as the angle 3834 of a light source fiber 3833.

E. ADDITIONAL EXAMPLES

Below are additional examples of a patient monitoring device or method of using the same.

Example 1: A system for measuring physiological parameters from a tissue site of a patient, the system comprising:
a plurality of non-invasive sensors configured to obtain physiological data associated with a patient;
one or more sensor heads comprising:
  a frame configured to support at least a portion of each of the plurality of noninvasive sensors;
  an interlocking component configured to couple to the frame and mate with a tissue site attachment component,
    wherein the tissue site attachment component is configured to couple to a tissue site of the patient, and
    wherein the tissue site attachment component has an opening configured to allow at least one of the plurality of noninvasive sensors to obtain physiological data associated with the patient at the tissue site.

Example 2: The system of example 1 wherein the interlocking component is configured to stabilize the tissue site while at least one of the plurality of noninvasive sensors obtains physiological data associated with the patient at the tissue site.

Example 3: The system of example 2, wherein the interlocking component is configured to stabilize the tissue site in relation to horizontal movement.

Example 4: The system of example 1, wherein the frame comprises an enclosure mechanism configured to receive a finger of the patient associated with the tissue site.

Example 5: The system of example 1, wherein the frame is configured to be received by an enclosure mechanism configured to receive a finger of the patient associated with the tissue site.

Example 6: The system of example 4, wherein the enclosure mechanism comprises a top portion and a bottom portion connected by a hinge configured to open and accept the finger of the patient.

Example 7: The system of example 4, wherein the enclosure mechanism comprises an opening to allow at least one of the plurality of sensors to measure the tissue site of the patient.

Example 8: The system of example 1, wherein the tissue site attachment component is configured to couple to the tissue site of the patient by an adhesive.

Example 9: The system of example 1, wherein the interlocking component comprises one or more electrical contacts.

Example 10: The system of example 9, wherein the frame comprises one or more spring loaded electrical contacts configured to electrically connect with the one or more electrical contacts of the interlocking attachment when the interlocking attachment is coupled to the frame.

Example 11: A system for measuring physiological parameters from a tissue site of a patient, the system comprising:
 a plurality of non-invasive sensors configured to obtain physiological data associated with a patient;
 one or more sensor heads comprising a frame configured to support at least a portion of each of the plurality of noninvasive sensors;
 a movement mechanism configured to couple to the one or more sensor heads, wherein the movement mechanism is configured to allow for a plurality of degrees of freedom of movement of the one or more sensor heads; and
 a movable cradle configured to accept a hand of a patient.

Example 12: The system of example 11, wherein the movement mechanism comprises a translational or rotational stage.

Example 13: The system of example 11, wherein the plurality of degrees of freedom comprises six degrees of freedom.

Example 14: The system of example 11, wherein the movable cradle comprises a movable palm rest.

Example 15: The system of example 14, wherein the movable palm rest comprises:
 a palm receiving portion configured to accept the hand of the patient; and
 a palm rest movement mechanism configured to adjust the location of the palm receiving portion.

Example 16: The system of example 15, wherein the palm rest movement mechanism comprises a translational or rotational stage.

Example 17: The system of example 15, wherein the palm rest movement mechanism comprises:
 a stopping mechanism configured to stop the palm receiving portion on a track; and
 a release mechanism configured to allow the palm receiving portion to move along the track.

Example 18: The system of example 15, wherein the palm rest comprises a heated surface configured to be in contact with at least a portion of the hand of the patient.

Example 19: The system of example 15, wherein the stopping mechanism comprises at least one of a brake or latch.

Example 20: The system of example 11, wherein the plurality of sensors comprises at least one of a Raman sensor, OCT sensor, or an absorbance sensor.

Example 21: The system of example 11, wherein the plurality of sensors comprises a fusion probe sensor configured to perform a plurality types of measurements.

Example 22: The system of example 11 comprising an imaging system configured to monitor the positioning of a tissue site of the patient in relation to at least one of the plurality of sensors.

Example 23: A system for measuring physiological parameters from a tissue site of a patient, the system comprising:
 a plurality of non-invasive sensors comprising:
  an emitter configured to emit excitation light; and
  a detector configured to detect light after interaction with a tissue site of a patient;
 one or more sensor heads comprising:
  a frame configured to support at least a portion of each of the plurality of noninvasive sensors;
  one or more scanning mechanisms configured to direct a path of light from the emitter towards a tissue site of a patient;
 one or more hardware processors configured to:
  determine a scanning pattern comprising a pattern of movement of the excitation light from the emitter towards the tissue site of the patient;
  actuate the one or more scanning mechanisms to cause the excitation light to follow a path on the tissue site of the patient based on the scanning pattern at a substantially constant speed;
  detect a plurality of physiological measurements at a plurality of points on the path based on the scanning pattern; and
  average the plurality of physiological measurements to determine a physiological parameter.

Example 24: The system of example 23, wherein the scanning pattern comprises a Lissajous pattern or a raster pattern.

Example 25: The system of example 23, wherein the scanning pattern is repeated periodically.

Example 26: The system of example 25, wherein the scanning pattern is repeated with a period of one minute.

Example 27: The system of example 23, wherein the path is within an interrogated area of 2.5 square centimeters.

Example 28: The system of example 23, wherein the path is within an interrogated area of 1 square centimeters.

Example 29: The system of example 23, wherein the tissue site of the patient comprises a nail bed of a digit of the patient.

Example 30: The system of example 23, wherein the one or more scanning mechanisms comprises at least one of a motorized mirror or a rotary wedge lens.

Example 31: The system of example 30, wherein the one or more scanning mechanisms comprises the motorized mirror and wherein the motorized mirror is configured to direct at least a portion of the excitation light towards the tissue site of the patient through the one or more sensor heads by movement of the mirror.

Example 32: The system of example 30, wherein the one or more scanning mechanisms comprises the rotary wedge lens and wherein the rotary wedge lens is configured to direct at least a portion of the excitation light towards the tissue site of the patient through the one or more sensor heads by rotation of the rotary wedge lens.

Example 33: A system for measuring physiological parameters from a tissue site of a patient, the system comprising:
  a plurality of non-invasive sensors configured to obtain physiological data associated with a patient;
  one or more sensor heads comprising a frame configured to support at least a portion of each of the plurality of noninvasive sensors; and
  a timing processor in communication with the plurality of non-invasive sensors, the timing processor comprising:
    a timing generator configured to generate a timing signal;
    a first programmable delay line configured to delay the timing signal according to a first delay;
    a first signal converter in communication with the plurality of non-invasive sensors, wherein the first signal converter is configured to receive physiological data from the non-invasive sensors according to the first delay of the timing signal;
    a second programmable delay line configured to delay the timing signal according to a second delay different from the first delay;
    a second signal converter in communication with the plurality of non-invasive sensors, wherein the second signal converter is configured to receive physiological data from the non-invasive sensors according to the second delay of the timing signal; and
    a deserializer configured to generate one or more data signals from serialized data received from the first signal converter or the second signal converter.

Example 34: The system of example 33, wherein the timing signal oscillates between a high and a low state.

Example 35: The system of example 33, wherein the second delay is longer than the first delay.

Example 36: The system of example 33, wherein the first delay comprises no delay.

Example 37: A multi-path length absorbance sensor comprising:
  at least one emitter;
  at least one detector; and
  a multi-path length fiber head bundle comprising:
    a set of short path length light source fibers configured to transmit light from the at least one emitter towards a tissue site of a patient;
    a set of long path length light source fibers from the at least one emitter towards the tissue site of the patient; and
    one or more detector fibers configured to transmit a detected signal to the at least one detector,
  wherein the one or more detector fibers are oriented in a central core of the fiber head bundle;
  wherein the set of short path length light source fibers are oriented to surround the detector fiber in the central core of the fiber head bundle; and
  wherein the set of long path length light source fibers are oriented to surround the central core of the fiber head bundle.

Example 38: The system of example 37, wherein at least one of the set of short path length light source fibers, the set of long path length light source fibers, and the one or more detector fibers has a hexagonal cross section.

Example 39: The system of example 37, wherein at least one of the set of short path length light source fibers, the set of long path length light source fibers, and the one or more detector fibers has a circular cross section.

Example 40: The system of example 37, wherein at least one of the set of short path length light source fibers, the set of long path length light source fibers, and the one or more detector fibers has a square cross section.

Example 41: The system of example 37, wherein the at least one of the set of short path length light source fibers or the set of long path length light source fibers has a substantially uniform illumination profile.

Example 42: The system of example 37, wherein the at least one of the set of short path length light source fibers, the set of long path length light source fibers, and the one or more detector fibers has a square core.

Example 43: The system of example 37, wherein a packing density of fibers in the multi-path length fiber head bundle is 84 percent.

Example 44: A system for measuring physiological parameters from a tissue site of a patient, the system comprising:
  a first non-invasive sensor comprising:
    a first emitter configured to emit first light towards a tissue site of a patient;
    a first detector configured to receive a first signal comprising physiological data associated with the tissue site of the patient;
  a second non-invasive sensor configured to:
    a second emitter configured to emit second light towards the tissue site of the patient;
    a second detector configured to receive a second signal comprising physiological data associated with the tissue site of the patient; and
  one or more sensor heads comprising:
    a lens system comprising collimating optics configured to:
      transmit the first light towards the tissue site of the patient along an outer perimeter of an optical path;
      transmit the first signal from the tissue site of the patient towards the first detector along a central core of the optical path;
      transmit the second signal from the tissue site of the patient towards the second detector along a different path than the first signal within the optical path.

Example 45: The system of example 44, wherein the first non-invasive sensor comprises a Raman sensor and wherein the second non-invasive sensor comprises an OCT sensor.

Example 46: The system of example 44, wherein the one or more sensor heads comprises a plurality of fiber bundles and an illumination source.

Example 47: The system of example 46, wherein the illumination source comprises an OCT illumination source.

Example 48: The system of example 44, wherein the lens system is to converge light from the first emitter near the tissue site of the patient.

Example 49: The system of example 44, wherein the lens system is to converge light from the second emitter near the tissue site of the patient.

Example 50: The system of example 44, wherein the one or more sensor heads comprises a window configured to be placed between the lens system and the tissue site of the patient.

Example 51: The system of example 50, wherein the window comprises Calcium Flouride, Magnesium Flouride, Sapphire, or Quartz.

Example 52: The system of example 50, wherein the window is 1 mm.

Example 53: The system of example 44, wherein the lens system comprises a prism lens.

Example 54: The system of example 53, wherein the prism lens is configured to orient an illumination source beam towards the collimating optics so that the illumination source beam is transmitted towards the tissue site of the patient.

Example 55: A heating system for increasing the temperature of the tissue site of a patient, the heating system comprising:
  a plurality of non-invasive sensors configured to measure a plurality of physiological parameters in an interrogation volume at a tissue site of a patient,
    wherein a first non-invasive sensor of the plurality of non-invasive sensors comprises a first emitter and a first detector configured to measure an absorbance in the interrogation volume; and
    wherein a second non-invasive sensor of the plurality of non-invasive sensors comprises a Raman sensor or an OCT sensor;
  a first temperature sensor configured to measure a surface temperature of the tissue site of the patient; and
  one or more hardware processors configured to:
    receive the surface temperature from the first temperature sensor;
    calculate a current temperature at a determined depth within the interrogation volume as a function of at least in part the surface temperature, absorbance of the tissue site, the size of the interrogation volume, a power of the first emitter, and ambient temperature;
    signal to a cooling device to cool the tissue of the patient based on the current temperature.

Example 56: A system for detecting an air gap between a surface of a sensor and a tissue site of a patient, the system comprising:
  a plurality of non-invasive sensors configured to obtain physiological data associated with a patient;
  one or more sensor heads comprising:
    a frame configured to support at least a portion of each of the plurality of noninvasive sensors; and
    a surface configured to contact a tissue site of the patient; and
  one or more hardware processors configured to:
    receive an image of the tissue site of the patient from at least one of the plurality of non-invasive sensors;
    process the image using a classifier trained by a neural network to determine a likelihood score that the surface of the one or more sensor heads is in contact with the tissue site of the patient; and
    cause at least one of the plurality of non-invasive sensors to obtain physiological data associated with the patient based on the likelihood score.

Example 57: The system of example 56, wherein the classifier is trained using a plurality of training images and wherein the neural network is configured to:
  for each training image of the plurality of training images:
    extract a plurality of one dimensional slices of the training image at different pixel locations within the image;
    process the plurality of one dimensional slices of the training images through a plurality of convolution layers or pooling layers; and
    output a weight that the surface of the one or more sensor heads is in contact with the tissue site of the patient in the one or more training images based on the processed plurality of one dimensional slices of the training images.

Example 58: The system of example 57, wherein the neural network comprises:
  a first plurality of convolutional layers configured to filter features from the training images and generate a first convolved image from a training image of the plurality of training images;
  a first activation layer configured to apply a nonlinear transformation to the first convolved image to generate a first activated image;
  a second plurality of convolutional layers configured to filter features from the activated image and generate a second convolved image;
  a second activation layer configured to apply a nonlinear transformation to the second convolved image to generate a second activated image;
  one or more pooling layers configured to reduce the dimensionality of the second activated image to generate a maxpooled image;
  a flattening layer configured to apply a transformation to the maxpooled image to generate a flattened image comprising a two-dimensional array of pixels.
  a fully connected layer configured to determine which features in the flattened image correlate to an air gap state of the training image;
  a third activation layer configured to apply a nonlinear function to the output of the fully connected layer; and
  a dropout layer configured to apply a drop a percentage of the output of the third activation layer.

Example 59: A spectroscopic system comprising:
  a Raman spectrometer configured to obtain Raman spectrographic data associated with a first band of wavenumbers and a second band of wavenumbers at least 500 $cm^{-1}$ away from the first band, the Raman spectrometer comprising:
    an emitter configured to emit light towards a tissue sample of a patient;
    a diffraction grating configured to diffract Raman scattered light from the tissue site of the patient towards a first detector and a second detector, wherein:
      the first detector is configured to detect Raman scattered light in the first band; and
      the second detector is configured to detect Raman scattered light in the second band.

Example 60: The spectroscopic system of example 59, wherein the diffraction grating is a holographic grating.

Example 61: The spectroscopic system of example 60, wherein the diffraction grating is a 1200 line per mm holographic grating.

Example 62: The spectroscopic system of example 59, wherein a blaze wavelength of the diffraction grating comprises 700 nm.

Example 63: The spectroscopic system of example 59, wherein the diffraction grating is configured to diffract light in one or more wavenumber ranges between 200 and 3800 cm'.

Example 64: The spectroscopic system of example 63, wherein the first band comprises wavenumbers in a range of 200 to 1800 cm'.

Example 65: The spectroscopic system of example 63, wherein the second band comprises wavenumber in a range of 2800 to 3800 cm'.

Example 66: The spectroscopic system of example 59, wherein the second band comprises a range of wavenumbers at least 1000 $cm^{-1}$ away from the first band.

Example 67: The spectroscopic system of example 59 comprising an entrance slit configured to allow light from one or more emitters to enter a detector plane of the Raman spectrometer.

Example 68: The spectroscopic system of example 67, wherein a slit width of the entrance slit corresponds to a wavenumber range of 20 cm$^{-1}$.

Example 69: A fiber sensor comprising:
  at least one light source fiber configured to transmit light to a tissue site of a patient;
  a plurality of multiple path length detector fibers configured to detect attenuated light from the tissue site of the patient;
  a tissue receiving portion configured to receive the tissue site of the patient, the tissue receiving portion comprising:
  a receiving cavity configured to accept the tissue site of the patient,
  wherein an end of the at least one light source fiber and an end of the plurality of multiple path length detector fibers are positioned to be adjacent to the tissue site of the patient in the receiving cavity,
  wherein the end of the at least one light source fiber forms a first angle with respect to a plane perpendicular to the length of the at least one light source fiber, and
  wherein the end of the plurality of multiple path length detector fibers forms a second angle with respect to a plane perpendicular to the length of the plurality of multiple path length detector.

Any of the above examples may be combined.

F. TERMINOLOGY

The term "and/or" herein has its broadest least limiting meaning which is the disclosure includes A alone, B alone, both A and B together, or A or B alternatively, but does not require both A and B or require one of A or one of B. As used herein, the phrase "at least one of" A, B, "and" C should be construed to mean a logical A or B or C, using a non-exclusive logical or.

The following description is merely illustrative in nature and is in no way intended to limit the disclosure, its application, or uses. For purposes of clarity, the same reference numbers will be used in the drawings to identify similar elements. It should be understood that steps within a method may be executed in different order without altering the principles of the present disclosure.

Features, materials, characteristics, or groups described in conjunction with a particular aspect, embodiment, or example are to be understood to be applicable to any other aspect, embodiment or example described herein unless incompatible therewith. All of the features disclosed in this specification (including any accompanying claims, abstract and drawings), or all of the steps of any method or process so disclosed, may be combined in any combination, except combinations where at least some of such features or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated or disclosed may differ from those shown in the figures. Depending on the embodiment, certain of the steps described above may be removed, others may be added. For example, the actual steps or order of steps taken in the disclosed processes may differ from those shown in the figures. Depending on the embodiment, certain of the steps described above may be removed, others may be added. For instance, the various components illustrated in the figures may be implemented as software or firmware on a processor, controller, ASIC, FPGA, or dedicated hardware. Hardware components, such as processors, ASICs, FPGAs, and the like, can include logic circuitry. Furthermore, the features and attributes of the specific embodiments disclosed above may be combined in different ways to form additional embodiments, all of which fall within the scope of the present disclosure.

User interface screens illustrated and described herein can include additional or alternative components. These components can include menus, lists, buttons, text boxes, labels, radio buttons, scroll bars, sliders, checkboxes, combo boxes, status bars, dialog boxes, windows, and the like. User interface screens can include additional or alternative information. Components can be arranged, grouped, displayed in any suitable order.

Although the present disclosure includes certain embodiments, examples and applications, it will be understood by those skilled in the art that the present disclosure extends beyond the specifically disclosed embodiments to other alternative embodiments or uses and obvious modifications and equivalents thereof, including embodiments which do not provide all of the features and advantages set forth herein. Accordingly, the scope of the present disclosure is not intended to be limited by the specific disclosures of preferred embodiments herein, and may be defined by claims as presented herein or as presented in the future.

Conditional language, such as "can," "could," "might," or "may," unless specifically stated otherwise, or otherwise understood within the context as used, is generally intended to convey that certain embodiments include, while other embodiments do not include, certain features, elements, or steps. Thus, such conditional language is not generally intended to imply that features, elements, or steps are in any way required for one or more embodiments or that one or more embodiments necessarily include logic for deciding, with or without user input or prompting, whether these features, elements, or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A system for measuring physiological parameters from a tissue site of a patient, the system comprising:
    a plurality of noninvasive sensors configured to obtain physiological data associated with a patient;
    a tissue site attachment component; and
    one or more sensor heads comprising:
        a frame configured to support at least a portion of each of the plurality of noninvasive sensors; and
        an interlocking component configured to mate with the tissue site attachment component so as to limit movement of the interlocking component with respect to the tissue site attachment component, wherein the tissue site attachment component is configured to couple to a tissue site of the patient, the interlocking component comprising:
            an opening configured to allow at least one of the plurality of noninvasive sensors to obtain physiological data associated with the patient at the tissue site; and
            a raised structure configured to be received into a recess of the tissue site attachment component at least partially formed by one or more raised walls of the tissue site attachment component.

2. The system of claim 1 wherein the interlocking component is configured to stabilize the tissue site while at least one of the plurality of noninvasive sensors obtains physiological data associated with the patient at the tissue site.

3. The system of claim 2, wherein the interlocking component is configured to stabilize the tissue site in relation to horizontal movement.

4. The system of claim 1, wherein the frame comprises an enclosure mechanism configured to receive a finger of the patient associated with the tissue site.

5. The system of claim 1, wherein the frame is configured to be received by an enclosure mechanism configured to receive a finger of the patient associated with the tissue site.

6. The system of claim 4, wherein the enclosure mechanism comprises a top portion and a bottom portion connected by a hinge configured to open and accept the finger of the patient.

7. The system of claim 4, wherein the enclosure mechanism comprises an opening to allow at least one of the plurality of noninvasive sensors to measure the tissue site of the patient.

8. The system of claim 1, wherein the tissue site attachment component is configured to couple to the tissue site of the patient by an adhesive.

9. The system of claim 1, wherein the interlocking component comprises one or more electrical contacts.

10. The system of claim 9, wherein the frame comprises one or more spring loaded electrical contacts configured to electrically connect with the one or more electrical contacts of the interlocking component when the interlocking component is coupled to the frame.

* * * * *